United States Patent
Cho et al.

(10) Patent No.: US 11,466,093 B2
(45) Date of Patent: Oct. 11, 2022

(54) ANTIBODY DERIVATIVES WITH CONDITIONALLY ENABLED EFFECTOR FUNCTION

(71) Applicant: The General Hospital Corporation, Boston, MA (US)

(72) Inventors: Glen S. Cho, Newton, MA (US); Brian Seed, Boston, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

(21) Appl. No.: 15/748,083

(22) PCT Filed: Jul. 27, 2016

(86) PCT No.: PCT/US2016/044177
§ 371 (c)(1),
(2) Date: Jan. 26, 2018

(87) PCT Pub. No.: WO2017/019729
PCT Pub. Date: Feb. 2, 2017

(65) Prior Publication Data
US 2018/0215831 A1 Aug. 2, 2018

Related U.S. Application Data

(60) Provisional application No. 62/197,262, filed on Jul. 27, 2015.

(51) Int. Cl.
| | |
|---|---|
| *C07K 16/46* | (2006.01) |
| *C12N 15/13* | (2006.01) |
| *C07K 16/28* | (2006.01) |
| *C07K 16/30* | (2006.01) |
| *C07K 16/32* | (2006.01) |

(52) U.S. Cl.
CPC ...... *C07K 16/2887* (2013.01); *C07K 16/2803* (2013.01); *C07K 16/3061* (2013.01); *C07K 16/32* (2013.01); *C07K 16/46* (2013.01); *C07K 2317/24* (2013.01); *C07K 2317/622* (2013.01); *C07K 2317/71* (2013.01); *C07K 2317/732* (2013.01); *C07K 2317/734* (2013.01); *C07K 2318/20* (2013.01); *C07K 2319/00* (2013.01); *C07K 2319/30* (2013.01); *C07K 2319/32* (2013.01); *C07K 2319/50* (2013.01)

(58) Field of Classification Search
CPC .......................... C07K 16/46; C07K 2319/50; C07K 2319/30; C07K 2317/71
USPC ............................................. 424/133.1, 178.1
See application file for complete search history.

(56) References Cited

U.S. PATENT DOCUMENTS

| | | |
|---|---|---|
| 5,475,096 A | 12/1995 | Gold et al. |
| 6,268,488 B1 | 7/2001 | Barbas, III et al. |
| 6,528,624 B1 | 3/2003 | Idusogie et al. |
| 6,737,056 B1 | 5/2004 | Presta |
| 7,101,977 B2 | 9/2006 | Rosenblum et al. |
| 7,276,585 B2 | 10/2007 | Lazar et al. |
| 8,008,443 B2 | 8/2011 | Dall et al. |
| 8,513,390 B2 | 8/2013 | Stagliano et al. |
| 8,518,404 B2 | 8/2013 | Daugherty et al. |
| 8,529,898 B2 | 9/2013 | Daugherty et al. |
| 8,541,203 B2 | 9/2013 | Daugherty et al. |
| 8,563,269 B2 | 10/2013 | Stagliano et al. |
| 8,618,252 B2 * | 12/2013 | Farrington ............... A61P 35/00 424/134.1 |
| 8,666,680 B2 | 3/2014 | Sondermann et al. |
| 2005/0038229 A1 | 2/2005 | Lipovsek et al. |
| 2006/0058510 A1 | 5/2006 | Skerra et al. |
| 2007/0148164 A1 * | 6/2007 | Farrington ............... A61P 43/00 435/328 |
| 2009/0304719 A1 | 12/2009 | Daugherty et al. |
| 2010/0055761 A1 | 3/2010 | Seed et al. |
| 2010/0136018 A1 | 6/2010 | Dolk et al. |
| 2010/0189651 A1 | 7/2010 | Stagliano et al. |
| 2011/0178279 A1 | 7/2011 | Williams et al. |
| 2012/0003210 A1 * | 1/2012 | Farrington ............. C07K 16/00 435/69.6 |
| 2012/0095193 A1 | 4/2012 | Burden et al. |
| 2012/0149061 A1 | 6/2012 | Stagliano et al. |
| 2013/0295085 A1 | 11/2013 | Noelle |
| 2015/0079088 A1 * | 3/2015 | Lowman ............. C07K 16/2809 424/135.1 |
| 2015/0110810 A1 | 4/2015 | Taylor et al. |
| 2021/0269547 A1 * | 9/2021 | Cobbold ............. C07K 16/2815 |

FOREIGN PATENT DOCUMENTS

| | | |
|---|---|---|
| EP | 2610268 | 7/2013 |
| WO | WO 1990/004413 | 5/1990 |
| WO | WO 93/19163 | 9/1993 |
| WO | WO 97/15669 | 5/1997 |

(Continued)

OTHER PUBLICATIONS

Chen et al. (Adv Drug Delivery Rev 65:(10):1357-1369 (Oct. 15, 2013)).*
Annand et al., "Caspase-1 (interleukin-1b-converting enzyme) is inhibited by the human serpin analogue proteinase inhibitor 9," Biochem. J, 1999, 342:655.
Appella et al., "The receptor-binding sequence of urokinase. A biological function for the growth-factor module of proteases," J Biol Chem, Apr. 1987, 262:4437-40.
Baum et al., "beta-Galactosidase containing a human immunodeficiency virus protease cleavage site is cleaved and inactivated by human immunodeficiency virus protease," PNAS, Dec. 1990, 87:10023-10027.
Beck et al., "Rapid and sensitive oligonucleotide ligation assay for detection of mutations in human immunodeficiency virus type 1 associated with high-level resistance to protease inhibitors," Apr. 2002, 40: 1413-9.

(Continued)

*Primary Examiner* — Lynn A Bristol
(74) *Attorney, Agent, or Firm* — Fish & Richardson P.C.

(57) ABSTRACT

Antibody derivatives that have diminished effector function in the initial state owing to the presence of one or more disabling moieties that substantially prevent engagement of the antibody regions responsible for interaction with humoral and cellular immune system effector molecules, and methods of use thereof.

11 Claims, 24 Drawing Sheets

Specification includes a Sequence Listing.

(56) References Cited

FOREIGN PATENT DOCUMENTS

| WO | WO 1998/005787 | 2/1998 |
|---|---|---|
| WO | WO 1998/033914 | 8/1998 |
| WO | WO 99/43713 | 9/1999 |
| WO | WO 1999/058572 | 11/1999 |
| WO | WO 2000/042072 | 7/2000 |
| WO | WO 2002/060955 | 8/2002 |
| WO | WO 2004/035752 | 4/2004 |
| WO | WO 2005/077981 | 8/2005 |
| WO | WO 2006/085967 | 8/2006 |
| WO | WO 2008/090959 | 5/2010 |
| WO | WO 2011/109789 | 9/2011 |
| WO | WO 2013/163631 | 10/2013 |
| WO | WO 2013/164694 | 11/2013 |

OTHER PUBLICATIONS

Berry and Davies, "Use of antibody fragments in immunoaffinity chromatography. Comparison of FV fragments, VH fragments and paralog peptides," J Chromatogr, 1992, 597:239-45.
Boder and Wittrup, "Yeast surface display for screening combinatorial polypeptide libraries," Nat Biotechnol, 1997, 15:553-7.
Bruhns et al., "Specificity and affinity of human Fcgamma receptors and their polymorphic variants for human IgG subclasses," Blood, Apr. 2009, 113(16):3716-25.
Casciola-Rosen et al.,"Mouse and human granzyme B have distinct tetrapeptide specificities and abilities to recmit the bid pathway," J. Biol, Chem, Feb. 2007, 282:4545-4552.
Chen et al., "Fusion protein linkers: property, design and functionality," Adv Drug Deliv Rev, Oct. 2013, 65:1357-69.
Chu et al., "Aptamer:toxin conjugates that specifically target prostate tumor cells," Cancer Res, 2006, 66:5989-92.
Cordingley et al., "Substrate requirements of human rhinovirus 3C protease for peptide cleavage in vitro," J. Biol. Chem, 1990, 265(16):9062-9065.
Dalken et al., "Targeted induction of apoptosis by chimeric granzyme B fusion proteins carrying antibody and growth factor domains for cell recognition," Cell Death Differ, Apr. 2006, 13:576-585.
Ebihara, et al., "Preparation of a claudin-targeting molecule using a C-terminal fragment of Clostridium perfringens enterotoxin," J Pharmacol Exp Ther, Jan. 2006, 316:255-60.
Ellington and Szostak, "In vitro selection of RNA molecules that bind specific ligands," Nature, Aug. 1990, 346:818-22.
Fan et al., "The substrate specificity of SARS coronavirus 3C-like proteinase," Biochem. Biophys. Res. Commun, 2005, 329(3):934-940.
Fields and Song, "A novel genetic system to detect protein-protein interactions," Nature, Jul. 1989, 340:245-6.
Fynbo et al., "Characterization of a recombinant granzyme B derivative as a "restriction" protease," Protein Expr. Purif. 2005, 39:209.
Galvin et al., "Apoptosis induced by granzyme B-glycosaminoglycan complexes: implications for granule-mediated apoptosis in vivo," J. Immunol, 1999, 162:5345.
Gronwall and Stahl, "Engineered affinity proteins—generation and applications," J Biotechnol, 2009, 140:254-69.
Gyuris, et al., "Cdi1, a human G1 and S phase protein phosphatase that associates with Cdk2," Cell, 1993, 75:791-803.
Han et al., "Engineering of Kex2 variants exhibiting altered substrate specificity," Biochem. Biophy. Res. Commun, 2005, 337:1102-1106.
Hosse et al., "A new generation of protein display scaffolds for molecular recognition," Protein Sci, 2006, 15:14-27.
Huston et al., "Protein engineering of single-chain Fv analogs and fusion proteins," Methods Enzymol, 1991, 203:46-88.
Huston, et al., "Protein engineering of antibody binding sites: recovery of specific activity in an anti-digoxin single-chain Fv analogue produced in *Escherichia coli*," PNAS, 1988, 85:5879-83.

Idusogie et al., "Mapping of the C1q binding site on rituxan, a chimeric antibody with a human IgG1 Fc," Apr. 2000, 164: 4178-84.
International Preliminary Report on Patentability in International Application No. PCT/US2016/044177, dated Jan. 30, 2018.
Kellermann and Green, "Antibody discovery: the use of transgenic mice to generate human monoclonal antibodies for therapeutics," Curr Opin Biotechnol, Dec. 2002, 13:593-7.
Kipriyanov, "Generation and characterization of bispecific tandem diabodies for tumor therapy," Methods Mol Biol, 2003, 207:323-33.
Knappik, et al., "Fully synthetic human combinatorial antibody libraries (HuCAL) based on modular consensus frameworks and CDRs randomized with trinucleotides," J Mol Biol, 2000, 296:57-86.
Koide et al., "Target-binding proteins based on the 10th human fibronectin type III domain ($^{10}$Fn)," Methods Enzymol, 2012, 503:135-56.
Lipovsek, et al., "Evolution of an interloop disulfide bond in high-affinity antibody mimics based on fibronectin type III domain and selected by yeast surface display: molecular convergence with single-domain camelid and shark antibodies," J Mol Biol, 2007, 368:1024-41.
Liu et al., "Targeted apoptosis activation with GrB/scFvMEL modulates melanoma growth, metastatic spread, chemosensitivity, and radiosensitivity," Neoplasia, Feb. 2006, 8:125-135.
Mahrus et al., "Granzyme M is a regulatory protease that inactivates proteinase inhibitor 9, an endogenous inhibitor of granzyme B," J. Biol. Chem, Dec. 2004, 279:54275.
Martin et al., "Affinity selection of a camelized VH domain antibody inhibitor of hepatitis C virus NS3 protease," Protein Eng, 1997, 10:607-14.
Mattheakis, et al., "An in vitro polysome display system for identifying ligands from very large peptide libraries," PNAS, Sep. 1994, 91:9022-6.
Melnick et al., "An *Escherichia coli* expression assay and screen for human immunodeficiency virus protease variants with decreased susceptibility to indinavir," Antimicrob. Agents Chemother, Dec. 1998, 42:3256.
Mendez et al., "Functional transplant of megabase human immunoglobulin loci recapitulates human antibody response in mice," Nat Genet, Feb. 1997, 15:146-56.
Michaelsen et al., "Structural difference in the complement activation site of human IgG1 and IgG3S," J Immunol, Dec. 2009, 70(6):553-64.
Mosavi, et al., "The ankyrin repeat as molecular architecture for protein recognition," Protein Sci, 2004, 13:1435-48.
Nunn et al., "Crystal structure of tobacco etch virus protease shows the protein C terminus bound within the active site," J. Mol. Biol, 2005, 350:145.
Nuttall et al., "Design and expression of soluble CTLA-4 variable domain as a scaffold for the display of functional polypeptides," Proteins, 1999, 36:217-27.
O'Loughlin et al., Mol. Biol. Evol, 2006, 23:764-722.
Patel et al., "Specificity of staphylococcal superantigen-like protein 10 toward the human IgG1 Fc domain," J Immunol, 2010, 184(11):6283-92.
Poe et al., "Human cytotoxic lymphocyte granzyme B. Its purification from granules and the characterization of substrate and inhibitor specificity," J. Biol. Chem, Jan. 1991, 266:98.
Rao et al., "Molecular and biotechnological aspects of microbial proteases," Microbiol. Mol. Biol. Rev, 1998, 62(3):597-635.
Roberts and Szostak, "RNA-peptide fusions for the in vitro selection of peptides and proteins," PNAS, Nov. 1997, 94:12297-302.
Shuker et al., "Understanding HTLV-I protease," Chem. Biol, 2003, 10:373.
Siberil et al., "Molecular aspects of human FcgammaR interactions with IgG: functional and therapeutic consequences," Immunol Lett, 2006, 106(2):111-8.
Sices and Kristie, "A genetic screen for the isolation and characterization of site-specific proteases," PNAS, 1998, 95:2828-2833.
Silverman, et al., "Multivalent avimer proteins evolved by exon shuffling of a family of human receptor domains," Nat Biotechnol, Dec. 2005, 23:1556-61.

(56) References Cited

OTHER PUBLICATIONS

Sipione et al., "Identification of a novel human granzyme B inhibitor secreted by cultured sertoli cells," J. Immunol, 2006, 177:5051-5058.
Spaeny-Dekking et al., "Extracellular granzyme A, complexed to proteoglycans, is protected against inactivation by protease inhibitors," Blood, Feb. 2000, 95:1465.
Sun et al., "A cytosolic granzyme B inhibitor related to the viral apoptotic regulator cytokine response modifier A is present in cytotoxic lymphocytes," J. Biol. Chem, Nov. 1996, 271:27802.
Takahashi et al., "Role of C-terminal regions of the C-terminal fragment of Clostridium perfringens enterotoxin in its interaction with claudin-4," J Control Release, 2005, 108:56-62.
Tanha, et al., "Optimal design features of camelized human single-domain antibody libraries," J Biol Chem, 2001, 276:24774-80.
Timmer and Salvesen, "Caspase substrates," Cell Death Diff, 2007, 14:66-72.
Tozser et al., "Comparison of the substrate specificity of two potyvirus proteases," FEBS J, 2005, 272:514.
Travis and Salvesen, "Human plasma proteinase inhibitors," Annu. Rev. Biochem, 1983, 52:655.
Tuerk and MacDougal-Waugh, "In vitro evolution of functional nucleic acids: high-affinity RNA ligands of HIV-1 proteins," Gene, Dec. 1993, 137:33-9.
Van de Velde et al., "The B-cell surface protein CD72/Lyb-2 is the ligand for CD5," Nature, 1991, 351:662-5.
Venekei et al., A"rapid and effective procedure for screening protease mutants," Protein Eng, 1996, 9:85-93.
Vogt and Skerra, "Construction of an artificial receptor protein ("anticalin") based on the human apolipoprotein D," Chembiochem, Feb. 2004, 5:191-9.
Wilson and Szostak, "In vitro selection of functional nucleic acids," Annu Rev Biochem, 1999, 68:611-47.
Zhao et al., "Secreted antibody/granzyme B fusion protein stimulates selective killing of HER2-overexpressing tumor cells," J. Biol. Chem, May 2004, 279:21343-21348.
Extended European Search Report in Application No. 16831265.0, dated Nov. 13, 2018, 8 pages.
Perez et al., "Antibody-drug conjugates: current status and future directions," Drug Discovery Today, Jul. 2014, 19: 869-881.
Weidle et al., "Proteases as activators for cytotoxic prodrugs in antitumor therapy," Cancer Genomics & Proteomics, Mar. 2014, 11: 67-80.
International Search Report and Written Opinion dated Oct. 21, 2016 in International Application No. PCT/US2016/044177, 11 pgs.
Daley et al., "Fc-disabled anti-mouse CD40L antibodies retain efficacy in promoting transplantation tolerance," Am J Transplant 8: 2265-71 (Sep. 8, 2008).

\* cited by examiner

1: anti-CD20-CH1-CH2-CH3 + CLk-CD32
2: anti-CD19-CH1-CH2-CH3 + CLk-CD32

1. anti-CD20-CH1-CH2-CH3 + CLk-CD32
2. anti-CD19-CH1-CH2-CH3 + CLk-CD32

1) aCD20-Fc-CD32
2) aCD19-Fc-CD32
3) CCPE-Fc-CD32
4) CD2ECD-Fc-CD32
5) H10-2G3-Fc-CD32

SEQUENCE LISTING

<160> NUMBER OF SEQ ID NOS: 80

<210> SEQ ID NO 1
<211> LENGTH: 1530
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 1

```
ggtaccgccg ccaccatgga ctggacctgg aggattctct tcttggtggc agcagccaca     60
ggagcccact cccaggtgca gctgcagcag cccggcgccg agttagttaa acccggcgcc    120
agcgtgaaga tgagctgcaa ggccagcggc tacaccttca ccagctacaa catgcactgg    180
gtgaagcaga cccccggcag gggcctggag tggatcggcg ccatctaccc cggcaacggc    240
gacaccagct acaaccagaa gttcaagggc aaggccaccc tgaccgccga caagagcagc    300
agcaccgcct acatgcagct gagcagcctg accagcgagg acagcgccgt gtactactgc    360
gccaggagca cctactacgg cggcgactgg tacttcaacg tgtggggcgc cggcaccacc    420
gtgaccgtga gcgccgcctc caccaagggc ccatcggtct tccccctggc acctcctcc     480
aagagcacct ctgggggcac agcggccctg ggctgcctgg tcaaggacta cttccccgag    540
ccggtgacgg tgtcgtggaa ctcaggcgcc ctgaccagcg gcgtgcacac cttcccggct    600
gtcctacagt cctcaggact ctactccctc tcttccgtgg tgaccgtgcc ctccagcagc    660
ttgggcaccc agacctacat ctgcaacgtg aatcacaagc ccagcaacac caaggtggac    720
aagaaagttg agcccaaatc ttgtgacaaa actcacacat gcccaccgtg cccagcacct    780
gaactcctgg ggggaccgtc agtcttcctc ttccccccaa aacccaagga caccctcatg    840
atctcccgga cccctgaggt cacatgcgtg gtggtggacg tgagccacga agaccctgag    900
gtcaagttca actggtacgt ggacggcgtg gaggtgcata atgccaagac aaagccgcgg    960
gaggagcagt acaacagcac gtaccgggtg gtcagcgtcc tcaccgtcct gcaccaggac   1020
tggctgaatg gcaaggagta caagtgcaaa gtctccaaca aagccctgcc tgcccccatc   1080
gagaaaacca tctccaaagc caaagggcag ccccgagaac cacaggtgta caccctgccc   1140
ccatcccggg atgagctgac caagaaccag gtcagcctga cctgcctggt caaaggcttc   1200
tatcccagcg acatcgccgt ggagtgggag agcaatgggc agccggagaa caactacaag   1260
accacgcctc ccgtgctgga ctccgacggc tccttcttcc tctactcaaa gctcaccgtg   1320
gacaagagca ggtggcagca ggggaacgtc ttctcatgct ccgtgatgca tgaggctctg   1380
cacaaccact acacgcagaa gagcctctcc ctgtctccgg gtaaaggtgg aggtggttca   1440
catcatcacc atcatcaccc tggcggagga ctaaacgaca tcttcgaggc tcagaaaatc   1500
gaatggcacg aaggtccttg ataatctaga                                    1530
```

<210> SEQ ID NO 2
<211> LENGTH: 501
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Met Asp Trp Thr Trp Arg Ile Leu Phe Leu Val Ala Ala Ala Thr Gly
 1               5                  10                  15

Ala His Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45
```

```
Thr Ser Tyr Asn Met His Trp Val Lys Gln Thr Pro Gly Arg Gly Leu
 50                  55                  60

Glu Trp Ile Gly Ala Ile Tyr Pro Gly Asn Gly Asp Thr Ser Tyr Asn
 65                  70                  75                  80

Gln Lys Phe Lys Gly Lys Ala Thr Leu Thr Ala Asp Lys Ser Ser Ser
                 85                  90                  95

Thr Ala Tyr Met Gln Leu Ser Ser Leu Thr Ser Glu Asp Ser Ala Val
                100                 105                 110

Tyr Tyr Cys Ala Arg Ser Thr Tyr Tyr Gly Gly Asp Trp Tyr Phe Asn
                115                 120                 125

Val Trp Gly Ala Gly Thr Thr Val Thr Val Ser Ala Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
                195                 200                 205

Val Thr Val Pro Ser Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
                275                 280                 285

Val Ser His Glu Asp Pro Glu Val Lys Phe Asn Trp Tyr Val Asp Gly
                290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
450                 455                 460

Ser Leu Ser Pro Gly Lys Gly Gly Gly Gly Ser His His His His His
```

```
465                 470                 475                 480
His Pro Gly Gly Gly Leu Asn Asp Ile Phe Glu Ala Gln Lys Ile Glu
                485                 490                 495
Trp His Glu Gly Pro
            500

<210> SEQ ID NO 3
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
ggtaccgccg ccaccatgga ctggacctgg aggattctct tcttggtggc agcagccaca      60
ggagcccact cccagatcgt gctgagccag agccccgcca tcctgagcgc cagccccggc     120
gagaaggtga ccatgacctg cagggccagc agcagcgtga gctacatcca ctggttccag     180
cagaagcccg gcagcagccc caagccctgg atctacgcca ccagcaacct ggccagcggc     240
gtgcccgtga ggttcagcgg cagcggcagc ggcaccagct acagcctgac catcagcagg     300
gtggaggccg aggacgccgc cacctactac tgccagcagt ggaccagcaa cccccccacc     360
ttcggcggcg gcaccaagct ggagatcaag aggaccgtgg ccgccccag cgtgttcatc      420 ttcccaccat ctgacgagca gctgaagagc ggcaccgcca gcgtggtgtg cctgctgaac     480
aacttctacc ccagggaggc caaggtgcag tggaaggtgg acaacgccct gcagagcggc     540
aacagccagg agagcgtgac cgagcaggac agcaaggaca gcacctacag cctgagcagc     600
accctgaccc tgagcaaggc cgactacgag aagcacaagg tgtacgcctg cgaggtgacc     660
caccagggcc tgagcagccc cgtgaccaag agcttcaaca ggggcgagtg ctgataatct     720
aga                                                                  723

<210> SEQ ID NO 4
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Asp Trp Thr Trp Arg Ile Leu Phe Leu Val Ala Ala Ala Thr Gly
1               5                   10                  15

Ala His Ser Gln Ile Val Leu Ser Gln Ser Pro Ala Ile Leu Ser Ala
            20                  25                  30

Ser Pro Gly Glu Lys Val Thr Met Thr Cys Arg Ala Ser Ser Ser Val
        35                  40                  45

Ser Tyr Ile His Trp Phe Gln Gln Lys Pro Gly Ser Ser Pro Lys Pro
    50                  55                  60

Trp Ile Tyr Ala Thr Ser Asn Leu Ala Ser Gly Val Pro Val Arg Phe
65                  70                  75                  80

Ser Gly Ser Gly Ser Gly Thr Ser Tyr Ser Leu Thr Ile Ser Arg Val
                85                  90                  95

Glu Ala Glu Asp Ala Ala Thr Tyr Tyr Cys Gln Gln Trp Thr Ser Asn
            100                 105                 110

Pro Pro Thr Phe Gly Gly Gly Thr Lys Leu Glu Ile Lys Arg Thr Val
        115                 120                 125
```

```
Ala Ala Pro Ser Val Phe Ile Phe Pro Pro Ser Asp Glu Gln Leu Lys
        130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
        210                 215                 220

Lys Ser Phe Asn Arg Gly Glu Cys
225                 230
```

<210> SEQ ID NO 5
<211> LENGTH: 2283
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
ggtaccgccg ccaccatgga ctggacctgg aggattctct tcttggtggc agcagccaca     60
ggagcccact cccaggtgca gctgcagcag cccggcgccg agttagttaa acccggcgcc    120
agcgtgaaga tgagctgcaa ggccagcggc tacaccttca ccagctacaa catgcactgg    180
gtgaagcaga cccccggcag gggcctggag tggatcggcg ccatctaccc cggcaacggc    240
gacaccagct acaaccagaa gttcaagggc aaggccaccc tgaccgccga caagagcagc    300
agcaccgcct acatgcagct gagcagcctg accagcgagg acagcgccgt gtactactgc    360
gccaggagca cctactacgg cggcgactgg tacttcaacg tgtggggcgc cggcaccacc    420
gtgaccgtga gcgccgcctc caccaagggc ccatcggtct tccccctggc acctcctcc    480 aagagcacct ctgggggcac agcggccctg ggctgcctgg tcaaggacta cttccccgag    540
ccggtgacgg tgtcgtggaa ctcaggcgcc ctgaccagcg gcgtgcacac cttcccggct    600
gtcctacagt cctcaggact ctactccctc tcttccgtgg tgaccgtgcc ctccagcagc    660
ttgggcaccc agacctacat ctgcaacgtg aatcacaagc ccagcaacac caaggtggac    720
aagaaagttg agcccaaatc ttgtgacaaa actcacacat gcccaccgtg cccagcacct    780
gaactcctgg ggggaccgtc agtcttcctc ttccccccaa acccaaggac accctcatg    840 atctcccgga cccctgaggt cacatgcgtg gtggtggacg tgagccacga agaccctgag    900
gtcaagttca actggtacgt ggacggcgtg gaggtgcata atgccaagac aaagccgcgg    960
gaggagcagt acaacagcac gtaccgggtg gtcagcgtcc tcaccgtcct gcaccaggac   1020
tggctgaatg gcaaggagta caagtgcaaa gtctccaaca aagccctgcc tgccccatc   1080 gagaaaacca tctccaaagc caaagggcag ccccgagaac cacaggtgta caccctgccc   1140
ccatcccggg atgagctgac caagaaccag gtcagcctga cctgcctggt caaaggcttc   1200
tatcccagcg acatcgccgt ggagtgggag agcaatgggc agccggagaa caactacaag   1260
accacgcctc ccgtgctgga ctccgacggc tccttcttcc tctactcaaa gctcaccgtg   1320
gacaagagca ggtggcagca ggggaacgtc ttctcatgct ccgtgatgca tgaggctctg   1380
```

```
cacaaccact acacgcagaa gagcctctcc ctgtctccgg gtaaaggtgg aggtggttca    1440
catcatcacc atcatcaccc tggcggagga ctaaacgaca tcttcgaggc tcagaaaatc    1500
gaatggcacg aaggtcctga attcggcgga ggcggctccg gcggaggcgg cgaatccggc    1560
ggaggcggct ccggaggcgg cggctccgaa ggcggcggag gtattgaacc ttttagcggt    1620
ggaggtggct ccgaaggcgg tggcggctcc ggaggcggcg gcgaatccgg cggcggcgga    1680
tctggaggcg gcggcgaatc cggcgcgccc ggtagcacta gtggtattat accttttagc    1740
gcggccgcac ctggcggagg cccaaaggct gtggtgttcc tggagcctca atggtacagc    1800
gtgcttgaga aggacagtgt gactctgaag tgccagggag cctactcccc tgaggacaat    1860
tccacacagt ggtttcacaa tgagagcctc atctcaagcc aggcctcgag ctacttcatt    1920
gacgctgcca cagtcaacga cagtggagag tacaggtgcc agacaaacct ctccaccctc    1980
agtgacccgg tgcagctaga agtccatatc ggctggctgt tgctccaggc ccctcggtgg    2040
gtgttcaagg aggaagaccc tattcacctg aggtgtcaca gctggaagaa cactgctctg    2100
cataaggtca catatttaca gaatggcaaa gacaggaagt attttcatca taattctgac    2160
ttccacattc caaaagccac actcaaagat agcggctcct acttctgcag ggggcttgtt    2220
gggagtaaaa atgtgtcttc agagactgtg aacatcacca tcactcaagg ttgataatct    2280
aga                                                                  2283
```

<210> SEQ ID NO 6
<211> LENGTH: 752
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Asp Trp Thr Trp Arg Ile Leu Phe Leu Val Ala Ala Ala Thr Gly
1               5                   10                  15

Ala His Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190
```

Phe Pro Ala Val Leu Gln Ser Ser Gly Leu Tyr Ser Leu Ser Ser Val
            195                 200                 205

Val Thr Val Pro Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
            245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
450                 455                 460

Ser Leu Ser Pro Gly Lys Gly Gly Gly Ser His His His His His
465                 470                 475                 480

His Pro Gly Gly Gly Leu Asn Asp Ile Phe Glu Ala Gln Lys Ile Glu
            485                 490                 495

Trp His Glu Gly Pro Glu Phe Gly Gly Gly Ser Gly Gly Gly Gly
            500                 505                 510

Glu Ser Gly Gly Gly Gly Ser Gly Gly Gly Gly Ser Glu Gly Gly Gly
            515                 520                 525

Gly Ile Glu Pro Phe Ser Gly Gly Gly Ser Glu Gly Gly Gly Gly
            530                 535                 540

Ser Gly Gly Gly Gly Glu Ser Gly Gly Gly Gly Ser Gly Gly Gly Gly
545                 550                 555                 560

Glu Ser Gly Ala Pro Gly Ser Thr Ser Gly Ile Ile Pro Phe Ser Ala
            565                 570                 575

Ala Ala Pro Gly Gly Pro Lys Ala Val Val Phe Leu Glu Pro Gln
            580                 585                 590

Trp Tyr Ser Val Leu Glu Lys Asp Ser Val Thr Leu Lys Cys Gln Gly
            595                 600                 605

Ala Tyr Ser Pro Glu Asp Asn Ser Thr Gln Trp Phe His Asn Glu Ser

Leu Ile Ser Ser Gln Ala Ser Ser Tyr Phe Ile Asp Ala Ala Thr Val
625                 630                 635                 640

Asn Asp Ser Gly Glu Tyr Arg Cys Gln Thr Asn Leu Ser Thr Leu Ser
            645                 650                 655

Asp Pro Val Gln Leu Glu Val His Ile Gly Trp Leu Leu Leu Gln Ala
                660                 665                 670

Pro Arg Trp Val Phe Lys Glu Glu Asp Pro Ile His Leu Arg Cys His
            675                 680                 685

Ser Trp Lys Asn Thr Ala Leu His Lys Val Thr Tyr Leu Gln Asn Gly
        690                 695                 700

Lys Asp Arg Lys Tyr Phe His His Asn Ser Asp Phe His Ile Pro Lys
705                 710                 715                 720

Ala Thr Leu Lys Asp Ser Gly Ser Tyr Phe Cys Arg Gly Leu Val Gly
                725                 730                 735

Ser Lys Asn Val Ser Ser Glu Thr Val Asn Ile Thr Ile Thr Gln Gly
            740                 745                 750

<210> SEQ ID NO 7
<211> LENGTH: 2283
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
ggtaccgccg ccaccatgga ctggacctgg aggattctct tcttggtggc agcagccaca      60
ggagcccact cccaggtgca gctgcagcag cccggcgccg agttagttaa acccggcgcc     120
agcgtgaaga tgagctgcaa ggccagcggc tacaccttca ccagctacaa catgcactgg     180
gtgaagcaga cccccggcag gggcctggag tggatcggcg ccatctaccc cggcaacggc     240
gacaccagct acaaccagaa gttcaagggc aaggccaccc tgaccgccga caagagcagc     300
agcaccgcct acatgcagct gagcagcctg accagcgagg acagcgccgt gtactactgc     360
gccaggagca cctactacgg cggcgactgg tacttcaacg tgtggggcgc cggcaccacc     420
gtgaccgtga gcgccgcctc caccaagggc ccatcggtct tccccctggc acctcctcc     480 aagagcacct ctgggggcac agcggccctg ggctgcctgg tcaaggacta cttccccgag     540
ccggtgacgg tgtcgtggaa ctcaggcgcc ctgaccagcg gcgtgcacac cttcccggct     600
gtcctacagt cctcaggact ctactccctc agcagcgtgg tgaccgtgcc ctccagcagc     660
ttgggcaccc agacctacat ctgcaacgtg aatcacaagc ccagcaacac caaggtggac     720
aagaaagttg agcccaaatc ttgtgacaaa actcacacat gcccaccgtg cccagcacct     780
gaactcctgg ggggaccgtc agtcttcctc ttccccccaa aacccaagga caccctcatg     840
atctcccgga cccctgaggt cacatgcgtg gtggtggacg tgagccacga agaccctgag     900
gtcaagttca actggtacgt ggacggcgtg gaggtgcata atgccaagac aaagccgcgg     960
gaggagcagt acaacagcac gtaccgggtg gtcagcgtcc tcaccgtcct gcaccaggac    1020
tggctgaatg gcaaggagta caagtgcaaa gtctccaaca aagccctgcc tgcccccatc    1080
gagaaaacca tctccaaagc caaagggcag ccccgagaac cacaggtgta caccctgccc    1140
ccatcccggg atgagctgac caagaaccag gtcagcctga cctgcctggt caaaggcttc    1200
tatcccagcg acatcgccgt ggagtgggag agcaatgggc agccggagaa caactacaag    1260

```
accacgcctc ccgtgctgga ctccgacggc tccttcttcc tctactcaaa gctcaccgtg    1320
gacaagagca ggtggcagca ggggaacgtc ttctcatgct ccgtgatgca tgaggctctg    1380
cacaaccact acacgcagaa gagcctctcc ctgtctccgg gtaaaggtgg aggtggttca    1440
catcatcacc atcatcaccc tggcggagga ctaaacgaca tcttcgaggc tcagaaaatc    1500
gaatggcacg aaggtcctga attcggcgga ggcggctccg gcggaggcgg cgaatccggc    1560
ggaggcggct ccggaggcgg cggctccgaa ggcggcggag gtattgaacc ttttagcggt    1620
ggaggtggct ccgaaggcgg tggcggctcc ggaggcggcg gcgaatccgg cggcggcgga    1680
tctggaggcg gcggcgaatc cggcgcgccc ggtagcacta gtggtattat acctttagc     1740 gcggccgcac ctggcggagg cccaaaggct gtgctgaaac ttgagccccc gtggatcaac    1800
gtgctccagg aggactctgt gactctgaca tgccagggg  ctcgcagccc tgagagcgac    1860
tccattcagt ggttccacaa tgggaatctc attccaccc  acacgcagcc cagctacagg    1920
ttcaaggcca acaacaatga cagcgggag tacacgtgcc agactggcca gaccagcctc    1980
agcgaccctg tgcatctgac tgtgctttcc gaatggctgg tgctccagac ccctcacctg    2040
gagttccagg agggagaaac catcatgctg aggtgccaca gctggaagga caagcctctg    2100
gtcaaggtca cattcttcca gaatggaaaa tcccagaaat ctcccgtttt ggatcccacc    2160
ttctccatcc cacaagcaaa ccacagtcac agtggtgatt accactgcac aggaaacata    2220
ggctacacgc tgttctcatc caagcctgtg accatcactg tccaagtgcc ctgataatct    2280
aga                                                                 2283
```

<210> SEQ ID NO 8
<211> LENGTH: 752
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

Met Asp Trp Thr Trp Arg Ile Leu Phe Leu Val Ala Ala Thr Gly
1               5                   10                  15

Ala His Ser Gln Val Gln Leu Gln Gln Pro Gly Ala Glu Leu Val Lys
                20                  25                  30

Pro Gly Ala Ser Val Lys Met Ser Cys Lys Ala Ser Gly Tyr Thr Phe
            35                  40                  45

Thr Ser Tyr Asn Met His Trp Val Lys Gln Thr Pro Gly Arg Gly Leu
        50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

-continued

```
Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Leu Gly Thr Gln Thr Tyr Ile Cys Asn
            210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
450                 455                 460

Ser Leu Ser Pro Gly Lys Gly Gly Gly Ser His His His His
465                 470                 475                 480

His Pro Gly Gly Gly Leu Asn Asp Ile Phe Glu Ala Gln Lys Ile Glu
                485                 490                 495

Trp His Glu Gly Pro Glu Phe Gly Gly Gly Ser Gly Gly Gly Gly
            500                 505                 510

Glu Ser Gly Gly Gly Gly Ser Gly Gly Gly Gly Ser Glu Gly Gly Gly
            515                 520                 525

Gly Ile Glu Pro Phe Ser Gly Gly Gly Ser Gly Gly Gly Gly
            530                 535                 540

Ser Gly Gly Gly Gly Glu Ser Gly Gly Gly Gly Ser Gly Gly Gly Gly
545                 550                 555                 560

Glu Ser Gly Ala Pro Gly Ser Thr Ser Gly Ile Ile Pro Phe Ser Ala
                565                 570                 575

Ala Ala Pro Gly Gly Gly Pro Lys Ala Val Leu Lys Leu Glu Pro Pro
            580                 585                 590
```

```
Trp Ile Asn Val Leu Gln Glu Asp Ser Val Thr Leu Thr Cys Gln Gly
            595                 600                 605
Ala Arg Ser Pro Glu Ser Asp Ser Ile Gln Trp Phe His Asn Gly Asn
        610                 615                 620
Leu Ile Pro Thr His Thr Gln Pro Ser Tyr Arg Phe Lys Ala Asn Asn
625                 630                 635                 640
Asn Asp Ser Gly Glu Tyr Thr Cys Gln Thr Gly Gln Thr Ser Leu Ser
                645                 650                 655
Asp Pro Val His Leu Thr Val Leu Ser Glu Trp Leu Val Leu Gln Thr
            660                 665                 670
Pro His Leu Glu Phe Gln Glu Gly Glu Thr Ile Met Leu Arg Cys His
        675                 680                 685
Ser Trp Lys Asp Lys Pro Leu Val Lys Val Thr Phe Phe Gln Asn Gly
    690                 695                 700
Lys Ser Gln Lys Phe Ser Arg Leu Asp Pro Thr Phe Ser Ile Pro Gln
705                 710                 715                 720
Ala Asn His Ser His Ser Gly Asp Tyr His Cys Thr Gly Asn Ile Gly
                725                 730                 735
Tyr Thr Leu Phe Ser Ser Lys Pro Val Thr Ile Thr Val Gln Val Pro
            740                 745                 750
```

<210> SEQ ID NO 9
<211> LENGTH: 2286
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
ggtaccgccg ccaccatgga ctggacctgg aggattctct tcttggtggc agcagccaca     60
ggagcccact cccaggtgca gctgcagcag cccggcgccg agttagttaa cccggcgcc    120
agcgtgaaga tgagctgcaa ggccagcggc tacaccttca ccagctacaa catgcactgg    180
gtgaagcaga cccccggcag gggcctggag tggatcggcg ccatctaccc cggcaacggc    240
gacaccagct acaaccagaa gttcaagggc aaggccaccc tgaccgccga caagagcagc    300
agcaccgcct acatgcagct gagcagcctg accagcgagg acagcgccgt gtactactgc    360
gccaggagca cctactacgg cggcgactgg tacttcaacg tgtggggcgc cggcaccacc    420
gtgaccgtga gcgccgcctc caccaagggc ccatcggtct tccccctggc accctcctcc    480
aagagcacct ctgggggcac agcggccctg ggctgcctgg tcaaggacta cttccccgag    540
ccggtgacgg tgtcgtggaa ctcaggcgcc ctgaccagcg gcgtgcacac cttcccggct    600
gtcctacagt cctcaggact ctactccctc agcagcgtgg tgaccgtgcc ctccagcagc    660
ttgggcaccc agacctacat ctgcaacgtg aatcacaagc ccagcaacac caaggtggac    720
aagaaagttg agcccaaatc ttgtgacaaa actcacacat gcccaccgtg cccagcacct    780
gaactcctgg ggggaccgtc agtcttcctc ttccccccaa aacccaagga caccctcatg    840
atctcccgga cccctgaggt cacatgcgtg gtggtggacg tgagccacga agaccctgag    900
gtcaagttca actggtacgt ggacggcgtg gaggtgcata atgccaagac aaagccgcgg    960
gaggagcagt acaacagcac gtaccgggtg gtcagcgtcc tcaccgtcct gcaccaggac    1020
tggctgaatg gcaaggagta caagtgcaaa gtctccaaca aagccctgcc tgcccccatc    1080
gagaaaacca tctccaaagc caaagggcag ccccgagaac cacaggtgta caccctgccc    1140
```

-continued

```
ccatcccggg atgagctgac caagaaccag gtcagcctga cctgcctggt caaaggcttc    1200
tatcccagcg acatcgccgt ggagtgggag agcaatgggc agccggagaa caactacaag    1260
accacgcctc ccgtgctgga ctccgacggc tccttcttcc tctactcaaa gctcaccgtg    1320
gacaagagca ggtggcagca ggggaacgtc ttctcatgct ccgtgatgca tgaggctctg    1380
cacaaccact acacgcagaa gagcctctcc ctgtctccgg gtaaaggtgg aggtggttca    1440
catcatcacc atcatcaccc tggcggagga ctaaacgaca tcttcgaggc tcagaaaatc    1500
gaatggcacg aaggtcctga attcggcgga ggcggctccg gcggaggcgg cgaatccggc    1560
ggaggcggct ccggaggcgg cggctccgaa ggcggcggag gtattgaacc ttttagcggt    1620
ggaggtggct ccgaaggcgg tggcggctcc ggaggcggcg cgaatccggg cggcggcgga    1680
tctggaggcg gcggcgaatc cggcgcgccc ggtagcacta gtggtattat accttttagc    1740
gcggccgcac ctggcggagg cacaaaggca gtgatcactt tgcagcctcc atgggtcagc    1800
gtgttccaag aggaaaccgt aaccttgcac tgtgaggtgc tccatctgcc tgggagcagc    1860
tctacacagt ggtttctcaa tggcacagcc actcagacct cgaccccag ctacagaatc     1920 acctctgcca gtgtcaatga cagtggtgaa tacaggtgcc agagaggtct ctcagggcga    1980
agtgacccca tacagctgga aatccacaga ggctggctac tactgcaggt ctccagcaga    2040
gtcttcacgg aaggagaacc tctggccttg aggtgtcatg cgtggaagga taagctggtg    2100
tacaatgtgc tttactatcg aaatggcaaa gcctttaagt tttccactg gaattctaac     2160 ctcaccattc tgaaaaccaa cataagtcac aatggcacct accattgctc aggcatggga    2220
aagcatcgct acacatcagc aggaatatct gtcactgtga agagctatt tccatgataa     2280 tctaga                                                                2286
```

<210> SEQ ID NO 10
<211> LENGTH: 753
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Asp Trp Thr Trp Arg Ile Leu Phe Leu Val Ala Ala Thr Gly
1               5                   10                  15

Ala His Ser Gln Val Gln Leu Gln Gln Pro Gly Ala Glu Leu Val Lys
                20                  25                  30

Pro Gly Ala Ser Val Lys Met Ser Cys Lys Ala Ser Gly Tyr Thr Phe
            35                  40                  45

Thr Ser Tyr Asn Met His Trp Val Lys Gln Thr Pro Gly Arg Gly Leu
        50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Thr Lys
    130                 135                 140

Gly Pro Ser Val Phe Pro Leu Ala Pro Ser Ser Lys Ser Thr Ser Gly
```

-continued

```
            145                 150                 155                 160
Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
                195                 200                 205

Val Thr Val Pro Ser Ser Leu Gly Thr Gln Thr Tyr Ile Cys Asn
210                 215                 220

Val Asn His Lys Pro Ser Asn Thr Lys Val Asp Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
                275                 280                 285

Val Ser His Glu Asp Pro Glu Val Lys Phe Asn Trp Tyr Val Asp Gly
                290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Asp Glu Leu Thr Lys Asn
                370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
450                 455                 460

Ser Leu Ser Pro Gly Lys Gly Gly Gly Ser His His His His
465                 470                 475                 480

His Pro Gly Gly Gly Leu Asn Asp Ile Phe Glu Ala Gln Lys Ile Glu
                485                 490                 495

Trp His Glu Gly Pro Glu Phe Gly Gly Gly Ser Gly Gly Gly Gly
                500                 505                 510

Glu Ser Gly Gly Gly Ser Gly Gly Gly Ser Glu Gly Gly Gly
                515                 520                 525

Gly Ile Glu Pro Phe Ser Gly Gly Gly Ser Glu Gly Gly Gly Gly
                530                 535                 540

Ser Gly Gly Gly Gly Glu Ser Gly Gly Gly Ser Gly Gly Gly Gly
545                 550                 555                 560

Glu Ser Gly Ala Pro Gly Ser Thr Ser Gly Ile Ile Pro Phe Ser Ala
                565                 570                 575
```

```
Ala Ala Pro Gly Gly Gly Thr Lys Ala Val Ile Thr Leu Gln Pro Pro
                580                 585                 590

Trp Val Ser Val Phe Gln Glu Thr Val Thr Leu His Cys Glu Val
        595                 600                 605

Leu His Leu Pro Gly Ser Ser Ser Thr Gln Trp Phe Leu Asn Gly Thr
    610                 615                 620

Ala Thr Gln Thr Ser Thr Pro Ser Tyr Arg Ile Thr Ser Ala Ser Val
625                 630                 635                 640

Asn Asp Ser Gly Glu Tyr Arg Cys Gln Arg Gly Leu Ser Gly Arg Ser
                645                 650                 655

Asp Pro Ile Gln Leu Glu Ile His Arg Gly Trp Leu Leu Leu Gln Val
            660                 665                 670

Ser Ser Arg Val Phe Thr Glu Gly Glu Pro Leu Ala Leu Arg Cys His
        675                 680                 685

Ala Trp Lys Asp Lys Leu Val Tyr Asn Val Leu Tyr Tyr Arg Asn Gly
    690                 695                 700

Lys Ala Phe Lys Phe Phe His Trp Asn Ser Asn Leu Thr Ile Leu Lys
705                 710                 715                 720

Thr Asn Ile Ser His Asn Gly Thr Tyr His Cys Ser Gly Met Gly Lys
                725                 730                 735

His Arg Tyr Thr Ser Ala Gly Ile Ser Val Thr Val Lys Glu Leu Phe
            740                 745                 750

Pro
```

<210> SEQ ID NO 11
<211> LENGTH: 1386
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
ggtaccgccg ccaccatgga ctggacctgg aggattctct tcttggtggc agcagccaca   60
ggagcccact cccagatcgt gctgagccag agccccgcca tcctgagcgc cagccccggc  120
gagaaggtga ccatgacctg cagggccagc agcagcgtga gctacatcca ctggttccag  180
cagaagcccg gcagcagccc caagccctgg atctacgcca ccagcaacct ggccagcggc  240
gtgcccgtga ggttcagcgg cagcggcagc ggcaccagct acagcctgac catcagcagg  300
gtggaggccg aggacgccgc cacctactac tgccagcagt ggaccagcaa cccccccacc  360
ttcggcggcg gcaccaagct ggagatcaag aggaccgtgg ccgcccccag cgtgttcatc  420
ttccaccat ctgacgagca gctgaagagc ggcaccgcca gcgtggtgtg cctgctgaac  480
aacttctacc ccagggaggc caaggtgcag tggaaggtgg acaacgccct gcagagcggc  540
aacagccagg agagcgtgac cgagcaggac agcaaggaca gcacctacag cctgagcagc  600
accctgaccc tgagcaaggc cgactacgag aagcacaagg tgtacgcctg cgaggtgacc  660
caccagggcc tgagcagccc cgtgaccaag agcttcaaca ggggcgagtg cggtggaggt  720
ggatcagaat tctcccccagg cggcggctcc gaaggcggcg aggtattga accttttagc  780
ggtggaggtg gctccgaagg cggtggcgcg cccggtagca ctagtggtat taccctttt  840
agcgcggccg cacctggcgg aggcccaaag gctgtggtgt tcctggagcc tcaatggtac  900
agcgtgcttg agaaggacag tgtgactctg aagtgccagg agcctactc ccctgaggac  960
```

-continued

```
aattccacac agtggtttca caatgagagc ctcatctcaa gccaggcctc gagctacttc    1020
attgacgctg ccacagtcaa cgacagtgga gagtacaggt gccagacaaa cctctccacc    1080
ctcagtgacc cggtgcagct agaagtccat atcggctggc tgttgctcca ggcccctcgg    1140
tgggtgttca aggaggaaga ccctattcac ctgaggtgtc acagctggaa gaacactgct    1200
ctgcataagg tcacatattt acagaatggc aaagacagga agtattttca tcataattct    1260
gacttccaca ttccaaaagc cacactcaaa gatagcggct cctacttctg caggggcctt    1320
gttgggagta aaaatgtgtc ttcagagact gtgaacatca ccatcactca aggttgataa    1380
tctaga                                                               1386
```

```
<210> SEQ ID NO 12
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Asp Trp Thr Trp Arg Ile Leu Phe Leu Val Ala Ala Ala Thr Gly
1               5                   10                  15

Ala His Ser Gln Ile Val Leu Ser Gln Ser Pro Ala Ile Leu Ser Ala
            20                  25                  30

Ser Pro Gly Glu Lys Val Thr Met Thr Cys Arg Ala Ser Ser Ser Val
        35                  40                  45

Ser Tyr Ile His Trp Phe Gln Gln Lys Pro Gly Ser Ser Pro Lys Pro
    50                  55                  60

Trp Ile Tyr Ala Thr Ser Asn Leu Ala Ser Gly Val Pro Val Arg Phe
65                  70                  75                  80

Ser Gly Ser Gly Ser Gly Thr Ser Tyr Ser Leu Thr Ile Ser Arg Val
                85                  90                  95

Glu Ala Glu Asp Ala Ala Thr Tyr Tyr Cys Gln Gln Trp Thr Ser Asn
            100                 105                 110

Pro Pro Thr Phe Gly Gly Gly Thr Lys Leu Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys Gly Gly Gly Ser Glu Phe Ser
225                 230                 235                 240

Pro Gly Gly Gly Ser Glu Gly Gly Gly Ile Glu Pro Phe Ser Gly
                245                 250                 255

Gly Gly Gly Ser Glu Gly Gly Gly Ala Pro Gly Ser Thr Ser Gly Ile
            260                 265                 270

Ile Pro Phe Ser Ala Ala Ala Pro Gly Gly Gly Pro Lys Ala Val Val
```

|   |   | 275 |   |   | 280 |   |   | 285 |   |   |   |
|---|---|---|---|---|---|---|---|---|---|---|---|

Phe Leu Glu Pro Gln Trp Tyr Ser Val Leu Glu Lys Asp Ser Val Thr
290                 295                 300

Leu Lys Cys Gln Gly Ala Tyr Ser Pro Glu Asp Asn Ser Thr Gln Trp
305                 310                 315                 320

Phe His Asn Glu Ser Leu Ile Ser Ser Gln Ala Ser Ser Tyr Phe Ile
                325                 330                 335

Asp Ala Ala Thr Val Asn Asp Ser Gly Glu Tyr Arg Cys Gln Thr Asn
                340                 345                 350

Leu Ser Thr Leu Ser Asp Pro Val Gln Leu Glu Val His Ile Gly Trp
                355                 360                 365

Leu Leu Leu Gln Ala Pro Arg Trp Val Phe Lys Glu Glu Asp Pro Ile
370                 375                 380

His Leu Arg Cys His Ser Trp Lys Asn Thr Ala Leu His Lys Val Thr
385                 390                 395                 400

Tyr Leu Gln Asn Gly Lys Asp Arg Lys Tyr Phe His His Asn Ser Asp
                405                 410                 415

Phe His Ile Pro Lys Ala Thr Leu Lys Asp Ser Gly Ser Tyr Phe Cys
                420                 425                 430

Arg Gly Leu Val Gly Ser Lys Asn Val Ser Ser Glu Thr Val Asn Ile
                435                 440                 445

Thr Ile Thr Gln Gly
        450

<210> SEQ ID NO 13
<211> LENGTH: 1386
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

| ggtaccgccg | ccaccatgga | ctggacctgg | aggattctct | tcttggtggc | agcagccaca | 60 |
|---|---|---|---|---|---|---|
| ggagcccact | cccagatcgt | gctgagccag | agccccgcca | tcctgagcgc | cagccccggc | 120 |
| gagaaggtga | ccatgacctg | cagggccagc | agcagcgtga | gctacatcca | ctggttccag | 180 |
| cagaagcccg | gcagcagccc | caagccctgg | atctacgcca | ccagcaacct | ggccagcggc | 240 |
| gtgcccgtga | ggttcagcgg | cagcggcagc | ggcaccagct | acagcctgac | catcagcagg | 300 |
| gtggaggccg | aggacgccgc | cacctactac | tgccagcagt | ggaccagcaa | ccccccacc | 360 |
| ttcggcggcg | gcaccaagct | ggagatcaag | aggaccgtgg | ccgcccccag | cgtgttcatc | 420 |
| ttcccaccat | ctgacgagca | gctgaagagc | ggcaccgcca | gcgtggtgtg | cctgctgaac | 480 |
| aacttctacc | ccagggaggc | caaggtgcag | tggaaggtgg | acaacgccct | gcagagcggc | 540 |
| aacagccagg | agagcgtgac | cgagcaggac | agcaaggaca | gcacctacag | cctgagcagc | 600 |
| accctgaccc | tgagcaaggc | cgactacgag | aagcacaagg | tgtacgcctg | cgaggtgacc | 660 |
| caccagggcc | tgagcagccc | cgtgaccaag | agcttcaaca | ggggcgagtg | cggtggaggt | 720 |
| ggatcagaat | tctcccccagg | cggcggctcc | gaaggcggcg | gaggtattga | accttttagc | 780 |
| ggtggaggtg | gctccgaagg | cggtggcgcg | cccggtagca | ctagtggtat | tatacctttt | 840 |
| agcgcggccg | cacctggcgg | aggcccaaag | gctgtgctga | acttgagcc | ccgtggatc | 900 |
| aacgtgctcc | aggaggactc | tgtgactctg | acatgccagg | gggctcgcag | ccctgagagc | 960 |
| gactccattc | agtggttcca | caatgggaat | ctcattccca | cccacacgca | gcccagctac | 1020 |

-continued

```
aggttcaagg ccaacaacaa tgacagcggg gagtacacgt gccagactgg ccagaccagc 1080
ctcagcgacc ctgtgcatct gactgtgctt tccgaatggc tggtgctcca gacccctcac 1140
```

```
ctggagttcc aggagggaga aaccatcatg ctgaggtgcc acagctggaa ggacaagcct 1200
ctggtcaagg tcacattctt ccagaatgga aaatcccaga aattctcccg tttggatccc 1260
accttctcca tcccacaagc aaaccacagt cacagtggtg attaccactg cacaggaaac 1320
ataggctaca cgctgttctc atccaagcct gtgaccatca ctgtccaagt gccctgataa 1380
tctaga 1386
```

<210> SEQ ID NO 14
<211> LENGTH: 453
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 14

```
Met Asp Trp Thr Trp Arg Ile Leu Phe Leu Val Ala Ala Ala Thr Gly
1 5 10 15

Ala His Ser Gln Ile Val Leu Ser Gln Ser Pro Ala Ile Leu Ser Ala
20 25 30

Ser Pro Gly Glu Lys Val Thr Met Thr Cys Arg Ala Ser Ser Ser Val
35 40 45

Ser Tyr Ile His Trp Phe Gln Gln Lys Pro Gly Ser Ser Pro Lys Pro
50 55 60

Trp Ile Tyr Ala Thr Ser Asn Leu Ala Ser Gly Val Pro Val Arg Phe
65 70 75 80

Ser Gly Ser Gly Ser Gly Thr Ser Tyr Ser Leu Thr Ile Ser Arg Val
85 90 95

Glu Ala Glu Asp Ala Ala Thr Tyr Tyr Cys Gln Gln Trp Thr Ser Asn
100 105 110

Pro Pro Thr Phe Gly Gly Gly Thr Lys Leu Glu Ile Lys Arg Thr Val
115 120 125

Ala Ala Pro Ser Val Phe Ile Phe Pro Pro Ser Asp Glu Gln Leu Lys
130 135 140

Ser Gly Thr Ala Ser Val Val Cys Leu Leu Asn Asn Phe Tyr Pro Arg
145 150 155 160

Glu Ala Lys Val Gln Trp Lys Val Asp Asn Ala Leu Gln Ser Gly Asn
165 170 175

Ser Gln Glu Ser Val Thr Glu Gln Asp Ser Lys Asp Ser Thr Tyr Ser
180 185 190

Leu Ser Ser Thr Leu Thr Leu Ser Lys Ala Asp Tyr Glu Lys His Lys
195 200 205

Val Tyr Ala Cys Glu Val Thr His Gln Gly Leu Ser Ser Pro Val Thr
210 215 220

Lys Ser Phe Asn Arg Gly Glu Cys Gly Gly Gly Gly Ser Glu Phe Ser
225 230 235 240

Pro Gly Gly Gly Ser Glu Gly Gly Gly Gly Ile Glu Pro Phe Ser Gly
245 250 255

Gly Gly Gly Ser Glu Gly Gly Gly Ala Pro Gly Ser Thr Ser Gly Ile
260 265 270

Ile Pro Phe Ser Ala Ala Ala Pro Gly Gly Gly Pro Lys Ala Val Leu
275 280 285
```

```
Lys Leu Glu Pro Pro Trp Ile Asn Val Leu Gln Glu Asp Ser Val Thr
    290                 295                 300

Leu Thr Cys Gln Gly Ala Arg Ser Pro Glu Ser Asp Ser Ile Gln Trp
305                 310                 315                 320

Phe His Asn Gly Asn Leu Ile Pro Thr His Thr Gln Pro Ser Tyr Arg
                325                 330                 335

Phe Lys Ala Asn Asn Asn Asp Ser Gly Glu Tyr Thr Cys Gln Thr Gly
                340                 345                 350

Gln Thr Ser Leu Ser Asp Pro Val His Leu Thr Val Leu Ser Glu Trp
            355                 360                 365

Leu Val Leu Gln Thr Pro His Leu Glu Phe Gln Glu Gly Glu Thr Ile
    370                 375                 380

Met Leu Arg Cys His Ser Trp Lys Asp Lys Pro Leu Val Lys Val Thr
385                 390                 395                 400

Phe Phe Gln Asn Gly Lys Ser Gln Lys Phe Ser Arg Leu Asp Pro Thr
                405                 410                 415

Phe Ser Ile Pro Gln Ala Asn His Ser His Ser Gly Asp Tyr His Cys
                420                 425                 430

Thr Gly Asn Ile Gly Tyr Thr Leu Phe Ser Ser Lys Pro Val Thr Ile
            435                 440                 445

Thr Val Gln Val Pro
            450
```

<210> SEQ ID NO 15
<211> LENGTH: 1389
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

```
ggtaccgccg ccaccatgga ctggacctgg aggattctct tcttggtggc agcagccaca      60
ggagcccact cccagatcgt gctgagccag agccccgcca tcctgagcgc cagccccggc     120
gagaaggtga ccatgacctg cagggccagc agcagcgtga gctacatcca ctggttccag     180
cagaagcccg gcagcagccc caagccctgg atctacgcca ccagcaacct ggccagcggc     240
gtgcccgtga ggttcagcgg cagcggcagc ggcaccagct acagcctgac catcagcagg     300
gtggaggccg aggacgccgc cacctactac tgccagcagt ggaccagcaa cccccccacc     360
ttcggcggcg gcaccaagct ggagatcaag aggaccgtgg ccgccccag cgtgttcatc      420
ttcccaccat ctgacgagca gctgaagagc ggcaccgcca gcgtggtgtg cctgctgaac     480
aacttctacc ccagggaggc caaggtgcag tggaaggtgg acaacgccct gcagagcggc     540
aacagccagg agagcgtgac cgagcaggac agcaaggaca gcacctacag cctgagcagc     600
accctgaccc tgagcaaggc cgactacgag aagcacaagg tgtacgcctg cgaggtgacc     660
caccagggcc tgagcagccc cgtgaccaag agcttcaaca ggggcgagtg cggtggaggt     720
ggatcagaat ctcccccagg cggcggctcc gaaggcggcg gaggtattga accttttagc     780
ggtggaggtg gctccgaagg cggtggcgcg cccgtagcac tagtggtat tatacctttt      840
agcgcggccg cacctggcgg aggcacaaag gcagtgatca ctttgcagcc tccatgggtc     900
agcgtgttcc aagaggaaac cgtaaccttg cactgtgagg tgctccatct gcctgggagc     960
agctctacac agtggtttct caatggcaca gccactcaga cctcgacccc cagctacaga    1020
```

```
atcacctctg ccagtgtcaa tgacagtggt gaatacaggt gccagagagg tctctcaggg    1080
cgaagtgacc ccatacagct ggaaatccac agaggctggc tactactgca ggtctccagc    1140
agagtcttca cggaaggaga acctctggcc ttgaggtgtc atgcgtggaa ggataagctg    1200
gtgtacaatg tgctttacta tcgaaatggc aaagccttta agttttccca ctggaattct    1260
aacctcacca ttctgaaaac caacataagt cacaatggca cctaccattg ctcaggcatg    1320
ggaaagcatc gctacacatc agcaggaata tctgtcactg tgaaagagct atttccatga    1380
taatctaga                                                            1389
```

<210> SEQ ID NO 16
<211> LENGTH: 454
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Met Asp Trp Thr Trp Arg Ile Leu Phe Leu Val Ala Ala Thr Gly
1               5                   10                  15

Ala His Ser Gln Ile Val Leu Ser Gln Ser Pro Ala Ile Leu Ser Ala
            20                  25                  30

Ser Pro Gly Glu Lys Val Thr Met Thr Cys Arg Ala Ser Ser Val
        35                  40                  45

Ser Tyr Ile His Trp Phe Gln Gln Lys Pro Gly Ser Ser Pro Lys Pro
    50                  55                  60

Trp Ile Tyr Ala Thr Ser Asn Leu Ala Ser Gly Val Pro Val Arg Phe
65                  70                  75                  80

Ser Gly Ser Gly Ser Gly Thr Ser Tyr Ser Leu Thr Ile Ser Arg Val
                85                  90                  95

Glu Ala Glu Asp Ala Ala Thr Tyr Tyr Cys Gln Gln Trp Thr Ser Asn
            100                 105                 110

Pro Pro Thr Phe Gly Gly Gly Thr Lys Leu Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys Gly Gly Gly Ser Glu Phe Ser
225                 230                 235                 240

Pro Gly Gly Gly Ser Glu Gly Gly Gly Ile Glu Pro Phe Ser Gly
                245                 250                 255

Gly Gly Gly Ser Glu Gly Gly Gly Ala Pro Gly Ser Thr Ser Gly Ile
            260                 265                 270

Ile Pro Phe Ser Ala Ala Pro Gly Gly Gly Thr Lys Ala Val Ile
        275                 280                 285
```

Thr Leu Gln Pro Pro Trp Val Ser Val Phe Gln Glu Thr Val Thr
        290                 295                 300

Leu His Cys Glu Val Leu His Leu Pro Gly Ser Ser Thr Gln Trp
305                 310                 315                 320

Phe Leu Asn Gly Thr Ala Thr Gln Thr Ser Thr Pro Ser Tyr Arg Ile
                325                 330                 335

Thr Ser Ala Ser Val Asn Asp Ser Gly Glu Tyr Arg Cys Gln Arg Gly
                340                 345                 350

Leu Ser Gly Arg Ser Asp Pro Ile Gln Leu Glu Ile His Arg Gly Trp
                355                 360                 365

Leu Leu Leu Gln Val Ser Ser Arg Val Phe Thr Glu Gly Glu Pro Leu
        370                 375                 380

Ala Leu Arg Cys His Ala Trp Lys Asp Lys Leu Val Tyr Asn Val Leu
385                 390                 395                 400

Tyr Tyr Arg Asn Gly Lys Ala Phe Lys Phe His Trp Asn Ser Asn
                405                 410                 415

Leu Thr Ile Leu Lys Thr Asn Ile Ser His Asn Gly Thr Tyr His Cys
                420                 425                 430

Ser Gly Met Gly Lys His Arg Tyr Thr Ser Ala Gly Ile Ser Val Thr
                435                 440                 445

Val Lys Glu Leu Phe Pro
        450

<210> SEQ ID NO 17
<211> LENGTH: 777
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
ccatggataa tataaatcgc gctcgcaaaa agcgcgttat cggtggtcat gaagctaaac      60
cgcactcccg tccgtacatg gcttacctga tgatctctgg tccaagcggt tcgaaacgtt     120
gcggtggttt cctgatccag gacgacttcg ttctgaccgc tgctcactgc tggggttcct     180
ccatcaacgt taccctgggt gctcacaaca tcaaagaaca ggaaccgacc cagcagttca     240
tcccggttaa cgtgctatcc gcacccggt cttacaaccc gaaaaacttc tccaacgaca     300
tcatgctgct gcagctggaa cagaaagcta acagaccca ggctgttcag ccgctgcgtc     360
tgccgtccaa caaagctcag gttaaaccgg gtcagacctg ctccgttgct ggttggggtc     420
agaccgctcc gctgggtaaa cactcccaca ctctgcagga agttaaaatg accgttcagg     480
aagatcgtaa atgcgaatcc gacctgcgtc actactacga ctccaccatc gaactgtgcg     540
ttggtgatcc ggaaatcaaa aaaacctcct tcaaggtga ctccggtggt ccgctggttt     600
gcaacaaagt tgctcagggt atcgtttcct acggtcgtac caacggtatg ccgccgatcg     660
cttacaccaa agtttcctcc ttcgttcact ggatcgaaaa aactatggaa cgttacaccg     720
gttccggact gcctgagact ggaagcggcc accaccatca tcaccattag cggccgc        777

<210> SEQ ID NO 18
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Asp Asn Ile Asn Arg Ala Arg Lys Lys Arg Val Ile Gly Gly His
1               5                   10                  15
Glu Ala Lys Pro His Ser Arg Pro Tyr Met Ala Tyr Leu Met Ile Ser
                20                  25                  30
Gly Pro Ser Gly Ser Lys Arg Cys Gly Gly Phe Leu Ile Gln Asp Asp
            35                  40                  45
Phe Val Leu Thr Ala Ala His Cys Trp Gly Ser Ser Ile Asn Val Thr
    50                  55                  60
Leu Gly Ala His Asn Ile Lys Glu Gln Glu Pro Thr Gln Gln Phe Ile
65                  70                  75                  80
Pro Val Lys Arg Ala Ile Pro His Pro Ala Tyr Asn Pro Lys Asn Phe
                85                  90                  95
Ser Asn Asp Ile Met Leu Leu Gln Leu Glu Gln Lys Ala Lys Gln Thr
            100                 105                 110
Gln Ala Val Gln Pro Leu Arg Leu Pro Ser Asn Lys Ala Gln Val Lys
        115                 120                 125
Pro Gly Gln Thr Cys Ser Val Ala Gly Trp Gly Gln Thr Ala Pro Leu
130                 135                 140
Gly Lys His Ser His Thr Leu Gln Glu Val Lys Met Thr Val Gln Glu
145                 150                 155                 160
Asp Arg Lys Cys Glu Ser Asp Leu Arg His Tyr Tyr Asp Ser Thr Ile
                165                 170                 175
Glu Leu Cys Val Gly Asp Pro Glu Ile Lys Lys Thr Ser Phe Lys Gly
            180                 185                 190
Asp Ser Gly Gly Pro Leu Val Cys Asn Lys Val Ala Gln Gly Ile Val
        195                 200                 205
Ser Tyr Gly Arg Thr Asn Gly Met Pro Pro Ile Ala Tyr Thr Lys Val
    210                 215                 220
Ser Ser Phe Val His Trp Ile Glu Lys Thr Met Glu Arg Tyr Thr Gly
225                 230                 235                 240
Ser Gly Leu Pro Glu Thr Gly Ser Gly His His His His His His
                245                 250                 255

<210> SEQ ID NO 19
<211> LENGTH: 900
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

| | |
|---|---|
| atgaaatacc tgctgccgac cgctgctgct ggtctgctgc tcctcgctgc ccagccggcg | 60 |
| atggccggta aggtggtgg ctctccagct agccaggtgc agctgcagca gtccggcccg | 120 |
| ggcatcgtga aaccgagcca gaccctgacc ctgacctgct ccttcagcgg cttctccctg | 180 |
| tccaccccgg gcatgggcgt tcctggatt cgccagccgc cgggcaaagc gccagagtgg | 240 |
| ctggctcaca tctactggga cgacgacaaa cgctacaacc cgcagctgaa atcccgcctg | 300 |
| actatctcca agacaccctc caaaaaccag gttgtgctga ccatgaccaa catggacagc | 360 |
| gaggacaccg ctacctacta ctgcacccgc cgcgttccgt cccggggtat gaccacctcc | 420 |
| ggctacttcg acgtttgggg ccagggcacc acggtgaccg tgagcagcgg tggcggcggt | 480 |
| agcggtggtg gcggcagcgg cggtggcggt agcgggagct ccgacatcgt tctgacccag | 540 |

```
tccccggatt ccctggctgt ttccctgggc gaacgcgcta ccatcaactg ccgcgcttcc      600
cagtccgttt ccacctccac ctactcctac atgcactggt accagcagaa accgggccag      660
ccgccgaaac tgctgatcaa atacgcttcc aacctggagt ccggcgttcc ggctcgcttc      720
tccggctccg gctccgaaac cgacttcacc ctgaccatcc acagcatgga gccggaagac      780
ttcgctacct actactgcca gcactcctgg gagaacccgt ggaccttcgg cggcggcacc      840
aaagtggaga tcaaggggga tccggcggcc gcactcgagc accaccacca ccaccactga      900
```

```
<210> SEQ ID NO 20
<211> LENGTH: 299
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Lys Tyr Leu Leu Pro Thr Ala Ala Gly Leu Leu Leu Leu Ala
1               5                   10                  15

Ala Gln Pro Ala Met Ala Gly Lys Gly Gly Ser Pro Ala Ser Gln
                20                  25                  30

Val Gln Leu Gln Gln Ser Gly Pro Gly Ile Val Lys Pro Ser Gln Thr
                35                  40                  45

Leu Thr Leu Thr Cys Ser Phe Ser Gly Phe Ser Leu Ser Thr Pro Gly
50                  55                  60

Met Gly Val Ser Trp Ile Arg Gln Pro Pro Gly Lys Ala Pro Glu Trp
65                  70                  75                  80

Leu Ala His Ile Tyr Trp Asp Asp Lys Arg Tyr Asn Pro Gln Leu
                85                  90                  95

Lys Ser Arg Leu Thr Ile Ser Lys Asp Thr Ser Lys Asn Gln Val Val
                100                 105                 110

Leu Thr Met Thr Asn Met Asp Ser Glu Asp Thr Ala Thr Tyr Tyr Cys
                115                 120                 125

Thr Arg Arg Val Pro Ser Arg Val Met Thr Thr Ser Gly Tyr Phe Asp
                130                 135                 140

Val Trp Gly Gln Gly Thr Thr Val Thr Val Ser Ser Gly Gly Gly Gly
145                 150                 155                 160

Ser Gly Gly Gly Gly Ser Gly Gly Gly Gly Ser Gly Ser Ser Asp Ile
                165                 170                 175

Val Leu Thr Gln Ser Pro Asp Ser Leu Ala Val Ser Leu Gly Glu Arg
                180                 185                 190

Ala Thr Ile Asn Cys Arg Ala Ser Gln Ser Val Ser Thr Ser Thr Tyr
                195                 200                 205

Ser Tyr Met His Trp Tyr Gln Gln Lys Pro Gly Gln Pro Pro Lys Leu
                210                 215                 220

Leu Ile Lys Tyr Ala Ser Asn Leu Glu Ser Gly Val Pro Ala Arg Phe
225                 230                 235                 240

Ser Gly Ser Gly Ser Glu Thr Asp Phe Thr Leu Thr Ile His Ser Met
                245                 250                 255

Glu Pro Glu Asp Phe Ala Thr Tyr Tyr Cys Gln His Ser Trp Glu Asn
                260                 265                 270

Pro Trp Thr Phe Gly Gly Gly Thr Lys Val Glu Ile Lys Gly Asp Pro
                275                 280                 285

Ala Ala Ala Leu Glu His His His His His His
                290                 295
```

<210> SEQ ID NO 21
<211> LENGTH: 523
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Asp Asn Ile Asn Arg Ala Arg Lys Lys Arg Val Ile Gly Gly His
1               5                   10                  15

Glu Ala Lys Pro His Ser Arg Pro Tyr Met Ala Tyr Leu Met Ile Ser
            20                  25                  30

Gly Pro Ser Gly Ser Lys Arg Cys Gly Gly Phe Leu Ile Gln Asp Asp
        35                  40                  45

Phe Val Leu Thr Ala Ala His Cys Trp Gly Ser Ser Ile Asn Val Thr
    50                  55                  60

Leu Gly Ala His Asn Ile Lys Glu Gln Glu Pro Thr Gln Gln Phe Ile
65                  70                  75                  80

Pro Val Lys Arg Ala Ile Pro His Pro Ala Tyr Asn Pro Lys Asn Phe
                85                  90                  95

Ser Asn Asp Ile Met Leu Leu Gln Leu Glu Gln Lys Ala Lys Gln Thr
            100                 105                 110

Gln Ala Val Gln Pro Leu Arg Leu Pro Ser Asn Lys Ala Gln Val Lys
        115                 120                 125

Pro Gly Gln Thr Cys Ser Val Ala Gly Trp Gly Gln Thr Ala Pro Leu
    130                 135                 140

Gly Lys His Ser His Thr Leu Gln Glu Val Lys Met Thr Val Gln Glu
145                 150                 155                 160

Asp Arg Lys Cys Glu Ser Asp Leu Arg His Tyr Tyr Asp Ser Thr Ile
                165                 170                 175

Glu Leu Cys Val Gly Asp Pro Glu Ile Lys Lys Thr Ser Phe Lys Gly
            180                 185                 190

Asp Ser Gly Gly Pro Leu Val Cys Asn Lys Val Ala Gln Gly Ile Val
        195                 200                 205

Ser Tyr Gly Arg Thr Asn Gly Met Pro Pro Ile Ala Tyr Thr Lys Val
    210                 215                 220

Ser Ser Phe Val His Trp Ile Glu Lys Thr Met Glu Arg Tyr Thr Gly
225                 230                 235                 240

Ser Gly Leu Pro Glu Thr Gly Lys Gly Gly Ser Pro Ala Ser Gln
                245                 250                 255

Val Gln Leu Gln Gln Ser Gly Pro Gly Ile Val Lys Pro Ser Gln Thr
            260                 265                 270

Leu Thr Leu Thr Cys Ser Phe Ser Gly Phe Ser Leu Ser Thr Pro Gly
        275                 280                 285

Met Gly Val Ser Trp Ile Arg Gln Pro Pro Gly Lys Ala Pro Glu Trp
    290                 295                 300

Leu Ala His Ile Tyr Trp Asp Asp Lys Arg Tyr Asn Pro Gln Leu
305                 310                 315                 320

Lys Ser Arg Leu Thr Ile Ser Lys Asp Thr Ser Lys Asn Gln Val Val
                325                 330                 335

Leu Thr Met Thr Asn Met Asp Ser Glu Asp Thr Ala Thr Tyr Tyr Cys
            340                 345                 350

Thr Arg Arg Val Pro Ser Arg Val Met Thr Thr Ser Gly Tyr Phe Asp

-continued

```
                355                 360                 365
Val Trp Gly Gln Gly Thr Thr Val Thr Val Ser Ser Gly Gly Gly Gly
            370                 375                 380
Ser Gly Gly Gly Ser Gly Gly Gly Ser Gly Ser Ser Asp Ile
385                 390                 395                 400
Val Leu Thr Gln Ser Pro Asp Ser Leu Ala Val Ser Leu Gly Glu Arg
                405                 410                 415
Ala Thr Ile Asn Cys Arg Ala Ser Gln Ser Val Ser Thr Ser Thr Tyr
            420                 425                 430
Ser Tyr Met His Trp Tyr Gln Gln Lys Pro Gly Gln Pro Pro Lys Leu
        435                 440                 445
Leu Ile Lys Tyr Ala Ser Asn Leu Glu Ser Gly Val Pro Ala Arg Phe
    450                 455                 460
Ser Gly Ser Gly Ser Glu Thr Asp Phe Thr Leu Thr Ile His Ser Met
465                 470                 475                 480
Glu Pro Glu Asp Phe Ala Thr Tyr Tyr Cys Gln His Ser Trp Glu Asn
                485                 490                 495
Pro Trp Thr Phe Gly Gly Gly Thr Lys Val Glu Ile Lys Gly Asp Pro
            500                 505                 510
Ala Ala Ala Leu Glu His His His His His His
        515                 520

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ile Glu Pro Asp
1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Val Pro Leu
1

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(7)
```

```
<223> OTHER INFORMATION: Ser or Gly

<400> SEQUENCE: 24

Glu Xaa Xaa Tyr Xaa Gln Xaa
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 25

Leu Pro Xaa Thr Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asn Pro Gln Thr Asn
1               5

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Leu Leu Gln Gly
1

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Leu Pro Glu Thr Gly
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Val Arg Arg Ala Ser
```

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ile Glu Pro Phe
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ile Ile Pro Phe
1

<210> SEQ ID NO 32
<211> LENGTH: 146
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
gaattcggta tcgagccttt cagcggttcc ccaggcggcg gctccgaagg cggcggaggt    60
attgaacctt ttagcggtgg aggtggctcc gaaggcggtg gcgcgcccgg tagcactagt   120
ggtattatac cttttagcgc ggccgc                                        146

<210> SEQ ID NO 33
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
ggtaccgccg ccaccatgga ctggacctgg aggattctct tcttggtggc agcagccaca    60
ggagcccact cccagatcgt gctgagccag agccccgcca tcctgagcgc cagccccggc   120
gagaaggtga ccatgacctg cagggccagc agcagcgtga gctacatcca ctggttccag   180
cagaagcccg gcagcagccc caagccctgg atctacgcca ccagcaacct ggccagcggc   240
gtgcccgtga ggttcagcgg cagcggcagc ggcaccagct acagcctgac catcagcagg   300
gtggaggccg aggacgccgc cacctactac tgccagcagt ggaccagcaa cccccccacc   360
ttcggcggcg gcaccaagct ggagatcaag gaccgtgg ccgcccccag cgtgttcatc   420
ttcccaccat ctgacgagca gctgaagagc ggcaccgcca gcgtggtgtg cctgctgaac   480
aacttctacc ccagggaggc caaggtgcag tggaaggtgg acaacgccct gcagagcggc   540
aacagccagg agagcgtgac cgagcaggac agcaaggaca gcacctacag cctgagcagc   600
accctgaccc tgagcaaggc cgactacgag aagcacaagg tgtacgcctg cgaggtgacc   660

```
caccagggcc tgagcagccc cgtgaccaag agcttcaaca ggggcgagtg cggtggaggt    720
ggatcagaat tcggtatcga gcctttcagc ggttccccag gcggcggctc cgaaggcggc    780
ggaggtattg aaccttttag cggtggaggt ggctccgaag gcggtggcgc gcccggtagc    840
actagtggta ttatacettt tagcgcggcc gcacctggcg gaggcccaaa ggctgtgctg    900
aaacttgagc cccgtggat caacgtgctc caggaggact ctgtgactct gacatgccag    960
ggggctcgca gccctgagag cgactccatt cagtggttcc acaatgggaa tctcattccc   1020
acccacacgc agcccagcta caggttcaag gccaacaaca atgacagcgg ggagtacacg   1080
tgccagactg ccagaccag cctcagcgac cctgtgcatc tgactgtgct ttccgaatgg   1140
ctggtgctcc agacccctca cctggagttc aggagggag aaaccatcat gctgaggtgc   1200
cacagctgga aggacaagcc tctggtcaag gtcacattct cccagaatgg aaaatcccag   1260
aaattctccc gtttggatcc caccttctcc atcccacaag caaaccacag tcacagtggt   1320
gattaccact gcacaggaaa cataggctac acgctgttct catccaagcc tgtgaccatc   1380
actgtccaag tgccctgata atctaga                                       1407
```

<210> SEQ ID NO 34
<211> LENGTH: 460
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 34

```
Met Asp Trp Thr Trp Arg Ile Leu Phe Leu Val Ala Ala Thr Gly
1               5                   10                  15

Ala His Ser Gln Ile Val Leu Ser Gln Ser Pro Ala Ile Leu Ser Ala
            20                  25                  30

Ser Pro Gly Glu Lys Val Thr Met Thr Cys Arg Ala Ser Ser Ser Val
        35                  40                  45

Ser Tyr Ile His Trp Phe Gln Gln Lys Pro Gly Ser Ser Pro Lys Pro
    50                  55                  60

Trp Ile Tyr Ala Thr Ser Asn Leu Ala Ser Gly Val Pro Val Arg Phe
65                  70                  75                  80

Ser Gly Ser Gly Ser Gly Thr Ser Tyr Ser Leu Thr Ile Ser Arg Val
                85                  90                  95

Glu Ala Glu Asp Ala Ala Thr Tyr Tyr Cys Gln Gln Trp Thr Ser Asn
            100                 105                 110

Pro Pro Thr Phe Gly Gly Gly Thr Lys Leu Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220
```

Lys Ser Phe Asn Arg Gly Glu Cys Gly Gly Gly Ser Glu Phe Gly
225                 230                 235                 240

Ile Glu Pro Phe Ser Gly Ser Pro Gly Gly Gly Ser Glu Gly Gly
                245                 250                 255

Gly Ile Glu Pro Phe Ser Gly Gly Gly Ser Glu Gly Gly Gly Ala
                260                 265                 270

Pro Gly Ser Thr Ser Gly Ile Ile Pro Phe Ser Ala Ala Pro Gly
            275                 280                 285

Gly Gly Pro Lys Ala Val Leu Lys Leu Glu Pro Pro Trp Ile Asn Val
        290                 295                 300

Leu Gln Glu Asp Ser Val Thr Leu Thr Cys Gln Gly Ala Arg Ser Pro
305                 310                 315                 320

Glu Ser Asp Ser Ile Gln Trp Phe His Asn Gly Asn Leu Ile Pro Thr
                325                 330                 335

His Thr Gln Pro Ser Tyr Arg Phe Lys Ala Asn Asn Asn Asp Ser Gly
                340                 345                 350

Glu Tyr Thr Cys Gln Thr Gly Gln Thr Ser Leu Ser Asp Pro Val His
            355                 360                 365

Leu Thr Val Leu Ser Glu Trp Leu Val Leu Gln Thr Pro His Leu Glu
370                 375                 380

Phe Gln Glu Gly Glu Thr Ile Met Leu Arg Cys His Ser Trp Lys Asp
385                 390                 395                 400

Lys Pro Leu Val Lys Val Thr Phe Phe Gln Asn Gly Lys Ser Gln Lys
                405                 410                 415

Phe Ser Arg Leu Asp Pro Thr Phe Ser Ile Pro Gln Ala Asn His Ser
                420                 425                 430

His Ser Gly Asp Tyr His Cys Thr Gly Asn Ile Gly Tyr Thr Leu Phe
            435                 440                 445

Ser Ser Lys Pro Val Thr Ile Thr Val Gln Val Pro
450                 455                 460

<210> SEQ ID NO 35
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
ggtaccgccg ccaccatgga ctggacctgg aggattctct tcttggtggc agcagccaca      60
ggagcccact ccgacatcca gatgacccag agccccagca gcctgagcgc cagcgtgggc     120
gacagggtga ccatcacctg cagggccagc caggacgtga acaccgccgt ggcctggtat     180
cagcagaagc ccggcaaggc ccccaagctg ctgatctaca gcgccagctt cctgtacagc     240
ggcgtgccca gcaggttcag cggcagcagg agcggcaccg acttcaccct gaccatcagc     300
agcctgcagc ccgaggactt cgccacctac tactgccagc agcactacac caccccccc      360 accttcggcc agggcaccaa ggtggagatc aagaggaccg tggccgcccc cagcgtgttc     420
atcttcccac catctgacga gcagctgaag agcggcaccg ccagcgtggt gtgcctgctg     480
aacaacttct accccaggga ggccaaggtg cagtggaagg tggacaacgc cctgcagagc     540
ggcaacagcc aggagagcgt gaccgagcag gacagcaagg acagcaccta cagcctgagc     600
agcaccctga ccctgagcaa ggccgactac gagaagcaca aggtgtacgc ctgcgaggtg     660

```
acccaccagg gcctgagcag ccccgtgacc aagagcttca acaggggcga gtgcggtgga    720
ggtggatcag aattcggtat cgagcctttc agcggttccc caggcggcgg ctccgaaggc    780
ggcggaggta ttgaaccttt tagcggtgga ggtggctccg aaggcggtgg cgcgcccggt    840
agcactagtg gtattatacc ttttagcgcg gccgcacctg gcggaggccc aaaggctgtg    900
ctgaaacttg agccccgtg atcaacgtg ctccaggagg actctgtgac tctgacatgc    960 caggggctc gcagcctga gagcgactcc attcagtggt tccacaatgg gaatctcatt    1020
cccacccaca cgcagcccag ctacaggttc aaggccaaca acaatgacag cggggagtac    1080
acgtgccaga ctggccagac cagcctcagc gaccctgtgc atctgactgt gctttccgaa    1140
tggctggtgc tccagacccc tcacctggag ttccaggagg agaaaccat catgctgagg    1200 tgccacagct ggaaggacaa gcctctggtc aaggtcacat tcttccagaa tggaaaatcc    1260
cagaaattct cccgtttgga tcccaccttc tccatcccac aagcaaacca cagtcacagt    1320
ggtgattacc actgcacagg aaacataggc tacacgctgt tctcatccaa gcctgtgacc    1380
atcactgtcc aagtgccctg ataatctaga                                    1410
```

<210> SEQ ID NO 36
<211> LENGTH: 461
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Asp Trp Thr Trp Arg Ile Leu Phe Leu Val Ala Ala Ala Thr Gly
1               5                   10                  15

Ala His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Val
        35                  40                  45

Asn Thr Ala Val Ala Trp Tyr Gln Gln Lys Pro Gly Lys Ala Pro Lys
    50                  55                  60

Leu Leu Ile Tyr Ser Ala Ser Phe Leu Tyr Ser Gly Val Pro Ser Arg
65                  70                  75                  80

Phe Ser Gly Ser Arg Ser Gly Thr Asp Phe Thr Leu Thr Ile Ser Ser
                85                  90                  95

Leu Gln Pro Glu Asp Phe Ala Thr Tyr Tyr Cys Gln Gln His Tyr Thr
            100                 105                 110

Thr Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

```
Thr Lys Ser Phe Asn Arg Gly Glu Cys Gly Gly Gly Ser Glu Phe
225                 230                 235                 240

Gly Ile Glu Pro Phe Ser Gly Pro Gly Gly Gly Ser Glu Gly Gly
            245                 250                 255

Gly Gly Ile Glu Pro Phe Ser Gly Gly Gly Ser Glu Gly Gly Gly
        260                 265                 270

Ala Pro Gly Ser Thr Ser Gly Ile Ile Pro Phe Ser Ala Ala Pro
            275                 280                 285

Gly Gly Gly Pro Lys Ala Val Leu Lys Leu Glu Pro Trp Ile Asn
        290                 295                 300

Val Leu Gln Glu Asp Ser Val Thr Leu Thr Cys Gln Gly Ala Arg Ser
305                 310                 315                 320

Pro Glu Ser Asp Ser Ile Gln Trp Phe His Asn Gly Asn Leu Ile Pro
                325                 330                 335

Thr His Thr Gln Pro Ser Tyr Arg Phe Lys Ala Asn Asn Asn Asp Ser
            340                 345                 350

Gly Glu Tyr Thr Cys Gln Thr Gly Gln Thr Ser Leu Ser Asp Pro Val
        355                 360                 365

His Leu Thr Val Leu Ser Glu Trp Leu Val Leu Gln Thr Pro His Leu
370                 375                 380

Glu Phe Gln Glu Gly Glu Thr Ile Met Leu Arg Cys His Ser Trp Lys
385                 390                 395                 400

Asp Lys Pro Leu Val Lys Val Thr Phe Phe Gln Asn Gly Lys Ser Gln
                405                 410                 415

Lys Phe Ser Arg Leu Asp Pro Thr Phe Ser Ile Pro Gln Ala Asn His
            420                 425                 430

Ser His Ser Gly Asp Tyr His Cys Thr Gly Asn Ile Gly Tyr Thr Leu
        435                 440                 445

Phe Ser Ser Lys Pro Val Thr Ile Thr Val Gln Val Pro
450                 455                 460

<210> SEQ ID NO 37
<211> LENGTH: 1527
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
ggtaccgccg ccaccatgga ctggacctgg aggattctct tcttggtggc agcagccaca     60
ggagcccact ccgaggtgca gctggtggag agcggcggcg gcctggtgca gcccggcggc    120
agcctgaggc tgagctgcgc cgccagcggc ttcaacatca aggacaccta catccactgg    180
gtgaggcagg cccccggcaa gggcctggag tgggtggcca ggatctaccc caccaacggc    240
tacaccaggt acgccgacag cgtgaagggc aggttcacca tcagcgccga caccagcaag    300
aacaccgcct acctgcagat gaacagcctg agggccgagg acaccgccgt gtactactgc    360
agcaggtggg gcggcgacgg cttctacgct atggactact ggggccaggg caccctggtg    420
accgtgagca gcgcctccac caagggccca tcggtcttcc ccctggcacc ctcctccaag    480
agcacctctg ggggcacagc ggccctgggc tgcctggtca aggactactt ccccgagccg    540
gtgacggtgt cgtggaactc aggcgccctg accagcggcg tgcacacctt cccggctgtc    600
ctacagtcct caggactcta ctccctctct tccgtggtga ccgtgccctc cagcagcttg    660
ggcacccaga cctacatctg caacgtgaat cacaagccca gcaacaccaa ggtggacaag    720
```

```
aaagttgagc ccaaatcttg tgacactcca ccaccttgcc caaggtgccc agcacctgaa      780
ctcctggggg gaccgtcagt cttcctcttc cccccaaaac ccaaggacac cctcatgatc      840
tcccggaccc ctgaggtcac atgcgtggtg gtggacgtga gccacgaaga ccctgaggtc      900
aagttcaact ggtacgtgga cggcgtggag gtgcataatg ccaagacaaa gccgcgggag      960
gagcagtaca acagcacgta ccgggtggtc agcgtcctca ccgtcctgca ccaggactgg     1020
ctgaatggca aggagtacaa gtgcaaagtc tccaacaaag ccctgcctgc ccccatcgag     1080
aaaaccatct ccaaagccaa agggcagccc cgagaaccac aggtgtacac cctgccccca     1140
tcccgggatg agctgaccaa gaaccaggtc agcctgacct gcctggtcaa aggcttctat     1200
cccagcgaca tcgccgtgga gtgggagagc aatgggcagc cggagaacaa ctacaagacc     1260
acgcctcccg tgctggactc cgacggctcc ttcttcctct actcaaagct caccgtggac     1320
aagagcaggt ggcagcaggg gaacgtcttc tcatgctccg tgatgcatga ggctctgcac     1380
aaccactaca cgcagaagag cctctccctg tctccgggta aggtggagg tggttcacat      1440 catcaccatc atcaccctgg cggaggacta aacgacatct tcgaggctca gaaaatcgaa     1500
tggcacgaag gtccttgata atctaga                                          1527
```

<210> SEQ ID NO 38
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Met Asp Trp Thr Trp Arg Ile Leu Phe Leu Val Ala Ala Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205
```

Thr Val Pro Ser Ser Ser Leu Gly Thr Gln Thr Tyr Ile Cys Asn Val
210                 215                 220

Asn His Lys Pro Ser Asn Thr Lys Val Asp Lys Val Glu Pro Lys
225                 230                 235                 240

Ser Cys Asp Thr Pro Pro Cys Pro Arg Cys Pro Ala Pro Glu Leu
            245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly Lys Gly Gly Gly Ser His His His His His His
465                 470                 475                 480

Pro Gly Gly Gly Leu Asn Asp Ile Phe Glu Ala Gln Lys Ile Glu Trp
            485                 490                 495

His Glu Gly Pro
            500

<210> SEQ ID NO 39
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
ggtaccgccg ccaccatgga ctggacctgg aggattctct tcttggtggc agcagccaca      60
ggagcccact ccgacatcca gatgacccag agcccagca gcctgagcgc agcgtgggc      120 gacagggtga ccatcacctg cagggccagc caggacgtga acaccgccgt ggcctggtat     180
cagcagaagc ccggcaaggc ccccaagctg ctgatctaca gcgccagctt cctgtacagc     240
ggcgtgccca gcaggttcag cggcagcagg agcggcaccg acttcaccct gaccatcagc     300
agcctgcagc ccgaggactt cgccacctac tactgccagc agcactacac cacccccccc     360

```
accttcggcc agggcaccaa ggtggagatc aagaggaccg tggccgcccc cagcgtgttc    420
atcttcccac catctgacga gcagctgaag agcggcaccg ccagcgtggt gtgcctgctg    480
aacaacttct accccaggga ggccaaggtg cagtggaagg tggacaacgc cctgcagagc    540
ggcaacagcc aggagagcgt gaccgagcag gacagcaagg acagcaccta cagcctgagc    600
agcaccctga ccctgagcaa ggccgactac gagaagcaca aggtgtacgc ctgcgaggtg    660
acccaccagg gcctgagcag ccccgtgacc aagagcttca caggggcga gtgctgataa     720 tctaga                                                              726
```

<210> SEQ ID NO 40
<211> LENGTH: 233
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 40

```
Met Asp Trp Thr Trp Arg Ile Leu Phe Leu Val Ala Ala Thr Gly
1               5                   10                  15

Ala His Ser Asp Ile Gln Met Thr Gln Ser Pro Ser Ser Leu Ser Ala
                20                  25                  30

Ser Val Gly Asp Arg Val Thr Ile Thr Cys Arg Ala Ser Gln Asp Val
            35                  40                  45

Asn Thr Ala Val Ala Trp Tyr Gln Gln Lys Pro Gly Lys Ala Pro Lys
        50                  55                  60

Leu Leu Ile Tyr Ser Ala Ser Phe Leu Tyr Ser Gly Val Pro Ser Arg
65                  70                  75                  80

Phe Ser Gly Ser Arg Ser Gly Thr Asp Phe Thr Leu Thr Ile Ser Ser
                85                  90                  95

Leu Gln Pro Glu Asp Phe Ala Thr Tyr Tyr Cys Gln Gln His Tyr Thr
            100                 105                 110

Thr Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 41
<211> LENGTH: 1262
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 41

```
ccatggataa tataaatcgc gctcgcaaaa agcgcgttat cggtggtcat gaagctaaac      60
cgcactcccg tccgtacatg gcttacctga tgatctctgg tccaagcggt tcgaaacgtt     120
gcggtggttt cctgatccag gacgacttcg ttctgaccgc tgctcactgc tggggttcct     180
ccatcaacgt taccctgggt gctcacaaca tcaaagaaca ggaaccgacc cagcagttca     240
tcccggttaa acgtgctatc ccgcacccgg cttacaaccc gaaaaacttc tccaacgaca     300
tcatgctgct gcagctggaa cagaaagcta acagaccca ggctgttcag ccgctgcgtc      360
tgccgtccaa caaagctcag gttaaaccgg tcagacctg ctccgttgct ggttggggtc      420
agaccgctcc gctgggtaaa cactcccaca ctctgcagga agttaaaatg accgttcagg     480
aagatcgtaa atgcgaatcc gacctgcgtc actactacga ctccaccatc gaactgtgcg     540
ttggtgatcc ggaaatcaaa aaaacctcct tcaaggtga ctccggtggt ccgctggttt      600
gcaacaaagt tgctcagggt atcgtttcct acggtcgtac caacggtatg ccgccgatcg     660
cttacaccaa agtttcctcc ttcgttcact ggatcgaaaa aactatggaa cgttacaccg     720
gtcctggtgg cggcggttct ggtgctagcg gtggtcctgg cgagctcgaa agatccgttt     780
taacagttcc atctacagat atagaaaaag aaatccttga tttagctgct gctacagaaa     840
gattaaattt aactgatgca ttaaactcaa atccagctgg taatttatat gattggcgtt     900
cttctaactc ataccttgg actcaaaagc tcaatttaca cttaacaatt acagctactg      960
gacaaaaata tagaatctta gctagcaaaa ttgttgattt taatatttat tcaaataatt    1020
ttaataatct agtgaaatta gaacagtcct taggtgatgg agtaaaagat cattatgttg    1080
atataagttt agatgctgga caatatgttc ttgtaatgaa agctaattca tcatatagtg    1140
gaaattaccc ttattcaata ttatttcaaa aatttaagct tgaaggtaag cctatcccta    1200
accctctcct cggtcttgat tctacgcgtg cggccgcact cgagcaccac caccaccacc    1260
ac                                                                    1262
```

<210> SEQ ID NO 42
<211> LENGTH: 420
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

```
Met Asp Asn Ile Asn Arg Ala Arg Lys Lys Arg Val Ile Gly Gly His
1               5                   10                  15

Glu Ala Lys Pro His Ser Arg Pro Tyr Met Ala Tyr Leu Met Ile Ser
                20                  25                  30

Gly Pro Ser Gly Ser Lys Arg Cys Gly Gly Phe Leu Ile Gln Asp Asp
            35                  40                  45

Phe Val Leu Thr Ala Ala His Cys Trp Gly Ser Ser Ile Asn Val Thr
        50                  55                  60

Leu Gly Ala His Asn Ile Lys Glu Gln Glu Pro Thr Gln Gln Phe Ile
65                  70                  75                  80

Pro Val Lys Arg Ala Ile Pro His Pro Ala Tyr Asn Pro Lys Asn Phe
                85                  90                  95

Ser Asn Asp Ile Met Leu Leu Gln Leu Glu Gln Lys Ala Lys Gln Thr
                100                 105                 110
```

Gln Ala Val Gln Pro Leu Arg Leu Pro Ser Asn Lys Ala Gln Val Lys
            115                 120                 125

Pro Gly Gln Thr Cys Ser Val Ala Gly Trp Gly Gln Thr Ala Pro Leu
        130                 135                 140

Gly Lys His Ser His Thr Leu Gln Glu Val Lys Met Thr Val Gln Glu
145                 150                 155                 160

Asp Arg Lys Cys Glu Ser Asp Leu Arg His Tyr Tyr Asp Ser Thr Ile
                165                 170                 175

Glu Leu Cys Val Gly Asp Pro Glu Ile Lys Lys Thr Ser Phe Lys Gly
            180                 185                 190

Asp Ser Gly Gly Pro Leu Val Cys Asn Lys Val Ala Gln Gly Ile Val
        195                 200                 205

Ser Tyr Gly Arg Thr Asn Gly Met Pro Pro Ile Ala Tyr Thr Lys Val
    210                 215                 220

Ser Ser Phe Val His Trp Ile Glu Lys Thr Met Glu Arg Tyr Thr Gly
225                 230                 235                 240

Pro Gly Gly Gly Gly Ser Gly Ala Ser Gly Gly Pro Gly Glu Leu Glu
                245                 250                 255

Arg Ser Val Leu Thr Val Pro Ser Thr Asp Ile Glu Lys Glu Ile Leu
            260                 265                 270

Asp Leu Ala Ala Ala Thr Glu Arg Leu Asn Leu Thr Asp Ala Leu Asn
        275                 280                 285

Ser Asn Pro Ala Gly Asn Leu Tyr Asp Trp Arg Ser Ser Asn Ser Tyr
    290                 295                 300

Pro Trp Thr Gln Lys Leu Asn Leu His Leu Thr Ile Thr Ala Thr Gly
305                 310                 315                 320

Gln Lys Tyr Arg Ile Leu Ala Ser Lys Ile Val Asp Phe Asn Ile Tyr
                325                 330                 335

Ser Asn Asn Phe Asn Asn Leu Val Lys Leu Glu Gln Ser Leu Gly Asp
            340                 345                 350

Gly Val Lys Asp His Tyr Val Asp Ile Ser Leu Asp Ala Gly Gln Tyr
        355                 360                 365

Val Leu Val Met Lys Ala Asn Ser Ser Tyr Ser Gly Asn Tyr Pro Tyr
    370                 375                 380

Ser Ile Leu Phe Gln Lys Phe Lys Leu Glu Gly Lys Pro Ile Pro Asn
385                 390                 395                 400

Pro Leu Leu Gly Leu Asp Ser Thr Arg Ala Ala Ala Leu Glu His His
                405                 410                 415

His His His His
        420

<210> SEQ ID NO 43
<211> LENGTH: 1938
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
ggtaccgccg ccaccatgga ctggacctgg aggattctct tcttggtggc agcagccaca      60
ggagcccact ccgcagcgaa ttctcaggtg cagctggtcc agtctggcgc cgaggtcaag     120
aaacctggcg cctccgtgaa agtcagctgc aaggccagcg gctacacctt caccagctac     180
aacatgcact gggtccggca gccccctggc aagggcctgg aatggatcgg cgccatctac     240

```
cccggcaacg gcgacacctc ctacaaccag aagttcaagg gcagagtcac catcaccgcc    300
gacaagagca ccagcaccgc ctacatggaa ctgagcagcc tgcggagcga ggacaccgcc    360
gtgtactact gcgccagaag cacctactac ggcggcgact ggtacttcaa cgtgtgggc     420 cagggcacca ccgtgaccgt gtccggtggc ggcggcagcg gcggcggcgg cagcggcggt    480
ggctcgagcc agatcgtgct gacccagagc cccgccaccc tgtctctgag ccctggcgag    540
agagccaccc tgagctgtag agccagcagc agcgtgtcct acatccactg gttccagcag    600
aagcccggca aggcccccaa gcctggatc tacgccacca gcaacctggc cagcggcgtg    660
cccgacagat tttctggcag cggcagcggc accgactaca ccctgaagat cagccgggtg    720
gaagccgagg acgtgggcac ctactactgc cagcagtgga ccagcaaccc ccccaccttc    780
ggccagggca ccaagctgga aatcaagcgc accgtggccg gtgcggccgc aggaccatct    840
ggagcctcca ccaagggccc atcggtcttc ccctggcac cctcctccaa gagcacctct    900
gggggcacag cggccctggg ctgcctggtc aaggactact ccccgagcc ggtgacggtg    960 tcgtggaact caggcgccct gaccagcggc gtgcacacct tcccggctgt cctacagtcc    1020
tcaggactct actccctctc ttccgtggtg accgtgccct ccagcagctt gggcacccag    1080
acctacatct gcaacgtgaa tcacaagccc agcaacacca aggtggacaa gaaagttgag    1140
cccaaatctt gtgacaaaac tcacacatgc ccaccgtgcc cagcacctga actcctgggg    1200
ggaccgtcag tcttcctctt ccccccaaaa cccaaggaca ccctcatgat ctcccggacc    1260
cctgaggtca catgcgtggt ggtggacgtg agccacgaag accctgaggt caagttcaac    1320
tggtacgtgg acggcgtgga ggtgcataat gccaagacaa agccgcggga ggagcagtac    1380
aacagcacgt accgggtggt cagcgtcctc accgtcctgc accaggactg gctgaatggc    1440
aaggagtaca agtgcaaagt ctccaacaaa gccctgcctg cccccatcga gaaaaccatc    1500
tccaaagcca aagggcagcc ccgagaacca caggtgtaca ccctgccccc atcccgggat    1560
gagctgacca agaaccaggt cagcctgacc tgcctggtca aaggcttcta tcccagcgac    1620
atcgccgtgg agtgggagag caatgggcag ccggagaaca actacaagac cacgcctccc    1680
gtgctggact ccgacggctc cttcttcctc tactcaaagc tcaccgtgga caagagcagg    1740
tggcagcagg ggaacgtctt ctcatgctcc gtgatgcatg aggctctgca caaccactac    1800
acgcagaaga gcctctccct gtctccgggt aaaggtggag gtggttcaca tcatcaccat    1860
catcaccctg gcggaggact aaacgacatc ttcgaggctc agaaaatcga atggcacgaa    1920
ggtccttgat aatctaga                                                  1938
```

<210> SEQ ID NO 44
<211> LENGTH: 637
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Asp Trp Thr Trp Arg Ile Leu Phe Leu Val Ala Ala Ala Thr Gly
1               5                   10                  15

Ala His Ser Ala Ala Asn Ser Gln Val Gln Leu Val Gln Ser Gly Ala
                20                  25                  30

Glu Val Lys Lys Pro Gly Ala Ser Val Lys Val Ser Cys Lys Ala Ser
        35                  40                  45

Gly Tyr Thr Phe Thr Ser Tyr Asn Met His Trp Val Arg Gln Pro Pro

-continued

```
            50                  55                  60
Gly Lys Gly Leu Glu Trp Ile Gly Ala Ile Tyr Pro Gly Asn Gly Asp
 65                  70                  75                  80

Thr Ser Tyr Asn Gln Lys Phe Lys Gly Arg Val Thr Ile Thr Ala Asp
                 85                  90                  95

Lys Ser Thr Ser Thr Ala Tyr Met Glu Leu Ser Ser Leu Arg Ser Glu
            100                 105                 110

Asp Thr Ala Val Tyr Tyr Cys Ala Arg Ser Thr Tyr Tyr Gly Gly Asp
            115                 120                 125

Trp Tyr Phe Asn Val Trp Gly Gln Gly Thr Thr Val Thr Val Ser Gly
        130                 135                 140

Gly Gly Gly Ser Gly Gly Gly Gly Ser Gly Gly Ser Ser Gln Ile
145                 150                 155                 160

Val Leu Thr Gln Ser Pro Ala Thr Leu Ser Leu Ser Pro Gly Glu Arg
                165                 170                 175

Ala Thr Leu Ser Cys Arg Ala Ser Ser Ser Val Ser Tyr Ile His Trp
            180                 185                 190

Phe Gln Gln Lys Pro Gly Lys Ala Pro Lys Pro Trp Ile Tyr Ala Thr
        195                 200                 205

Ser Asn Leu Ala Ser Gly Val Pro Asp Arg Phe Ser Gly Ser Gly Ser
210                 215                 220

Gly Thr Asp Tyr Thr Leu Lys Ile Ser Arg Val Glu Ala Glu Asp Val
225                 230                 235                 240

Gly Thr Tyr Tyr Cys Gln Gln Trp Thr Ser Asn Pro Pro Thr Phe Gly
                245                 250                 255

Gln Gly Thr Lys Leu Glu Ile Lys Arg Thr Val Ala Gly Ala Ala Ala
            260                 265                 270

Gly Pro Ser Gly Ala Ser Thr Lys Gly Pro Ser Val Phe Pro Leu Ala
        275                 280                 285

Pro Ser Ser Lys Ser Thr Ser Gly Gly Thr Ala Ala Leu Gly Cys Leu
290                 295                 300

Val Lys Asp Tyr Phe Pro Glu Pro Val Thr Val Ser Trp Asn Ser Gly
305                 310                 315                 320

Ala Leu Thr Ser Gly Val His Thr Phe Pro Ala Val Leu Gln Ser Ser
                325                 330                 335

Gly Leu Tyr Ser Leu Ser Ser Val Val Thr Val Pro Ser Ser Ser Leu
            340                 345                 350

Gly Thr Gln Thr Tyr Ile Cys Asn Val Asn His Lys Pro Ser Asn Thr
        355                 360                 365

Lys Val Asp Lys Lys Val Glu Pro Lys Ser Cys Asp Lys Thr His Thr
370                 375                 380

Cys Pro Pro Cys Pro Ala Pro Glu Leu Leu Gly Gly Pro Ser Val Phe
385                 390                 395                 400

Leu Phe Pro Pro Lys Pro Lys Asp Thr Leu Met Ile Ser Arg Thr Pro
                405                 410                 415

Glu Val Thr Cys Val Val Val Asp Val Ser His Glu Asp Pro Glu Val
            420                 425                 430

Lys Phe Asn Trp Tyr Val Asp Gly Val Glu Val His Asn Ala Lys Thr
        435                 440                 445

Lys Pro Arg Glu Glu Gln Tyr Asn Ser Thr Tyr Arg Val Val Ser Val
450                 455                 460

Leu Thr Val Leu His Gln Asp Trp Leu Asn Gly Lys Glu Tyr Lys Cys
465                 470                 475                 480
```

Lys Val Ser Asn Lys Ala Leu Pro Ala Pro Ile Glu Lys Thr Ile Ser
                485                 490                 495

Lys Ala Lys Gly Gln Pro Arg Glu Pro Gln Val Tyr Thr Leu Pro Pro
            500                 505                 510

Ser Arg Asp Glu Leu Thr Lys Asn Gln Val Ser Leu Thr Cys Leu Val
        515                 520                 525

Lys Gly Phe Tyr Pro Ser Asp Ile Ala Val Glu Trp Glu Ser Asn Gly
    530                 535                 540

Gln Pro Glu Asn Asn Tyr Lys Thr Thr Pro Pro Val Leu Asp Ser Asp
545                 550                 555                 560

Gly Ser Phe Phe Leu Tyr Ser Lys Leu Thr Val Asp Lys Ser Arg Trp
            565                 570                 575

Gln Gln Gly Asn Val Phe Ser Cys Ser Val Met His Glu Ala Leu His
        580                 585                 590

Asn His Tyr Thr Gln Lys Ser Leu Ser Leu Ser Pro Gly Lys Gly Gly
    595                 600                 605

Gly Gly Ser His His His His His His Pro Gly Gly Leu Asn Asp
        610                 615                 620

Ile Phe Glu Ala Gln Lys Ile Glu Trp His Glu Gly Pro
625                 630                 635

<210> SEQ ID NO 45
<211> LENGTH: 1968
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
ggtaccgccg ccaccatgga ctggacctgg aggattctct tcttggtggc agcagccaca      60
ggagcccact ccgcagcgaa ttctcaggtg cagctggtcc agtccggcgc ggaagtgaaa     120
aaaccgggct cctccgtgaa aatctcctgc aaagcgtccg gctacgcgtt ctcctcctac     180
tggatgaact gggtgcgcca ggcgccgggc cagggcctgg aatggatcgg ccagatctgg     240
ccgggcgatg gcgataccaa ctacaacggc aaattcaaag gccgcgtgac cctgaccgcg     300
gatgaatcca cctccaccgc gtacatggaa ctgtcctccc tgcgctccga agataccgcg     360
gtgtacttct gcgcgcgccg cgaaaccacc accgtgggcc gctattacta tgcgatggat     420
tactggggcc agggcaccac ggtgaccgtg tcctccggag cggtggcag cggtggaggt     480 ggcagcggcg gcggggtag cgggagctcc gatatcctgc tgacccagag cccggattcc     540
ctggccgtgt ccctgggcga gcgcgcaacc atcaactgca aagcgtccca gagcgtggat     600
tacgacggcg atagctacct gaactggtac cagcagaaac cgggccagcc gccgaaactg     660
ctgatctacg atgcgagcaa cctggtgtcc ggcatcccga gccgcttctc cggtagtggc     720
agcggcaccg acttcacgct gaccatcagc agtctgcagc cggaagatgt cgccacctac     780
cactgccagc agagcaccga agaccgtgg accttcggcc agggcaccaa gctggagatc     840
aagcgcggtg gtgcggccgc aggaccatct ggagcctcca ccaagggccc atcggtcttc     900 ccctggcac cctcctccaa gagcacctct ggggcacag cggccctggg ctgcctggtc     960
aaggactact ccccgagcc ggtgacggtg tcgtggaact caggcgccct gaccagcggc    1020
gtgcacacct tcccggctgt cctacagtcc tcaggactct actccctctc ttccgtggtg    1080
accgtgccct ccagcagctt gggcacccag acctacatct gcaacgtgaa tcacaagccc    1140

```
agcaacacca aggtggacaa gaaagttgag cccaaatctt gtgacaaaac tcacacatgc    1200
ccaccgtgcc cagcacctga actcctgggg ggaccgtcag tcttcctctt ccccccaaaa    1260
cccaaggaca ccctcatgat ctcccggacc cctgaggtca catgcgtggt ggtggacgtg    1320
agccacgaag accctgaggt caagttcaac tggtacgtgg acggcgtgga ggtgcataat    1380
gccaagacaa agccgcggga ggagcagtac aacagcacgt accgggtggt cagcgtcctc    1440
accgtcctgc accaggactg gctgaatggc aaggagtaca agtgcaaagt ctccaacaaa    1500
gccctgcctg cccccatcga gaaaaccatc tccaaagcca agggcagccc cgagaaccca    1560
caggtgtaca ccctgccccc atcccgggat gagctgacca agaaccaggt cagcctgacc    1620
tgcctggtca aaggcttcta tcccagcgac atcgccgtgg agtgggagag caatgggcag    1680
ccggagaaca actacaagac cacgcctccc gtgctggact ccgacggctc cttcttcctc    1740
tactcaaagc tcaccgtgga caagagcagg tggcagcagg ggaacgtctt ctcatgctcc    1800
gtgatgcatg aggctctgca caaccactac acgcagaaga gcctctccct gtctccgggt    1860
aaaggtggag gtggttcaca tcatcaccat catcaccctg gcggaggact aaacgacatc    1920
ttcgaggctc agaaaatcga atggcacgaa ggtccttgat aatctaga                 1968
```

<210> SEQ ID NO 46
<211> LENGTH: 647
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Met Asp Trp Thr Trp Arg Ile Leu Phe Leu Val Ala Ala Ala Thr Gly
1               5                   10                  15

Ala His Ser Ala Ala Asn Ser Gln Val Gln Leu Val Gln Ser Gly Ala
            20                  25                  30

Glu Val Lys Lys Pro Gly Ser Ser Val Lys Ile Ser Cys Lys Ala Ser
        35                  40                  45

Gly Tyr Ala Phe Ser Ser Tyr Trp Met Asn Trp Val Arg Gln Ala Pro
    50                  55                  60

Gly Gln Gly Leu Glu Trp Ile Gly Gln Ile Trp Pro Gly Asp Gly Asp
65                  70                  75                  80

Thr Asn Tyr Asn Gly Lys Phe Lys Gly Arg Val Thr Leu Thr Ala Asp
                85                  90                  95

Glu Ser Thr Ser Thr Ala Tyr Met Glu Leu Ser Ser Leu Arg Ser Glu
            100                 105                 110

Asp Thr Ala Val Tyr Phe Cys Ala Arg Arg Glu Thr Thr Thr Val Gly
        115                 120                 125

Arg Tyr Tyr Tyr Ala Met Asp Tyr Trp Gly Gln Gly Thr Thr Val Thr
    130                 135                 140

Val Ser Ser Gly Gly Gly Gly Ser Gly Gly Gly Gly Ser Gly Gly Gly
145                 150                 155                 160

Gly Ser Gly Ser Ser Asp Ile Leu Leu Thr Gln Ser Pro Asp Ser Leu
                165                 170                 175

Ala Val Ser Leu Gly Glu Arg Ala Thr Ile Asn Cys Lys Ala Ser Gln
            180                 185                 190

Ser Val Asp Tyr Asp Gly Asp Ser Tyr Leu Asn Trp Tyr Gln Gln Lys
        195                 200                 205
```

```
Pro Gly Gln Pro Pro Lys Leu Leu Ile Tyr Asp Ala Ser Asn Leu Val
    210             215                 220
Ser Gly Ile Pro Ser Arg Phe Ser Gly Ser Gly Ser Gly Thr Asp Phe
225             230                 235                 240
Thr Leu Thr Ile Ser Ser Leu Gln Pro Glu Asp Val Ala Thr Tyr His
                245                 250                 255
Cys Gln Gln Ser Thr Glu Asp Pro Trp Thr Phe Gly Gln Gly Thr Lys
            260                 265                 270
Leu Glu Ile Lys Arg Gly Gly Ala Ala Gly Pro Ser Gly Ala Ser
        275                 280                 285
Thr Lys Gly Pro Ser Val Phe Pro Leu Ala Pro Ser Ser Lys Ser Thr
    290             295                 300
Ser Gly Gly Thr Ala Ala Leu Gly Cys Leu Val Lys Asp Tyr Phe Pro
305             310                 315                 320
Glu Pro Val Thr Val Ser Trp Asn Ser Gly Ala Leu Thr Ser Gly Val
                325                 330                 335
His Thr Phe Pro Ala Val Leu Gln Ser Ser Gly Leu Tyr Ser Leu Ser
            340                 345                 350
Ser Val Val Thr Val Pro Ser Ser Ser Leu Gly Thr Gln Thr Tyr Ile
        355                 360                 365
Cys Asn Val Asn His Lys Pro Ser Asn Thr Lys Val Asp Lys Lys Val
    370             375                 380
Glu Pro Lys Ser Cys Asp Lys Thr His Thr Cys Pro Pro Cys Pro Ala
385             390                 395                 400
Pro Glu Leu Leu Gly Gly Pro Ser Val Phe Leu Phe Pro Pro Lys Pro
                405                 410                 415
Lys Asp Thr Leu Met Ile Ser Arg Thr Pro Glu Val Thr Cys Val Val
            420                 425                 430
Val Asp Val Ser His Glu Asp Pro Glu Val Lys Phe Asn Trp Tyr Val
        435                 440                 445
Asp Gly Val Glu Val His Asn Ala Lys Thr Lys Pro Arg Glu Glu Gln
    450             455                 460
Tyr Asn Ser Thr Tyr Arg Val Val Ser Val Leu Thr Val Leu His Gln
465             470                 475                 480
Asp Trp Leu Asn Gly Lys Glu Tyr Lys Cys Lys Val Ser Asn Lys Ala
                485                 490                 495
Leu Pro Ala Pro Ile Glu Lys Thr Ile Ser Lys Ala Lys Gly Gln Pro
            500                 505                 510
Arg Glu Pro Gln Val Tyr Thr Leu Pro Pro Ser Arg Asp Glu Leu Thr
        515                 520                 525
Lys Asn Gln Val Ser Leu Thr Cys Leu Val Lys Gly Phe Tyr Pro Ser
    530             535                 540
Asp Ile Ala Val Glu Trp Glu Ser Asn Gly Gln Pro Glu Asn Asn Tyr
545             550                 555                 560
Lys Thr Thr Pro Pro Val Leu Asp Ser Asp Gly Ser Phe Phe Leu Tyr
                565                 570                 575
Ser Lys Leu Thr Val Asp Lys Ser Arg Trp Gln Gln Gly Asn Val Phe
            580                 585                 590
Ser Cys Ser Val Met His Glu Ala Leu His Asn His Tyr Thr Gln Lys
        595                 600                 605
Ser Leu Ser Leu Ser Pro Gly Lys Gly Gly Gly Ser His His His
    610             615                 620
His His His Pro Gly Gly Gly Leu Asn Asp Ile Phe Glu Ala Gln Lys
```

```
625              630              635              640
Ile Glu Trp His Glu Gly Pro
                645
```

<210> SEQ ID NO 47
<211> LENGTH: 1152
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
ggtaccgccg ccaccatgga ctggacctgg aggattctct tcttggtggc agcagccaca      60
ggagcccact ccgcagcgaa ttctgaagga tctaccgtgg ccgccccag cgtgttcatc      120
ttcccaccat ctgacgagca gctgaagagc ggcaccgcca gcgtggtgtg cctgctgaac      180
aacttctacc ccagggaggc caaggtgcag tggaaggtgg acaacgccct gcagagcggc      240
aacagccagg agagcgtgac cgagcaggac agcaaggaca gcacctacag cctgagcagc      300
accctgaccc tgagcaaggc cgactacgag aagcacaagg tgtacgcctg cgaggtgacc      360
caccagggcc tgagcagccc cgtgaccaag agcttcaaca ggggcgagtg cggtggaggt      420
ggatcagaat tcggtatcga gcctttcagc ggttccccag gcggcggctc cgaaggcggc      480
ggaggtattg aaccttttag cggtggaggt ggctccgaag gcggtggcgc gcccggtagc      540
actagtggta ttatacccttt tagcgcggcc gcacctggcg gaggcccaaa ggctgtgctg      600
aaacttgagc ccccgtggat caacgtgctc caggaggact ctgtgactct gacatgccag      660
ggggctcgca gccctgagag cgactccatt cagtggttcc acaatgggaa tctcattccc      720
acccacacgc agcccagcta caggttcaag gccaacaaca atgacagcgg ggagtacacg      780
tgccagactg ccagaccag cctcagcgac cctgtgcatc tgactgtgct ttccgaatgg      840
ctggtgctcc agacccctca cctggagttc caggagggag aaaccatcat gctgaggtgc      900
cacagctgga aggacaagcc tctggtcaag gtcacattct ccagaatgga aaatcccag      960
aaattctccc gtttggatcc caccttctcc atcccacaag caaaccacag tcacagtggt      1020
gattaccact gcacaggaaa cataggctac acgctgttct catccaagcc tgtgaccatc      1080
actgtccaag tgcccggtgg tggttctggt ggaggatggt ctcacccaca gttcgaaaag      1140
tgataatcta ga                                                         1152
```

<210> SEQ ID NO 48
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Met Asp Trp Thr Trp Arg Ile Leu Phe Leu Val Ala Ala Thr Gly
 1               5                  10                  15

Ala His Ser Ala Ala Asn Ser Glu Gly Ser Thr Val Ala Pro Ser
                20                  25                  30

Val Phe Ile Phe Pro Pro Ser Asp Glu Gln Leu Lys Ser Gly Thr Ala
                35                  40                  45

Ser Val Val Cys Leu Leu Asn Asn Phe Tyr Pro Arg Glu Ala Lys Val
        50                  55                  60
```

Gln Trp Lys Val Asp Asn Ala Leu Gln Ser Gly Asn Ser Gln Glu Ser
65                  70                  75                  80

Val Thr Glu Gln Asp Ser Lys Asp Ser Thr Tyr Ser Leu Ser Ser Thr
                85                  90                  95

Leu Thr Leu Ser Lys Ala Asp Tyr Glu Lys His Lys Val Tyr Ala Cys
            100                 105                 110

Glu Val Thr His Gln Gly Leu Ser Ser Pro Val Thr Lys Ser Phe Asn
        115                 120                 125

Arg Gly Glu Cys Gly Gly Gly Ser Glu Phe Gly Ile Glu Pro Phe
130                 135                 140

Ser Gly Ser Pro Gly Gly Gly Ser Glu Gly Gly Gly Ile Glu Pro
145                 150                 155                 160

Phe Ser Gly Gly Gly Gly Ser Glu Gly Gly Gly Ala Pro Gly Ser Thr
                165                 170                 175

Ser Gly Ile Ile Pro Phe Ser Ala Ala Ala Pro Gly Gly Pro Lys
            180                 185                 190

Ala Val Leu Lys Leu Glu Pro Pro Trp Ile Asn Val Leu Gln Glu Asp
            195                 200                 205

Ser Val Thr Leu Thr Cys Gln Gly Ala Arg Ser Pro Glu Ser Asp Ser
210                 215                 220

Ile Gln Trp Phe His Asn Gly Asn Leu Ile Pro Thr His Thr Gln Pro
225                 230                 235                 240

Ser Tyr Arg Phe Lys Ala Asn Asn Asn Asp Ser Gly Glu Tyr Thr Cys
                245                 250                 255

Gln Thr Gly Gln Thr Ser Leu Ser Asp Pro Val His Leu Thr Val Leu
            260                 265                 270

Ser Glu Trp Leu Val Leu Gln Thr Pro His Leu Glu Phe Gln Glu Gly
        275                 280                 285

Glu Thr Ile Met Leu Arg Cys His Ser Trp Lys Asp Lys Pro Leu Val
290                 295                 300

Lys Val Thr Phe Phe Gln Asn Gly Lys Ser Gln Lys Phe Ser Arg Leu
305                 310                 315                 320

Asp Pro Thr Phe Ser Ile Pro Gln Ala Asn His Ser His Ser Gly Asp
                325                 330                 335

Tyr His Cys Thr Gly Asn Ile Gly Tyr Thr Leu Phe Ser Ser Lys Pro
            340                 345                 350

Val Thr Ile Thr Val Gln Val Pro Gly Gly Ser Gly Gly Gly Trp
        355                 360                 365

Ser His Pro Gln Phe Glu Lys
370                 375

<210> SEQ ID NO 49
<211> LENGTH: 2367
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
ggtaccgccg ccaccatgga ctggacctgg aggattctct tcttggtggc agcagccaca    60
ggagcccact ccgcagcgaa ttctcaggtg cagctggtcc agtctggcgc cgaggtcaag   120
aaacctggcg cctccgtgaa agtcagctgc aaggccagcg gctacacctt caccagctac   180
aacatgcact gggtccggca gcccctggc aagggcctgg aatggatcgg cgccatctac   240

```
cccggcaacg gcgacacctc ctacaaccag aagttcaagg gcagagtcac catcaccgcc    300
gacaagagca ccagcaccgc ctacatggaa ctgagcagcc tgcggagcga ggacaccgcc    360
gtgtactact gcgccagaag cacctactac ggcggcgact ggtacttcaa cgtgtgggc    420 cagggcacca ccgtgaccgt gtccggtggc ggcggcagcg gcggcggcgg cagcggcggt    480
ggctcgagcc agatcgtgct gacccagagc cccgccaccc tgtctctgag ccctggcgag    540
agagccaccc tgagctgtag agccagcagc agcgtgtcct acatccactg gttccagcag    600
aagcccggca aggcccccaa gccctggatc tacgccacca gcaacctggc cagcggcgtg    660
cccgacagat tttctggcag cggcagcggc accgactaca ccctgaagat cagccgggtg    720
gaagccgagg acgtgggcac ctactactgc cagcagtgga ccagcaaccc ccccaccttc    780
ggccagggca ccaagctgga aatcaagcgc accgtggccg gtgcggccgg tggtactcac    840
acatgcccac cgtgcccagc acctgaactc ctgggggac cgtcagtctt cctcttcccc    900
ccaaaaccca aggacaccct catgatctcc cggacccctg aggtcacatg cgtggtggtg    960
gacgtgagcc acgaagaccc tgaggtcaag ttcaactggt acgtggacgg cgtggaggtg    1020
cataatgcca agacaaagcc gcgggaggag cagtacaaca gcacgtaccg ggtggtcagc    1080
gtcctcaccg tcctgcacca ggactggctg aatggcaagg agtacaagtg caaagtctcc    1140
aacaaagccc tgcctgcccc catcgagaaa accatctcca agccaaagg gcagccccga    1200 gaaccacagg tgtacaccct gcccccatcc cgggatgagc tgaccaagaa ccaggtcagc    1260
ctgacctgcc tggtcaaagg cttctatccc agcgacatcg ccgtggagtg ggagagcaat    1320
gggcagccgg agaacaacta caagaccacg cctcccgtgc tggactccga cggctccttc    1380
ttcctctact caaagctcac cgtggacaag agcaggtggc agcaggggaa cgtcttctca    1440
tgctccgtga tgcatgaggc tctgcacaac cactacacgc agaagagcct ctccctgtct    1500
ccgggtaaag gtggaggtgg ttcacatcat caccatcatc accctggcgg aggactaaac    1560
gacatcttcg aggctcagaa aatcgaatgg cacgaaggtc ctgaattcgg cggaggcggc    1620
tccggcggag gcggcgaatc cggcggaggc ggctccggag gcggcggctc cgaaggcggc    1680
ggaggtattg aaccttttag cggtggaggt ggctccgaag gcggtggcgg ctccggaggc    1740
ggcggcgaat ccggcggcgg cggatctgga ggcggcggcg aatccggcgc gcccggtagc    1800
actagtggta ttataccttt tagcgcggcc gcacctggcg gaggcccaaa ggctgtgctg    1860
aaacttgagc cccgtggat caacgtgctc caggaggact ctgtgactct gacatgccag    1920
ggggctcgca gccctgagag cgactccatt cagtggttcc acaatgggaa tctcattccc    1980
acccacacgc agcccagcta caggttcaag gccaacaaca tgacagcgg ggagtacacg    2040 tgccagactg ccagaccag cctcagcgac cctgtgcatc tgactgtgct ttccgaatgg    2100
ctggtgctcc agacccctca cctggagttc aggagggag aaaccatcat gctgaggtgc    2160
cacagctgga aggacaagcc tctggtcaag gtcacattct tccagaatgg aaaatcccag    2220
aaattctccc gtttggatcc caccttctcc atcccacaag caaccacag tcacagtggt    2280 gattaccact gcacaggaaa cataggctac acgctgttct catccaagcc tgtgaccatc    2340
actgtccaag tgccctgata atctaga                                        2367
```

<210> SEQ ID NO 50
<211> LENGTH: 780
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

Met Asp Trp Thr Trp Arg Ile Leu Phe Leu Val Ala Ala Thr Gly
1               5                   10                  15

Ala His Ser Ala Ala Asn Ser Gln Val Gln Leu Val Gln Ser Gly Ala
            20                  25                  30

Glu Val Lys Lys Pro Gly Ala Ser Val Lys Val Ser Cys Lys Ala Ser
        35                  40                  45

Gly Tyr Thr Phe Thr Ser Tyr Asn Met His Val Arg Gln Pro Pro
    50                  55                  60

Gly Lys Gly Leu Glu Trp Ile Gly Ala Ile Tyr Pro Gly Asn Gly Asp
65                  70                  75                  80

Thr Ser Tyr Asn Gln Lys Phe Lys Gly Arg Val Thr Ile Thr Ala Asp
                85                  90                  95

Lys Ser Thr Ser Thr Ala Tyr Met Glu Leu Ser Ser Leu Arg Ser Glu
            100                 105                 110

Asp Thr Ala Val Tyr Tyr Cys Ala Arg Ser Thr Tyr Tyr Gly Gly Asp
        115                 120                 125

Trp Tyr Phe Asn Val Trp Gly Gln Gly Thr Thr Val Thr Val Ser Gly
    130                 135                 140

Gly Gly Gly Ser Gly Gly Gly Ser Gly Gly Ser Ser Gln Ile
145                 150                 155                 160

Val Leu Thr Gln Ser Pro Ala Thr Leu Ser Leu Ser Pro Gly Glu Arg
                165                 170                 175

Ala Thr Leu Ser Cys Arg Ala Ser Ser Val Ser Tyr Ile His Trp
            180                 185                 190

Phe Gln Gln Lys Pro Gly Lys Ala Pro Lys Pro Trp Ile Tyr Ala Thr
        195                 200                 205

Ser Asn Leu Ala Ser Gly Val Pro Asp Arg Phe Ser Gly Ser Gly Ser
    210                 215                 220

Gly Thr Asp Tyr Thr Leu Lys Ile Ser Arg Val Glu Ala Glu Asp Val
225                 230                 235                 240

Gly Thr Tyr Tyr Cys Gln Gln Trp Thr Ser Asn Pro Pro Thr Phe Gly
                245                 250                 255

Gln Gly Thr Lys Leu Glu Ile Lys Arg Thr Val Ala Gly Ala Ala Gly
            260                 265                 270

Gly Thr His Thr Cys Pro Pro Cys Pro Ala Pro Glu Leu Leu Gly Gly
        275                 280                 285

Pro Ser Val Phe Leu Phe Pro Pro Lys Pro Lys Asp Thr Leu Met Ile
    290                 295                 300

Ser Arg Thr Pro Glu Val Thr Cys Val Val Val Asp Val Ser His Glu
305                 310                 315                 320

Asp Pro Glu Val Lys Phe Asn Trp Tyr Val Asp Gly Val Glu Val His
                325                 330                 335

Asn Ala Lys Thr Lys Pro Arg Glu Glu Gln Tyr Asn Ser Thr Tyr Arg
            340                 345                 350

Val Val Ser Val Leu Thr Val Leu His Gln Asp Trp Leu Asn Gly Lys
        355                 360                 365

Glu Tyr Lys Cys Lys Val Ser Asn Lys Ala Leu Pro Ala Pro Ile Glu
    370                 375                 380

Lys Thr Ile Ser Lys Ala Lys Gly Gln Pro Arg Glu Pro Gln Val Tyr
385                 390                 395                 400

Thr Leu Pro Pro Ser Arg Asp Glu Leu Thr Lys Asn Gln Val Ser Leu
            405                 410                 415

Thr Cys Leu Val Lys Gly Phe Tyr Pro Ser Asp Ile Ala Val Glu Trp
        420                 425                 430

Glu Ser Asn Gly Gln Pro Glu Asn Asn Tyr Lys Thr Thr Pro Pro Val
                435                 440                 445

Leu Asp Ser Asp Gly Ser Phe Phe Leu Tyr Ser Lys Leu Thr Val Asp
        450                 455                 460

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Leu Ser Pro
                485                 490                 495

Gly Lys Gly Gly Gly Gly Ser His His His His His His Pro Gly Gly
            500                 505                 510

Gly Leu Asn Asp Ile Phe Glu Ala Gln Lys Ile Glu Trp His Glu Gly
            515                 520                 525

Pro Glu Phe Gly Gly Gly Ser Gly Gly Gly Gly Glu Ser Gly Gly
            530                 535                 540

Gly Gly Ser Gly Gly Gly Ser Glu Gly Gly Gly Ile Glu Pro
545                 550                 555                 560

Phe Ser Gly Gly Gly Ser Glu Gly Gly Gly Ser Gly Gly Gly
                565                 570                 575

Gly Glu Ser Gly Gly Gly Ser Gly Gly Gly Glu Ser Gly Ala
            580                 585                 590

Pro Gly Ser Thr Ser Gly Ile Ile Pro Phe Ser Ala Ala Ala Pro Gly
            595                 600                 605

Gly Gly Pro Lys Ala Val Leu Lys Leu Glu Pro Pro Trp Ile Asn Val
610                 615                 620

Leu Gln Glu Asp Ser Val Thr Leu Thr Cys Gln Gly Ala Arg Ser Pro
625                 630                 635                 640

Glu Ser Asp Ser Ile Gln Trp Phe His Asn Gly Asn Leu Ile Pro Thr
                645                 650                 655

His Thr Gln Pro Ser Tyr Arg Phe Lys Ala Asn Asn Asn Asp Ser Gly
                660                 665                 670

Glu Tyr Thr Cys Gln Thr Gly Gln Thr Ser Leu Ser Asp Pro Val His
            675                 680                 685

Leu Thr Val Leu Ser Glu Trp Leu Val Leu Gln Thr Pro His Leu Glu
            690                 695                 700

Phe Gln Glu Gly Glu Thr Ile Met Leu Arg Cys His Ser Trp Lys Asp
705                 710                 715                 720

Lys Pro Leu Val Lys Val Thr Phe Phe Gln Asn Gly Lys Ser Gln Lys
                725                 730                 735

Phe Ser Arg Leu Asp Pro Thr Phe Ser Ile Pro Gln Ala Asn His Ser
            740                 745                 750

His Ser Gly Asp Tyr His Cys Thr Gly Asn Ile Gly Tyr Thr Leu Phe
            755                 760                 765

Ser Ser Lys Pro Val Thr Ile Thr Val Gln Val Pro
770                 775                 780

<210> SEQ ID NO 51
<211> LENGTH: 2397
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51

| | | | | | |
|---|---|---|---|---|---|
| ggtaccgccg | ccaccatgga | ctggacctgg | aggattctct | tcttggtggc | agcagccaca | 60 |
| ggagcccact | ccgcagcgaa | ttctcaggtg | cagctggtcc | agtccggcgc | ggaagtgaaa | 120 |
| aaaccgggct | cctccgtgaa | aatctcctgc | aaagcgtccg | gctacgcgtt | ctcctcctac | 180 |
| tggatgaact | gggtgcgcca | ggcgccgggc | cagggcctgg | aatggatcgg | ccagatctgg | 240 |
| ccgggcgatg | gcgataccaa | ctacaacggc | aaattcaaag | gccgcgtgac | cctgaccgcg | 300 |
| gatgaatcca | cctccaccgc | gtacatggaa | ctgtcctccc | tgcgctccga | agataccgcg | 360 |
| gtgtacttct | gcgcgcgccg | cgaaaccacc | accgtgggcc | gctattacta | tgcgatggat | 420 |
| tactggggcc | agggcaccac | ggtgaccgtg | tcctccggag | cggtggcag | cggtggaggt | 480 |
| ggcagcggcg | gcggggtag | cgggagctcc | gatatcctgc | tgacccagag | cccggattcc | 540 |
| ctggccgtgt | ccctgggcga | gcgcgcaacc | atcaactgca | aagcgtccca | gagcgtggat | 600 |
| tacgacggcg | atagctacct | gaactggtac | cagcagaaac | cgggccagcc | gccgaaactg | 660 |
| ctgatctacg | atgcgagcaa | cctggtgtcc | ggcatcccga | gccgcttctc | cggtagtggc | 720 |
| agcggcaccg | acttcacgct | gaccatcagc | agtctgcagc | cggaagatgt | cgccacctac | 780 |
| cactgccagc | agagcaccga | agacccgtgg | accttcggcc | agggcaccaa | gctggagatc | 840 |
| aagcgcggtg | gtgcggccgg | tggtactcac | acatgcccac | cgtgcccagc | acctgaactc | 900 |
| ctggggggac | cgtcagtctt | cctcttcccc | ccaaaaccca | aggacaccct | catgatctcc | 960 |
| cggacccctg | aggtcacatg | cgtggtggtg | gacgtgagcc | acgaagaccc | tgaggtcaag | 1020 |
| ttcaactggt | acgtggacgg | cgtggaggtg | cataatgcca | agacaaagcc | gcgggaggag | 1080 |
| cagtacaaca | gcacgtaccg | ggtggtcagc | gtcctcaccg | tcctgcacca | ggactggctg | 1140 |
| aatggcaagg | agtacaagtg | caaagtctcc | aacaaagccc | tgcctgcccc | catcgagaaa | 1200 |
| accatctcca | aagccaaagg | gcagccccga | gaaccacagg | tgtacaccct | gcccccatcc | 1260 |
| cgggatgagc | tgaccaagaa | ccaggtcagc | ctgacctgcc | tggtcaaagg | cttctatccc | 1320 |
| agcgacatcg | ccgtggagtg | ggagagcaat | gggcagccgg | agaacaacta | caagaccacg | 1380 |
| cctcccgtgc | tggactccga | cggctccttc | ttcctctact | caaagctcac | cgtggacaag | 1440 |
| agcaggtggc | agcaggggaa | cgtcttctca | tgctccgtga | tgcatgaggc | tctgcacaac | 1500 |
| cactacacgc | agaagagcct | ctccctgtct | ccgggtaaag | gtggaggtgg | ttcacatcat | 1560 |
| caccatcatc | accctggcgg | aggactaaac | gacatcttcg | aggctcagaa | aatcgaatgg | 1620 |
| cacgaaggtc | ctgaattcgg | cggaggcggc | tccggcggag | gcggcgaatc | cggcggaggc | 1680 |
| ggctccggag | gcggcggctc | cgaaggcggc | ggaggtattg | aaccttttag | cggtggaggt | 1740 |
| ggctccgaag | gcggtggcgg | ctccggaggc | ggcggcgaat | ccggcggcgg | cggatctgga | 1800 |
| ggcggcggca | atccggcgc | gcccggtagc | actagtggta | ttatacccttt | tagcgcggcc | 1860 |
| gcacctggcg | gaggcccaaa | ggctgtgctg | aaacttgagc | ccccgtggat | caacgtgctc | 1920 |
| caggaggact | ctgtgactct | gacatgccag | ggggctcgca | gccctgagag | cgactccatt | 1980 |
| cagtggttcc | acaatgggaa | tctcattccc | acccacacgc | agcccagcta | caggttcaag | 2040 |
| gccaacaaca | atgacagcgg | ggagtacacg | tgccagactg | gccagaccag | cctcagcgac | 2100 |
| cctgtgcatc | tgactgtgct | ttccgaatgg | ctggtgctcc | agaccccctca | cctggagttc | 2160 |
| caggaggagg | aaaccatcat | gctgaggtgc | cacagctgga | aggacaagcc | tctggtcaag | 2220 |
| gtcacattct | tccagaatgg | aaaatcccag | aaattctccc | gtttggatcc | caccttctcc | 2280 |

```
atcccacaag caaaccacag tcacagtggt gattaccact gcacaggaaa cataggctac    2340
acgctgttct catccaagcc tgtgaccatc actgtccaag tgccctgata atctaga      2397
```

<210> SEQ ID NO 52
<211> LENGTH: 790
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Met Asp Trp Thr Trp Arg Ile Leu Phe Leu Val Ala Ala Thr Gly
1               5                   10                  15

Ala His Ser Ala Ala Asn Ser Gln Val Gln Leu Val Gln Ser Gly Ala
            20                  25                  30

Glu Val Lys Lys Pro Gly Ser Ser Val Lys Ile Ser Cys Lys Ala Ser
        35                  40                  45

Gly Tyr Ala Phe Ser Ser Tyr Trp Met Asn Trp Val Arg Gln Ala Pro
    50                  55                  60

Gly Gln Gly Leu Glu Trp Ile Gly Gln Ile Trp Pro Gly Asp Gly Asp
65                  70                  75                  80

Thr Asn Tyr Asn Gly Lys Phe Lys Gly Arg Val Thr Leu Thr Ala Asp
                85                  90                  95

Glu Ser Thr Ser Thr Ala Tyr Met Glu Leu Ser Ser Leu Arg Ser Glu
            100                 105                 110

Asp Thr Ala Val Tyr Phe Cys Ala Arg Arg Glu Thr Thr Thr Val Gly
        115                 120                 125

Arg Tyr Tyr Tyr Ala Met Asp Tyr Trp Gly Gln Gly Thr Thr Val Thr
    130                 135                 140

Val Ser Ser Gly Gly Gly Gly Ser Gly Gly Gly Gly Ser Gly Gly Gly
145                 150                 155                 160

Gly Ser Gly Ser Ser Asp Ile Leu Leu Thr Gln Ser Pro Asp Ser Leu
                165                 170                 175

Ala Val Ser Leu Gly Glu Arg Ala Thr Ile Asn Cys Lys Ala Ser Gln
            180                 185                 190

Ser Val Asp Tyr Asp Gly Asp Ser Tyr Leu Asn Trp Tyr Gln Gln Lys
        195                 200                 205

Pro Gly Gln Pro Pro Lys Leu Leu Ile Tyr Asp Ala Ser Asn Leu Val
    210                 215                 220

Ser Gly Ile Pro Ser Arg Phe Ser Gly Ser Gly Ser Gly Thr Asp Phe
225                 230                 235                 240

Thr Leu Thr Ile Ser Ser Leu Gln Pro Glu Asp Val Ala Thr Tyr His
                245                 250                 255

Cys Gln Gln Ser Thr Glu Asp Pro Trp Thr Phe Gly Gln Gly Thr Lys
            260                 265                 270

Leu Glu Ile Lys Arg Gly Gly Ala Gly Gly Thr His Thr Cys Pro
        275                 280                 285

Pro Cys Pro Ala Pro Glu Leu Leu Gly Gly Pro Ser Val Phe Leu Phe
    290                 295                 300

Pro Pro Lys Pro Lys Asp Thr Leu Met Ile Ser Arg Thr Pro Glu Val
305                 310                 315                 320

Thr Cys Val Val Val Asp Val Ser His Glu Asp Pro Glu Val Lys Phe
                325                 330                 335
```

Asn Trp Tyr Val Asp Gly Val Glu Val His Asn Ala Lys Thr Lys Pro
                340                 345                 350

Arg Glu Glu Gln Tyr Asn Ser Thr Tyr Arg Val Val Ser Val Leu Thr
            355                 360                 365

Val Leu His Gln Asp Trp Leu Asn Gly Lys Glu Tyr Lys Cys Lys Val
        370                 375                 380

Ser Asn Lys Ala Leu Pro Ala Pro Ile Glu Lys Thr Ile Ser Lys Ala
385                 390                 395                 400

Lys Gly Gln Pro Arg Glu Pro Gln Val Tyr Thr Leu Pro Pro Ser Arg
                405                 410                 415

Asp Glu Leu Thr Lys Asn Gln Val Ser Leu Thr Cys Leu Val Lys Gly
            420                 425                 430

Phe Tyr Pro Ser Asp Ile Ala Val Glu Trp Glu Ser Asn Gly Gln Pro
        435                 440                 445

Glu Asn Asn Tyr Lys Thr Thr Pro Pro Val Leu Asp Ser Asp Gly Ser
    450                 455                 460

Phe Phe Leu Tyr Ser Lys Leu Thr Val Asp Lys Ser Arg Trp Gln Gln
465                 470                 475                 480

Gly Asn Val Phe Ser Cys Ser Val Met His Glu Ala Leu His Asn His
                485                 490                 495

Tyr Thr Gln Lys Ser Leu Ser Leu Ser Pro Gly Lys Gly Gly Gly Gly
            500                 505                 510

Ser His His His His His His Pro Gly Gly Gly Leu Asn Asp Ile Phe
        515                 520                 525

Glu Ala Gln Lys Ile Glu Trp His Glu Gly Pro Glu Phe Gly Gly Gly
    530                 535                 540

Gly Ser Gly Gly Gly Gly Glu Ser Gly Gly Gly Ser Gly Gly Gly Gly
545                 550                 555                 560

Gly Ser Glu Gly Gly Gly Ile Glu Pro Phe Ser Gly Gly Gly
                565                 570                 575

Ser Glu Gly Gly Gly Gly Ser Gly Gly Gly Glu Ser Gly Gly Gly
            580                 585                 590

Gly Ser Gly Gly Gly Glu Ser Gly Ala Pro Gly Ser Thr Ser Gly
        595                 600                 605

Ile Ile Pro Phe Ser Ala Ala Ala Pro Gly Gly Gly Pro Lys Ala Val
        610                 615                 620

Leu Lys Leu Glu Pro Pro Trp Ile Asn Val Leu Gln Glu Asp Ser Val
625                 630                 635                 640

Thr Leu Thr Cys Gln Gly Ala Arg Ser Pro Glu Ser Asp Ser Ile Gln
                645                 650                 655

Trp Phe His Asn Gly Asn Leu Ile Pro Thr His Thr Gln Pro Ser Tyr
            660                 665                 670

Arg Phe Lys Ala Asn Asn Asn Asp Ser Gly Glu Tyr Thr Cys Gln Thr
        675                 680                 685

Gly Gln Thr Ser Leu Ser Asp Pro Val His Leu Thr Val Leu Ser Glu
    690                 695                 700

Trp Leu Val Leu Gln Thr Pro His Leu Glu Phe Gln Glu Gly Glu Thr
705                 710                 715                 720

Ile Met Leu Arg Cys His Ser Trp Lys Asp Lys Pro Leu Val Lys Val
                725                 730                 735

Thr Phe Phe Gln Asn Gly Lys Ser Gln Lys Phe Ser Arg Leu Asp Pro
            740                 745                 750

Thr Phe Ser Ile Pro Gln Ala Asn His Ser His Ser Gly Asp Tyr His

```
              755                 760                 765
Cys Thr Gly Asn Ile Gly Tyr Thr Leu Phe Ser Ser Lys Pro Val Thr
        770                 775                 780

Ile Thr Val Gln Val Pro
785                 790

<210> SEQ ID NO 53
<211> LENGTH: 1992
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
ggtaccgccg ccaccatgga ctggacctgg aggattctct tcttggtggc agcagccaca      60
ggagcccact ccgcagcgaa ttctgctgct gctacagaaa gattaaattt agctgatgca     120
ttaaactcaa atccagctgg taatttatat gattggcgtt cttctaactc ataccctttgg    180 actcaaaagc tcaatttaca cttaacaatt acagctactg acaaaaata tagaatctta     240 gctagcaaaa ttgttgattt taatattat tcaaataatt ttaataatct agtgaaatta     300
gaacagtcct taggtgatgg agtaaaagat cattatgttg atataagttt agatgctgga    360
caatatgttc ttgtaatgaa agctaattca gcatatagtg aaattaccc ttattcaata     420 ttatttcaaa aatttaaggg tggtcctgcg gccggtggta ctcacacatg cccaccgtgc    480
ccagcacctg aactcctggg gggaccgtca gtcttcctct ccccccaaa acccaaggac     540 accctcatga tctcccggac ccctgaggtc acatgcgtg tggtggacgt gagccacgaa     600
gaccctgagg tcaagttcaa ctggtacgtg gacggcgtgg aggtgcataa tgccaagaca    660
aagccgcggg aggagcagta caacagcacg taccgggtgg tcagcgtcct caccgtcctg    720
caccaggact ggctgaatgg caaggagtac aagtgcaaag tctccaacaa agccctgcct    780
gcccccatcg agaaaccat ctccaaagcc aaagggcagc ccgagaacc acaggtgtac      840 accctgcccc catcccggga tgagctgacc aagaaccagg tcagcctgac ctgcctggtc    900
aaaggcttct atcccagcga catcgccgtg gagtgggaga gcaatgggca gccggagaac    960
aactacaaga ccacgcctcc cgtgctggac tccgacggct ccttcttcct ctactcaaag   1020
ctcaccgtgg acaagagcag gtggcagcag gggaacgtct tctcatgctc cgtgatgcat   1080
gaggctctgc acaaccacta cacgcagaag agcctctccc tgtctccggg taaaggtgga   1140
ggtggttcac atcatcacca tcatcaccct ggcggaggac taaacgacat cttcgaggct   1200
cagaaaatcg aatggcacga aggtcctgaa ttcggcggag gcggctccgg cggaggcggc   1260
gaatccggcg gaggcggctc cggaggcggc ggctccgaag cggcggagg tattgaacct   1320 tttagcggtg gaggtggctc cgaaggcggt ggcggctccg gaggcggcgg cgaatccggc   1380
ggcggcggat ctgaggcggc ggcgaatcc ggcgcgcccg gtagcactag tggtattata    1440
ccttttagcg cggccgcacc tggcggaggc ccaaaggctg tgctgaaact tgagccccg    1500 tggatcaacg tgctccagga ggactctgtg actctgacat gccagggggc tcgcagccct   1560
gagagcgact ccattcagtg gttccacaat gggaatctca ttcccaccca cacgcagccc   1620
agctacaggt tcaaggccaa caacaatgac agcgggagt acacgtgcca gactggccag   1680
accagcctca cgaccctgt gcatctgact gtgctttccg aatggctggt gctccagacc   1740
cctcacctgg agttccagga gggagaaacc atcatgctga ggtgccacag ctggaaggac   1800
```

-continued

```
aagcctctgg tcaaggtcac attcttccag aatggaaaat cccagaaatt ctcccgtttg   1860
gatcccacct tctccatccc acaagcaaac cacagtcaca gtggtgatta ccactgcaca   1920
ggaaacatag ctacacgct gttctcatcc aagcctgtga ccatcactgt ccaagtgccc    1980
tgataatcta ga                                                       1992
```

<210> SEQ ID NO 54
<211> LENGTH: 655
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Met Asp Trp Thr Trp Arg Ile Leu Phe Leu Val Ala Ala Ala Thr Gly
1               5                   10                  15

Ala His Ser Ala Ala Asn Ser Ala Ala Ala Thr Glu Arg Leu Asn Leu
            20                  25                  30

Ala Asp Ala Leu Asn Ser Asn Pro Ala Gly Asn Leu Tyr Asp Trp Arg
        35                  40                  45

Ser Ser Asn Ser Tyr Pro Trp Thr Gln Lys Leu Asn Leu His Leu Thr
    50                  55                  60

Ile Thr Ala Thr Gly Gln Lys Tyr Arg Ile Leu Ala Ser Lys Ile Val
65                  70                  75                  80

Asp Phe Asn Ile Tyr Ser Asn Asn Phe Asn Asn Leu Val Lys Leu Glu
                85                  90                  95

Gln Ser Leu Gly Asp Gly Val Lys Asp His Tyr Val Asp Ile Ser Leu
            100                 105                 110

Asp Ala Gly Gln Tyr Val Leu Val Met Lys Ala Asn Ser Ala Tyr Ser
        115                 120                 125

Gly Asn Tyr Pro Tyr Ser Ile Leu Phe Gln Lys Phe Lys Gly Gly Pro
    130                 135                 140

Ala Ala Gly Gly Thr His Thr Cys Pro Pro Cys Pro Ala Pro Glu Leu
145                 150                 155                 160

Leu Gly Gly Pro Ser Val Phe Leu Phe Pro Pro Lys Pro Lys Asp Thr
                165                 170                 175

Leu Met Ile Ser Arg Thr Pro Glu Val Thr Cys Val Val Val Asp Val
            180                 185                 190

Ser His Glu Asp Pro Glu Val Lys Phe Asn Trp Tyr Val Asp Gly Val
        195                 200                 205

Glu Val His Asn Ala Lys Thr Lys Pro Arg Glu Glu Gln Tyr Asn Ser
    210                 215                 220

Thr Tyr Arg Val Val Ser Val Leu Thr Val Leu His Gln Asp Trp Leu
225                 230                 235                 240

Asn Gly Lys Glu Tyr Lys Cys Lys Val Ser Asn Lys Ala Leu Pro Ala
                245                 250                 255

Pro Ile Glu Lys Thr Ile Ser Lys Ala Lys Gly Gln Pro Arg Glu Pro
            260                 265                 270

Gln Val Tyr Thr Leu Pro Pro Ser Arg Asp Glu Leu Thr Lys Asn Gln
        275                 280                 285

Val Ser Leu Thr Cys Leu Val Lys Gly Phe Tyr Pro Ser Asp Ile Ala
    290                 295                 300

Val Glu Trp Glu Ser Asn Gly Gln Pro Glu Asn Asn Tyr Lys Thr Thr
305                 310                 315                 320
```

Pro Pro Val Leu Asp Ser Asp Gly Ser Phe Leu Tyr Ser Lys Leu
            325                 330                 335

Thr Val Asp Lys Ser Arg Trp Gln Gln Gly Asn Val Phe Ser Cys Ser
            340                 345                 350

Val Met His Glu Ala Leu His Asn His Tyr Thr Gln Lys Ser Leu Ser
            355                 360                 365

Leu Ser Pro Gly Lys Gly Gly Gly Ser His His His His His
        370                 375                 380

Pro Gly Gly Gly Leu Asn Asp Ile Phe Glu Ala Gln Lys Ile Glu Trp
385                 390                 395                 400

His Glu Gly Pro Glu Phe Gly Gly Gly Ser Gly Gly Gly Gly Glu
            405                 410                 415

Ser Gly Gly Gly Ser Gly Gly Gly Ser Glu Gly Gly Gly
            420                 425                 430

Ile Glu Pro Phe Ser Gly Gly Gly Ser Glu Gly Gly Gly Ser
            435                 440                 445

Gly Gly Gly Glu Ser Gly Gly Gly Ser Gly Gly Gly Glu
        450                 455                 460

Ser Gly Ala Pro Gly Ser Thr Ser Gly Ile Ile Pro Phe Ser Ala Ala
465                 470                 475                 480

Ala Pro Gly Gly Gly Pro Lys Ala Val Leu Lys Leu Glu Pro Pro Trp
            485                 490                 495

Ile Asn Val Leu Gln Glu Asp Ser Val Thr Leu Thr Cys Gln Gly Ala
            500                 505                 510

Arg Ser Pro Glu Ser Asp Ser Ile Gln Trp Phe His Asn Gly Asn Leu
        515                 520                 525

Ile Pro Thr His Thr Gln Pro Ser Tyr Arg Phe Lys Ala Asn Asn Asn
530                 535                 540

Asp Ser Gly Glu Tyr Thr Cys Gln Thr Gly Gln Thr Ser Leu Ser Asp
545                 550                 555                 560

Pro Val His Leu Thr Val Leu Ser Glu Trp Leu Val Leu Gln Thr Pro
            565                 570                 575

His Leu Glu Phe Gln Glu Gly Glu Thr Ile Met Leu Arg Cys His Ser
            580                 585                 590

Trp Lys Asp Lys Pro Leu Val Lys Val Thr Phe Phe Gln Asn Gly Lys
        595                 600                 605

Ser Gln Lys Phe Ser Arg Leu Asp Pro Thr Phe Ser Ile Pro Gln Ala
        610                 615                 620

Asn His Ser His Ser Gly Asp Tyr His Cys Thr Gly Asn Ile Gly Tyr
625                 630                 635                 640

Thr Leu Phe Ser Ser Lys Pro Val Thr Ile Thr Val Gln Val Pro
            645                 650                 655

<210> SEQ ID NO 55
<211> LENGTH: 2184
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
ggtaccgccg ccaccatgga ctggacctgg aggattctct tcttggtggc agcagccaca      60
ggagcccact ccgcagcgaa ttctaaagag attacgaatg ccttggaaac ctggggtgcc     120
ttgggtcagg acatcaactt ggacattcct agttttcaaa tgagtgatga tattgacgat    180

```
ataaaatggg aaaaaacttc agacaagaaa aagattgcac aattcagaaa agagaaagag    240
actttcaagg aaaaagatac atataagcta tttaaaaatg gaactctgaa aattaagcat    300
ctgaagaccg atgatcagga tatctacaag gtatcaatat atgatacaaa aggaaaaaat    360
gtgttggaaa aaatatttga tttgaagatt caagagaggg tctcaaaacc aaagatctcc    420
tggacttgta tcaacacaac cctgacctgt gaggtaatga atggaactga ccccgaatta    480
aacctgtatc aagatgggaa acatctaaaa ctttctcaga gggtcatcac acacaagtgg    540
accaccagcc tgagtgcaaa attcaagtgc acagcaggga acaaagtcag caaggaatcc    600
agtgtcgagc ctgtcagctg tccagagaaa ggtctggacg cggccggtgg tactcacaca    660
tgcccaccgt gcccagcacc tgaactcctg ggggaccgt cagtcttcct cttcccccca    720
aaacccaagg acaccctcat gatctcccgg acccctgagg tcacatgcgt ggtggtggac    780
gtgagccacg aagaccctga ggtcaagttc aactggtacg tggacggcgt ggaggtgcat    840
aatgccaaga caaagccgcg ggaggagcag tacaacagca cgtaccgggt ggtcagcgtc    900
ctcaccgtcc tgcaccagga ctggctgaat ggcaaggagt acaagtgcaa agtctccaac    960
aaagccctgc ctgcccccat cgagaaaacc atctccaaag ccaaagggca gccccgagaa   1020
ccacaggtgt acaccctgcc cccatcccgg gatgagctga ccaagaacca ggtcagcctg   1080
acctgcctgg tcaaaggctt ctatcccagc gacatcgccg tggagtggga gagcaatggg   1140
cagccggaga acaactacaa gaccacgcct cccgtgctgg actccgacgg ctccttcttc   1200
ctctactcaa agctcaccgt ggacaagagc aggtggcagc aggggaacgt cttctcatgc   1260
tccgtgatgc atgaggctct gcacaaccac tacacgcaga agagcctctc cctgtctccg   1320
ggtaaaggtg gaggtggttc acatcatcac catcatcacc ctggcggagg actaaacgac   1380
atcttcgagg ctcagaaaat cgaatggcac gaaggtcctg aattcggcgg aggcggctcc   1440
ggcggaggcg gcgaatccgg cggaggcggc tccggaggcg gcggctccga aggcggcgga   1500
ggtattgaac ttttagcgg tggaggtggc tccgaaggcg gtggcggctc cggaggcggc   1560
ggcgaatccg gcggcggcgg atctggaggc ggcggcgaat ccggcgcgcc cggtagcact   1620
agtggtatta taccttttag cgcggccgca cctggcggag gccaaaggc tgtgctgaaa    1680 cttgagcccc cgtggatcaa cgtgctccag gaggactctg tgactctgac atgccagggg   1740
gctcgcagcc ctgagagcga ctccattcag tggttccaca atgggaatct cattcccacc   1800
cacacgcagc ccagctacag gttcaaggcc aacaacaatg acagcgggga gtacacgtgc   1860
cagactggcc agaccagcct cagcgaccct gtgcatctga ctgtgctttc gaatggctg    1920 gtgctccaga cccctcacct ggagttccag gagggagaaa ccatcatgct gaggtgccac   1980
agctggaagg acaagcctct ggtcaaggtc acattcttcc agaatggaaa atcccagaaa   2040
ttctcccgtt tggatcccac cttctccatc ccacaagcaa accacagtca cagtggtgat   2100
taccactgca caggaaacat aggctacacg ctgttctcat ccaagccgtt gaccatcact   2160
gtccaagtgc cctgataatc taga                                         2184
```

<210> SEQ ID NO 56
<211> LENGTH: 719
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

-continued

```
Met Asp Trp Thr Trp Arg Ile Leu Phe Leu Val Ala Ala Thr Gly
1               5                   10                  15

Ala His Ser Ala Ala Asn Ser Lys Glu Ile Thr Asn Ala Leu Glu Thr
            20                  25                  30

Trp Gly Ala Leu Gly Gln Asp Ile Asn Leu Asp Ile Pro Ser Phe Gln
        35                  40                  45

Met Ser Asp Asp Ile Asp Asp Ile Lys Trp Glu Lys Thr Ser Asp Lys
    50                  55                  60

Lys Lys Ile Ala Gln Phe Arg Lys Glu Lys Glu Thr Phe Lys Glu Lys
65                  70                  75                  80

Asp Thr Tyr Lys Leu Phe Lys Asn Gly Thr Leu Lys Ile Lys His Leu
                85                  90                  95

Lys Thr Asp Asp Gln Asp Ile Tyr Lys Val Ser Ile Tyr Asp Thr Lys
            100                 105                 110

Gly Lys Asn Val Leu Glu Lys Ile Phe Asp Leu Lys Ile Gln Glu Arg
        115                 120                 125

Val Ser Lys Pro Lys Ile Ser Trp Thr Cys Ile Asn Thr Thr Leu Thr
    130                 135                 140

Cys Glu Val Met Asn Gly Thr Asp Pro Glu Leu Asn Leu Tyr Gln Asp
145                 150                 155                 160

Gly Lys His Leu Lys Leu Ser Gln Arg Val Ile Thr His Lys Trp Thr
                165                 170                 175

Thr Ser Leu Ser Ala Lys Phe Lys Cys Thr Ala Gly Asn Lys Val Ser
            180                 185                 190

Lys Glu Ser Ser Val Glu Pro Val Ser Cys Pro Glu Lys Gly Leu Asp
        195                 200                 205

Ala Ala Gly Gly Thr His Thr Cys Pro Pro Cys Pro Ala Pro Glu Leu
    210                 215                 220

Leu Gly Gly Pro Ser Val Phe Leu Phe Pro Pro Lys Pro Lys Asp Thr
225                 230                 235                 240

Leu Met Ile Ser Arg Thr Pro Glu Val Thr Cys Val Val Val Asp Val
                245                 250                 255

Ser His Glu Asp Pro Glu Val Lys Phe Asn Trp Tyr Val Asp Gly Val
            260                 265                 270

Glu Val His Asn Ala Lys Thr Lys Pro Arg Glu Glu Gln Tyr Asn Ser
        275                 280                 285

Thr Tyr Arg Val Val Ser Val Leu Thr Val Leu His Gln Asp Trp Leu
    290                 295                 300

Asn Gly Lys Glu Tyr Lys Cys Lys Val Ser Asn Lys Ala Leu Pro Ala
305                 310                 315                 320

Pro Ile Glu Lys Thr Ile Ser Lys Ala Lys Gly Gln Pro Arg Glu Pro
                325                 330                 335

Gln Val Tyr Thr Leu Pro Pro Ser Arg Asp Glu Leu Thr Lys Asn Gln
            340                 345                 350

Val Ser Leu Thr Cys Leu Val Lys Gly Phe Tyr Pro Ser Asp Ile Ala
        355                 360                 365

Val Glu Trp Glu Ser Asn Gly Gln Pro Glu Asn Asn Tyr Lys Thr Thr
    370                 375                 380

Pro Pro Val Leu Asp Ser Asp Gly Ser Phe Phe Leu Tyr Ser Lys Leu
385                 390                 395                 400

Thr Val Asp Lys Ser Arg Trp Gln Gln Gly Asn Val Phe Ser Cys Ser
                405                 410                 415
```

Val Met His Glu Ala Leu His Asn His Tyr Thr Gln Lys Ser Leu Ser
              420                 425                 430

Leu Ser Pro Gly Lys Gly Gly Gly Ser His His His His His
        435                 440                 445

Pro Gly Gly Gly Leu Asn Asp Ile Phe Glu Ala Gln Lys Ile Glu Trp
        450                 455                 460

His Glu Gly Pro Glu Phe Gly Gly Gly Ser Gly Gly Gly Gly Glu
465                 470                 475                 480

Ser Gly Gly Gly Gly Ser Gly Gly Gly Ser Glu Gly Gly Gly
                485                 490                 495

Ile Glu Pro Phe Ser Gly Gly Gly Ser Glu Gly Gly Gly Ser
            500                 505                 510

Gly Gly Gly Gly Glu Ser Gly Gly Gly Ser Gly Gly Gly Glu
            515                 520                 525

Ser Gly Ala Pro Gly Ser Thr Ser Gly Ile Ile Pro Phe Ser Ala Ala
        530                 535                 540

Ala Pro Gly Gly Gly Pro Lys Ala Val Leu Lys Leu Glu Pro Pro Trp
545                 550                 555                 560

Ile Asn Val Leu Gln Glu Asp Ser Val Thr Leu Thr Cys Gln Gly Ala
                565                 570                 575

Arg Ser Pro Glu Ser Asp Ser Ile Gln Trp Phe His Asn Gly Asn Leu
            580                 585                 590

Ile Pro Thr His Thr Gln Pro Ser Tyr Arg Phe Lys Ala Asn Asn Asn
        595                 600                 605

Asp Ser Gly Glu Tyr Thr Cys Gln Thr Gly Gln Thr Ser Leu Ser Asp
    610                 615                 620

Pro Val His Leu Thr Val Leu Ser Glu Trp Leu Val Leu Gln Thr Pro
625                 630                 635                 640

His Leu Glu Phe Gln Glu Gly Glu Thr Ile Met Leu Arg Cys His Ser
                645                 650                 655

Trp Lys Asp Lys Pro Leu Val Lys Val Thr Phe Phe Gln Asn Gly Lys
            660                 665                 670

Ser Gln Lys Phe Ser Arg Leu Asp Pro Thr Phe Ser Ile Pro Gln Ala
        675                 680                 685

Asn His Ser His Ser Gly Asp Tyr His Cys Thr Gly Asn Ile Gly Tyr
    690                 695                 700

Thr Leu Phe Ser Ser Lys Pro Val Thr Ile Thr Val Gln Val Pro
705                 710                 715

<210> SEQ ID NO 57
<211> LENGTH: 1989
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
ggtaccgccg ccaccatgga ctggacctgg aggattctct tcttggtggc agcagccaca      60
ggagcccact ccgcagcgaa ttctctgggc aagaagctgc tggaggccgc cagggccggc     120
caggacgacg aggttaggat cctgatggcc aacggcgccg acgtgaacgc caaggacgag     180
tacggcctga cccccctgta cctggccacc gcccacggcc acctggagat cgtggaggtg     240
ctgctgaaga tggagcaga tgttaatgct gtggacgcca tcggcttcac ccccctgcac     300
ctggccgcct tcatcggaca tcttgaaatt gccgaagtct tgcttaaaca cggtgctgac     360

```
gtcaatgcac aggacaagtt cggcaagacc gccttcgaca tcagcatcgg caacggcaac    420
gaggacctgg ccgagatcct gcaggcggcc ggtggtactc acacatgccc accgtgccca    480
gcacctgaac tcctgggggg accgtcagtc ttcctcttcc ccccaaaacc caaggacacc    540
ctcatgatct cccggacccc tgaggtcaca tgcgtggtgg tggacgtgag ccacgaagac    600
cctgaggtca agttcaactg gtacgtggac ggcgtggagg tgcataatgc aagacaaag    660 ccgcgggagg agcagtacaa cagcacgtac cgggtggtca gcgtcctcac cgtcctgcac    720
caggactggc tgaatggcaa ggagtacaag tgcaaagtct ccaacaaagc cctgcctgcc    780
cccatcgaga aaaccatctc caaagccaaa gggcagcccc gagaaccaca ggtgtacacc    840
ctgcccccat cccgggatga gctgaccaag aaccaggtca gcctgacctg cctggtcaaa    900
ggcttctatc ccagcgacat cgccgtggag tgggagagca atgggcagcc ggagaacaac    960
tacaagacca cgcctcccgt gctggactcc gacggctcct tcttcctcta tcaaagctc    1020 accgtggaca gagcaggtg gcagcagggg aacgtcttct catgctccgt gatgcatgag    1080
gctctgcaca accactacac gcagaagagc ctctcccctgt ctccgggtaa aggtggaggt   1140
ggttcacatc atcaccatca tcaccctggc ggaggactaa cgacatcttc cgaggctcag    1200
aaaatcgaat ggcacgaagg tcctgaattc ggcggaggcg gctccggcgg aggcggcgaa    1260
tccggcggag gcggctccgg aggcggcggc tccgaaggcg gcggaggtat tgaaccttt    1320 agcggtggag gtggctccga aggcggtggc ggctccggag gcggcggcga atccggcggc   1380
ggcggatctg gaggcggcgg cgaatccggc gcgcccggta gcactagtgg tattataccct   1440 tttagcgcgg ccgcacctgg cggaggccca aaggctgtgc tgaaacttga gccccgtgg   1500 atcaacgtgc tccaggagga ctctgtgact ctgacatgcc aggggggctcg cagccctgag   1560 agcgactcca ttcagtggtt ccacaatggg aatctcattc ccacccacac gcagcccagc   1620
tacaggttca aggccaacaa caatgacagc ggggagtaca cgtgccagac tggccagacc   1680
agcctcagcg accctgtgca tctgactgtg ctttccgaat ggctggtgct ccagaccct   1740 cacctggagt tccaggaggg agaaaccatc atgctgaggt gccacagctg aaggacaag   1800 cctctggtca aggtcacatt cttccagaat ggaaaatccc agaaattctc ccgtttggat   1860
cccaccttct ccatcccaca agcaaaccac agtcacagtg gtgattacca ctgcacagga   1920
aacataggct acacgctgtt ctcatccaag cctgtgacca tcactgtcca agtgccctga   1980
taatctaga                                                            1989
```

<210> SEQ ID NO 58
<211> LENGTH: 654
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Asp Trp Thr Trp Arg Ile Leu Phe Leu Val Ala Ala Ala Thr Gly
1               5                   10                  15

Ala His Ser Ala Ala Asn Ser Leu Gly Lys Lys Leu Leu Glu Ala Ala
            20                  25                  30

Arg Ala Gly Gln Asp Asp Glu Val Arg Ile Leu Met Ala Asn Gly Ala
        35                  40                  45

Asp Val Asn Ala Lys Asp Glu Tyr Gly Leu Thr Pro Leu Tyr Leu Ala
    50                  55                  60

```
Thr Ala His Gly His Leu Glu Ile Val Glu Val Leu Leu Lys Asn Gly
 65                  70                  75                  80

Ala Asp Val Asn Ala Val Asp Ala Ile Gly Phe Thr Pro Leu His Leu
                 85                  90                  95

Ala Ala Phe Ile Gly His Leu Glu Ile Ala Glu Val Leu Leu Lys His
            100                 105                 110

Gly Ala Asp Val Asn Ala Gln Asp Lys Phe Gly Lys Thr Ala Phe Asp
        115                 120                 125

Ile Ser Ile Gly Asn Gly Asn Glu Asp Leu Ala Glu Ile Leu Gln Ala
130                 135                 140

Ala Gly Gly Thr His Thr Cys Pro Pro Cys Pro Ala Pro Glu Leu Leu
145                 150                 155                 160

Gly Gly Pro Ser Val Phe Leu Phe Pro Pro Lys Pro Lys Asp Thr Leu
                165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
        195                 200                 205

Val His Asn Ala Lys Thr Lys Pro Arg Glu Glu Gln Tyr Asn Ser Thr
210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Ile Glu Lys Thr Ile Ser Lys Ala Lys Gly Gln Pro Arg Glu Pro Gln
            260                 265                 270

Val Tyr Thr Leu Pro Pro Ser Arg Asp Glu Leu Thr Lys Asn Gln Val
        275                 280                 285

Ser Leu Thr Cys Leu Val Lys Gly Phe Tyr Pro Ser Asp Ile Ala Val
        290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
        355                 360                 365

Ser Pro Gly Lys Gly Gly Gly Ser His His His His His His Pro
        370                 375                 380

Gly Gly Gly Leu Asn Asp Ile Phe Glu Ala Gln Lys Ile Glu Trp His
385                 390                 395                 400

Glu Gly Pro Glu Phe Gly Gly Gly Ser Gly Gly Gly Gly Glu Ser
                405                 410                 415

Gly Gly Gly Gly Ser Gly Gly Gly Ser Glu Gly Gly Gly Ile
            420                 425                 430

Glu Pro Phe Ser Gly Gly Gly Ser Glu Gly Gly Gly Ser Gly
        435                 440                 445

Gly Gly Gly Glu Ser Gly Gly Gly Ser Gly Gly Gly Glu Ser
        450                 455                 460

Gly Ala Pro Gly Ser Thr Ser Gly Ile Ile Pro Phe Ser Ala Ala Ala
465                 470                 475                 480
```

Pro Gly Gly Gly Pro Lys Ala Val Leu Lys Leu Glu Pro Pro Trp Ile
            485                 490                 495
Asn Val Leu Gln Glu Asp Ser Val Thr Leu Thr Cys Gln Gly Ala Arg
        500                 505                 510
Ser Pro Glu Ser Asp Ser Ile Gln Trp Phe His Asn Gly Asn Leu Ile
    515                 520                 525
Pro Thr His Thr Gln Pro Ser Tyr Arg Phe Lys Ala Asn Asn Asn Asp
530                 535                 540
Ser Gly Glu Tyr Thr Cys Gln Thr Gly Gln Thr Ser Leu Ser Asp Pro
545                 550                 555                 560
Val His Leu Thr Val Leu Ser Glu Trp Leu Val Leu Gln Thr Pro His
            565                 570                 575
Leu Glu Phe Gln Glu Gly Glu Thr Ile Met Leu Arg Cys His Ser Trp
        580                 585                 590
Lys Asp Lys Pro Leu Val Lys Val Thr Phe Phe Gln Asn Gly Lys Ser
    595                 600                 605
Gln Lys Phe Ser Arg Leu Asp Pro Thr Phe Ser Ile Pro Gln Ala Asn
    610                 615                 620
His Ser His Ser Gly Asp Tyr His Cys Thr Gly Asn Ile Gly Tyr Thr
625                 630                 635                 640
Leu Phe Ser Ser Lys Pro Val Thr Ile Thr Val Gln Val Pro
            645                 650

<210> SEQ ID NO 59
<211> LENGTH: 1151
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

```
ccatggataa tataaatcgc gctcgcaaaa agcgcgttat cggtggtcat gaagctaaac      60
cgcactcccg tccgtacatg cttacctga tgatctctgg tccaagcggt tcgaaacgtt     120
gcggtggttt cctgatccag gacgacttcg ttctgaccgc tgctcactgc tggggttcct     180
ccatcaacgt taccctgggt gctcacaaca tcaaagaaca ggaaccgacc cagcagttca     240
tcccggttaa cgtgctatc ccgcacccgg cttacaaccc gaaaaacttc tccaacgaca     300
tcatgctgct gcagctggaa cagaaagcta acagaccca ggctgttcag ccgctgcgtc     360
tgccgtccaa caaagctcag gttaaaccgg tcagacctg ctccgttgct ggttggggtc     420
agaccgctcc gctgggtaaa cactcccaca ctctgcagga agttaaaatg accgttcagg     480
aagatcgtaa atgcgaatcc gacctgcgtc actactacga ctccaccatc gaactgtgcg     540
ttggtgatcc ggaaatcaaa aaacctcct tcaaggtga ctccggtggt ccgctggttt      600
gcaacaaagt tgctcagggt atcgtttcct acggtcgtac caacggtatg ccgccgatcg     660
cttacaccaa agtttcctcc ttcgttcact ggatcgaaaa actatggaa cgttacaccg     720
gtcctggtgg cggcggttct ggtgctagcg gtggttctct gggcaagaag ctgctggagg     780
ccgccagggc cggccaggac gacgaggtta ggatcctgat ggccaacggc gccgacgtga     840
acgccaagga cgagtacggc ctgacccccc tgtacctggc caccgcccac ggccacctgg     900
agatcgtgga ggtgctgctg aagaatggag cagatgttaa tgctgtggac gccatcggct     960
tcacccccct gcacctggcc gccttcatcg gacatcttga aattgccgaa gtcttgctta    1020
aacacggtgc tgacgtcaat gcacaggaca gttcggcaa gaccgccttc gacatcagca    1080
```
tcggcaacgg caacgaggac ctggccgaga tcctgcaggc ggccgcactc gagcaccacc      1140
accaccacca c                                                           1151

<210> SEQ ID NO 60
<211> LENGTH: 383
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met Asp Asn Ile Asn Arg Ala Arg Lys Lys Arg Val Ile Gly Gly His
1               5                   10                  15

Glu Ala Lys Pro His Ser Arg Pro Tyr Met Ala Tyr Leu Met Ile Ser
                20                  25                  30

Gly Pro Ser Gly Ser Lys Arg Cys Gly Gly Phe Leu Ile Gln Asp Asp
            35                  40                  45

Phe Val Leu Thr Ala Ala His Cys Trp Gly Ser Ser Ile Asn Val Thr
        50                  55                  60

Leu Gly Ala His Asn Ile Lys Glu Gln Glu Pro Thr Gln Gln Phe Ile
65                  70                  75                  80

Pro Val Lys Arg Ala Ile Pro His Pro Ala Tyr Asn Pro Lys Asn Phe
                85                  90                  95

Ser Asn Asp Ile Met Leu Leu Gln Leu Glu Gln Lys Ala Lys Gln Thr
            100                 105                 110

Gln Ala Val Gln Pro Leu Arg Leu Pro Ser Asn Lys Ala Gln Val Lys
        115                 120                 125

Pro Gly Gln Thr Cys Ser Val Ala Gly Trp Gly Gln Thr Ala Pro Leu
130                 135                 140

Gly Lys His Ser His Thr Leu Gln Glu Val Lys Met Thr Val Gln Glu
145                 150                 155                 160

Asp Arg Lys Cys Glu Ser Asp Leu Arg His Tyr Tyr Asp Ser Thr Ile
                165                 170                 175

Glu Leu Cys Val Gly Asp Pro Glu Ile Lys Lys Thr Ser Phe Lys Gly
            180                 185                 190

Asp Ser Gly Gly Pro Leu Val Cys Asn Lys Val Ala Gln Gly Ile Val
        195                 200                 205

Ser Tyr Gly Arg Thr Asn Gly Met Pro Pro Ile Ala Tyr Thr Lys Val
    210                 215                 220

Ser Ser Phe Val His Trp Ile Glu Lys Thr Met Glu Arg Tyr Thr Gly
225                 230                 235                 240

Pro Gly Gly Gly Ser Gly Ala Ser Gly Gly Ser Leu Gly Lys Lys
                245                 250                 255

Leu Leu Glu Ala Ala Arg Ala Gly Gln Asp Asp Glu Val Arg Ile Leu
            260                 265                 270

Met Ala Asn Gly Ala Asp Val Asn Ala Lys Asp Glu Tyr Gly Leu Thr
        275                 280                 285

Pro Leu Tyr Leu Ala Thr Ala His Gly His Leu Glu Ile Val Glu Val
    290                 295                 300

Leu Leu Lys Asn Gly Ala Asp Val Asn Ala Val Asp Ala Ile Gly Phe
305                 310                 315                 320

Thr Pro Leu His Leu Ala Ala Phe Ile Gly His Leu Glu Ile Ala Glu
                325                 330                 335

Val Leu Leu Lys His Gly Ala Asp Val Asn Ala Gln Asp Lys Phe Gly
            340                 345                 350

Lys Thr Ala Phe Asp Ile Ser Ile Gly Asn Gly Asn Glu Asp Leu Ala
        355                 360                 365

Glu Ile Leu Gln Ala Ala Ala Leu Glu His His His His His His
    370                 375                 380

<210> SEQ ID NO 61
<211> LENGTH: 1488
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

| | |
|---|---|
| ggtaccgccg ccaccatgga ctggacctgg aggattctct tcttggtggc agcagccaca | 60 |
| ggagcccact cccagatcgt gctgagccag agccccgcca tcctgagcgc cagccccggc | 120 |
| gagaaggtga ccatgacctg cagggccagc agcagcgtga gctacatcca ctggttccag | 180 |
| cagaagcccg gcagcagccc caagccctgg atctacgcca ccagcaacct ggccagcggc | 240 |
| gtgcccgtga ggttcagcgg cagcggcagc ggcaccagct acagcctgac catcagcagg | 300 |
| gtggaggccg aggacgccgc cacctactac tgccagcagt ggaccagcaa cccccccacc | 360 |
| ttcggcggcg gcaccaagct ggagatcaag gaccgtgg ccgcccccag cgtgttcatc | 420 |
| ttcccaccat ctgacgagca gctgaagagc ggcaccgcca gcgtggtgtg cctgctgaac | 480 |
| aacttctacc ccagggaggc caaggtgcag tggaaggtgg acaacgccct gcagagcggc | 540 |
| aacagccagg agagcgtgac cgagcaggac agcaaggaca gcacctacag cctgagcagc | 600 |
| accctgaccc tgagcaaggc cgactacgag aagcacaagg tgtacgcctg cgaggtgacc | 660 |
| caccagggcc tgagcagccc cgtgaccaag agcttcaaca ggggcgagtg cggtggaggt | 720 |
| ggatcagaat tcggtatcga gcctttcagc ggttccccag cggcggctc cgaaggcggc | 780 |
| ggaggtattg aaccttttag cggtggaggt ggctccgaag gcggtggcgc gcccggtagc | 840 |
| actagtggta ttataccttt tagcgcggcc gcaagcggcc acgccaagca gaaccagaag | 900 |
| agcgtgaaca gcacgacaa ggaggccctg cacaggtact acaccggcaa cttcaaggag | 960 |
| atgaagaaca tcaacgccct gaagcacggc aagaacaacc tgaggttcaa gtacaggggc | 1020 |
| atgaagaccc aggtgctgct gcccggcaac gagtacagga agtaccagca gaggaggtac | 1080 |
| accggcctgg acgtgttctt cgtgcaggag aggagggaca gcacgacat cagctacacc | 1140 |
| gtgggcggcg tgaccaagac caacaaggcc agcggcttcg tgagcgagcc aggctgaac | 1200 |
| gtggccaagg agaacggcaa ggacgccttc gtgaagggct accctacca catcaacaag | 1260 |
| gaggagatca gcctgaagga gctggacttc aagctgagga agcacctgat cgagaagtac | 1320 |
| ggcctgtaca agaccatcag caaggagggc agggtgaaga tcagcctgaa ggacggcagc | 1380 |
| ttctacaacc tggacctgag gtacaagctg gacttcaagt acatgggcga ggtgatcgac | 1440 |
| agcaagcaga tcaaggacat cgaggttaac ctgaagtaat aatctaga | 1488 |

<210> SEQ ID NO 62
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Met Asp Trp Thr Trp Arg Ile Leu Phe Leu Val Ala Ala Ala Thr Gly
1               5                   10                  15

Ala His Ser Gln Ile Val Leu Ser Gln Ser Pro Ala Ile Leu Ser Ala
            20                  25                  30

Ser Pro Gly Glu Lys Val Thr Met Thr Cys Arg Ala Ser Ser Ser Val
        35                  40                  45

Ser Tyr Ile His Trp Phe Gln Gln Lys Pro Gly Ser Ser Pro Lys Pro
50                  55                  60

Trp Ile Tyr Ala Thr Ser Asn Leu Ala Ser Gly Val Pro Val Arg Phe
65                  70                  75                  80

Ser Gly Ser Gly Ser Gly Thr Ser Tyr Ser Leu Thr Ile Ser Arg Val
                85                  90                  95

Glu Ala Glu Asp Ala Ala Thr Tyr Tyr Cys Gln Gln Trp Thr Ser Asn
            100                 105                 110

Pro Pro Thr Phe Gly Gly Gly Thr Lys Leu Glu Ile Lys Arg Thr Val
        115                 120                 125

Ala Ala Pro Ser Val Phe Ile Phe Pro Pro Ser Asp Glu Gln Leu Lys
130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
210                 215                 220

Lys Ser Phe Asn Arg Gly Glu Cys Gly Gly Gly Ser Glu Phe Gly
225                 230                 235                 240

Ile Glu Pro Phe Ser Gly Ser Pro Gly Gly Gly Ser Glu Gly Gly Gly
                245                 250                 255

Gly Ile Glu Pro Phe Ser Gly Gly Gly Ser Glu Gly Gly Ala
            260                 265                 270

Pro Gly Ser Thr Ser Gly Ile Ile Pro Phe Ser Ala Ala Ala Ser Gly
        275                 280                 285

His Ala Lys Gln Asn Gln Lys Ser Val Asn Lys His Asp Lys Glu Ala
290                 295                 300

Leu His Arg Tyr Tyr Thr Gly Asn Phe Lys Glu Met Lys Asn Ile Asn
305                 310                 315                 320

Ala Leu Lys His Gly Lys Asn Asn Leu Arg Phe Lys Tyr Arg Gly Met
                325                 330                 335

Lys Thr Gln Val Leu Leu Pro Gly Asn Glu Tyr Arg Lys Tyr Gln Gln
            340                 345                 350

Arg Arg Tyr Thr Gly Leu Asp Val Phe Phe Val Gln Glu Arg Arg Asp
        355                 360                 365

Lys His Asp Ile Ser Tyr Thr Val Gly Val Thr Lys Thr Asn Lys
370                 375                 380

Ala Ser Gly Phe Val Ser Glu Pro Arg Leu Asn Val Ala Lys Glu Asn
385                 390                 395                 400

Gly Lys Asp Ala Phe Val Lys Gly Tyr Pro Tyr His Ile Asn Lys Glu
                405                 410                 415
```

Glu Ile Ser Leu Lys Glu Leu Asp Phe Lys Leu Arg Lys His Leu Ile
            420                 425                 430

Glu Lys Tyr Gly Leu Tyr Lys Thr Ile Ser Lys Glu Gly Arg Val Lys
            435                 440                 445

Ile Ser Leu Lys Asp Gly Ser Phe Tyr Asn Leu Asp Leu Arg Tyr Lys
450                 455                 460

Leu Asp Phe Lys Tyr Met Gly Glu Val Ile Asp Ser Lys Gln Ile Lys
465                 470                 475                 480

Asp Ile Glu Val Asn Leu Lys
            485

<210> SEQ ID NO 63
<211> LENGTH: 1323
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
ggtaccgccg ccaccatgga ctggacctgg aggattctct tcttggtggc agcagccaca      60
ggagcccact cccagatcgt gctgagccag agccccgcca tcctgagcgc cagccccggc     120
gagaaggtga ccatgacctg cagggccagc agcagcgtga gctacatcca ctggttccag     180
cagaagcccg gcagcagccc caagccctgg atctacgcca ccagcaacct ggccagcggc     240
gtgcccgtga ggttcagcgg cagcggcagc ggcaccagct acagcctgac catcagcagg     300
gtggaggccg aggacgccgc cacctactac tgccagcagt ggaccagcaa ccccccacc      360 ttcggcggcg gcaccaagct ggagatcaag aggaccgtgg ccgccccag cgtgttcatc      420 ttcccaccat ctgacgagca gctgaagagc ggcaccgcca gcgtggtgtg cctgctgaac     480
aacttctacc ccagggaggc caaggtgcag tggaaggtgg acaacgccct gcagagcggc     540
aacagccagg agagcgtgac cgagcaggac agcaaggaca gcacctacag cctgagcagc     600
accctgaccc tgagcaaggc cgactacgag aagcacaagg tgtacgcctg cgaggtgacc     660
caccagggcc tgagcagccc cgtgaccaag agcttcaaca ggggcgagtg cggtggaggt     720
ggatcagaat tcggtatcga gccttcagc ggttccccag cggcggctc cgaaggcggc      780 ggaggtattg aaccttttag cggtggaggt ggctccgaag gcggtggcgc gcccggtagc     840
actagtggta ttataccttt tagcgcggcc gcatcccccg gggagacgtt cagcacgaac     900
gtctccatcc atgccatcgc ccacgacgac cagacctact ccatgacgt cgtctggttg      960 aggttcgacg tgccgacctc gtgtgccgag atgcgaatat acgaatcgtg tctgtatcac    1020
ccgcagctcc cagaatgtct gtccccggcc gacgcgccgt cgccgcgag tacgtggacg    1080 tctcgcctgg ccgtccgcag ctacgcgggg tgttccagaa caaaccccc accgcgctgt    1140 tcggccgagg ctcacatgga gcccgtcccg gggctggcgt ggcaggcggc ctccgtcaat    1200
ctggagttcc gggacgcgtc cccacaacac tccggcctgt atctgtgtgt ggtgtacgtc    1260
aacgaccata ttcacgcctg gggccacatt accatcagca ccgcggcgca gtaataatct    1320
aga                                                                  1323

<210> SEQ ID NO 64
<211> LENGTH: 432
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 64

Met Asp Trp Thr Trp Arg Ile Leu Phe Leu Val Ala Ala Thr Gly
1               5                   10                  15

Ala His Ser Gln Ile Val Leu Ser Gln Ser Pro Ala Ile Leu Ser Ala
            20                  25                  30

Ser Pro Gly Glu Lys Val Thr Met Thr Cys Arg Ala Ser Ser Ser Val
        35                  40                  45

Ser Tyr Ile His Trp Phe Gln Gln Lys Pro Gly Ser Ser Pro Lys Pro
    50                  55                  60

Trp Ile Tyr Ala Thr Ser Asn Leu Ala Ser Gly Val Pro Val Arg Phe
65                  70                  75                  80

Ser Gly Ser Gly Ser Gly Thr Ser Tyr Ser Leu Thr Ile Ser Arg Val
                85                  90                  95

Glu Ala Glu Asp Ala Ala Thr Tyr Tyr Cys Gln Gln Trp Thr Ser Asn
            100                 105                 110

Pro Pro Thr Phe Gly Gly Gly Thr Lys Leu Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys Gly Gly Gly Ser Glu Phe Gly
225                 230                 235                 240

Ile Glu Pro Phe Ser Gly Ser Pro Gly Gly Gly Ser Glu Gly Gly Gly
                245                 250                 255

Gly Ile Glu Pro Phe Ser Gly Gly Gly Ser Glu Gly Gly Ala
            260                 265                 270

Pro Gly Ser Thr Ser Gly Ile Ile Pro Phe Ser Ala Ala Ser Pro
        275                 280                 285

Gly Glu Thr Phe Ser Thr Asn Val Ser Ile His Ala Ile Ala His Asp
290                 295                 300

Asp Gln Thr Tyr Ser Met Asp Val Val Trp Leu Arg Phe Asp Val Pro
                310                 315                 320
305

Thr Ser Cys Ala Glu Met Arg Ile Tyr Glu Ser Cys Leu Tyr His Pro
            325                 330                 335

Gln Leu Pro Glu Cys Leu Ser Pro Ala Asp Ala Pro Cys Ala Ala Ser
        340                 345                 350

Thr Trp Thr Ser Arg Leu Ala Val Arg Ser Tyr Ala Gly Cys Ser Arg
    355                 360                 365

Thr Asn Pro Pro Arg Cys Ser Ala Glu Ala His Met Glu Pro Val
370                 375                 380

Pro Gly Leu Ala Trp Gln Ala Ala Ser Val Asn Leu Glu Phe Arg Asp
385                 390                 395                 400

Ala Ser Pro Gln His Ser Gly Leu Tyr Leu Cys Val Val Tyr Val Asn
                405                 410                 415

Asp His Ile His Ala Trp Gly His Ile Thr Ile Ser Thr Ala Ala Gln
            420                 425                 430

<210> SEQ ID NO 65
<211> LENGTH: 1245
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

| | | | | | |
|---|---|---|---|---|---|
| ggtaccgccg | ccaccatgga | ctggacctgg | aggattctct | tcttggtggc | agcagccaca | 60 |
| ggagcccact | cccagatcgt | gctgagccag | agccccgcca | tcctgagcgc | cagccccggc | 120 |
| gagaaggtga | ccatgacctg | cagggccagc | agcagcgtga | gctacatcca | ctggttccag | 180 |
| cagaagcccg | gcagcagccc | caagccctgg | atctacgcca | ccagcaacct | ggccagcggc | 240 |
| gtgcccgtga | ggttcagcgg | cagcggcagc | ggcaccagct | acagcctgac | catcagcagg | 300 |
| gtggaggcca | ggacgccgc | cacctactac | tgccagcagt | ggaccagcaa | ccccccacc | 360 |
| ttcggcggcg | gcaccaagct | ggagatcaag | aggaccgtgg | ccgccccag | cgtgttcatc | 420 |
| ttcccaccat | ctgacgagca | gctgaagagc | ggcaccgcca | gcgtggtgtg | cctgctgaac | 480 |
| aacttctacc | ccagggaggc | caaggtgcag | tggaaggtgg | acaacgccct | gcagagcggc | 540 |
| aacagccaga | gagcgtgac | cgagcaggac | agcaaggaca | gcacctacag | cctgagcagc | 600 |
| accctgaccc | tgagcaaggc | cgactacgag | aagcacaagg | tgtacgcctg | cgaggtgacc | 660 |
| caccagggcc | tgagcagccc | cgtgaccaag | agcttcaaca | ggggcgagtg | cgtggaggt | 720 |
| ggatcagaat | tcggtatcga | gcctttcagc | ggttccccag | gcggcggctc | cgaaggcggc | 780 |
| ggaggtattg | aaccttttag | cggtggaggt | ggctccgaag | gcggtggcgc | gcccggtagc | 840 |
| actagtggta | ttataccttt | tagcgcggcc | gcactgggca | agaagctgct | ggaggccgcc | 900 |
| agggccggcc | aggacgacga | ggttaggatc | ctgatggcca | acggcgccga | cgtgaacgcc | 960 |
| agggacatgt | ctggctacac | cccctgcac | ctggccgccc | acatgggcca | cctggagatc | 1020 |
| gtggaggtgc | tgctgaagaa | tggagcagat | gttaatgcta | aagacaactg | ggcgacacc | 1080 |
| cccctgcacc | tggccgccat | cttcggacat | cttgaaattg | tcgaagtctt | gcttaaaaac | 1140 |
| ggtgctgacg | tcaatgcaca | ggacaagttc | ggcaagaccg | ccttcgacat | cagcatcgac | 1200 |
| aacggcaacg | aggacctggc | cgagatcctg | cagtaataat | ctaga | | 1245 |

<210> SEQ ID NO 66
<211> LENGTH: 406
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Asp Trp Thr Trp Arg Ile Leu Phe Leu Val Ala Ala Ala Thr Gly
1               5                   10                  15

Ala His Ser Gln Ile Val Leu Ser Gln Ser Pro Ala Ile Leu Ser Ala
            20                  25                  30

Ser Pro Gly Glu Lys Val Thr Met Thr Cys Arg Ala Ser Ser Ser Val
        35                  40                  45

Ser Tyr Ile His Trp Phe Gln Gln Lys Pro Gly Ser Pro Lys Pro
 50                  55                  60

Trp Ile Tyr Ala Thr Ser Asn Leu Ala Ser Gly Val Pro Val Arg Phe
 65                  70                  75                  80

Ser Gly Ser Gly Ser Gly Thr Ser Tyr Ser Leu Thr Ile Ser Arg Val
                 85                  90                  95

Glu Ala Glu Asp Ala Ala Thr Tyr Tyr Cys Gln Gln Trp Thr Ser Asn
                100                 105                 110

Pro Pro Thr Phe Gly Gly Gly Thr Lys Leu Glu Ile Lys Arg Thr Val
            115                 120                 125

Ala Ala Pro Ser Val Phe Ile Phe Pro Pro Ser Asp Glu Gln Leu Lys
        130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
210                 215                 220

Lys Ser Phe Asn Arg Gly Glu Cys Gly Gly Gly Ser Glu Phe Gly
225                 230                 235                 240

Ile Glu Pro Phe Ser Gly Ser Pro Gly Gly Gly Ser Glu Gly Gly Gly
            245                 250                 255

Gly Ile Glu Pro Phe Ser Gly Gly Gly Ser Glu Gly Gly Gly Ala
        260                 265                 270

Pro Gly Ser Thr Ser Gly Ile Ile Pro Phe Ser Ala Ala Leu Gly
        275                 280                 285

Lys Lys Leu Leu Glu Ala Ala Arg Ala Gly Gln Asp Asp Glu Val Arg
290                 295                 300

Ile Leu Met Ala Asn Gly Ala Asp Val Asn Ala Arg Asp Met Ser Gly
305                 310                 315                 320

Tyr Thr Pro Leu His Leu Ala Ala His Met Gly His Leu Glu Ile Val
                325                 330                 335

Glu Val Leu Leu Lys Asn Gly Ala Asp Val Asn Ala Lys Asp Asn Trp
            340                 345                 350

Gly Asp Thr Pro Leu His Leu Ala Ala Ile Phe Gly His Leu Glu Ile
        355                 360                 365

Val Glu Val Leu Leu Lys Asn Gly Ala Asp Val Asn Ala Gln Asp Lys
        370                 375                 380

Phe Gly Lys Thr Ala Phe Asp Ile Ser Ile Asp Asn Gly Asn Glu Asp
385                 390                 395                 400

Leu Ala Glu Ile Leu Gln
                405

<210> SEQ ID NO 67
<211> LENGTH: 1245
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

```
ggtaccgccg ccaccatgga ctggacctgg aggattctct tcttggtggc agcagccaca    60
ggagcccact cccagatcgt gctgagccag agccccgcca tcctgagcgc cagccccggc   120
gagaaggtga ccatgacctg cagggccagc agcagcgtga gctacatcca ctggttccag   180
cagaagcccg gcagcagccc caagccctgg atctacgcca ccagcaacct ggccagcggc   240
gtgcccgtga ggttcagcgg cagcggcagc ggcaccagct acagcctgac catcagcagg   300
gtggaggccg aggacgccgc cacctactac tgccagcagt ggaccagcaa cccccccacc   360
ttcggcggcg gcaccaagct ggagatcaag gaccgtggc cgcccccag cgtgttcatc   420
ttcccaccat ctgacgagca gctgaagagc ggcaccgcca gcgtggtgtg cctgctgaac   480
aacttctacc ccagggaggc caaggtgcag tggaaggtgg acaacgccct gcagagcggc   540
aacagccagg agagcgtgac cgagcaggac agcaaggaca gcacctacag cctgagcagc   600
accctgaccc tgagcaaggc cgactacgag aagcacaagg tgtacgcctg cgaggtgacc   660
caccagggcc tgagcagccc cgtgaccaag agcttcaaca ggggcgagtg cggtggaggt   720
ggatcagaat tcggtatcga gccttcagc ggttccccag gcggcggctc cgaaggcggc   780
ggaggtattg aaccttttag cggtggaggt ggctccgaag gcggtggcgc gcccggtagc   840
actagtggta ttatacccttt tagcgcggcc gcactgggca agaagctgct ggaggccgcc   900
agggccggcc aggacgacga ggttaggatc ctgatggcca acgcgccga cgtgaacgcc   960
gcggacaagt ctggctacac ccccctgcac ctggccgccc acattggcca cctggagatc  1020
gtggaggtgc tgctgaagca cggagcagat gttaatgctc atgacagctg gggcgacacc  1080
cccctgcacc tggccgccac cttcggacat cttgaaattg tcgaagtctt gcttaaacac  1140
ggtgctgacg tcaatgcaca ggacaagttc ggcaagaccg ccttcgacat cagcatcgac  1200
aacggcaacg aggacctggc cgagatcctg cagtaataat ctaga               1245
```

<210> SEQ ID NO 68
<211> LENGTH: 406
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Met Asp Trp Thr Trp Arg Ile Leu Phe Leu Val Ala Ala Thr Gly
1               5                   10                  15

Ala His Ser Gln Ile Val Leu Ser Gln Ser Pro Ala Ile Leu Ser Ala
            20                  25                  30

Ser Pro Gly Glu Lys Val Thr Met Thr Cys Arg Ala Ser Ser Ser Val
        35                  40                  45

Ser Tyr Ile His Trp Phe Gln Gln Lys Pro Gly Ser Ser Pro Lys Pro
    50                  55                  60

Trp Ile Tyr Ala Thr Ser Asn Leu Ala Ser Gly Val Pro Val Arg Phe
65                  70                  75                  80

Ser Gly Ser Gly Ser Gly Thr Ser Tyr Ser Leu Thr Ile Ser Arg Val
                85                  90                  95

Glu Ala Glu Asp Ala Ala Thr Tyr Tyr Cys Gln Gln Trp Thr Ser Asn
            100                 105                 110

Pro Pro Thr Phe Gly Gly Gly Thr Lys Leu Glu Ile Lys Arg Thr Val
        115                 120                 125
```

```
Ala Ala Pro Ser Val Phe Ile Phe Pro Pro Ser Asp Glu Gln Leu Lys
        130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys Gly Gly Gly Ser Glu Phe Gly
225                 230                 235                 240

Ile Glu Pro Phe Ser Gly Ser Pro Gly Gly Ser Glu Gly Gly Gly
                245                 250                 255

Gly Ile Glu Pro Phe Ser Gly Gly Gly Ser Glu Gly Gly Ala
            260                 265                 270

Pro Gly Ser Thr Ser Gly Ile Ile Pro Phe Ser Ala Ala Leu Gly
        275                 280                 285

Lys Lys Leu Leu Glu Ala Ala Arg Ala Gly Gln Asp Asp Glu Val Arg
290                 295                 300

Ile Leu Met Ala Asn Gly Ala Asp Val Asn Ala Asp Lys Ser Gly
305                 310                 315                 320

Tyr Thr Pro Leu His Leu Ala Ala His Ile Gly His Leu Glu Ile Val
                325                 330                 335

Glu Val Leu Leu Lys His Gly Ala Asp Val Asn Ala His Asp Ser Trp
            340                 345                 350

Gly Asp Thr Pro Leu His Leu Ala Ala Thr Phe Gly His Leu Glu Ile
        355                 360                 365

Val Glu Val Leu Leu Lys His Gly Ala Asp Val Asn Ala Gln Asp Lys
    370                 375                 380

Phe Gly Lys Thr Ala Phe Asp Ile Ser Ile Asp Asn Gly Asn Glu Asp
385                 390                 395                 400

Leu Ala Glu Ile Leu Gln
                405

<210> SEQ ID NO 69
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
ggtaccgccg ccaccatgga ctggacctgg aggattctct tcttggtggc agcagccaca      60
ggagcccact cccagatcgt gctgagccag agccccgcca tcctgagcgc cagccccggc     120
gagaaggtga ccatgacctg cagggccagc agcagcgtga gctacatcca ctggttccag     180
cagaagcccg gcagcagccc caagccctgg atctacgcca ccagcaacct ggccagcggc     240
gtgcccgtga ggttcagcgg cagcggcagc ggcaccagct acagcctgac catcagcagg     300
gtggaggcca aggacgccgc cacctactac tgccagcagt ggaccagcaa ccccccccac     360
ttcggcggcg gcaccaagct ggagatcaag aggaccgtgg ccgcccccag cgtgttcatc     420
```

```
ttcccaccat ctgacgagca gctgaagagc ggcaccgcca gcgtggtgtg cctgctgaac      480
aacttctacc ccagggaggc caaggtgcag tggaaggtgg acaacgccct gcagagcggc      540
aacagccagg agagcgtgac cgagcaggac agcaaggaca cacctacag cctgagcagc       600 accctgaccc tgagcaaggc cgactacgag aagcacaagg tgtacgcctg cgaggtgacc      660
caccagggcc tgagcagccc cgtgaccaag agcttcaaca ggggcgagtg cggtggaggt      720
ggatcagaat tcggtatcga gccttcagc ggttccccag cggcggctc cgaaggcggc        780 ggaggtattg aacctttag cggtggaggt ggctccgaag gcggtggcgc gcccggtagc       840
actagtggta ttatacctt tagcgcggcc gcactgggca agaagctgct ggaggccgcc       900
agggccggcc aggacgacga ggttaggatc ctgatggcca acgcgccga cgtgaacgcc      960 atcgacacta ttggcctgac ccccctgcac ctggccgccc acgacggcca cctggagatc      1020
gtggaggtgc tgctgaagaa cggagcagat gttaatgctg ctgacaactg gggcatcacc     1080 ccctgcacc tggccgcccg gcgcggacat cttgaaattg tcgaagtctt gcttaaacac      1140
ggtgctgacg tcaatgcaga cgacgtgcag ggcaacaccc ccctgcacct gaccgcccac     1200
cacggtcact tggagatagt tgaggtactt ctcaagcaag gagcagatgt taacgctcag     1260
gacaagttcg gcaagaccgc cttcgacatc agcatcgaca cggcaacga ggacctggcc      1320 gagatcctgc agtaataatc taga                                            1344
```

<210> SEQ ID NO 70
<211> LENGTH: 439
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

```
Met Asp Trp Thr Trp Arg Ile Leu Phe Leu Val Ala Ala Ala Thr Gly
1               5                   10                  15

Ala His Ser Gln Ile Val Leu Ser Gln Ser Pro Ala Ile Leu Ser Ala
            20                  25                  30

Ser Pro Gly Glu Lys Val Thr Met Thr Cys Arg Ala Ser Ser Ser Val
        35                  40                  45

Ser Tyr Ile His Trp Phe Gln Gln Lys Pro Gly Ser Ser Pro Lys Pro
    50                  55                  60

Trp Ile Tyr Ala Thr Ser Asn Leu Ala Ser Gly Val Pro Val Arg Phe
65                  70                  75                  80

Ser Gly Ser Gly Ser Gly Thr Ser Tyr Ser Leu Thr Ile Ser Arg Val
                85                  90                  95

Glu Ala Glu Asp Ala Ala Thr Tyr Tyr Cys Gln Gln Trp Thr Ser Asn
            100                 105                 110

Pro Pro Thr Phe Gly Gly Gly Thr Lys Leu Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190
```

```
Leu Ser Ser Thr Leu Thr Leu Ser Lys Ala Asp Tyr Glu Lys His Lys
            195                 200                 205

Val Tyr Ala Cys Glu Val Thr His Gln Gly Leu Ser Ser Pro Val Thr
    210                 215                 220

Lys Ser Phe Asn Arg Gly Glu Cys Gly Gly Gly Ser Glu Phe Gly
225                 230                 235                 240

Ile Glu Pro Phe Ser Gly Ser Pro Gly Gly Gly Ser Glu Gly Gly Gly
                245                 250                 255

Gly Ile Glu Pro Phe Ser Gly Gly Gly Ser Glu Gly Gly Gly Ala
            260                 265                 270

Pro Gly Ser Thr Ser Gly Ile Ile Pro Phe Ser Ala Ala Ala Leu Gly
            275                 280                 285

Lys Lys Leu Leu Glu Ala Ala Arg Ala Gly Gln Asp Asp Glu Val Arg
    290                 295                 300

Ile Leu Met Ala Asn Gly Ala Asp Val Asn Ala Ile Asp Thr Ile Gly
305                 310                 315                 320

Leu Thr Pro Leu His Leu Ala Ala His Asp Gly His Leu Glu Ile Val
                325                 330                 335

Glu Val Leu Leu Lys Asn Gly Ala Asp Val Asn Ala Ala Asp Asn Trp
            340                 345                 350

Gly Ile Thr Pro Leu His Leu Ala Ala Arg Arg Gly His Leu Glu Ile
            355                 360                 365

Val Glu Val Leu Leu Lys His Gly Ala Asp Val Asn Ala Asp Asp Val
    370                 375                 380

Gln Gly Asn Thr Pro Leu His Leu Thr Ala His His Gly His Leu Glu
385                 390                 395                 400

Ile Val Glu Val Leu Leu Lys Gln Gly Ala Asp Val Asn Ala Gln Asp
                405                 410                 415

Lys Phe Gly Lys Thr Ala Phe Asp Ile Ser Ile Asp Asn Gly Asn Glu
            420                 425                 430

Asp Leu Ala Glu Ile Leu Gln
            435

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Asp Asp Asp Lys
1               5

<210> SEQ ID NO 72
<211> LENGTH: 4
<212> TYPE: PRT
<213> ORGANISM: Artificial Sequence
<220> FEATURE:
<223> OTHER INFORMATION: Furin recognition site
<220> FEATURE:
<221> NAME/KEY: misc_feature
<222> LOCATION: (2)..(3)
<223> OTHER INFORMATION: Xaa can be any naturally occurring amino acid

<400> SEQUENCE: 72

Arg Xaa Xaa Arg
1
```

```
<210> SEQ ID NO 73
<211> LENGTH: 4
<212> TYPE: PRT
<213> ORGANISM: Artificial Sequence
<220> FEATURE:
<223> OTHER INFORMATION: Furin recognition site
<220> FEATURE:
<221> NAME/KEY: misc_feature
<222> LOCATION: (2)..(2)
<223> OTHER INFORMATION: Xaa can be any naturally occurring amino acid

<400> SEQUENCE: 73

Arg Xaa Lys Arg
1

<210> SEQ ID NO 74
<211> LENGTH: 4
<212> TYPE: PRT
<213> ORGANISM: Artificial Sequence
<220> FEATURE:
<223> OTHER INFORMATION: Furin recognition site
<220> FEATURE:
<221> NAME/KEY: misc_feature
<222> LOCATION: (2)..(2)
<223> OTHER INFORMATION: Xaa can be any naturally occurring amino acid

<400> SEQUENCE: 74

Arg Xaa Arg Arg
1

<210> SEQ ID NO 75
<211> LENGTH: 6
<212> TYPE: PRT
<213> ORGANISM: Artificial Sequence
<220> FEATURE:
<223> OTHER INFORMATION: Furin recognition site
<220> FEATURE:
<221> NAME/KEY: misc_feature
<222> LOCATION: (4)..(4)
<223> OTHER INFORMATION: Xaa can be any naturally occurring amino acid

<400> SEQUENCE: 75

Arg Ala Arg Xaa Arg Arg
1               5

<210> SEQ ID NO 76
<211> LENGTH: 6
<212> TYPE: PRT
<213> ORGANISM: Artificial Sequence
<220> FEATURE:
<223> OTHER INFORMATION: Furin recognition site
<220> FEATURE:
<221> NAME/KEY: misc_feature
<222> LOCATION: (4)..(4)
<223> OTHER INFORMATION: Xaa can be any naturally occurring amino acid

<400> SEQUENCE: 76

Arg Ala Arg Xaa Lys Arg
1               5

<210> SEQ ID NO 77
<211> LENGTH: 4
<212> TYPE: PRT
<213> ORGANISM: Artificial Sequence
<220> FEATURE:
<223> OTHER INFORMATION: granzyme B recognition site

<400> SEQUENCE: 77

Ile Glu Pro Asp
```

```
<210> SEQ ID NO 78
<211> LENGTH: 6
<212> TYPE: PRT
<213> ORGANISM: Artificial Sequence
<220> FEATURE:
<223> OTHER INFORMATION: granzyme M recognition site

<400> SEQUENCE: 78

Lys Val Tyr Pro Leu Met
1               5

<210> SEQ ID NO 79
<211> LENGTH: 5
<212> TYPE: PRT
<213> ORGANISM: Artificial Sequence
<220> FEATURE:
<223> OTHER INFORMATION: sortase A recognition site
<220> FEATURE:
<221> NAME/KEY: misc_feature
<222> LOCATION: (3)..(3)
<223> OTHER INFORMATION: Xaa can be any naturally occurring amino acid

<400> SEQUENCE: 79

Leu Pro Xaa Thr Gly
1               5

<210> SEQ ID NO 80
<211> LENGTH: 5
<212> TYPE: PRT
<213> ORGANISM: Artificial Sequence
<220> FEATURE:
<223> OTHER INFORMATION: sortase B recognition site

<400> SEQUENCE: 80

Asn Pro Gln Thr Asn
1               5
```

ANTIBODY DERIVATIVES WITH CONDITIONALLY ENABLED EFFECTOR FUNCTION

CLAIM OF PRIORITY

This application is a U.S. National Phase Application under 35 U.S.C. § 371 of International Patent Application No. PCT/US2016/044177, filed on Jul. 27, 2016, which claims priority under 35 USC § 119(e) to U.S. Patent Application Ser. No. 62/197,262, filed on Jul. 27, 2015. The entire contents of the foregoing are hereby incorporated by reference.

TECHNICAL FIELD

The present invention relates to antibody derivatives that have diminished effector function in the initial state owing to the presence of one or more disabling moieties that substantially prevent engagement of the antibody regions responsible for interaction with humoral and cellular immune system effector molecules, and methods of use thereof.

BACKGROUND

Selective killing of cell populations is desirable in a variety of clinical settings, including the treatment of human malignancies and autoimmune disorders. Antibodies have become widely employed for the targeted treatment of neoplastic diseases that are characterized by the elevated expression of specific cell surface proteins that demarcate the malignant cell, or for diseases in which the ablation of the corresponding normal cellular compartment can be tolerated, for example in the treatment of some types of leukemia and lymphoma, or the treatment of autoimmune disorders by ablation or substantial reduction in size of the B cell compartment. However the problem of off-target toxicity caused by antibody-mediated cytotoxic destruction of normal and essential tissues is not negligible.

SUMMARY

In part, the present invention relates to a therapeutic strategy for modulating the effector function of antibodies and antibody derivatives in a controllable way to reduce systemic adverse effects. Specifically, the invention relies on the use of an antibody derivative that has diminished effector function in its initial state owing to the presence of one or more disabling groups that substantially prevent engagement of the antibody regions responsible for interaction with humoral and cellular immune system effector molecules. An antibody derivative with disabled effector function loses its disabling moiety as a result of the action of an activator or endogenous activating factor on a disabling moiety cleavable linker and thereafter engages the effector functions of the immune system. In some embodiments, the disabled antibody derivative can be activated by endogenous activating factors found on or in the vicinity of a target cell. In other embodiments the invention provides a mechanism for enabling the effector function of the disabled antibody or antibody derivative by provision of a second activator composition that in turn can be activated by cell proximity or another activator.

Thus, described herein are compositions and methods useful for selective killing of cells that bear a first and second target while sparing cells that bear only one of the targets, by a mechanism that relies on the innate capacity of antibodies to engage the effector functions of the immune system. Fusion proteins are provided that comprise target recognition moieties and effector domains, wherein the effector domains are prevented from exerting their normal function by effector region disabling moieties (See FIG. 1A). The antibody effector region and effector region disabling moiety are linked through a disabling moiety cleavable linker.

Thus described herein are disabled antibody derivatives that include one or more target binding moieties that are operably linked to one or more antibody effector regions and one or more effector region disabling moieties. An effector region disabling moiety is operably linked to the remainder of the disabled antibody derivative through a linker that contains a disabling moiety cleavable linker. In one embodiment of this aspect, the disabling moiety cleavable linker is susceptible to cleavage by action of enzymes naturally found on the target cell that act as endogenous activating factors. In another embodiment, the disabling moiety cleavable linker is susceptible to cleavage by action of exogenous enzymes independently delivered to the target cell by one or more target binding moieties recognizing one or more targets different from those recognized by the disabled antibody derivative. In some embodiments, the effector region disabling moiety substantially prevents the engagement of effector functions of the immune system prior to the cleavage of the disabling moiety cleavable linker. In some embodiments the effector region disabling moiety substantially prevents the engagement of effector functions of the immune system and the disabled antibody derivative does not intrinsically produce a deleterious effect on the target cell to which it is bound prior to the cleavage of the disabling moiety cleavable linker. In some embodiments the disabled antibody derivative is non-toxic to a cell bearing the target of its one or more target binding moieties.

In addition, described herein are activators or proactivators that include one or more target binding moieties (which bind to the same or different moieties on same target cell) operably linked to an activator domain or proactivator domain. The action of the activator domain is to directly or indirectly cause the cleavage of the disabling moiety cleavable linker, thereby severing the operable linkage between the disabling moiety and the remainder of the disabled antibody derivative.

Thus in a first aspect the invention provides disabled antibody derivatives comprising: a target recognition moiety; an antibody effector region, preferably comprising an IgG CH2 domain, an IgM CH3 domain, or IgG CH2 and CH3 domains; a disabling moiety cleavable linker, and an effector region disabling moiety.

In some embodiments, the target recognition moiety comprises an antigen-binding antibody variable region; an artificially diversified polypeptide binder; or a peptide that binds to a cell surface protein.

In some embodiments, the target recognition moiety binds to target on a cancer cell or on an immune system cell.

In some embodiments, the antibody effector region comprises an IgG CH2 domain.

In some embodiments, the disabling moiety cleavable linker comprises a polypeptide sequence containing a protease cleavage site.

In some embodiments, the disabling moiety cleavable linker comprises a post-translationally modified protease cleavage site.

In some embodiments, the effector region disabling moiety comprises an extracellular soluble portion of an Fc receptor, e.g., an extracellular soluble domain of a human Fc receptor, e.g., of CD16, CD32, or CD64. In some embodiments, the effector region disabling moiety comprises an antibody-binding portion of an Fc-gamma receptor.

In some embodiments, the target recognition moiety and the antibody effector region comprise a variable region and constant region of an antibody, e.g., of a human IgG antibody.

In some embodiments, the target recognition moiety and the antibody effector region comprise a variable region and constant region of a human IgG antibody, and the disabling moiety cleavable linker is coupled to either the C terminus of the light chain or the C terminus of the heavy chain.

In some embodiments, the target recognition moiety and the antibody effector region comprise a variable region and constant region of a human IgG antibody, the disabling moiety cleavable linker is coupled to either the C terminus of the light chain or the C terminus of the heavy chain, and the effector region disabling moiety comprises an antibody binding portion of an Fc gamma receptor.

In some embodiments, the target recognition moiety and the antibody effector region comprise a variable region and constant region of a human IgG antibody, the disabling moiety cleavable linker is coupled to the C terminus of the light chain, and the effector region disabling moiety comprises an extracellular domain of human CD32. In additional aspects, the invention provides nucleic acids encoding the disabled antibody derivatives described herein; vectors comprising the nucleic acids; and host cells expressing the disabled antibody derivatives.

In another aspect, the invention provides kits comprising a disabled antibody derivatives described herein, or a nucleic acid encoding the disabled antibody derivatives, and an activator comprising a second target recognition moiety and an activation domain that cleaves the disabling moiety cleavable linker.

In some embodiments, the activator is a proactivator comprising a second target recognition moiety, an activation domain that cleaves the disabling moiety cleavable linker, and a proactivator activation linker that inactivates the activation domain.

In some embodiments, the target recognition moiety, an antibody effector region, a disabling moiety cleavable linker, and an effector region disabling moiety are assembled posttranslationally through enzymatic or chemical linkage from component parts.

In some embodiments, the target recognition moiety, an antibody effector region, a disabling moiety cleavable linker, and an effector region disabling moiety are non-covalently operably linked to one another.

In yet a further aspect, the invention provides methods of directing immune effector function against a cell, e.g., to kill the cell. The methods include contacting the cell with a disabled antibody derivative as described herein, and an activator comprising: a second target recognition moiety and an activation domain that cleaves the disabling moiety cleavable linker, wherein the target recognition domain and the second target recognition domain bind to targets present on the cell, thereby inducing one or both of a humoral immune response or a cellular immune response against that cell. Contacting the cell can include expressing the disabled antibody derivative in the cell, e.g., by contacting the cell with a nucleic acid expressing a disabled antibody derivative as described herein.

This invention also describes methods of directing immune effector function against a cell, e.g., to kill the cell without the use of an activator provided exogenously. The methods include contacting the cell with a disabled antibody derivative as described herein, wherein the target recognition domain binds to a target present on the cell, and the disabling moiety cleavable linker is cleaved by an endogenous activator, to thereby induce one or both of a humoral immune response or a cellular immune response against that cell.

Definitions

As used herein the specification, "a" or "an" can mean one or more; "another" can mean at least a second or more.

The terms "activate(s)," "activating" or "activation" refer to a process by which a composition is operably converted from an inactive or inert form to a functional form. Activation of a disabled antibody derivative describes the conversion of a disabled form of an antibody derivative to an enabled form. Activation of a proactivator describes the conversion of a proactivator to an activator.

The terms "activator," "proactivator," "proactivator activator" or "proactivator proactivator" as used herein refer to a composition that (i) comprises at least one activator domain that is capable of directly or indirectly inducing the cleavage of a disabling moiety cleavable linker or a proactivator activation linker of a proactivator, thereby substantially activating a modified antibody derivative or proactivator; (ii) is operably linked to a target binding moiety; and (iii) differs from a natural protein at least in the composition and/or organization of its domains. Any of these compositions, for convenience, can be referred to as a (pro)activator. The additional moiety of a (pro)activator can be peptide or non-peptide in nature. A proactivator comprises at least one additional proactivator activation linker. Additional peptide components can be derived by natural production or by chemical synthesis, and in the case of a peptide component that acts as a proactivator activation linker or a target binding moiety, the additional peptide components need not be based on any natural template but can be selected for the desired purpose from an artificial scaffold or random sequence or by diversification of an existing template such that substantially all of the primary sequence similarity is lost but the functional attributes are preserved. Non-peptide additional components can include one or more functional chemical species. The chemical species can comprise a linker or a cleavage site, each optionally substituted with one or more linkers that can provide flexible attachment of the chemical species to a polypeptide or to another chemical species. A (pro)activator can comprise additional domains, for example that provide favorable therapeutic properties, such as enhanced half-life, diminished immunogenicity, or reduced non-specific interaction with cellular structures. Alternatively, such additional domains can be inert.

The term "activator domain" is meant to refer to a protein domain that substantially activates a disabled antibody derivative or proactivator. In some embodiments the activator domain provides an enzyme catalytic function. In some embodiments the proactivator is a zymogen of an enzyme or enzyme domain and the action of the activator domain on said proactivator is to convert the zymogen to an active enzyme or enzyme domain.

The term "administering" and "co-administering" as used herein refer to the application of two or more agents, simultaneously and/or sequentially to an organism in need of treatment. The sequential order, time interval, and relative quantity of the application can be varied to achieve an optimized selective cytotoxic or cytostatic effect. It can be preferable to use one agent in large excess, or to use two agents in similar quantities. One agent can be applied significantly before the addition of the second agent, or they can be applied in closer intervals or at the same time. In addition administering and co-administering can include injection or delivery from more than one site, for example by injection into two different anatomical locations or by delivery by more than one modality, such as by aerosol and intravenous injection, or by intravenous and intramuscular injection or by intravenous and subcutaneous injection.

The term "amino acid" as used herein refers to a naturally occurring or unnatural alpha or beta amino acid, wherein such natural or unnatural amino acids can be optionally substituted by one to four substituents, such as halo, for example F, Br, Cl or I or CF3, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, optionally substituted amino, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

The phrase "antibody effector region" or "effector region" refers to a region on an antibody that interacts with components of the immune system that engage or deliver the immune response of the organism, i.e., the effector functions of the immune system. In some embodiments, an antibody effector region can be, the CH2 domain of IgG or the CH3 domain of IgM, or portions thereof that interact with complement C1q, or the CH2 domain of IgG, or portions thereof that interact with Fc receptors. An antibody effector region need not be a naturally occurring sequence, but may have been modified or engineered to provide enhanced or selective engagement of immune system effector function (e.g., binding to one or both of C1q or Fc, either a natural or engineered C1q or Fc as are known in the art).

The phrase "antibody or antibody derivative with disabled effector function" refers to a protein derivative that possesses one or more domain with an antibody effector region operably linked to target binding moieties, wherein the effector domains are disabled or otherwise prevented from engaging the effector functions of the immune system.

The phrase "antibody constant region" is defined as the domains comprising CH1, the hinge region, CH2, CH3, and CL1 in the antibody structure for IgG, IgA, and IgD isotypes. The constant region for the IgM and IgE isotypes comprises domains CH1, CH2, CH3, CH4, and CL1.

The phrase "antibody Fc region" is defined as the domains comprising CH2 and CH3 in the antibody structure for IgG, IgA, and IgD isotypes. The Fc region for the IgM and IgE isotypes comprises domains CH2, CH3, and CH4 of the antibody structure.

The phrase "artificially diversified polypeptide binder" as used herein refers to a peptide or polypeptide comprising at least one domain that has been made to comprise multiple embodiments as a result of natural or synthetic mutation, including addition, deletion and substitution, so as to provide an ensemble of peptides or polypeptides from which a high affinity variant capable of binding to the desired cell surface target can be isolated. Such artificially diversified binders can comprise peptides, for example as selected by phage display, ribosome display, RNA display, yeast display, cell surface display or related methods, or polypeptides, similarly selected, and typically diversified in flexible loops of robust scaffolds so as to provide antibody variable region mimetics or related binding compositions. In some examples, the artificially diversified binder is a nanobody, affibody, adnectin, camelbody, lipocalin, or DARPin.

By the term "cancer cell" is meant a component of a cell population characterized by inappropriate accumulation in a tissue. This inappropriate accumulation can be the result of a genetic or epigenetic variation that occurs in one or more cells of the cell population. This genetic or epigenetic variation causes the cells of the cell population to grow faster, die slower, or differentiate slower than the surrounding, normal tissue. The term "cancer cell" as used herein also encompasses cells that support the growth or survival of a malignant cell. Such supporting cells can include fibroblasts, vascular or lymphatic endothelial cells, inflammatory cells or co-expanded non-neoplastic cells that favor the growth or survival of the malignant cell. The term "cancer cell" is meant to include cancers of hematopoietic, epithelial, endothelial, or solid tissue origin. The term "cancer cell" is also meant to include cancer stem cells.

The term "cell surface target" as used herein refers to any structure operably exposed on the surface of a cell, including transient exposure as for example can be the consequence of fusion of intracellular vesicles with the plasma membrane, and that can be specifically recognized by a target binding moiety. A cell surface target can include one or more optionally substituted polypeptide, carbohydrate, nucleic acid, sterol or lipid moieties, or combinations thereof, as well as modifications of polypeptides, carbohydrate, nucleic acid, sterol or lipid moieties separately or in combination. A cell surface target can comprise a combination of optionally substituted polypeptide and optionally substituted carbohydrate, an optionally substituted carbohydrate and optionally substituted lipid or other structures operably recognized by a target binding moiety. A cell surface target can comprise one or more such optionally substituted polypeptides, carbohydrates, nucleic acid, sterol or lipids in complexes, for example heteromultimeric proteins, glycan-substituted heteromultimeric proteins, or other complexes, such as the complex of a peptide with a major histocompatibility complex antigen. A cell surface target can exist in a form operably linked to the target cell through another binding intermediary. A cell surface target can be created by some intervention to modify particular cells with an optionally substituted small molecule, polypeptide, carbohydrate, nucleic acid, sterol or lipid. For example a cell surface target can be created by the administration of a species that binds to a cell of interest and thereby affords a binding surface for any of the disabled antibody derivatives, disabled antibody derivative activators, disabled antibody derivative proactivators or proactivator activators of the present compositions and methods.

The phrase "complement system" refers to a process in the innate immune system that can deposit proteins on a cell surface through an protease amplification cascade, resulting in targeted cell destruction through a membrane attack complex or phagocytosis by immune cells. Antibody binding on the cell surface can initiate the complement cascade through interactions of complement proteins with the antibody effector domain.

The phrase "complement proteins" or "proteins of the complement system" refers to proteins involved in the complement cascade which is comprised of C1q, C2, C3, C4, C5, C6, C7, C8, and C9.

The phrase "contacts a cell" as used herein shall mean physically binds to or comes into the vicinity of a cell. A composition that has contacted a cell shall have bound at least once to a cell or components in the vicinity of a cell to which it is targeted. Examples of contact that do not involve direct binding to a cell include binding to cell elaborated matrix components, or secreted structures, such as enzymes, glycosaminoglycans, lipids, particles, exosomes or other cellular fragments or structures. Contact with a cell can produce a change in the composition contacting the cell without requiring the composition to come into direct physical association with a cell. In addition, a composition that directly binds to a cell can dissociate and rebind multiple times, resulting in an equilibrium state in which only a fraction of its duration in the vicinity of the cell represents the bound state. A composition in such equilibrium falls within the definition of a composition that has contacted a cell.

The term "coronaviral protease" refers to any of a variety of proteases encoded by members of the animal virus family Coronaviridae and exhibiting high cleavage specificity. "coronaviral protease" encompasses the natural proteases as well as engineered variants generated by genetic mutation or chemical or enzymatic modification.

The phrase "destroying or inhibiting a target cell" or "destroy or inhibit a target cell" is used herein to refer to reducing the rate of cellular division (cytostasis) or causing cell death (cytotoxicity) of a particular cell type (e.g., a cell expressing the desired cell surface targets). Cytostasis can result when a cell is targeted by immune system effector function, for example the action of secreted cytokines, interferons, or other mediators which cause cellular inhibition by the action of the mediators to induce a disruption of or decrease in cellular activity, or can result when the cell is physically limited in its ability to access nutrients or mitogenic signals, for example as a consequence of granuloma formation. Cytotoxicity can result when soluble mediators induce apoptosis in the target cell, or when the target cell is affected by deposition of the complement membrane attack complex, by formation of perforin-mediated pores, by delivery of cytotoxic proteases or other granule contents, by activation of a respiratory burst, or when the cell is affected by other mechanisms of immune system effector function that cause the death of the target cell. Cytotoxicity can occur by any of a variety of mechanisms such as necrosis, apoptosis, necroptosis, or other specialized pathways; no distinction here is made between the different mechanisms.

By "the effector functions of the immune system" is meant the capacity of the immune system to respond to a pathogen, pathogen-infected cell or pathogen-mimetic signal that induces or mobilizes the resources of the immune system to attempt to kill or eliminate the pathogen, pathogen-infected cell or source of the pathogen-mimetic signal. The effector function of the immune system can be classified as cytotoxic and/or assistive. The assistive effector function comprises the secretion of cytokines, chemokines and other mediators that attract other immune system cells or promote their activation, replication or differentiation to increase the potency of the immune response. The cytotoxic effector function either directly or indirectly leads to the death or cytostasis of the pathogen, pathogen-infected cell, or source of the pathogen-mimetic signal. The cytotoxic effector function can involve a response of cells, in which case it is known as cellular effector function, or can involve only acellular reactions resulting from proteins present in bodily fluids such as plasma, cerebrospinal fluid, extracellular exudates or secretions, in which case it is known as humoral effector function. In some cases effector functions can have both cellular and humoral components, and both assistive and cytotoxic functions. For example in the course of complement activation, complement fragments such as C5a are formed, that act as assistive mediators to elicit immune cell migration and activation. Similarly, some assistive mediators such as inflammatory cytokines and interferons can have direct deleterious effects on cells, producing cytostasis or cytotoxicity.

An "effector region disabling moiety" is a moiety that substantially prevents the effector region of a disabled antibody derivative from engaging at least one effector function of the immune system. In the present compositions, the disabling moiety does not substantially reduce the ability of the target binding moiety to bind its target, i.e., does not increase the Kd of binding of the target binding moiety to its target by more than 10 fold.

The term "endogenous" refers to a composition that is natively operably present, and particularly refers to compositions that are natively operably present on, in, or in the vicinity of the target cell.

The phrase "endogenous activating factor" refers to an endogenous composition that is capable of acting on a disabling moiety cleavable linker to sever the linkage between the disabling moiety and the effector region. An example of an endogenous activating factor is a protease that is natively operably present on, in or in the vicinity of the target cell that cleaves the disabling moiety cleavable linker.

The term "enzyme" as used herein refers to a protein catalyst that mediates a specific chemical modification (e.g., the addition, removal, or substitution of a chemical component) of a substrate. The term enzyme is meant to include proteases, phosphatases, phosphodiesterases, nucleases, glycohydrolases, esterases, or other catalysts that can remove chemical modifications as described herein.

The term "exogenous" or "exogenously" as used herein refers to any composition that is provided in, on, or to the vicinity of a target in an action intended to induce one or more favorable consequences of the invention.

The term "Fc receptor family" refers to a group of cell surface proteins that recognize and specifically interact with the Ig Fc domains of circulating antibodies. These receptors possess extracellular domains that bind with varying affinities regions in the CH2 and CH3 domains for IgG, IgA, and IgD. Family members comprise receptors that can bind to the CH2, CH3, and CH4 domains for IgM and IgE isotypes. Fc receptors comprise proteins from the Fc-gamma, Fc-alpha, Fc-epsilon, FcRn receptor families.

The phrase "Fc gamma receptor" is defined as a set of cell surface proteins found on immune effector cells that can interact with regions of the CH2 domain of immunoglobulins inducing lysis, opsinization, and phagocytosis. Specifically, Fc-gamma receptors include CD16, CD32, and CD64 and mutant variations of said domains.

The phrase "fusion protein" refers to a composition that incorporates at least one polypeptide component and at least one additional moiety that can be one or more peptides or polypeptides or synthetic ligands and linkers that are required to constitute the modified antibody derivatives and activators or proactivators of the invention. The polypeptide component of the modified antibody derivative is expected to comprise at minimum a natural or engineered antibody effector region and the polypeptide component of the activator or proactivator is expected to comprise at minimum the enzyme domain that effects the direct or indirect cleavage of the disabling moiety cleavable linker.

The term "glycosylation" refers to covalent modifications of proteins with carbohydrates. Glycosylation can be achieved through N-glycosylation or 0-glycosylation. An introduction of consensus N-linked glycosylation sites can be preferred when the proteins are to be produced in a mammalian cell line or cell lines that create a glycosylation pattern that is innocuous to humans.

The term "granzyme B" (GrB) refers to a member of the granzyme family of serine proteases known to be involved in apoptosis. Specifically, GrB has been shown to cleave only a limited number of natural substrates, e.g., pro-caspase-3 and Bid. It has been shown that GrB is an enzyme with high substrate sequence specificity because of the requirement for interactions with an extended peptide sequence in the substrate for efficient catalysis. GrB is thought to have a consensus recognition sequence of IEPD (SEQ ID NO: 22). GrB is a single chain and single domain serine protease and is synthesized in a pro-form, which is activated by removal of an amino terminal two amino acid pro-peptide by dipeptidyl peptidase I (DPPI. In the present compositions and methods, the term GrB for example refers to the mature form, i.e., the form without the propeptide).

The term "granzyme M" (GrM) refers to another member of the granzyme family of serine proteases that is specifically found in granules of natural killer cells and is implicated in the induction of target cell death. It has been shown that GrM is an enzyme with high substrate sequence specificity because of the requirement for interactions with at least four amino acids in the peptide substrate for efficient catalysis, i.e., a preferred recognition sequence of KVPL (SEQ ID NO: 23).

The term "heterologous" as used herein refers to a composition or state that is not native or naturally found, for example, that can be achieved by replacing an existing natural composition or state with one that is derived from another source. Thus replacement of a naturally existing, for example, furin-sensitive, cleavage site with the cleavage site for another enzyme, constitutes the replacement of the native site with a heterologous site. Similarly the expression of a protein in an organism other than the organism in which that protein is naturally expressed constitutes a heterologous expression system and a heterologous protein.

An "immune system cell" is a cell or cell fragment, such as a platelet, that participates in the function of the immune system. Subsets of immune system cells that have specialized functions in the immune system, and/or that are thought to mediate the inappropriate immune responses that give rise to autoimmune diseases, are targeted by the disabled antibody derivatives of the present invention to improve immune function or restrain or prevent autoimmune activity.

The phrase "disabled antibody derivative" refers to a composition comprising at least one antibody effector region operably linked to at least one target binding moiety and at least one effector region disabling moiety that is associated with the remainder of the disabled antibody derivative by a disabling moiety cleavable linker and that is non-toxic to a target cell. A disabled antibody derivative can comprise additional moieties that provide for desirable pharmaceutical properties, for example to enhance half-life, tissue penetration or organ localization, or to facilitate manufacturing, storage or distribution, or to reduce immunogenicity or nonspecific interactions with targets. Alternatively, the additional moieties can be inert. Non-peptide additional moieties can include one or more functional chemical species. The chemical species can comprise a linker or a cleavage site, each optionally substituted with one or more linkers that can provide flexible attachment of the chemical species to a polypeptide or to another chemical species.

The phrase "disabling moiety cleavable linker" as used herein refers to a linker by which an effector region disabling moiety is operably joined to the remainder of the disabled antibody derivative. The disabling moiety cleavable linker contains at least one susceptible chemical bond that, upon cleavage, causes the effector region disabling moiety to lose its operable linkage to the remainder of the disabled antibody derivative. The disabling moiety cleavable linker susceptible chemical bond can be found in an amide, carbamate, ester, glycosyl, peptide, phosphoester, phosphodiester, phosphoramide, thioester, urea or other grouping for which a cleavage function can be provided. The disabling moiety cleavable linker can be a polypeptide or a synthetic chain that includes a polypeptide, or a synthetic linker that contains at least one chemical grouping providing a susceptible chemical bond.

The term "modified" as used herein refers to a composition that has been operably changed from one or more predominant forms found naturally to an altered form by any of a variety of methods, including genetic alteration or chemical substitution or degradation and comprising addition, subtraction, or alteration of biological components or substituents such as amino acid or nucleic acid residues, as well as the addition, subtraction or modification of protein post-translational modifications such as, without limitation, glycan, lipid, phosphate, sulfate, methyl, acetyl, ADP-ribosyl, ubiquitinyl, sumoyl, neddoyl, hydroxyl, carboxyl, amino, aminoacyl or formyl moieties. "Modified" also comprises alteration by chemical or enzymatic substitution or degradation to add, subtract, or alter chemical moieties to provide a form not found in the composition as it exists in its natural abundance comprising a proportion of greater than 10%, or greater than 1%, or greater than 0.1%. The term "modified" is not intended to refer to a composition that has been altered incidentally as a consequence of manufacturing, purification, storage, or expression in a novel host and for which such alteration does not operably change the character of the composition.

The term "natively activatable" as used herein refers to a composition or state that can be converted from an inactive form to an active form by the action of natural factors or environmental variables on, in, or in the vicinity of a target cell. In one embodiment "natively activatable" refers to disabled antibody derivatives or disabled antibody derivative activators that, either as a consequence of modification on a disabling moiety cleavable linker or proactivator activation linker, or not, have the property of being converted from an inactive form to an active form as a result of natural factors on, in, or in the vicinity of a target cell. In one embodiment, the natively activatable protein possesses a cleavage site for a ubiquitously distributed protease such as a furin/kexin protease. In another embodiment, the natively activatable protein possesses a cleavage site for a target cell-specific protease, such as a tumor-enriched protease. In yet another embodiment, the natively activatable protein can be activated by low pH in, on, or in the vicinity of, a target cell. In another embodiment, the natively activatable protein possesses a post-translational modification that is removable by an enzyme found in, on, or in the vicinity of a target cell. In another embodiment the natively activatable protein possesses a disabling moiety cleavable linker or proactivator activation linker that can be modified by an enzyme found in, on, or in the vicinity of a target cell. Examples of such non-protease enzymes include esterases, glycolhydrolases, phosphatases, phosphodiesterases and nucleases.

The phrase "natively operably present" means that the composition is operably present on, in or in the vicinity of a target cell or tissue prior to the application of the compositions of the invention. A composition can be natively operably present on a target cell that has been rendered distinct from the normal cells or tissues of an organism by the action of disease. For example a neoplastic cell that expresses a protease that is active or can be readily activated without recourse to the compositions of the invention is considered to exhibit the protease in a natively operably present form, even though that protease can only be found on neoplastic and not normal cells of that lineage.

The phrase "nontoxic to a target cell" is used herein to refer to compositions that, when contacted with a target cell (i.e., the target cell to which the target binding moiety of the disabled antibody derivative activator is directed) under the conditions of use described in the present compositions and methods, do not significantly destroy or inhibit the growth of a target cell, that is do not reduce the proportion of viable cells in a target population, or the proportion of dividing cells in a target population, or the total proportion of cells in a target population by more than 50%, or 10%, or 1% or 0.1% under the preferred conditions of use. This phrase does not include fusion proteins that, when administered to a subject or contacted with a target cell, become activated by an endogenous factor, rendering them toxic to a target cell. By "target population" is meant cells that express targets for the target binding moieties of the present compositions and methods.

The terms "operably linked" or "operable linkage" encompass the joining of two or more peptide components covalently or noncovalently or both covalently and noncovalently as well as the joining of one or more peptide components with one or more chemical species covalently or noncovalently or both covalently and noncovalently, as well as the joining of two or more chemical species covalently. Among suitable forms of covalent linkage for peptide components are direct translational fusion, in which a single polypeptide is formed upon translation of mRNA, or post-translational fusion, achieved by operable linkage through chemical or enzymatic means or by operable linkage through natural intermolecular reactions such as the formation of disulfide bonds. Operable linkage can be performed through chemical or enzymatic activation of various portions of a donor molecule to result in the attachment of the activated donor molecule to a recipient molecule. Following operable linkage two moieties can have additional linker species between them, or no additional species, or can have undergone covalent joining that results in the loss of atoms from one or more moieties, for example as can occur following enzymatically induced operable linkage.

The phrase "operably present" means that the composition is present in sufficient quantity or concentration to have a desired effect on the compositions on which it is intended to act. Examples of an activating moiety that can be present but not operably present include, for example, intracellular proteases, phosphatases or hydrolases, which are not operably present because they are in a different compartment than a therapeutically supplied protease, phosphatase or hydrolase (which when therapeutically supplied is either present on the surface of the cell or in a vesicular compartment topologically equivalent to the exterior of the cell) and cannot act on the disabled antibody derivative in a way that would cause its activation. A protein can also be present but not operably present if it is found in such low quantities as not to significantly affect the rate of activation of the disabled antibody derivative or disabled antibody derivative proactivator, for example to provide a form not operably found in, on, or in the vicinity of, a targeted cell in a proportion of greater than 10%, or greater than 1%, or greater than 0.1% of the proportion that can be achieved by exogenous supply of a minimum therapeutically effective dose. As a further non-limiting example, replacement of a furin-sensitive site in a therapeutic protein with a site for a protease naturally found operably present on, in, or in the vicinity of a targeted host cell constitutes a heterologous replacement that can be acted on by an endogenous protease. Replacement of a furin-sensitive site in a therapeutic protein with a site for a protease not naturally found operably present in the vicinity of a targeted host cell constitutes a heterologous replacement that can be acted on by an exogenous protease.

The phrase "PCSK family member" refers to any member of the proprotein convertase subtilisin kexin family of serine proteases that express demonstrable proteolytic activity, for example human PCSKn where n takes the values from 1 to 7.

The term "PEG" refers to an optionally substituted polyethylene glycol moiety that can exist in various sizes and geometries, such as linear, branched or dendrimer and can refer to block copolymers or modified polymers with additional functionality, such as can be useful for the therapeutic action of a modified antibody derivative, an activator or a proactivator. The number of optionally substituted or unsubstituted ethylene glycol moieties in a PEG moiety is at least two.

The term "PEGylated" refers to a composition that has undergone reversible or irreversible attachment of a PEG moiety.

The term "PEGylation" refers to covalent or noncovalent modifications of proteins with polyethylene glycol polymers of various sizes and geometries, such as linear, branched and dendrimer and can refer to block copolymers incorporating polyethylene glycol polymers or modified polymers with additional functionality, such as can be useful for the therapeutic action of a modified antibody derivative. For example a polyethylene glycol moiety can join a modifiable activation sequence to an optional inhibitor sequence or can join one or more target binding moieties to a modified antibody derivative. Many strategies for PEGylating proteins in a manner that is consistent with retention of activity of the conjugated protein have been described in the art. These include conjugation to a free thiol such as a cysteine by alkylation or Michael addition, attachment to the N-terminus by acylation or reductive alkylation, attachment to the side chain amino groups of lysine residues, attachment to glutamine residues using transglutaminase, attachment to the N-terminus by native ligation or Staudinger ligation, or attachment to endogenous glycans, such as N-linked glycans or O-linked glycans. Numerous glycan addition strategies are known; including hydrazone formation with aldehydes generated by periodate oxidation, Staudinger ligation with glycan azides incorporated by metabolic labeling, and glycan substitution technology. Examples of noncovalent modification include the reaction of a high affinity ligand-substituted PEG with a protein domain binding such ligand, as for example the reaction of a biotin-substituted PEG moiety with a streptavidin or avidin fusion protein.

The term "polypeptide" or "peptide" as used herein refers to two or more amino acids linked by an amide bond between the carboxyl terminus of one amino acid and the amino terminus of another.

The prefix "(pro)" indicates that the word that immediately follows can be interpreted either as the word itself or the word prefixed with "pro." For example (pro)activator shall be understood to mean "activator or proactivator".

The phrase "proactivator activation linker" refers to a moiety operably linking a target recognition moiety to an activator or proactivator, wherein the linker must undergo cleavage or modification to convert the proactivator to an activator, that is, to enable the activity of the activator domain to be expressed. In some embodiments the proactivator activation linker is a substrate for an enzyme. In some embodiments the proactivator activation linker comprises a modified substrate for an enzyme. In some embodiments the enzyme is an endogenous protease, either a cell-lineage specific endogenous protease or a ubiquitous protease. In some embodiments the enzyme is an exogenous protease, in which case it can be either an activator or a proactivator.

The term "protease" as used herein refers to compositions that possess proteolytic activity, and preferably those that can recognize and cleave certain peptide sequences specifically. In one particular embodiment, the specific recognition site is equal to or longer than that of the native furin cleavage sequence of four amino acids, thus providing activation stringency comparable to, or greater than, that exemplified by native substrates. A protease can be a native, engineered, or synthetic composition having the desired proteolytic activity. Proteolytic specificity can be enhanced by genetic mutation, in vitro modification, or addition or subtraction of binding moieties that control activity.

The term "picornaviral protease" refers to any of a variety of proteases encoded by members of the animal virus family Picornaviridae and exhibiting high cleavage specificity. "picornaviral protease" encompasses the natural proteases as well as engineered variants generated by genetic mutation or chemical or enzymatic modification. The term "human Rhinovirus 3C consensus protease" refers to a synthetic picornaviral protease that is created by choice of a consensus sequence derived from multiple examples of specific rhinoviral proteases.

The term "potyviral protease" refers to any of a variety of proteases encoded by members of the plant virus family Potyviridae and exhibiting high cleavage specificity. "Potyviral protease" encompasses the natural proteases as well as engineered variants generated by genetic mutation or chemical modification. The term "tobacco etch virus protease" or "TEV protease" refers to natural or engineered variants of a 27 kDa cysteine protease exhibiting stringent sequence specificity. It is widely used in biotechnology for removal of affinity tags of recombinant proteins. TEV protease recognizes a seven amino acid recognition sequence EXXYXQ↓S/G (SEQ ID NO: 24), where X is any residue.

The term "retroviral protease" refers to any of a variety of proteases encoded by members of the virus family Retroviridae. "HIV protease" encompasses the natural proteases as well as engineered variants generated by genetic mutation or chemical or enzymatic modification.

The phrase "selective killing" is used herein to refer to the killing, destroying, or inhibiting of more cells of one particular population than another, e.g., by a margin of 99:1 or above, 95:5 or above, 90:10 or above, 85:15 or above, 80:20 or above, 75:25 or above, 70:30 or above, 65:35 or above, or 60:40 or above.

The term "sortase" refers to a protein from gram-positive bacteria that can recognize a conserved carboxylic sorting motif and catalyze a transpeptidation reaction to anchor surface proteins to the cell wall envelope (Dramsi et al., Res. Microbiol. 156(3):289-297 (2005)). A preferred embodiment comprises the use of *Staphylococcus aureus* sortase A or B to catalyze a transpeptidation reaction between a first moiety that is tagged with LPXTG (SEQ ID NO: 25) or NPQTN (SEQ ID NO: 26) at or near C-terminus, respectively for sortase A and sortase B, and a second moiety containing the dipeptide GG or GK at the N-terminus, or a primary amine group.

The phrase "substantially activates" as used herein means to increase the referenced action or activity that would otherwise occur by 50%, or by 100%, or more.

By "substantially identical" is meant a nucleic acid or amino acid sequence that, when optimally aligned, for example using the methods described below, share at least 60%, 65%, 70%, 75%, 80%, 85%, 90%, 95%, 96%, 97%, 98%, 99%, or 100% sequence identity with a second nucleic acid or amino acid sequence, e.g., a SAA sequence. "Substantial identity" can be used to refer to various types and lengths of sequence, such as full-length sequence, epitopes or immunogenic peptides, functional domains, coding and/or regulatory sequences, exons, introns, promoters, and genomic sequences. Percent identity between two polypeptides or nucleic acid sequences is determined in various ways that are within the skill in the art, for instance, using publicly available computer software such as Smith Waterman Alignment (Smith, T. F. and M. S. Waterman (1981) J Mol Biol 147:195-7); "BestFit" (Smith and Waterman, Advances in Applied Mathematics, 482-489 (1981)) as incorporated into GeneMatcher Plus, Schwarz and Dayhof (1979) Atlas of Protein Sequence and Structure, Dayhof, M. O., Ed, pp 353-358; BLAST program (Basic Local Alignment Search Tool; (Altschul, S. F., W. Gish, et al. (1990) J Mol Biol 215: 403-10), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins or nucleic acids, the length of comparison can be any length, up to and including full length (e.g., 5%, 10%, 20%, 30%, 40%, 50%, 60%, 70%, 80%, 90%, 95%, or 100%). For purposes of the present compositions and methods, at least 80% of the full length of the sequence is aligned using the BLAST algorithm and the default parameters.

Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

The phrase "substantially prevent" or "substantially prevents" as used herein means to decrease the referenced action or activity that would otherwise occur by 50%, or by 90%, or by 99%, or by 99.9% or more.

The term "substrate" as used herein refers to the specific composition, or portion of a composition, that is recognized and chemically modified by an enzyme.

The phrase "target binding moiety" as used herein refers to one or more moieties that can bind to one or more cell surface targets, and thus can direct disabled antibody derivatives, disabled antibody derivative (pro)activators, or proactivator (pro)activators to those cells. Target binding moieties can include, among others, the natural variable regions of antibodies or antibody fragments, single antibody domains and related compositions, such as scFv or diabodies, as well as artificially diversified polypeptide binders, which as defined above can include engineered nanobody, affibody, adnectin, camelbody, lipocalin, DARPin and related structures. Also included are soluble mediators, cytokines, growth factors, soluble receptor fragments, matrix fragments, or other structures that are known to have cognate binding structures on the targeted cell. Target binding moieties can also include combinations of moieties (e.g., an scFv with a cytokine and an scFv with a second scFv). Alternatively the target binding moiety can be a carbohydrate, a lipid or a synthetic molecule that acts as a binding agent, for example as an agonist or an antagonist of a receptor or ectoenzyme. Target binding moieties can also include combinations of moieties (e.g., an scFv with a cytokine and an scFv with a second scFv).

The phrase "targeted cell" or "target cell" is used herein to refer to any cell that expresses at least two cell surface targets, which are the intended targets of one or more disabled antibody derivatives or disabled antibody derivative (pro)activators or disabled antibody derivative proactivator (pro)activators.

The term "transglutaminase" refers to a protein that catalyzes the formation of a covalent bond between a free amine group (e.g., protein- or peptide-bound lysine, or substituted aminoalkane such as a substituted cadaverine) and the gamma-carboxamide group of protein- or peptide bound glutamine. Examples of this family of proteins are transglutaminases of many different origins, including thrombin, factor XIII, and tissue transglutaminase from human and animals. A preferred embodiment comprises the use of a microbial transglutaminase (Yokoyama et al., Appl. Microbiol. Biotechnol. 64(4):447-454 (2004)) to catalyze an acyl transfer reaction between a first moiety containing a glutamine residue (acyl donor), located within a preferred sequence such as LLQG (SEQ ID NO: 27), and a second moiety containing a primary amine group (acyl acceptor). It is preferable that the reactive glutamine residue is solvent exposed and located in an unstructured, i.e. flexible, segment of the polypeptide.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

SEQUENCE LISTING

The instant application contains a Sequence Listing which has been submitted electronically in ASCII format and is hereby incorporated by reference in its entirety. Said ASCII copy, created on Jul. 20, 2016, is named 29539-0130WO1_SL.txt and is 202,373 bytes in size.

| SEQ ID NO: | Description |
|---|---|
| 1 | DNA: Rituximab Antibody heavy chain |
| 2 | Protein: Rituximab Antibody heavy chain |
| 3 | DNA: Rituximab Antibody light chain |
| 4 | Protein: Rituximab Antibody light chain |
| 5 | DNA: HC-CD16 |
| 6 | Protein: HC-CD16 |
| 7 | DNA: HC-CD32 |
| 8 | Protein: HC-CD32 |
| 9 | DNA: HC-CD64 |
| 10 | Protein: HC-CD64 |
| 11 | DNA: LC-CD16 |
| 12 | Protein: LC-CD16 |
| 13 | DNA: LC-CD32 |
| 14 | Protein: LC-CD32 |
| 15 | DNA: LC-CD64 |
| 16 | Protein: LC-CD64 |
| 17 | DNA: Pro-granzyme B (version 3) |
| 18 | Protein: Pro-granzyme B (version 3) |
| 19 | DNA: anti-CD5 (A2D5) |
| 20 | Protein: anti-CD5 (A2D5 scFv) |
| 21 | Protein: conjugated Pro-granzyme B (version 3) - anti-CD5 (A2D5 scFv) |
| 22 | consensus recognition sequence IEPD |
| 23 | recognition sequence KVPL |
| 24 | seven amino acid recognition sequence EXXYXQ↓S/G |
| 25 | LPXTG tag for sortase A |
| 26 | NPQTN tag for sortase B |
| 27 | LLQG |
| 28 | tag sequence LPETG |
| 29 | furin site having the sequence RVRRAS |
| 30 | IEPF cleavage site |
| 31 | IIPF cleavage site |
| 32 | DNA: Linker 2 |
| 33 | DNA: Rituximab LC-L2-CD32, LC-CD32 Linker 2 |
| 34 | Protein: Rituximab LC-L2-CD32, LC-CD32 Linker 2 |
| 35 | DNA: Herceptin LC-L2-CD32, |
| 36 | Protein: Herceptin LC-L2-CD32, |
| 37 | DNA: Herceptin HC, |
| 38 | Protein: Herceptin HC, |
| 39 | DNA: Herceptin LC-wt, |
| 40 | Protein: Herceptin LC-wt, |
| 41 | DNA: Granzyme BV3-CCPE, |
| 42 | Protein: Granzyme BV3-CCPE, |
| 43 | DNA: anti-CD20 scFv—CH1—CH2—CH3 |
| 44 | Protein: anti-CD20 scFv—CH1—CH2—CH3 |
| 45 | DNA: anti-CD19—CH1—CH2—CH3 (HD37) |
| 46 | Protein: anti-CD19—CH1—CH2—CH3 (HD37) |
| 47 | DNA: CLk-CD32 |
| 48 | Protein: CLk-CD32 |
| 49 | DNA: anti-CD20-Fc-CD32 |
| 50 | Protein: anti-CD20-Fc-CD32 |
| 51 | DNA: anti-CD19-Fc-CD32 |
| 52 | Protein: anti-CD19-Fc-CD32 |
| 53 | DNA: CCPE-Fc-CD32 |
| 54 | Protein: CCPE-Fc-CD32 |
| 55 | DNA: CD2(ECD)-Fc-CD32 |
| 56 | Protein: CD2(ECD)-Fc-CD32 |
| 57 | DNA: H10-2-G3-Fc-CD32 |
| 58 | Protein: H10-2-G3-Fc-CD32 |
| 59 | DNA: Granzyme BV3-H10-2-G3 |
| 60 | Protein: Granzyme BV3-H10-2-G3 |
| 61 | DNA: Rituximab LC-SSL10 |
| 62 | Protein: Rituximab LC-SSL10 |
| 63 | DNA: Rituximab LC-HSVgE |
| 64 | Protein: Rituximab LC-HSVgE |
| 65 | DNA: Rituximab LC-I_02 |
| 66 | Protein: Rituximab LC-I_02 |
| 67 | DNA: Rituximab LC-I_07 |
| 68 | Protein: Rituximab LC-I_07 |
| 69 | DNA: Rituximab LC-I_11 |
| 70 | Protein: Rituximab LC-I_11 |
| 71 | DDDDK enterokinase site |

Figure 10A:
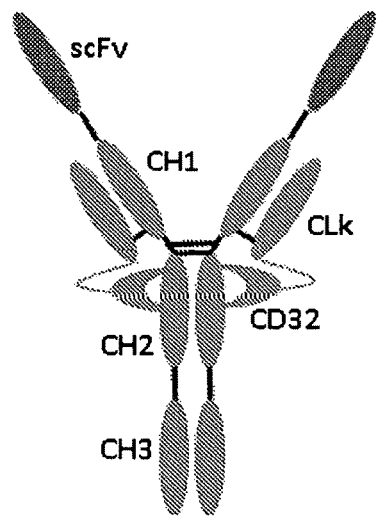
Figure 10B:
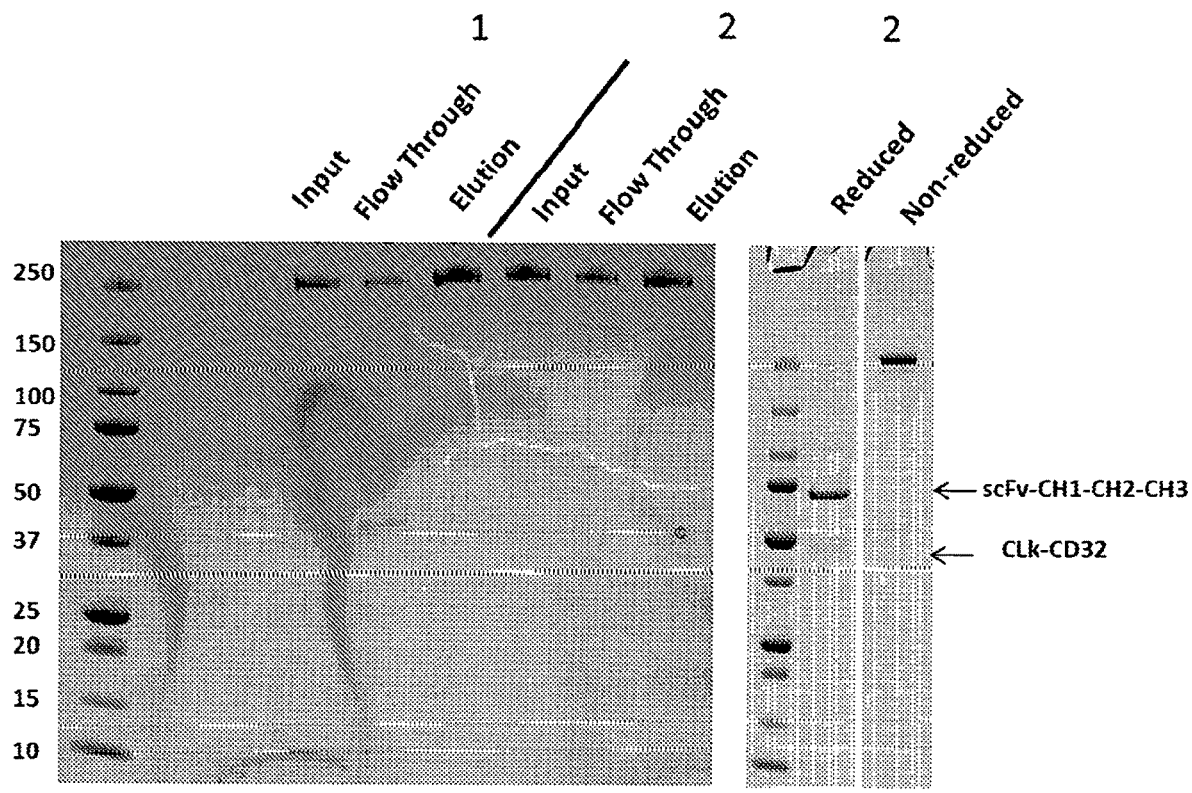

FIGS. 10A-B. Exemplary structures of an alternative disabled antibody derivative. (A) The variable domain from both the heavy chain and light chain-CD32 fusion were deleted and a scFv domain was fused to the N-terminus of the heavy chain CH1 domain. The modified heavy chain (scFv-CH1-hinge-CH2-CH3) and truncated light chain-CD32 fusion (CLk-CD32) were co-expressed in a mammalian expression system and purified using Ni-NTA agarose. (B) The Ni-NTA purified protein was further purified using the strep-tag II epitope on the C-terminus of the light chain on Streptactin agarose. The purified protein was analyzed using SDS-PAGE under reducing and non-reducing conditions. The bands corresponding to the two chains of the antibody derivative are identified on the right.

Figure 11A:
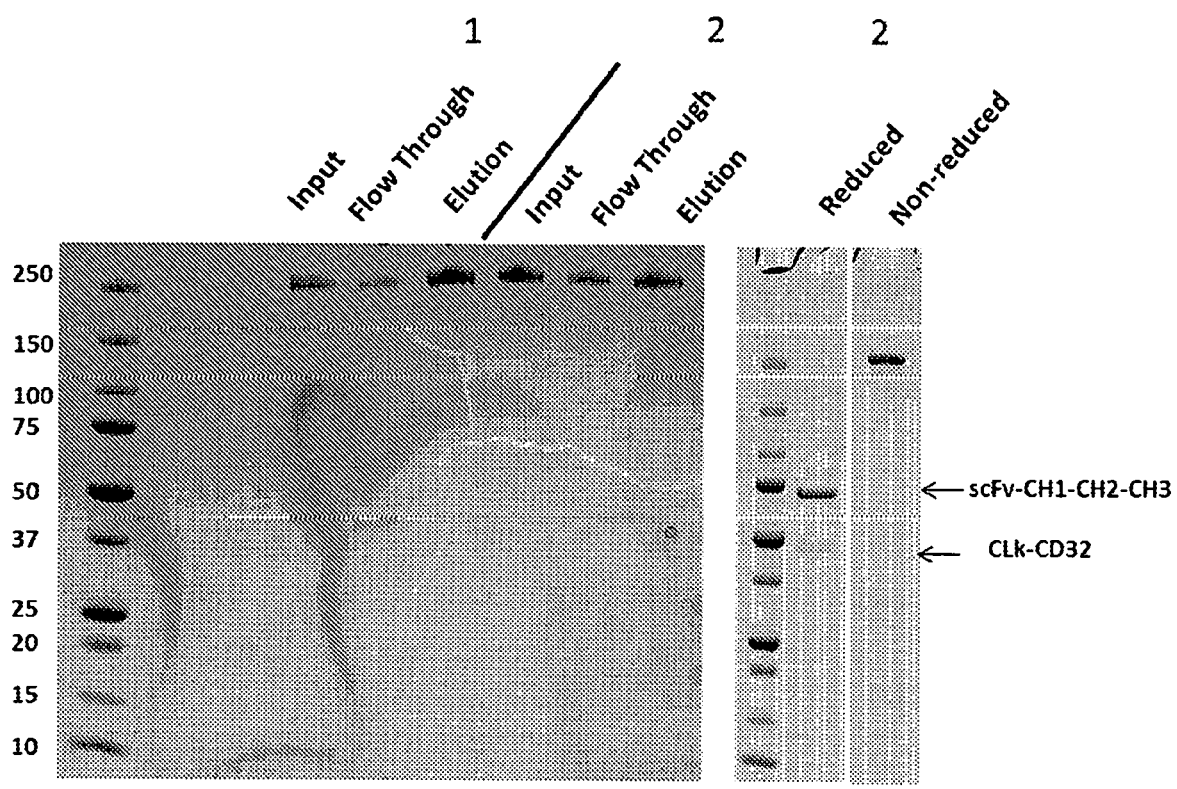
Figure 11B:
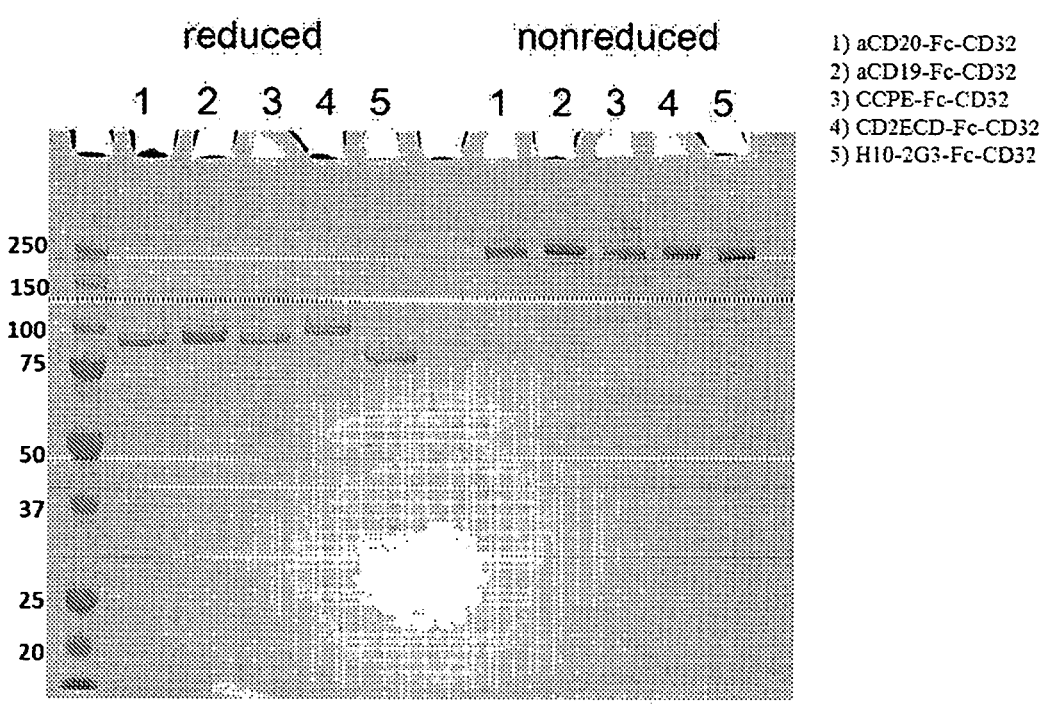

FIGS. 11A-B. Exemplary structures of an alternative disabled antibody derivative in which variations of the binding moiety are fused to Fc-CD32 fusion. (A) A diversity of different binding moieties was fused to the N-terminus of the Fc domain of IgG1 heavy chain (CH2 and CH3 domains). The disabling moiety, CD32 domain, was fused to the C-terminus of the CH3 domain via a long linker. (B) These proteins were transfected as a single construct into a mammalian expression system and purified using Ni-NTA agarose. The protein was analyzed using SDS-PAGE under reducing and non-reducing conditions. The mature protein exists as a dimer based on the disulfide bridges in the hinge region of the antibody derivative.

Figure 12A:
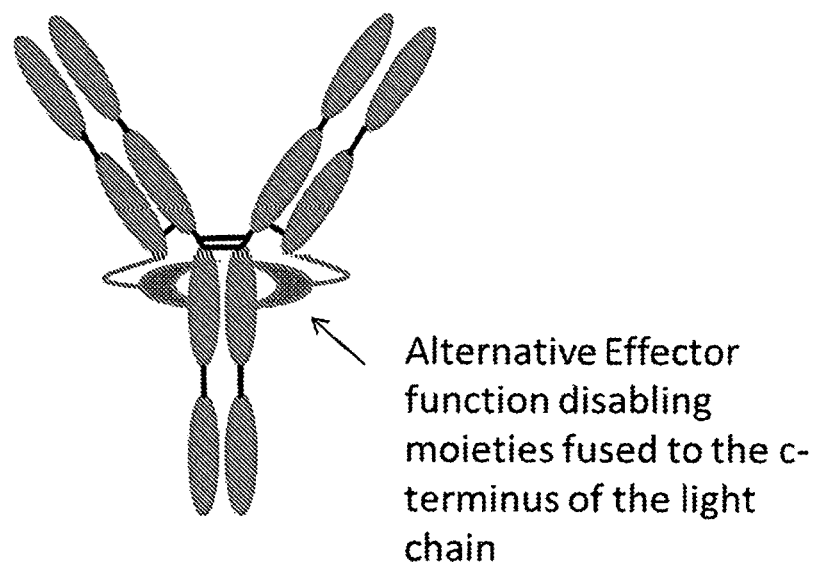
Figure 12B:
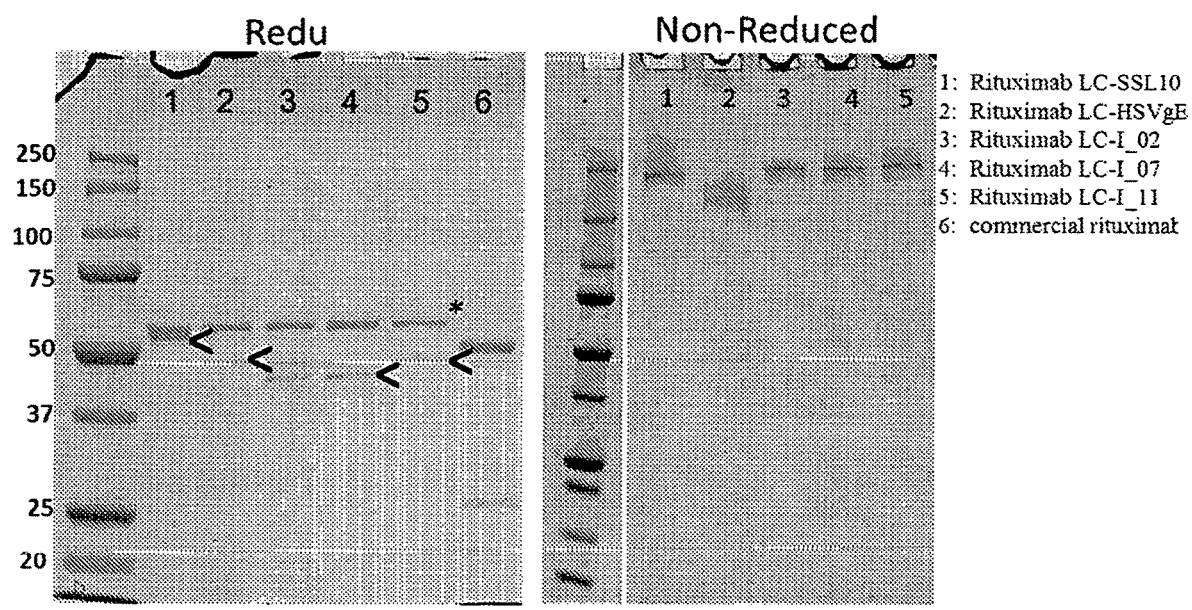
Figure 13A:
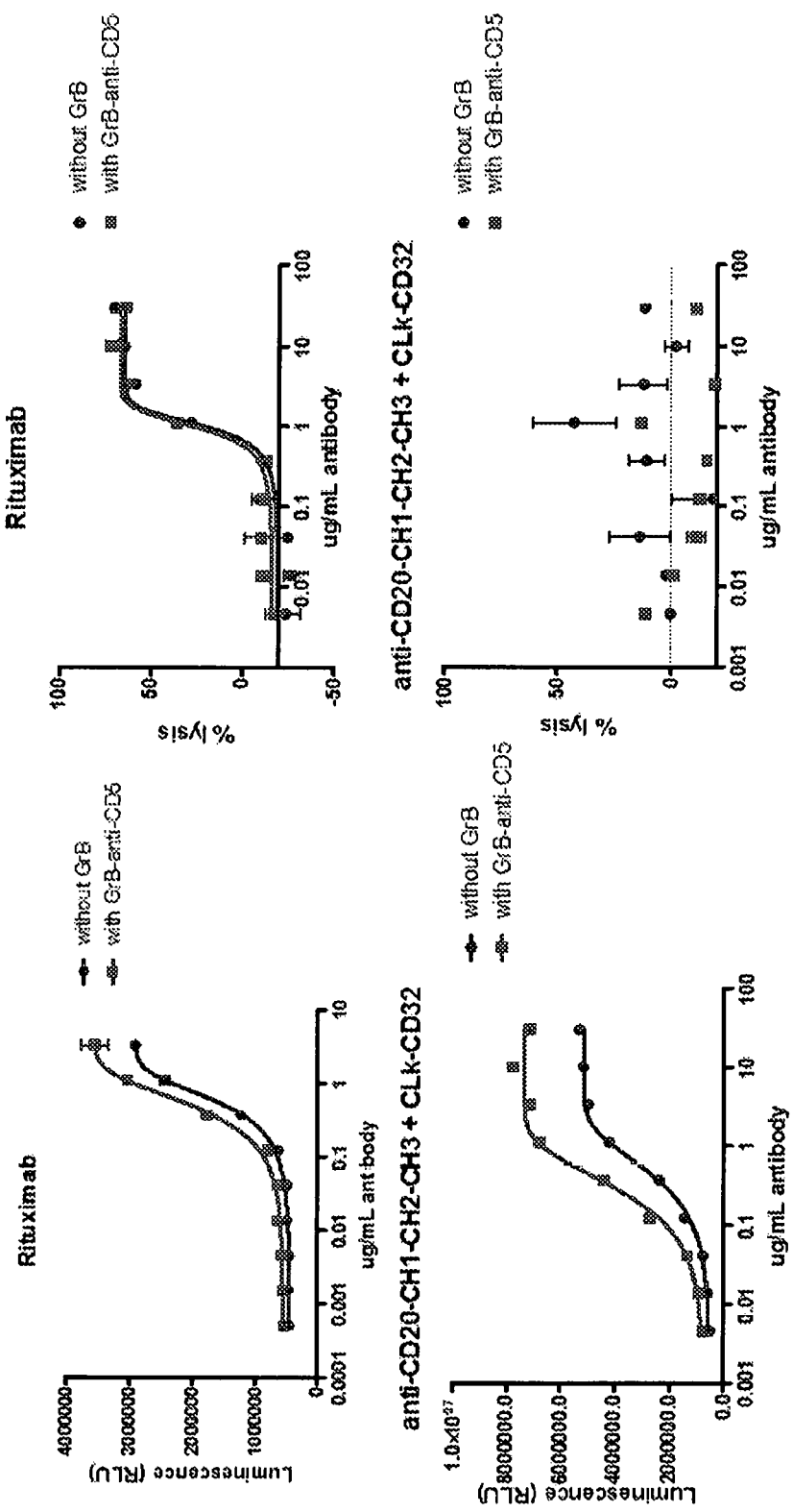
Figure 13B:
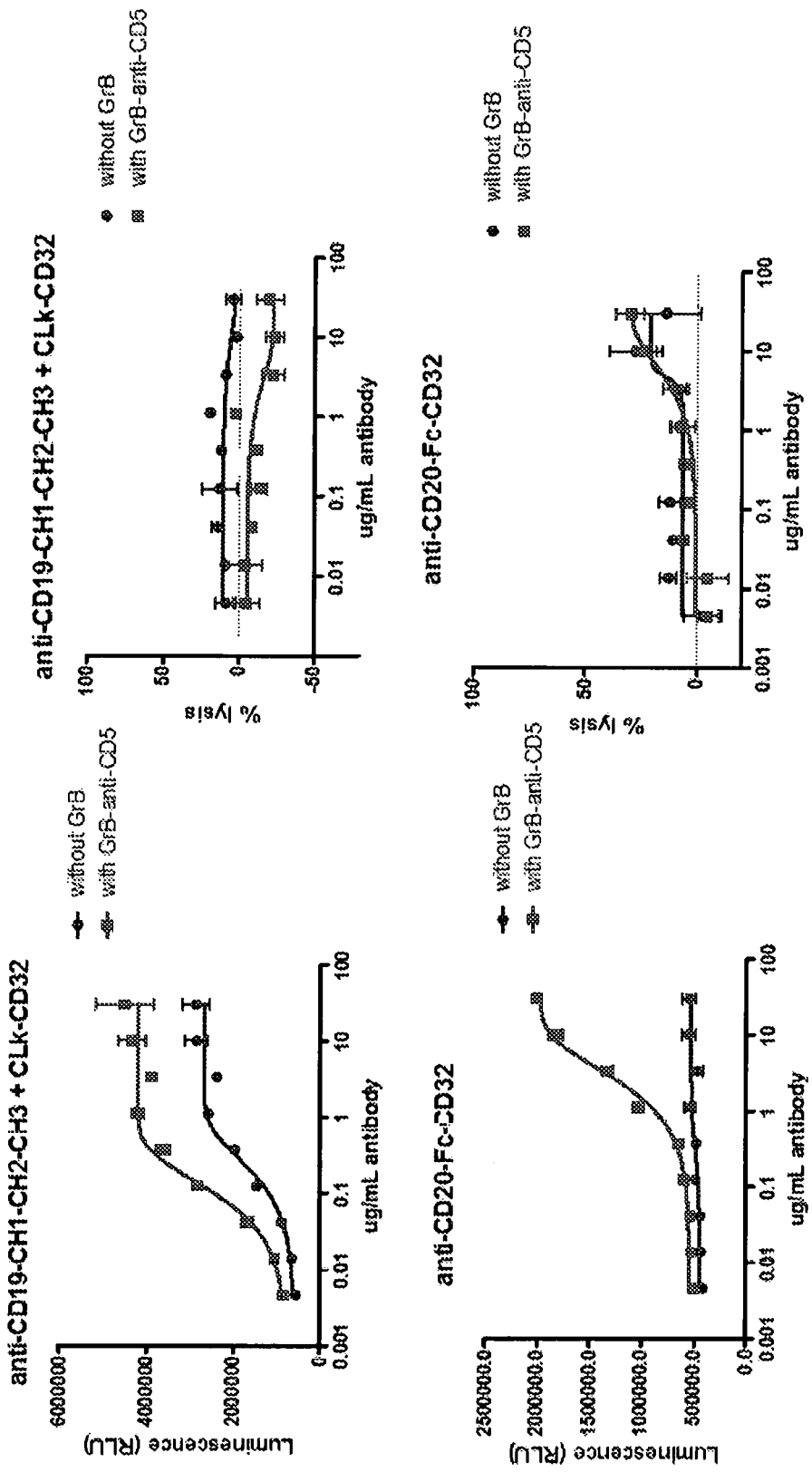
Figure 13C:
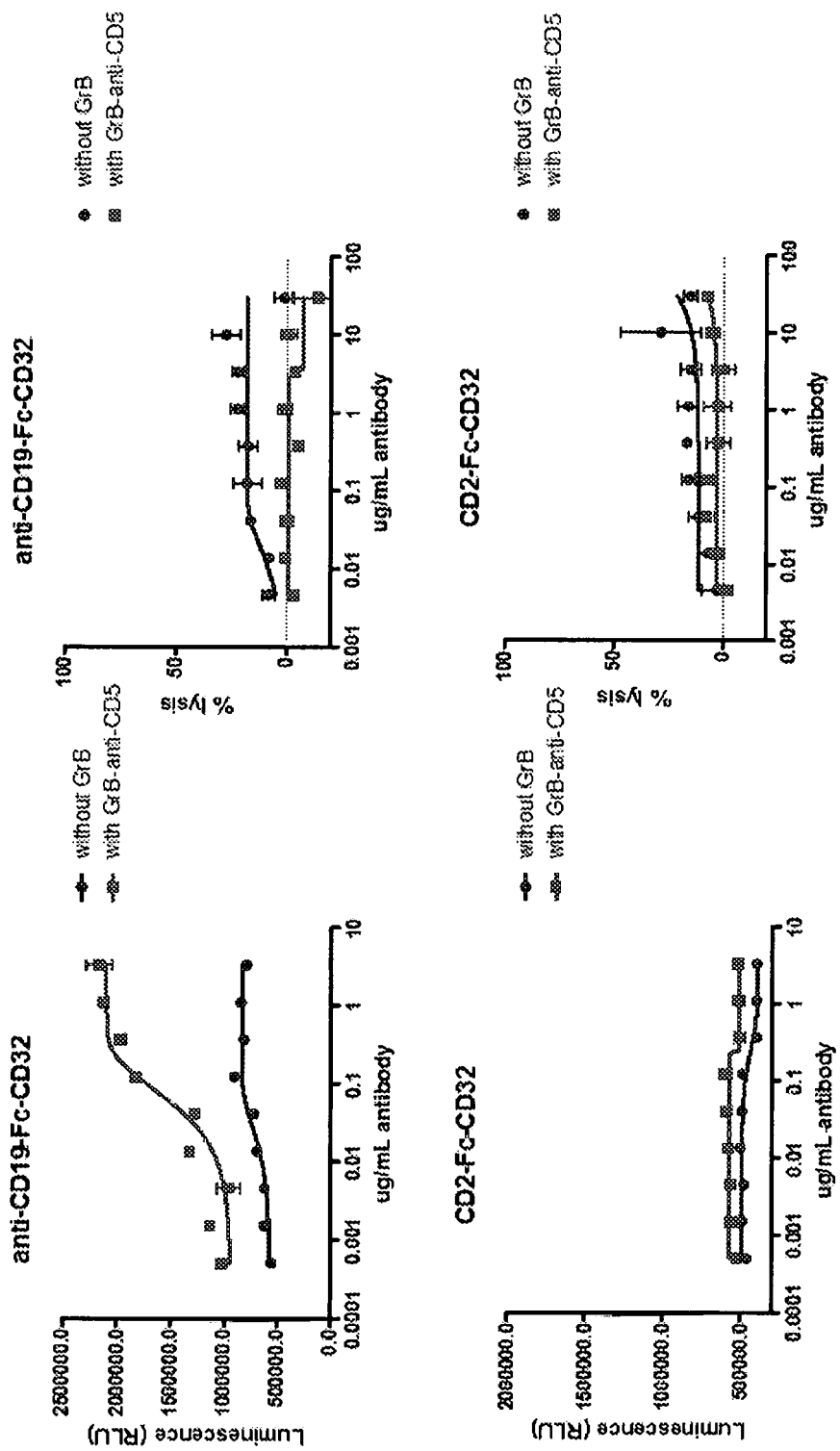
Figure 13D:
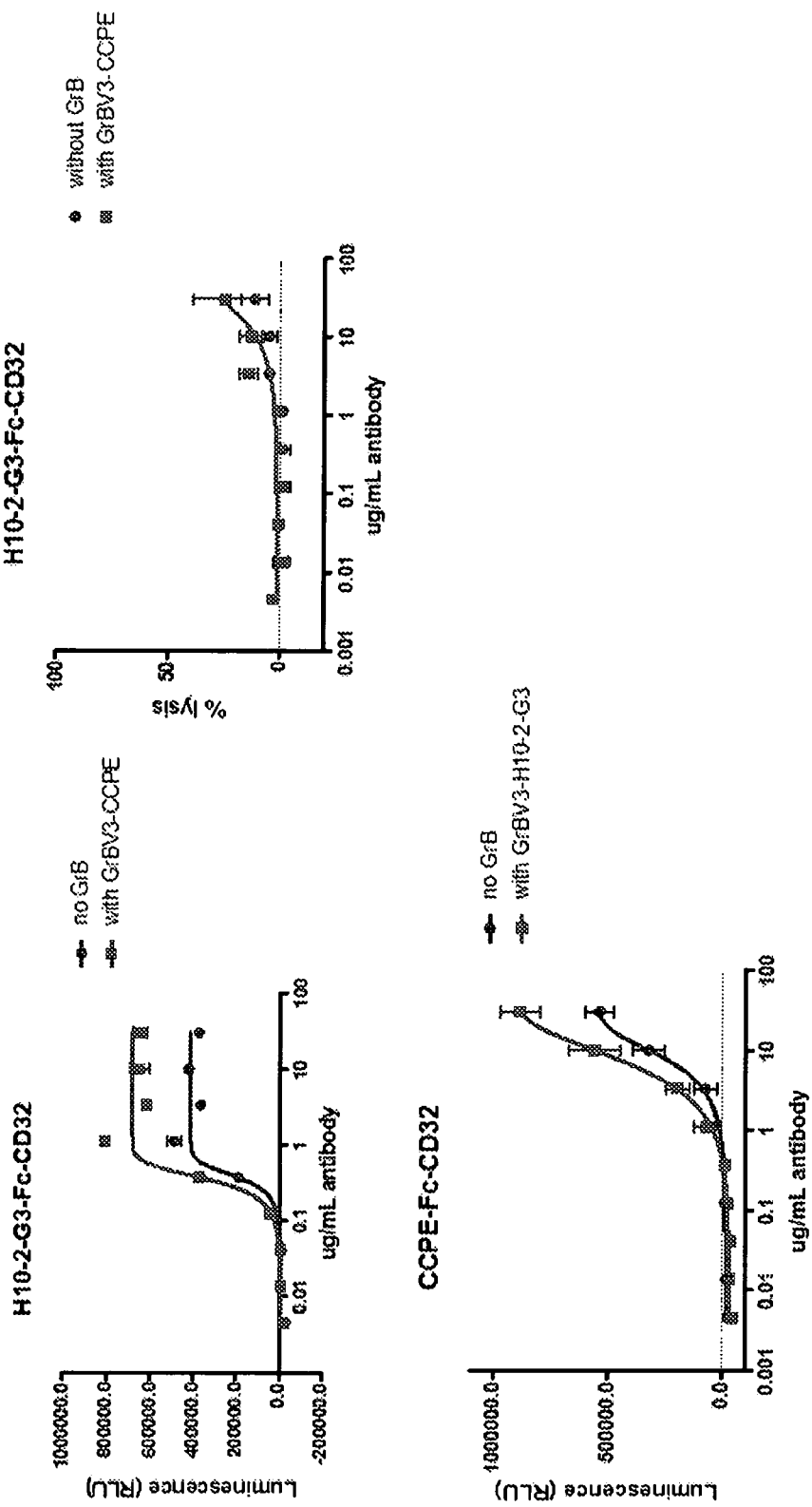
Figure 13E:
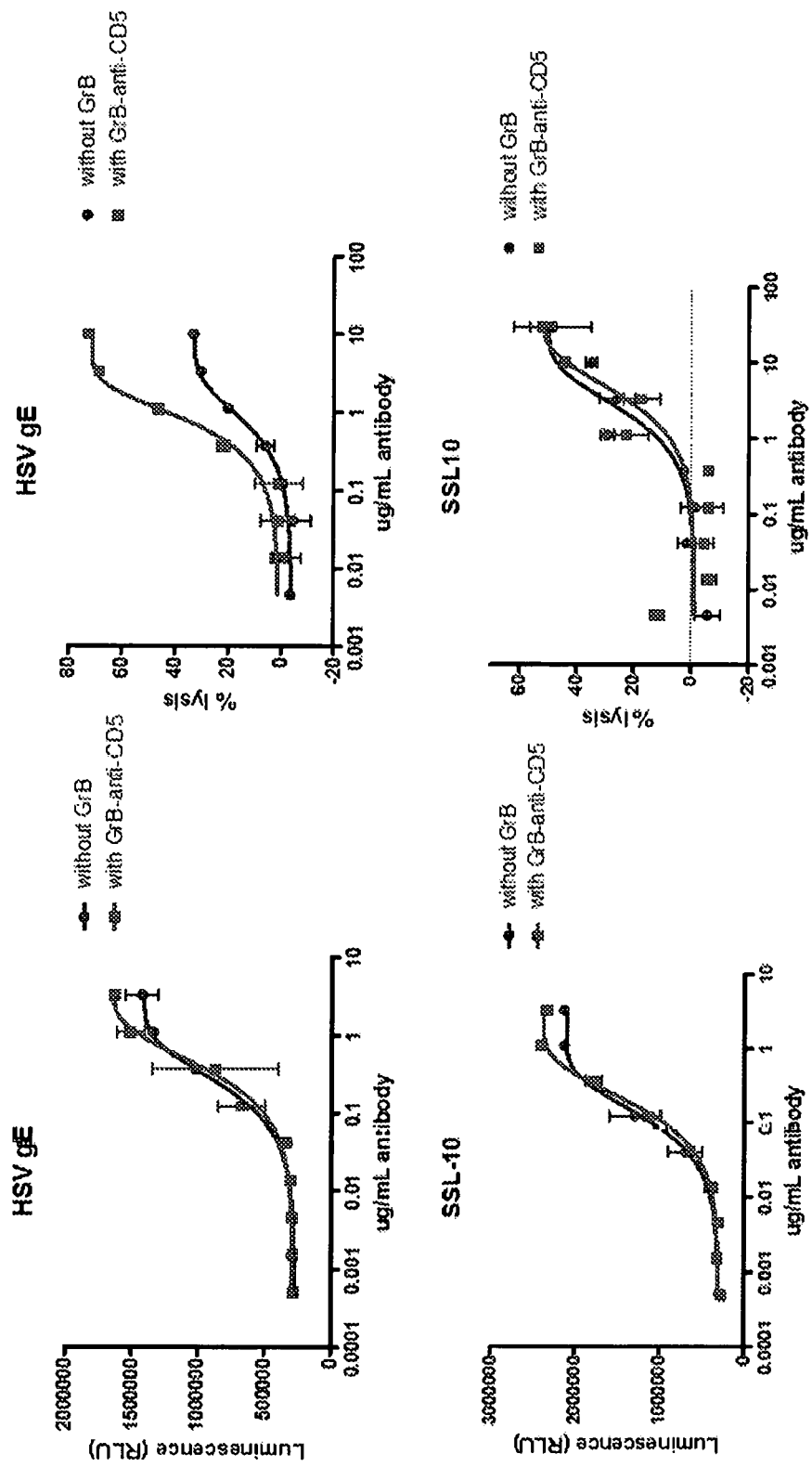
Figure 13F:
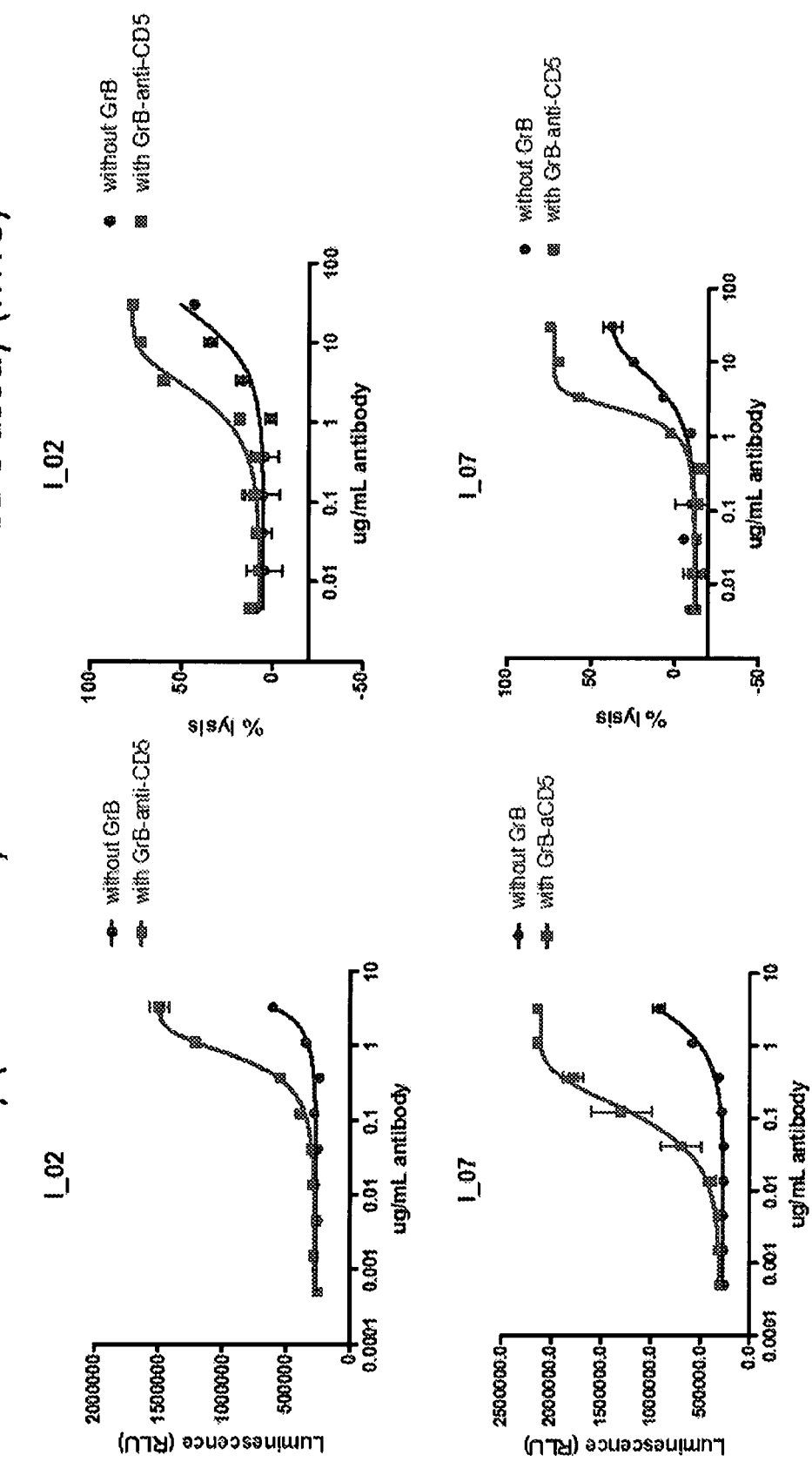
Figure 13G:
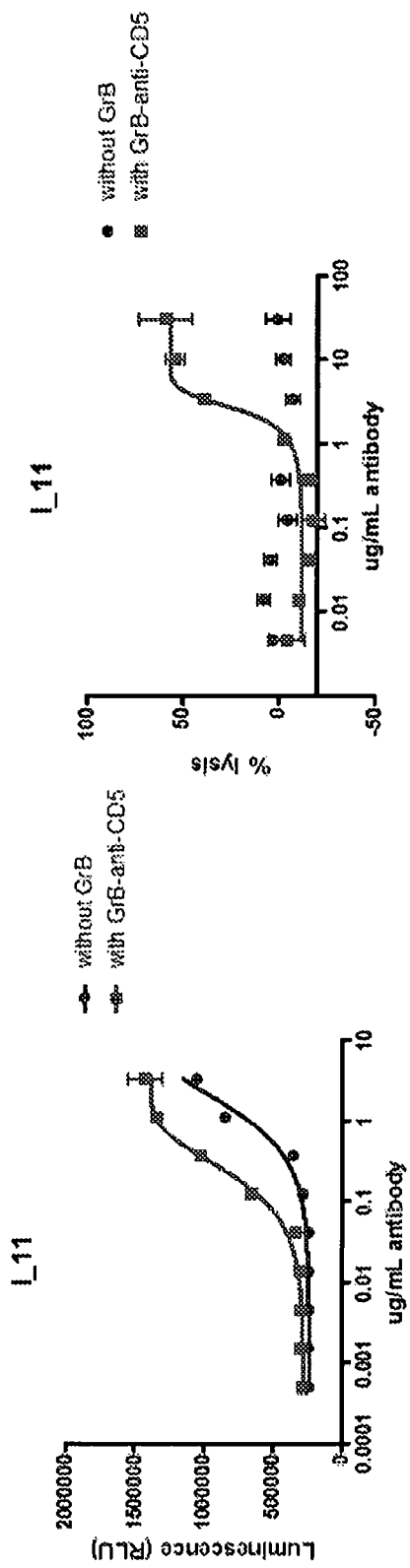

FIGS. 12A-B. Exemplary structures of an alternative disabled antibody derivative with a diverse set of disabling moieties. (A) The Rituximab LC-L2-CD32 construct was modified such that the CD32 domain disabling moiety was replaced by alternative domains that have Fc binding properties. These constructs were co-transfected with the Rituximab HC construct to form new antibody derivatives. (B) The proteins were produced in a mammalian expression system and purified with Ni-NTA agarose. The proteins were analyzed using reducing and non-reducing SDS-PAGE. The star indicates the heavy chain and the arrow heads indicate the various modified light chains fused to different disabling moieties. WT Rituximab is shown as a control.

FIGS. 13A-G Testing the conditional activation of ADCC and CDC of the disabled antibody variants in the presence and absence of the granzyme B activator reagent. The graphs on the left side are the results of ADCC assays of each of the antibody derivatives indicated. The level of luminescence produced is plotted against the antibody derivative concentration. The graphs on the right side are the CDC total lysis results from the same antibody derivative. These are the assay results of the variants depicted in FIGS. 10A-B, 11A-B, and 12A-B; the identification of the modified antibody is indicated on each of the graphs. The results are presented in order in which the constructs are mentioned in the text. Rituximab, anti-CD20, anti-CD19, CD2ECD variants were tested with Raji cells expressing CD5, and H10-2-G3 and CCPE variants were tested with SKBr3 cells.

DETAILED DESCRIPTION

Many cell surface proteins that are expressed at high levels on tumors are also expressed in moderate abundance on healthy cells and the consequences of destruction of the latter can preclude deployment of antibodies against the former. In some cases, a cell surface protein that is expressed at high level on the tumor cells can be found in the context of additional proteins that are expressed at moderate or high level on the same tumor cells as well. Each protein might be found on other normal tissues, but the presence of both at high or moderate levels on the same cell is not otherwise encountered in the vital tissues of the organism. In such cases it is possible to take advantage of the unusual presence of both proteins on the same cell to target the cell for ablation. Similarly, to selectively destroy a subpopulation of cells in the immune system that are harmful to the organism, for example that are sustaining an autoimmune reaction, it is useful to be able to apply therapeutic agents that require two or more targets to be coexpressed in order for the agent to act.

Described herein are methods and compositions for treating diseases through selective killing of targeted cells by an approach that modulates the ability of antibody effector regions to engage the effector functions of the immune system. In one aspect, the invention features disabled antibody derivatives containing a target binding moiety, an antibody effector region, an effector region disabling moiety, and a disabling moiety cleavable linker that is directly or indirectly cleaved by an activator moiety not naturally operably found in, on, or in the vicinity of a target cell. These methods also include the combinatorial use of two or more therapeutic agents, at minimum comprising a disabled antibody derivative and an activator or proactivator, to target and destroy or inhibit a specific cell population. Each of these therapeutic agents contains at least one target binding moiety binding to an independent cell surface target of the targeted cells. The disabled antibody derivative contains a disabling moiety cleavable linker that can be acted upon by the activator or the activated form of the proactivator. The activator or activated form of the proactivator comprises an enzymatic activity that, upon acting on the disabling moiety cleavable linker, converts, or allows to be converted, the disabled antibody derivative to an active antibody derivative by allowing the release of the effector region disabling moiety. The targeted cells are then inhibited or destroyed by the effector functions of the immune system engaged by the active antibody derivative.

Effector Regions

Antibodies engage both the humoral and cellular arms of the immune system to mediate destruction of pathogens or cells infected by pathogens. The humoral effector function of the immune system results in the deposition of complement on the target pathogen or pathogen-infected cell, which can cause cytolysis of the target through the creation of a membrane pore called the membrane attack complex (MAC). The formation of the MAC proceeds through the sequential activation of a series of serine protease zymogens that successively amplify the signal initiated by complement binding to clustered antibodies and result in the controlled deposition of the terminal components of the cascade in the MAC.

The cellular arm of the immune system can be stimulated either directly, by cellular recognition of clustered antibodies on the target pathogen or pathogen-infected cell, or indirectly, by recognition of deposited complement proteins. In the latter pathway, a pathogen that is resistant to the action of the MAC can be engulfed by myeloid cells or destroyed by the oxidative effect of a respiratory burst that is triggered by the encounter by macrophages or granulocytes with a target bearing deposited complement.

Antibody isotypes differ in their ability to engage humoral and cellular effector programs; thus, effector regions can be selected that have more humoral or more cellular effector activity. IgM antibodies are especially effective at eliciting complement deposition, but have relatively little capacity to mediate direct cellular cytotoxicity. IgG antibodies are less effective at initiating the complement cascade, but are considerably more effective at provoking cellular cytotoxic responses. IgA has more humoral than cellular activity, and IgE has essentially only cellular activity. In the case of IgE the effector cells are typically only those cells that bear high affinity IgE receptors, principally the mast cells, basophils and eosinophils. Among the IgG subtypes in humans, IgG1 and IgG3 effectively initiate humoral immune responses, whereas IgG2 and IgG4 have much less activity. IgG1 and IgG3 also bind more effectively to the receptors for immunoglobulin, called Fc receptors, which initiate signaling in the immune system. IgG4 interacts strongly only with the high affinity Fc receptor, FcRγI, whereas IgG2 has much less interaction than IgG1 and IgG3 for all of the receptors (Bruhns et al., Blood. 2009 113(16):3716-25).

Generally, the segments of antibodies that are principally responsible for engaging humoral or cellular immunity can be found in the constant regions. Among IgG subtypes, the CH2 domain provides the most important contact residues for binding to complement C1q and IgG receptors, whereas for IgM, it is the CH3 domain that largely interacts with C1q.

Mutational analyses have shown that the binding of C1q to the therapeutic antibody rituximab can be diminished by mutation of residues Asp270, Lys322, Pro329, and Pro331 to alanine (Idusogie et al., 2000). Michaelsen et al. (Scand J Immunol. 2009 70(6):553-64) confirmed that Asp270, Lys322, Pro329 and Pro331 on IgG1 are important for interaction with complement, and showed that for IgG3, Asp270 is less critical, whereas Leu334 and Leu335 are more important.

On IgG1, the key residues for binding to Fc receptors are found at amino acids 233-236 (Glu Leu Leu Gly), Pro238, Asp265, Asn297, Ala327 and Pro329 (Siberil et al. Immunol Lett. 2006 106(2):111-8), indicating that the contact surfaces for Clq and Fc receptors at least partially overlap.

Effector Region Disabling Moieties

The disabled antibody derivatives described herein also include effector region disabling moieties that inhibit the activity of the effector domains by physically occluding or sterically obstructing the effector domains.

The effector region disabling moieties can be naturally occurring proteins, such as complement Clq or Fc receptor domains, or can be composed of elements that arise from synthetically diversified natural protein fragments that have been selected for the capacity to bind to or disable the effector regions, or that can have been generated by immunization of an appropriate species with the effector domains to produce antibodies or antibody fragments that recognize the effector regions. Some examples of disabling moieties derived from naturally occurring proteins include but are not limited to the antibody binding portions of the Fc-gamma receptors, Fc-alpha receptors, Fc-epsilon receptors and the Clq protein from the complement system. The effector region disabling moieties can also be derived from naturally occurring proteins that bind to the IgG CH2 domain and block effector functions from non-mammalian sources, such as the staphylococcal superantigen-like protein 10 (SSL10; Patel et al., J Immunol. 2010 184(11):6283-92). The effector region disabling moieties need not bind directly to residues that make contact with proteins that initiate effector function, but can exert their action by impeding access of the proteins that initiate effector function to the critical contact residues. To act by steric obstruction, effector region disabling moieties need not have an affinity for the effector contact residues or antibody domain, but can simply act by providing a barrier to the engagement of the effector region contact residues. Such a barrier can be provided by proteinaceous or non-proteinaceous disabling moieties. Effector region disabling moieties also need not be employed in their natural composition but can be engineered to improve their binding affinity, ease of production by fermentation or other synthetic process, or decreased interaction with other elements of the apparatus they naturally engage, for example, to prevent induction of complement deposition.

In the present compositions, the disabling moiety does not substantially reduce the ability of the target binding moiety to bind its target, i.e., does not increase the Kd of binding of the target binding moiety to its target by more than 10 fold.

Target Recognition Moieties

Disclosed herein are target binding moieties that act to localize modified antibody derivative and/or (pro)activators to the surface of target cells.

The target recognition moieties can be, for example, an antibody or antigen-binding antibody derivative, e.g., a native antibody, an engineered antibody, or an antibody derivative in which the target recognition function is provided by a single chain antibody fragment such as a scFv, or by a non-antibody target recognition moiety. Examples of non-antibody target recognition moieties can include, without limitation, an extracellular domain of a cell surface protein, a natural or engineered ligand for a cellular receptor, or an artificially diversified polypeptide binder such as a nanobody, affibody, adnectin, camelbody, lipocalin, or DARPin. Non-antibody target recognition moieties can be attached to the amino terminus of the antibody derivative or to the carboxyl terminus. Antibody derivatives can include one or more target recognition domains wherein increased selectivity or affinity is provided by the combined interaction of a plurality of target recognition domains with the target.

The target binding moieties can include fragments derived from antibodies, antibody mimetics, ligands specific for certain receptors expressed on a target cell surface, carbohydrates, peptides that specifically bind cell surface molecules, as well as naturally occurring ligands for receptors, or chemically synthesized equivalents that can be agonists, antagonists, or compounds that bind with influence on the function of the target composition.

One embodiment of the target binding moiety is a protein domain that can specifically recognize a target on the cell surface. The most widely used form of target binding moieties today occurs in the form of antibodies, and it is expected that antibodies, e.g., furnished with an effector region disabling moiety and a disabling moiety cleavable linker or an activator/proactivator domain, can be used in the present compositions. Thus in some embodiments the invention provides a natural antibody or an engineered antibody, such as an effector function engineered antibody, that possesses the natural organization of an antibody in the form of variable and constant regions composing heavy and light chains associated in the manner typically found for antibodies in their native configuration; in these cases the antibody includes both the target recognition moiety and the effector region.

Alternatively, the target binding moiety can be a fragment or reengineered version of an antibody variable region, such as a scFv (Huston, et al. 1991. Methods Enzymol. 203:46-88, Huston, et al. 1988. Proc Natl Acad Sci USA. 85:5879-

83). In one embodiment the target binding moiety is a variable region fragment or fragments of human, murine, goat, rat, rabbit, or camel antibody origin. In another embodiment the target binding moiety is a humanized version of animal antibodies in which the CDR regions have been grafted onto a human antibody framework (for example as taught by Queen and Harold. 1996. U.S. Pat. No. 5,530,101). Human antibodies to human epitopes can be isolated from transgenic mice bearing human antibodies as well as from phage display libraries based on human antibodies (Kellermann and Green. 2002. Curr Opin Biotechnol. 13:593-7, Mendez, et al. 1997. Nat Genet. 15:146-56, Knappik, et al. 2000. J Mol Biol. 296:57-86). The binding moiety can also be molecules from the immune system that are structurally related to antibodies such as engineered T-cell receptors, single chain T-cell receptors, CTLA-4, monomeric VH or VL domains (nanobodies), and camelized antibodies (Berry and Davies. 1992. J Chromatogr. 597:239-45, Martin, et al. 1997. Protein Eng. 10:607-14, Tanha et al. 2001. J Biol Chem. 276:24774-80, Nuttall, et al. 1999. Proteins. 36:217-27). A further embodiment can comprise diabodies, which are genetic fusions of two single chain variable fragments that have specificity for two distinct epitopes on the same cell. As an example, a diabody with an anti-CD19 and anti-CD22 scFv can be fused to an antibody effector region or a (pro)activator in order to increase the affinity to B-cell targets (Kipriyanov. 2003. Methods Mol Biol. 207:323-33).

In another embodiment the target binding moiety can also be an artificially diversified polypeptide binder. Artificially diversified polypeptide binders have portions of their native sequence replaced by sequences that can bind to heterologous targets. Such binders can be superior to antibodies in terms of stability, production, and size. Examples include nanobodies, affibodies, adnectins, camelbodies, lipocalins, or DARPins. One category of such binders is based on the fibronectin type III domain, which has been used previously to isolate affinity reagents to various structures (Koide et al. Methods Enzymol. 2012; 503:135-56, Lipovsek, et al. 2007. J Mol Biol. 368:1024-41, Lipovsek, Wagner, and Kuimelis. 2004. U.S. Patent 20050038229). Lipocalins are another class of polypeptide that have been used for molecular diversification and selection of novel affinity reagents (Skerra et al. 2005. U.S. Patent 20060058510). Lipocalins are a class of proteins that bind to steroids and metabolites in the plasma. Functional lipocalin binders to CTLA4 and VEGF have been isolated using phage display techniques (Vogt and Skerra. 2004. Chembiochem. 5:191-9). C-type lectin domains, A-domains and ankyrin repeats provide frameworks that can be oligomerized in order to increase the binding surface of the scaffold (Mosavi, et al. 2004. Protein Sci. 13:1435-48). Other artificially diversified polypeptide binders have been formed from human serum albumin, green fluorescent protein, PDZ domains, Kunitz domains, charybdotoxin, plant homeodomain, and beta-lactamase. There are several comprehensive reviews on the use of artificially diversified polypeptide binders (Hosse, et al. 2006. Protein Sci. 15:14-27; Gronwall and Stahl 2009, J Biotechnol 140:254-69). Those skilled in the art understand that many diverse proteins or protein domains have the potential to be diversified and can be developed and used as affinity reagents, and these can serve as cell-binding moieties in the context of combinatorial targeting therapy. In another embodiment, the target binding moiety can be a naturally occurring ligand, adhesion molecule, or receptor for an epitope expressed on the cell surface. Compositions of the ligand can be a peptide, lectin, hormone, fatty acid, nucleic acid, or steroid. For example, human growth hormone could be used as a target binding moiety for cells expressing human growth hormone receptor. Solubilized receptor ligands can also be used in cases in which the natural ligand is an integral membrane protein. Such solubilized integral membrane proteins are well-known in the art and are easily prepared by the formation of a functional fragment of a membrane protein by removing the transmembrane or membrane anchoring domains to afford a soluble active ligand; for example soluble CD72 could be used as a ligand to localize modified antibody derivatives to CD5 containing cells (Van de Velde, et al. 1991. Nature. 351: 662-5). Another example is the binding of urokinase type plasminogen activator (uPA) to its receptor uPAR. It has been shown that the region of u-PA responsible for high affinity binding (Kd≈0.5 nM) to uPAR is entirely localized within the first 46 amino acids, called N-terminal growth factor like domain (N-GFD) (Appella, et al. 1987. J Biol Chem. 262:4437-40). Avemers refer to multiple receptor binder domains that have been shuffled in order to increase the avidity and specificity to specific targets (Silverman, et al. 2005. Nat Biotechnol. 23:1556-61). These receptor binding domains and ligands can be genetically fused and produced as a contiguous polypeptide with the modified antibody derivative or (pro)activator or they can be isolated separately and then chemically or enzymatically attached. They can also be non-covalently associated with the modified antibody derivative or (pro)activator.

A target binding moiety comprising a carbohydrate such as mannose, mannose 6-phosphate, galactose, N-acetylglucosamine, or sialyl-Lewis X, can be used to target the mannose receptor, mannose 6-phosphate receptor, asialoglycoprotein receptor, N-acetylglucosamine receptor, or E-selectin, respectively. A moiety comprising a sialyl-Lewis X glycan operably linked to a tyrosine sulfated peptide or a sulfated carbohydrate can be used to target P-selectin or L-selectin, respectively.

As another example, the target binding moiety can be drawn from bacterial or plant toxins. The C-terminal domain of the *Clostridium perfringens* enterotoxin (C-CPE) binds with high affinity and specificity to the mammalian claudin3/4 adhesion molecules. Although claudins are components of most cells tight junctions, they are not typically exposed on the apical surface. The C-CPE can be appended to the modified antibody derivative or (pro)activator in order to localize one of the components of the combinatorial targeting to cells overexpressing unengaged claudin3/4, a condition of many types of cancers (Takahashi, et al. 2005. J Control Release. 108:56-62, Ebihara, et al. 2006. J Pharmacol Exp Ther. 316:255-60).

Another embodiment is afforded by the use of a peptide agonist or antagonist to localize complexes to cells expressing the cognate peptide receptor. In another embodiment, the binding peptide could be an unnatural peptide selected from a random sequence library. In order to increase binding affinity, peptides can be multimerized through sequential repeated fusions or attaching them to a dendrimer which can then be attached to the modified antibody derivative or (pro)activators of the invention.

In another embodiment, the target binding moiety can be a nucleic acid that consists of DNA, RNA, PNA or other analogs thereof. Nucleic acid aptamers have been identified to many protein targets and bind with very high affinity through a process of in vitro evolution (Gold. 1991. U.S. Pat. No. 5,475,096, Wilson and Szostak. 1999. Annu Rev Biochem. 68:611-47). RNA aptamers specific for PSMA have been shown to specifically localized conjugated gelonin toxin to cells overexpressing PSMA (Chu, et al. 2006. Cancer Res. 66:5989-92). The nucleic acid can be chemically synthesized or biochemically transcribed and then modified to include an attachment group for conjugation to the modified antibody derivative or (pro)activator. The nucleic acid can be directly conjugated using common crosslinking reagents or enzymatically coupled by processes known in the art. The nucleic acid can also be non-covalently associated with the fusion proteins of the invention.

Additional target binding moieties can be identified using a number of techniques described in the art. Typically natural hormones and peptide ligands can be identified through reported interactions found in the literature. Additionally, antibody mimics and nucleic acid aptamers can be identified using selection technologies that can isolate rare binding molecules toward epitopes of interest, such as those expressed on cancer cells or other diseased states. These techniques include SELEX, phage display, bacterial display, yeast display, mRNA display, in vivo complementation, yeast two-hybrid system, and ribosome display (Roberts and Szostak. 1997. Proc Natl Acad Sci USA. 94:12297-302, Boder and Wittrup. 1997. Nat Biotechnol. 15:553-7, Ellington and Szostak. 1990. Nature. 346:818-22, Tuerk and MacDougal-Waugh. 1993. Gene. 137:33-9, Gyuris, et al. 1993. Cell. 75:791-803, Fields and Song. 1989. Nature. 340:245-6, Mattheakis, et al. 1994. Proc Natl Acad Sci USA. 91:9022-6). Antibodies can be generated using the aforementioned techniques or in a traditional fashion by immunizing animals and generating hybridomas or by sequencing heavy and light chain repertoires from plasma cells of immunized animals.

The targets of the target binding moieties (i.e., to which the target binding moieties bind) can be protein receptors, carbohydrates, and lipids on or around the cell surface. Examples of polypeptide modifications known in the art that can advantageously comprise elements of a cell surface target include glycosylation, sulfation, phosphorylation, ADP-ribosylation, and ubiquitination. Examples of carbohydrate modifications that can be distinctive for a specific lineage of cells include sulfation, acetylation, dehydrogenation and dehydration. Examples of lipid modification include glycan substitution and sulfation. Examples of lipids that can be distinctive for a specific targeted cell include sphingolipids and their derivatives, such as gangliosides, globosides, ceramides and sulfatides, or lipid anchor moieties, such as the glycosyl phosphatidyl inositol-linked protein anchor.

The target binding moiety can indirectly bind to the target cell through another binding intermediary that directly binds to a cell surface epitope, as long as the target binding moiety acts to localize the modified antibody derivative or (pro)activator to the cell surface. The targets of these binding modules can be resident proteins, receptors, carbohydrates, lipids, cholesterol, and other modifications to the target cell surface. The target binding moiety can be joined to the disabled antibody derivative or (pro)activator either through direct translational fusions if the DNA encoding both species is joined. Alternatively, chemical coupling methods and enzymatic crosslinking can also join the two components. The target binding moiety can contain sequences not involved in the structure or binding of the agent, but involved with other processes such as attachment or interaction with the disabled antibody derivative or (pro)activator.

In some embodiments, the target binding moiety is one or more single-chain variable fragment (scFv) that specifically recognizes epitopes on cells of patients with B-CLL. In another embodiment the target binding moiety is one or more single-chain variable fragment (scFv) that specifically recognizes CD5. In yet another embodiment the target binding moiety is a single-chain variable fragment (scFv) that specifically recognizes B-cell markers CD19, CD20, or CD22. In one embodiment the scFv fragment includes one or more specific tag sequence (LPETG (SEQ ID NO: 28)) that is used for enzymatic crosslinking induced by SortaseA. The tag sequence can be at the N-terminus, C-terminus, or at an internal position. In another embodiment the LPETG (SEQ ID NO: 28) tag sequence is located near or at the C-terminus. The expression and functional reproduction of scFv is well-known in the art. The scFvs were produced through the expression in the E. coli periplasm and refolded in vitro using reported procedures for obtaining functional scFvs.

The target binding moieties of the invention are typically selected to recognize a specific cell type, e.g., a cancer cell, a cell of hematopoietic origin, a cell contributing to organ hypertrophy or an excessively activated cell contributing to a disease state, or a nociceptive neuron. It will be recognized by those skilled in the art that there are many cell surface targets that can be used for targeting the modified antibody derivatives or activators/proactivators of the invention to selectively destroy or inhibit neoplastic tissues, and the recitations of US20100055761A1 teaching exemplary combinations of such targets are incorporated herein by reference.

Linkers

Each of the domains and moieties in the compositions described herein can be linked to the next domain or moiety directly or with an intervening linker. For example, the effector region disabling moiety can be attached to the antibody or antibody derivative by chemical or enzymatic derivatization or by translational fusion. If by the latter, the translational fusion can be made to the amino terminus or the carboxyl terminus of an antibody heavy chain or light chain, or to both. If the antibody derivative comprises a non-antibody target recognition moiety, the effector region disabling moiety can be attached to the amino terminus of the antibody derivative or the carboxyl terminus. If the non-antibody target recognition moiety is comprised of more than one chain, the effector region disabling moiety can also be attached to the amino terminus or carboxyl terminus of one or more of said chains.

If the effector region disabling moiety is attached to the antibody or antibody derivative by chemical means it is preferred to attach the moiety in proximity to the effector contact residues, for example by site selective chemical modification. Such site selective modification can be accomplished by introduction of specific natural or non-natural amino acid residues at specific locations near the effector contact residues. Convenient locations known in the art include the carboxyl terminus of the light chain or residues spatially proximate to the carboxyl terminus, or in the antibody constant domains CH2 for IgG or CH3 for IgM.

In constructs wherein the effector region disabling moiety has an affinity for the effector surface of the antibody constant region, the effector region disabling moiety is preferably operably linked to the antibody or antibody derivative by a flexible linker that allows the disabling moiety to appropriately position itself to occlude the effector surface of the antibody constant region. Effector region disabling moieties that have an intrinsic affinity for the effector surface residues are preferred, but effector region disablement can also be achieved by steric obstruction, for example by fusion of a large protein or protein fragment to the carboxyl terminus of the light chain of an antibody. The bulk of the protein or protein fragment thereby prevents contact of the effector domain with the effector molecules of the immune system. Non-proteinaceous moieties can be used to provide a steric obstruction function as long as they include a facility for release of the disabling moiety by the activator or endogenous activating factor.

Thus, in some embodiments, each moiety within a modified antibody derivative (e.g., one or more target binding moieties, one or more antibody effector regions, one or more effector region disabling moieties, and one or more disabling moiety cleavable linkers) or a (pro)activator fusion, (e.g., one or more target binding moieties, one or activator domains, and optionally one or more natively activatable domain) can function independently but each is operably linked. Within each fusion protein the operable linkage between the two functional moieties acts as a molecular bridge, which can be covalent or non-covalent. The moieties of each fusion protein can be operably linked in any orientation with respect to each other, that is, C-terminal of one to N-terminal of the other, or C-terminal of one to C-terminal of the other, or N-terminal of one to N-terminal of the other, or by internal residues to terminal residues or internal residues to internal residues. An optional linker can serve as a glue to physically join the two moieties, as a separator to allow spatial independence, or as a means to provide additional functionality to each other, or a combination thereof. For example, it can be desirable to separate the target binding moiety from the operably linked enzyme moiety to prevent them from interfering with each other's activity. In this case the linker provides freedom from steric conflict between the operably linked moieties. The linker can also provide, for example, lability to the connection between the two moieties, an enzyme cleavage site (e.g., a cleavage site for protease or a hydrolytic site for esterase), a stability sequence, a molecular tag, a detectable label, or various combinations thereof.

Polypeptide linkers have recently been reviewed by Chen et al., (2013) Adv Drug Deliv Rev. 65:1357-69. Polypeptide linkers can be designed to be disordered (flexible) or ordered (stiff) and can in some embodiments be cleavable, for example by disulfide reduction or proteolytic action. Disordered linkers frequently bear a large fraction of glycine residues whereas ordered linkers contain either sequence motifs that favor alpha helix formation or a large fraction of proline residues, which typically have reduced rotational freedom. Increasing the length or changing the degree of order in a linker can have major effects on the production, stability and activity of recombinant proteins bearing linkers (Chen et al., 2013).

Chemical activation of amino acid residues can be carried out through a variety of methods well known in the art that result in the joining of the side chain of amino acid residues on one molecule with side chains of residues on another molecule, or through the joining of side chains to the alpha amino group or by the joining of two or more alpha amino groups. Typically the joining induced by chemical activation is accomplished through a linker which can be a small molecule, an optionally substituted branched or linear polymer of identical or nonidentical subunits adapted with specific moieties at two or more termini to attach to polypeptides or substitutions on polypeptides, or an optionally substituted polypeptide. Examples of common covalent protein operable linkage agents can be found in various vendor offerings, including those offered for sale by Pierce Chemical Corporation. In general it is preferable to be able to induce operable linkage of components in a site-specific manner, to afford a simple reproducibly manufactured substance. Operable linkage by chemical activation can be the result of chemical activation targeted to specific residues that are functionally unique, i.e., are present only once in the moiety to be activated or are preferentially activatable because of a unique chemical environment, for example, such as would produce a reduction in pK of an epsilon amino unit of a lysine residue. Potential groups for chemical activation can be made functionally unique by genetic removal of all other residues having the same properties, for example to remove all but a single cysteine residue, or all but a single lysine reside. Amino terminal residues can be favorably targeted by virtue of the low pK of the alpha amino group, or by suitable chemistry exploiting the increased reactivity of the alpha amino group in close proximity to another activatable group. Examples of the latter include native chemical ligation, Staudinger ligation, and oxidation of amino terminal serine to afford an aldehyde substituent. Chemical activation can also be carried out through reactions that activate naturally occurring protein substituents, such as oxidation of glycans, or other naturally occurring protein modifications such as those formed by biotin or lipoic acid, or can be based on chemical reactions that convert the functionality of one side chain into that of another, or that introduce a novel chemical reactive group that can subsequently activated to produce the desired operable linkage. Examples of the latter include the use of iminodithiolane to endow a lysine residue with a sulfhydryl moiety or the reaction of a cysteine moiety with an appropriate maleimide or haloacetamide to change the functionality of the thiol to another desired reactive moiety. Chemical activation can also be carried out on both species to be operably linked to provide reactive species that interact with one another to provide an operable linkage, for example the introduction of a hydrazide, hydrazine or hydroxylamine on one moiety and an aldehyde on the other.

Noncovalent operable linkage can be obtained by providing a complementary surface between one moiety and another to provide a complex which is stable for the intended useful persistence of the operably linked moieties in therapeutic use. Such noncovalent linkages can be created from either two or more polypeptides that can be the same or dissimilar or one or more polypeptide and a small molecule or ligand attached to the second moiety. Attachment of the small molecule or ligand can take place through in vitro or in vivo processes, such as the incorporation of biotin or lipoic acid into their specific acceptor sequences which can be natural or artificial biotin or lipoic acid acceptor domains and which can be achieved either by natural incorporation in vivo or by enzymatic biotinylation or lipoylation in vitro. Alternatively, the protein can be substituted with biotin or other moieties by chemical reaction with biotin derivatives. Common examples of biotin derivatives used to couple with proteins include aldehydes, amines, haloacetamides, hydrazides, maleimides, and activated esters, such as N-hydroxysuccinimide esters, Examples of commonly employed noncovalent linkage include the linkage induced by binding of biotin and its derivatives or biotin-related substituents such as iminobiotin or diaminobiotin or thiobiotin to streptavidin or avidin or variants thereof, the binding of enzymes to their covalent or noncovalent specific inhibitors, such as the binding of methotrexate to mammalian dihydrofolate reductase, the binding of natural or synthetic leucine zippers to one another, the binding of enzymes to specific or nonspecific inhibitors, such as antitrypsin or leupeptin or alpha-2-macroglobulin, the binding of aryl bis-arsenates to alpha helices bearing appropriately positioned cysteine residues, the binding between a nucleic acid aptamer and its target; between a peptide and a nucleic acid such as Tat-TAR interaction.

Enzymatic activation of one polypeptide to afford coupling with another polypeptide can also be employed. Enzymes or enzyme domains that undergo covalent modification by reaction with substrate-like molecules can also be used to create fusions. Examples of such enzymes or enzyme domains include O6-alkylguanine DNA-alkyltransferase (Gronemeyer et al. Protein Eng Des Sel. 2006 19(7):309-16), thymidylate synthase, or proteases that are susceptible to covalent or stable noncovalent modification of the active site, as for example DPP4.

The present compositions and methods also feature the use of bifunctional or multifunctional linkers, which contain at least two interactive or reactive functionalities that are positioned near or at opposite ends, each can bind to or react with one of the moieties to be linked. The two or more functionalities can be the same (i.e., the linker is homobifunctional) or they can be different (i.e., the linker is heterobifunctional). A variety of bifunctional or multifunctional cross-linking agents are known in the art are suitable for use as linkers. For example, cystamine, m-maleimidobenzoyl-N-hydroxysuccinimide-ester, N-succinimidyl-3-(2-pyridyldithio)-propionate, methylmercaptobutyrimidate, dithiobis(2-nitrobenzoic acid), and many others are commercially available, e.g., from Pierce Chemical Co. Rockford, Ill. Additional chemically orthogonal reactions suitable for such specific operable linkage reactions include, for example, Staudinger ligation, Cu[I] catalyzed [2+3] cycloaddition, and native ligation.

The bifunctional or multifunctional linkers can be interactive but non-reactive. Such linkers include the composite use of any examples of non-covalent interactions discussed above.

The length and composition of the linker can be varied considerably provided that it can fulfill its purpose as a molecular bridge. The length and composition of the linker are generally selected taking into consideration the intended function of the linker, and optionally other factors such as ease of synthesis, stability, resistance to certain chemical and/or temperature parameters, and biocompatibility. For example, the linker should not significantly interfere with the regulatory ability of the target binding moiety relating to targeting of the modified antibody derivative or (pro)activator, or with the activity of the modified antibody derivative or (pro)activator or the effector functions of the immune system that have been engaged.

Linkers suitable for use according to the present compositions and methods can be branched, unbranched, saturated, or unsaturated hydrocarbon chains, including peptides as noted above.

Furthermore, if the linker is a peptide, the linker can be attached by cotranslational expression using recombinant DNA technology.

In one embodiment of the present compositions and methods, the linker is a branched or unbranched, saturated or unsaturated, hydrocarbon chain having from 1 to 100 carbon atoms, wherein one or more of the carbon atoms is optionally replaced by —O— or —NR— (wherein R is H, or C1 to C6 alkyl), and wherein the chain is optionally substituted on carbon with one or more substituents selected from the group of (C1-C6) alkoxy, (C3-C6) cycloalkyl, (C1-C6) alkanoyl, (C1-C6) alkanoyloxy, (C1-C6) alkoxycarbonyl, (C1-C6) alkylthio, amide, azido, cyano, nitro, halo, hydroxy, oxo (=O), carboxy, aryl, aryloxy, heteroaryl, and heteroaryloxy.

Examples of suitable linkers include, but are not limited to, peptides having a chain length of 1 to 100 atoms, and linkers derived from groups such as ethanolamine, ethylene glycol, polyethylene with a chain length of 6 to 100 carbon atoms, polyethylene glycol with 3 to 30 repeating units, phenoxyethanol, propanolamide, butylene glycol, butyleneglycolamide, propyl phenyl, and ethyl, propyl, hexyl, steryl, cetyl, and palmitoyl alkyl chains.

In one embodiment, the linker is a branched or unbranched, saturated or unsaturated, hydrocarbon chain, having from 1 to 50 carbon atoms, wherein one or more of the carbon atoms is optionally replaced by —O— or —NR— (wherein R is as defined above), and wherein the chain is optionally substituted on carbon with one or more substituents selected from the group of (C1-C6) alkoxy, (C1-C6) alkanoyl, (C1-C6) alkanoyloxy, (C1-C6) alkoxycarbonyl, (C1-C6) alkylthio, amide, hydroxy, oxo (=O), carboxy, aryl and aryloxy.

In another embodiment, the linker is an unbranched, saturated hydrocarbon chain having from 1 to 50 carbon atoms, wherein one or more of the carbon atoms is optionally replaced by —O— or —NR— (wherein R is as defined above), and wherein the chain is optionally substituted on carbon with one or more substituents selected from the group of (C1-C6) alkoxy, (C1-C6) alkanoyl, (C1-C6) alkanoyloxy, (C1-C6) alkoxycarbonyl, (C1-C6) alkylthio, amide, hydroxy, oxo (=O), carboxy, aryl and aryloxy.

In a specific embodiment of the present compositions and methods, the linker is a peptide having a chain length of 1 to 50 atoms. In another embodiment, the linker is a peptide having a chain length of 1 to 40 atoms.

As known in the art, the attachment of a linker to a modified antibody derivative (or of a linker element to a target binding moiety or a target binding moiety to an activator domain or an antibody effector region) need not be a particular mode of attachment or reaction. Various non-covalent interactions or reactions providing a product of suitable stability and biological compatibility are acceptable.

One preferred embodiment of the present compositions and methods relies on enzymatic reaction to provide an operable linkage between the moieties of a modified antibody derivative or a (pro)activator. Among the enzymatic reactions that produce such operable linkage, it is well-known in the art that transglutaminase ligation, sortase ligation, and intein-mediated ligation provide for high specificity.

The preferred peptide substrate sequences listed above are for example and non-limiting. It is known in the art that these families of enzymes can recognize and utilize different sequences as substrates, and those sequences are included here as embodiments for the present compositions and methods.

Cleavable Linkers

In the disabled antibody derivative compositions described herein, a cleavable linker is present between the disabling moiety and the effecter region (this linker is referred to as disabling moiety cleavable linkers), and optionally between the target recognition moiety and the activator domain (this linker is referred to as proactivator activation linker). Typically these linkers will differ, i.e., will be activated (cleaved) by different activators. In general, the disabling moiety cleavable linker will be activated (cleaved) by the active form of the activator or proactivator.

In one example, natively activatable linkers can be used. Such linkers are cleaved by enzymes of the complement system, urokinase, tissue plasminogen activator, trypsin, plasmin, or another enzyme having proteolytic activity that can be used in one embodiment of the present compositions and methods. According to another embodiment of the present compositions and methods, a disabling moiety cleavable linker is susceptible to cleavage by tissue-specific enzymes having a proteolytic activity such as a urokinase, a tissue plasminogen activator, plasmin, thrombin or trypsin.

In one embodiment of the invention, the disabling moiety cleavable linker can be cleaved by a protease that is up-regulated or associated with cancers in general. Examples of such proteases are uPA, the matrix metalloproteinase (MMP) family, the caspases, elastase, and the plasminogen activator family, as well as fibroblast activation protein. In still another embodiment, the cleavage site is cleaved by a protease secreted by cancer-associated cells. Examples of these proteases include matrix metalloproteases, elastase, plasmin, thrombin, and uPA. In another embodiment, the protease cleavage site is one that is up-regulated or associated with a specific cancer. In yet another embodiment, the proteolytic activity can be provided by a protease fusion targeted to the same cell. Various cleavage sites recognized by proteases are known in the art and the skilled person will have no difficulty in selecting a suitable cleavage site. Non-limiting examples of cleavage sites are provided elsewhere in this document. As is known in the art, other protease cleavage sites recognized by these proteases can also be used. In one embodiment, the cleavable linker region is one which is targeted by endocellular proteases.

Chemical linkers can also be designed to be substrates for carboxylesterases, so that they can be selectively cleaved by these carboxyltransferases or corresponding fusion proteins with a target binding moiety. One preferred embodiment comprises the use of a carboxyl transferase activity to activate the cleavage of an ester linker. For example but without limitation, secreted human carboxyltransferase-1, -2, and -3 can be used for this purpose. Additional examples include carboxyl transferase of other origins.

Another embodiment of the cleavable linkers comprises nucleic acid units that are specifically susceptible to sequence specific endonucleases.

Preferable cleavable linkers include those that are stable to in vivo conditions but susceptible to the action of an activator as described herein. Many examples of suitable linkers have been provided in the context of attempts to develop antibody-directed enzyme prodrug therapy. For example a large class of enzyme substrates that lead to release of an active moiety, such as a fluorophore, have been devised through the use of what are known as self-immolative linkers. Self-immolative linkers are designed to liberate an active moiety upon release of an upstream conjugation linkage, for example between a sugar and an aryl moiety. Such linkers are often based on glycosides of aryl methyl ethers, for example the phenolic glycosides of 3-nitro, 4-hydroxy benzyl alcohol; see for example Ho et al. Chembiochem, 2007 Mar. 26; 8(5):560-6, or the phenolic amides of 4-amino benzyl alcohol, for example Niculescu-Duvaz et al. J Med Chem. 1998 Dec. 17; 41(26):5297-309 or Toki et al. J Org Chem. 2002 Mar. 22; 67(6):1866-72.

To create self-immolative linkers based on glycosides the phenolic hydroxyl is glycated by reaction with a 1-Br-substituted sugar such as alpha-1-Br galactose or alpha-1-Br glucuronic acid to provide the substrate for the activating enzyme, and the benzyl alcohol moiety is then activated with a carbonylation reagent such as phosgene or carbonyl diimidazole and reacted with a primary amine to afford a carbamate linkage. Upon scission of the aryl glycosidic bond or the aryl ester, the aryl moiety eliminates, leaving a carbamoyl moiety that in turn eliminates, affording $CO_2$ and the regenerated amine. Said amine can be the alpha amino group of a polypeptide chain or the epsilon amino of a lysine side chain.

To create self-immolative linkers based on amide bonds the phenyl amine of 4-amino benzyl alcohol is reacted with an activated carboxyl group of a suitable peptide or amino acid to create a phenyl amide that can be a substrate for an appropriate peptidase, for example carboxypeptidase G2, see Niculescu-Duvaz et al. J Med Chem. 41(26):5297-309 (1998). The benzyl alcohol moiety is then activated with a carbonylation reagent such as phosgene or carbonyl diimidazole and reacted with a primary amine to afford a carbamate linkage. Upon scission of the aryl amide bond, the aryl moiety eliminates, leaving a carbamoyl moiety that in turn eliminates, affording $CO_2$ and the regenerated amine. Said amine can be the alpha amino group of a polypeptide chain or the epsilon amino of a lysine side chain.

For the creation of an appropriate self-immolating activation moiety according to the present compositions and methods the aryl group is substituted with a reactive moiety that provides a linkage to one element of the modified antibody derivative or (pro)activator, such as the domain comprising an antibody effector region.

Similar forms of self-immolative linker are also well-known in the art. For example Papot et al. Bioorg Med Chem Lett. 8(18):2545-8 (1998) teach the creation of glucuronide prodrugs based on aryl malonaldehydes that undergo elimination of the aryl linker moiety upon cleavage by a glucuronidase. Suitable linkers based on aryl malonaldehydes in the context of the present compositions and methods provide a disabling moiety cleavable linker or proactivator activation linker in which the aryl substituent is operably linked to one terminus of the moiety, for example at the location of the furin cleavage site, and the carbamoyl functionality is operably linked to another moiety. In the system devised by Papot et al, cleavage by glucuronidase will result in elimination of the aryl malonaldehyde and activation of the modified antibody derivative or proactivator. Similar elimination events are known to take place following hydrolysis of the lactam moiety of linkers based on 7-aminocephalosporanic acid, and enzymatically activated prodrugs based on beta-lactam antibiotics or related structures are well known in the art. For example Alderson et al. Bioconjug Chem. 17(2):410-8 (2006) teach the creation of a 7-aminocephalosporanic acid-based linker that undergoes elimination and scission of a carbamate moiety in similar fashion to that of the aryl malonaldehydes disclosed by Papot et al. In addition, Harding et al. Mol Cancer Ther. 4(11):1791-800 (2005) teach a beta-lactamase that has reduced immunogenicity that can be favorably applied as an activator for a prodrug moiety based on a 7-aminocephalosporanic acid nucleus.

In yet another embodiment the disabling moiety cleavable linker or proactivator activation linker is a peptide but is operably linked by a flexible nonpeptide linker at either or both termini in the same location as the natural furin-like protease cleavage site, or in parallel to the natural furin-like cleavage site. In such embodiments the activator is a cognate protease or peptide hydrolase recognizing the peptide of the disabling moiety cleavable linker or proactivator activation linker. In a doubly triggered disabled antibody derivative, the proactivator activation linker is the substrate of another (pro)activator, either an activator or a natively activatable proactivator. In such a disabled antibody derivative the action of two (pro)activators is required to activate the disabled antibody derivative.

Activators and Proactivators

The present compositions and methods provides a facility for multiple independent targeting events to further restrict or make selective the recognition of cells that are desired to be inhibited or destroyed, through the use of disabled antibody derivatives and activators or proactivators. The activators include a target recognition moiety as described above and an activator domain. Proactivators include a target recognition moiety as described above and an activator domain that is provided in an inactive form but is activated at the cell surface, e.g., by another activator or by an enzyme present in the environment of the cell.

As described herein, to allow the effector region disabling moiety to be released and the effector region enabled, the disabling moiety cleavable linker must be severed. Thus an activator or endogenous activating factor acts on the disabling moiety cleavable linker to directly or indirectly sever the linkage between the antibody or antibody derivative and the effector region disabling moiety. Several methods of direct or indirect severance are known in the art, for example as taught by US20100055761A1, which is incorporated by reference herein. Exemplary severance methods of the latter reference include by protease cleavage, or by phosphatase removal of a phosphate blocking an endogenous cleavage site, such as a furin or furin-family protease cleavage site. Upon removal of the blocking phosphate, the endogenous furin or furin-family proteases of the target cell cause cleavage of the activator target sequence.

In some embodiments, the action of the activator or endogenous activating factor results in a residual fragment or moiety attached to the antibody or antibody derivative that does not interfere with the engagement of the effector functions of the immune system. In some cases the residual fragment can actively participate in the engagement of effector functions, e.g., by contributing to the affinity of the antibody or antibody derivative for one or more immune system effector molecules; the residual fragment could be selected to favor Fc receptor engagement or complement deposition.

Proactivators

An activator can be provided in a latent form called a proactivator that is activated by another activator or by the environment of a cell surface. Proactivators are preferred for use in the present methods because they provide the activator domain in an inert form, and thereby reduce the likelihood of adverse reactions caused by the active form of the activator domain, such as the cleavage of undesired substrates by an activator that is an enzyme. As noted above, the proactivators described herein contain a proactivator activation linker, which when cleaved leaves the activator domain in an active state. The proactivator activation linker has a function similar to that of the activating cleavage site of a zymogen. Prior to modification of the proactivator activation linker the proactivators are inactive (i.e., they cannot directly or indirectly cleave, and thereby activate, the modified antibody derivative). Examples of such proactivators include proteases specific for the modified antibody derivative disabling moiety cleavable linker that are presented in zymogen form, such that the cleavage of the zymogen to convert the proactivator to an activator requires a second protease. Examples of proactivators that are themselves the target of natively present activators or exogenous activators or proactivators include zymogens of targeted granzyme B bearing an enterokinase-susceptible peptide at the location of the zymogen activating cleavage, and zymogens of targeted granzyme B bearing a furin-susceptible peptide at the location of the zymogen activating cleavage.

An example of a proactivator activator would be an enterokinase fusion protein that can be independently targeted to the target cell and act upon a zymogen of granzyme B bearing an enterokinase-susceptible peptide at the location of the zymogen-activating cleavage. Such enterokinase would be presented in a proactivator form if it were itself a zymogen, such as zymogen form that could be activated by cleavage by furin or furin-like (PCSK family) protease.

The activation of proactivators can occur through events that cleave or modify proactivator activation moieties that allow the proactivators to be activated or converted to a form that can be natively activated. Proactivator activation moieties can be polypeptide cleavage sequences, altered polypeptide cleavage sequences, or cleavable linkers that restrict or make selective the activation of the proactivator. Each proactivator activation linker must have a corresponding activator capable of modifying such proactivator activation linker in a way that causes the proactivators bearing such proactivator activation linker to be activated or converted to a form that can be natively activated.

Of particular utility are proactivators that are activated by proprotein convertase subtilisin kexin (PCSK) family proteases, ubiquitous proteases that are found in the secretory pathway and/or on the cell surface of nearly all eukaryotic cells. PCSK family protease-activatable proactivators are a preferred embodiment of proactivators that are not themselves activated by other activators in this disclosure.

Furin is the most widely known member of the PCSK family of membrane-anchored serine proteases. With the exception of PCSK9, the members of this family are thought to cleave substrates that present themselves in the course of transit and maturation along the secretory pathway of eukaryotic cells. There are 8 members of the family encoded in the human genome, and furin itself is also known as PCSK3. With the exception of PCSK9, members of the family typically recognize sequences of the form 100(R (SEQ ID NO:72), preferably, RXKR (SEQ ID NO:73) or RXRR (SEQ ID NO:74), and can exert higher activity against sequences that contain flanking RA, for example RARXRR (SEQ ID NO:75) or RARXKR (SEQ ID NO:76).

Activator Domains

A number of activator domains can be used in the present compositions and methods. As used herein, an activator domain is one that acts on the disabling moiety cleavable linker, or that acts on the proactivator activation linker of a proactivator. In preferred embodiments, the activator domain will cleave the linker directly.

As one example, the activator domain can be the catalytic domain of a hydrolytic enzyme, such as a human hydrolytic enzyme, such as a human protease, nuclease, phosphodiesterase, phosphatase or glycohydrolase, and more preferably an exogenous human protease, nuclease, phosphodiesterase, phosphatase or glycohydrolase, or a nonhuman hydrolytic enzyme, including a viral protease, such as a retroviral protease or a potyviral protease or a flaviviral protease or picornaviral protease or a coronaviral protease.

In some embodiments, the action of the activator domain is not to cause direct cleavage of the disabling moiety cleavable linker or proactivator activation linker but to transform, modify, or expose a cleavage site on the disabling moiety cleavable linker or proactivator activation linker, making it susceptible to the action of enzymes natively present on or in the vicinity of the target cell or other activators, for example by removing a phosphate moiety that blocks the action of a furin protease, e.g., as taught by US 2010/0055761. The disabling moiety cleavable linker can contain a cleavage site for an enzyme that in its native state is insusceptible to cleavage because of one or more synthetic or post-translational modifications to the cleavage site or its vicinity that impair the action of the enzyme, e.g., as taught by US 2010/0055761. In these cases, the action of the activator domain is to remove or alter such modifications in order to allow the enzyme to cleave the linker. In the example presented in US 2010/0055761, a furin site having the sequence RVRRAS (SEQ ID: 29) was shown to be recognized by the protein Ser/Thr kinase PKA, allowing the serine residue to be phosphorylated. In the phosphorylated state the sequence was not recognized by furin. However upon treatment of the phosphorylated site with a protein phosphatase, the furin sensitivity was restored. The enzyme natively present on or in the vicinity of the target cell can be ubiquitously present, such as a PCSK family enzyme, or can be selectively present, for example an enzyme that is present only on or in the vicinity of cells of a particular developmental lineage, such as the prostate specific membrane antigen or the prostate specific antigen, found on or in the vicinity of prostate cells, respectively, or the hepatic protease prostasin. Several matrix metalloproteinases such as MMP-2 and MMP-9 are enriched in the vicinity of human cancers (Roomi et al. Oncol. Rep. 21(5): 1323-33 (2009)), and so can also be used.

Endogenous Activating Factors

In some embodiments, the invention provides for a disabling moiety cleavable linker or proactivator activation linker that is susceptible to the action of an endogenous activating factor. Such a factor can be a protease operably present on, in, or in the vicinity of a target cell, such as secreted protease, such as prostate specific antigen (a chymotryptic-like protease), or a cell-surface-linked protease, such as a member of the family of matrix metalloproteases such as TACE or a member of the transmembrane protease, serine (TMPRSS) family, such as TMPRSS2. The endogenous activating factor can also be a phosphatase, such as prostatic acid phosphatase, that is capable of activating a disabling moiety cleavable linker that is protected from cleavage by endogenous proteases such as furin by a phosphorylated amino acid residue. In some embodiments, endogenous activating factors confer specificity on the action of the disabled antibody derivatives of the invention by providing for a therapeutically favorable restriction of the activation confined to the vicinity of the target, thereby preventing the activation of the disabled antibody derivative on, in or in the vicinity of other cells or tissues on which the action of the antibody would be undesirable.

Exogenous Protease Selection

In some embodiments, the activator domain of the activator or proactivator comprises an exogenous protease. An exogenous protease and corresponding cleavage site can be chosen for the present compositions and methods based on the following considerations. The protease is preferably capable of cleaving a disabling moiety cleavable linker or a proactivator activation linker without significantly inactivating the targets of its action or itself. The protease is preferably not naturally found in or on cells that are desired to be spared, with the exception that the protease can be naturally found in such cells if its natural location does not allow it to activate an externally administered disabled antibody derivative or (pro)activator. For example, an intracellular protease such as a caspase can be used if the modified antibody derivative or (pro)activator must be activated at the surface of the cell or in some intracellular vesicular compartment that does not naturally contain the intracellular protease, such as the endosome, golgi, or endoplasmic reticulum. In such cases the cells that are desired to be spared could contain the protease but the protease would not activate the disabled antibody derivative or the proactivator.

The catalytic activity of the protease is preferably stable to in vivo conditions for the time required to exert its therapeutic effect in vivo. If the therapeutic program requires the repeat administration of the protease, the protease is preferably resistant to interference by the formation of antibodies that impair its function, for example neutralizing antibodies. In some embodiments the protease has low immunogenicity or can be optionally modified or substituted to reduce immunogenicity or can be optionally modified or substituted to reduce the effect of antibodies on its activity. The protease preferably has low toxicity itself or has low toxicity in the form of its operable linkage with one or more target binding moieties. The protease is preferably stable or can be made to be stable to conditions associated with the manufacturing, storage and distribution of therapeutic products. The protease is preferably a natural protease, a modified protease, or an artificial enzyme.

Desirable proteases of the present compositions and methods include those known to have highly specific substrate selectivities, either by virtue of an extended catalytic site or by the presence of specific substrate-recognition modules that endow a relatively nonselective protease with appropriate specificity. Proteases of limited selectivity can also be made more selective by genetic mutation or chemical modification of residues close to the substrate-binding pocket.

As is known in the art, many proteases recognize certain cleavage sites, and some specific, non-limiting examples are given below. One of skill in the art would understand that cleavage sites other than those listed are recognized by the listed proteases, and can be used as a general protease cleavage site according to the present compositions and methods.

Proteases of human origin are preferred embodiments of the present compositions and methods due to their reduced likelihood of eliciting a neutralizing immune reaction. A human protease utilizing any catalytic mechanism, i.e., the nature of the amino acid residue or cofactor at the active site that is involved in the hydrolysis of the peptides and proteins, including aspartic proteases, cysteine proteases, metalloproteases, serine proteases, and threonine proteases, can be useful for the present compositions and methods.

Because model studies of a potential therapeutic agent must be conducted in animals to determine such properties as toxicity, efficacy, and pharmacokinetics prior to clinical trials in human, the presence of proteinase inhibitors in the plasma of animals could also limit the development of therapeutics comprising proteolytic activities. The proteinase inhibitors in animal plasma can possess inhibitory properties that are different from their human counterparts. For example human GrB has been found to be inhibited by mouse serpina3n, which is secreted by cultured Sertoli cells and is the major component of serpina3 ($\alpha$1-antichymotrypsin) present in mouse plasma (Sipione et al., J. Immunol. 177:5051-5058 (2006)). However, the human $\alpha$1-antichymotrypsin has not been shown to be an inhibitor of human GrB. The difference between mouse and human plasma protease inhibitors can be traced to their genetic differences. Whereas the major human plasma protease inhibitors, $\alpha$1-antitrypsin and $\alpha$1-antichymotrypsin, are each encoded by a single gene, in the mouse they are represented by clusters of 5 and 14 genes, respectively. Even though there is a high degree of overall sequence similarity within these clusters of inhibitors, the reactive-center loop (RCL) domain, which determines target protease specificity, is markedly divergent. To overcome inhibition by mouse protease inhibitors, the screening and mutagenesis strategies described herein can be applied to identify mutant proteases that are resistant to inhibition by inhibitors present in the animal model of choice.

Human Granzymes

Recombinant human granzyme B (GrB) and/or one or more of its derivatives can be used as an exogenous protease within the activator domain of the (pro)activator fusion protein. GrB has high substrate sequence specificity with a consensus recognition sequence of IEPD (SEQ ID NO:77) and is known to cleave only a limited number of natural substrates. GrB is found in cytoplasmic granules of cytotoxic T-lymphocytes and natural killer cells, and thus should be useful for the present compositions and methods provided these cells are not the targeted cells. The optimum pH for GrB activity is around pH 8, but it retains its activity between pH 5.5 and pH 9.5 (Fynbo et al., Protein Expr. Purif. 39:209 (2005)). GrB cleaves peptides containing IEPD (SEQ ID NO:77) with high efficiency and specificity (Casciola-Rosen et al., J. Biol. Chem. 282:4545-4552 (2007)). Because GrB is involved in regulating programmed cell death, it is tightly regulated in vivo. In addition, GrB is a single chain and single domain serine protease, which could contribute to a simpler composite structure of the fusion protein. Moreover, GrB has recently been found to be very stable in general, and it performs very well in the cleavage of different fusion proteins (Fynbo et al., Protein Expr. Purif. 39:209 (2005)).

Any member of the granzyme family of serine proteases, e.g., granzyme A and granzyme M, can be used as the recombinant protease component of the protease fusion in this invention. For example, granzyme M (GrM) is specifically found in the granules of natural killer cells and can hydrolyze the peptide sequence KV(Y)PL(M) (SEQ ID NO:78) with high efficiency and specificity (Mahrus et al., J. Biol. Chem. 279:54275 (2004)).

In designing and utilizing protease fusions of the invention, it should be noted that proteinase inhibitors can hamper the proteolytic activities of protease fusion proteins. For example, GrB is specifically inhibited by intracellular proteinase inhibitor 9 (PI-9), a member of the serpin superfamily that primarily exists in cytotoxic lymphocytes (Sun et al., J. Biol. Chem. 271:27802 (1996)) and has been detected in human plasma. GrB can also be inhibited by α1-protease inhibitor (α1PI) that is present in human plasma (Poe et al., J. Biol. Chem. 266:98 (1991)). GrM is inhibited by α1-antichymotrypsin (ACT) and α1PI (Mahrus et al., J. Biol. Chem. 279:54275 (2004)), and GrA is inhibited in vitro by protease inhibitors antithrombin III (ATIII) and α2-macroglobulin (a2M) (Spaeny-Dekking et al., Blood 95:1465 (2000)). These proteinase inhibitors are also present in human plasma (Travis and Salvesen, Annu. Rev. Biochem. 52:655 (1983)).

One approach to preserve proteolytic activities of granzymes is to utilize complexation with proteoglycan, since the mature and active form of GrA has been observed in human plasma as a complex with serglycin, a granule-associated proteoglycan (Spaeny-Dekking et al., Blood 95:1465 (2000)). Glycosaminglycan complexes of GrB have also been found proteolytically active (Galvin et al., J. Immunol. 162:5345 (1999)). Thus, it can be possible to keep granzyme fusion proteins active in plasma through formulations using chondroitin sulfates.

Engineered Granzymes

Granzymes can be subjected to diversification by systematic or random alteration of the primary sequence to generate enzyme variants with altered specificities or other properties beneficial for their role as (pro)activators, or proactivator (pro)activators. Granzyme variants that recognize sequences other than IEPD and related motifs are useful for the present compositions and methods because they can be produced in mammalian cells without causing toxicity to the cell in which they are expressed. In addition, such enzymes have lower toxicity against cells to which they are targeted, since they do not induce the cleavage of caspases and other proteins that can induce apoptosis or damage the cell. A preferred form of engineered (pro)granzyme B for this invention is the enzyme identified as (pro)granzyme B v3 (SEQ ID NO: 18).

Cathepsins and Caspases

Any member of the cathepsins (Chwieralski et al., Apoptosis 11:143 (2006)), e.g., cathepsin A, B, C, D, E, F, G, H, K, L, S, W, and X, can also be used as the recombinant protease for the present compositions and methods. Cathepsins are proteases that are localized intralysosomally under physiologic conditions, and therefore have optimum activity in acidic environments. Cathepsins comprise proteases of different enzyme classes; e.g., cathepsins A and G are serine proteases, cathepsins D and E are aspartic proteases. Certain cathepsins are caspases, a unique family of cysteine proteases that play a central role in the initiation and execution phases of apoptosis. Among all known mammalian proteases, only the serine protease granzyme B has substrate specificity similar to the caspases.

All caspases, including caspase-1, -2, -3, -4, -5, -6, -7, -8, -9 and more, show high selectivity and cleave proteins adjacent to an aspartate residue (Timmer and Salvesen, Cell Death Diff 14:66-72 (2007)). Because the naturally occurring inhibitors of caspases, e.g., IAPB, are usually located intracellularly (LeBlanc, Prog. Neuropsychopharmacol. Biol. Psychiatry 27:215 (2003)), the probability of inhibition in plasma is dramatically reduced. Although PI-9 inhibits caspase-1 and caspase-4 at moderate rates, it does not inhibit caspase-3 (Annand et al., Biochem. J. 342:655 (1999)).

Other Human Proteases

Many human proteases, including those have been identified as certain disease markers secreted by diseased cells, or associated with cancer invasion and metastasis, can be useful for the present compositions and methods as the heterologous protease. These proteases are well studied and detailed information on proteolytic activity and sequence selectivity is available. Examples of such proteases include urokinase plasminogen activator (uPA), prostate-specific antigen (PSA), renin, and MMP-2. Additional examples include the caspases, elastase, kallikreins, the matrix metalloprotease (MMP) family, the plasminogen activator family, as well as fibroblast activation protein.

In certain cases, the protease involved in one disease can be useful for the treatment of another disease that does not usually involve its overexpression. In other instances, the concentration of the secreted protease at native level can not be sufficient to activate corresponding modified antibody derivative or (pro)activator to the extent that is necessary for targeted cell killing, i.e., is not operably present on the targeted cells. Additional proteolytic activity delivered to the cells through targeted protease fusion would provide desired modified antibody derivative or (pro)activator activation. In one embodiment, the protease fusion could have the same sequence specificity as the protease secreted by the diseased cells. In another embodiment, it can be desirable to use a combination of multiple, different, proteolytic cleavage activities to increase overall cleavage efficiency, with at least one of the proteolytic activity being provided by a targeted protease fusion.

Additional examples of endogenous proteases include those have been identified as certain disease markers, which are upregulated in certain disease. Non-limiting examples of such proteases include urokinase plasminogen activator (uPA) prostate-specific antigen (PSA), renin, and MMP-2

Alternatively, potential candidate proteases can be screened in vitro by interactions with known proteinase inhibitors in plasma or with human plasma directly to avoid potential complications posed by these proteinase inhibitors. Alternatively, proteases for which cognate inhibitors are found in plasma can be engineered to provide mutant forms that resist inhibition. For example, in vitro E. coli expression-screening methods have been developed to select mutant proteases that are resistant to known HIV-1 protease inhibitors (Melnick et al., Antimicrob. Agents Chemother. 42:3256 (1998)).

Retroviral Proteases

Recombinant human retroviral proteases can also be used for the present compositions and methods. Human retroviral proteases, including that of human immunodeficiency virus type 1 (HIV-1) (Beck et al., 2002), human T cell leukemia viruses (HTLV) (Shuker et al., Chem. Biol. 10:373 (2003)), and severe acute respiratory syndrome coronavirus (SARS), have been extensively studied as targets of anti-viral therapy. These proteases often have long recognition sequences and high substrate selectivity.

Coronaviral Proteases

Coronaviral or toroviral proteases are encoded by members of the animal virus family Coronaviridae and exhibit high cleavage specificity. Such proteases are another preferred embodiment for the present compositions and methods (Fan et al. Biochem. Biophys. Res. Commun. 329(3): 934-940 (2005)).

Picornaviral Proteases

Picornaviral proteases can also be used for the present compositions and methods. Such picornaviral proteases have been studied as targets of anti-viral therapy, for example human Rhinovirus (HRV) 3C protease (Cordingley et al. J. Biol. Chem. 265(16):9062-9065 (1990)).

Potyviral Proteases

Potyviral proteases are encoded by members of the plant virus family Potyviridae and exhibiting high cleavage specificity, and are another preferred embodiment for the present compositions and methods. For example, tobacco etch virus (TEV) protease has very high substrate specificity and catalytic efficiency, and is used widely as a tool to remove peptide tags from overexpressed recombinant proteins (Nunn et al., J. Mol. Biol. 350:145 (2005)). TEV protease recognizes an extended seven amino acid residue consensus sequence E-X—X—Y—X-Q↓S/G (where X is any residue) (SEQ ID NO: 24) that is present at protein junctions. Those skilled in the art would recognize that it is possible to engineer a particular protease such that its sequence specificity is altered to prefer another substrate sequence (Tozser et al., FEBS J. 272:514 (2005)).

Proteases of Other Origins

Since proteases are physiologically necessary for living organisms, they are ubiquitous, being found in a wide range of sources such as plants, animals, and microorganisms (Rao et al. Microbiol. Mol. Biol. Rev. 62(3):597-635 (1998)). All these proteases are potential candidates for the present compositions and methods.

In a preferred embodiment, PEGylation can be utilized to reduce the immunological potential of proteases for the present compositions and methods, particularly for those that are of non-human origins. PEGylation can confer additional benefits to protease fusion proteins, such as improved plasma persistence and reduced non-specific cell binding.

Recombinant DNA Construct Design and Sequence Modification

Many proteases found in nature are synthesized as zymogens, i.e., as catalytically inactive forms in which an inhibitory peptide binds to and masks (disables) the active site, or in which the active site is nonfunctional in the initial state because the presence of an inhibitory peptide alters the conformation of the active site. Zymogens are typically activated by cleavage of the inhibitory peptide. In one embodiment of the present compositions and methods, the exogenous protease of the disabled antibody derivative or (pro)activator activator is in the form of a zymogen, which can be activated by another exogenous protease or by an endogenous protease. Depending on the location of the inhibitory peptide in the primary sequence, such zymogens are either favorably N-terminally situated (when the inhibitory peptide is located at the N-terminus of the zymogen) or C-terminally situated (when the inhibitory peptide is located at the C-terminus of the zymogen). When the protease moiety of the disabled antibody derivative or (pro)activator activator is linked to the target binding moiety by chemical or enzymatic linkage, the inhibitory peptide can be located at either the N-terminus or the C-terminus, since either or both termini can be free as a result of an operable linkage to a target binding moiety taking place at a location other than the N- or C-terminus.

Accordingly, one embodiment of the present compositions comprises a recombinant proactivator that can be activated by another protease. Such a proactivator comprises a proactivator activation linker, an activator domain, and a target binding moiety. The action of the other protease either cleaves the proactivator activation linker to afford an active protease fusion. The other protease can be naturally found on or in the vicinity of the target cell, in which case the proactivator is said to be natively activatable, and the activating protease is said to be an endogenous protease; or the other protease can be conveyed to the vicinity of the target cell by one or more target binding moieties provided by the invention, in which case it is considered to be an exogenous protease.

Many zymogens comprise active enzymatic moieties in which the inhibitory peptide physically occupies the active site substrate binding cleft, and for which the cleavage site that releases the inhibitory peptide lies distal to the cleft. Among members of a class of proteases for which the active site is composed of residues at the N-terminus of the polypeptide chain, and for which the alpha amino group comprises the active site nucleophile or an important determinant of catalytic efficacy, artificial zymogens can be formed by directly appending a protease cleavage site to the N-terminus. In such cases the activating protease must be capable of cleaving the bond between the recognition site and the desired N-terminal residue. In a preferred embodiment, the activating protease has no sequence requirement for the residue directly following the cleavage location, or preferentially cleaves substrates for which the residue directly following the cleavage location is the same as the reside at the N-terminus of the mature protease. Examples of activating proteases that directly cleave the disabling moiety cleavable linker or proactivator activation linker and their corresponding cleavage sites include, but are not limited to thrombin, Factor Xa and enterokinase. Specifically, a GrB fusion containing DDDDK (SEQ ID NO: 71), attached to its N-terminus can be generated and activated by treatment with enterokinase. Specifically, GrB-anti-CD19, GrB-anti-CD5, and GrB-(YSA)2 fusions are so constructed.

In another embodiment of the present compositions and methods, the proactivator can be activated in vivo by a proteolytic activity that is endogenous to the targeted cells. One example of such endogenous protease is furin, an endosomal protease that is ubiquitously expressed in various mammalian cells. Specifically, a furin recognition site can replace a natural zymogen cleavage site to provide a zymogen that is activated by proximity to the cell surface or by internalization. In the case of proteases for which the N-terminal residues comprise important determinants of the active site, such a furin recognition site can be directly appended to the N-terminus of the proactivator. For example, a furin cleavage site can be added to the N-terminus of Granzyme B or Granzyme M to provide an natively activatable proactivator. Specifically, a GrB fusion construct containing two C-terminal 12 residue target binding YSA peptides and an N-terminal furin cleavage site is prepared for the production of GrB-(YSA)2.

Proactivators containing a furin cleavage site are preferably produced in expression systems that do not contain native furin activity, e.g., in *E. coli*. A proactivator that is activatable in the targeted human cells by contact with PCSK family members such as furin is an example of a natively-activatable proactivator. One important advantage of such a proactivator, as compared to an activator, is that the proactivator can be combined with a modified antibody derivative for simplified therapeutic delivery. Such mixtures of modified antibody derivatives and proactivators will show reduced activation prior to accumulation upon the targeted cells.

Proactivator proteins that are activated by proteolytic cleavage by an endogenous protease activity of the target cell can be designed so that the proteolytic cleavage severs the operable linkage between the target binding moiety and the activator domain. For example in a translational fusion, the inhibitory peptide might lie between the target binding moiety and the activator domain. Or in a chemically or enzymatically induced crosslinking of target binding moiety to the activator domain, the crosslinking can be induced via residues on the proactivator activation linker that are not functionally required for inhibition of the activator domain.

Strategies to Reduce Potential Side Effects of Protease Fusions

Application of human proteases for modified antibody derivative activation can encounter complications if the protease of choice is capable of eliciting unintended biological effects in addition to the designed disabled antibody derivative activation. For example, many proteases, including granzymes and caspases, can promote cell death through involvement in an apoptotic cascade. Immunotoxins composed of granzyme B and a cell surface targeting domain have been developed as cytotoxic agents against certain diseased cell populations (Liu et al. Neoplasia 8:125-135 (2006), Dalken et al. Cell Death Differ. 13:576-585, Zhao et al. J. Biol. Chem. 279:21343-21348 (2004), U.S. Ser. No. 07/101,977). To eliminate such potential side effects in the context of present compositions and methods, it is preferable to use a cell surface target that does not internalize upon binding as the intended target for the protease fusion protein. In such a case the disabled antibody derivative activation can be accomplished on the cell surface, but a toxic effect will not be generated by the activator acting alone.

Another approach is to mutate the candidate proteases so that they confer altered sequence specificity, thus are no longer preferentially bound to and cleaving at the native cleavage sites. Such engineered proteases are likely to have lower toxicities that are caused by biological cascade downstream from the proteolytic processing at the naturally occurring cleavage sequence. Selection or screening methods that are suited for such applications have been developed (e.g., Sices et al. Proc. Natl. Acad. Sci. USA 95:2828-2833 (1998) and Baum et al. Proc. Natl. Acad. Sci. USA 87:10023-10027 (1990)), and have been used select mutant proteases that are capable of cleaving a sequence that is different from the native proteolytic site of the original protease (e.g., O'Loughlin et al. Mol. Biol. Evol. 23:764-722 (2006), Han et al. Biochem. Biophy. Res. Commun. 337:1102-1106 (2005), and Venekei et al. Protein Eng. 9:85-93 (1996)). Because the cleavage site and the inhibitor RCL often possess sequence similarity, changing the proteolytic specificity of a protease can also result in its resistance to inhibition by its known proteinase inhibitors. Examples are available where the selection or screening for altered cleavage site, lower cytotoxicity, and altered inhibition profile are accomplished to simultaneously (O'Loughlin et al. Mol. Biol. Evol. 23:764-722 (2006)). Specifically, granzyme B is modified to provide altered forms of granzyme with reduced spontaneous toxicity through altered substrate specificity.

Further modifications can be engineered to increase the activity and/or specificity of proteases. These modifications include PEGylation to increase stability to serum or to lower immunogenicity, and genetic engineering/selection can produce mutant proteases that possess altered properties such as resistance to certain inhibitors, increased thermal stability, and improved solubility.

Strategies to Prevent Inhibition by Proteinase Inhibitors in Plasma and in Cells In designing and utilizing protease fusions of the invention, it should be noted that proteinase inhibitors can hamper the proteolytic activities of protease fusion proteins. For example, GrB is specifically inhibited by intracellular proteinase inhibitor 9 (PI-9), a member of the serpin superfamily that primarily exists in cytotoxic lymphocytes (Sun et al., J. Biol. Chem. 271:27802 (1996)) and has been detected in human plasma. GrB can also be inhibited by α1-protease inhibitor (α1PI) that is present in human plasma (Poe et al., J. Biol. Chem. 266:98 (1991)). GrM is inhibited by α1-antichymotrypsin (ACT) and α1PI (Mahrus et al., J. Biol. Chem. 279:54275 (2004)), and GrA is inhibited in vitro by protease inhibitors antithrombin III (ATIII) and a2-macroglobulin (a2M) (Spaeny-Dekking et al., Blood 95:1465 (2000)). These proteinase inhibitors are also present in human plasma (Travis and Salvesen, Annu. Rev. Biochem. 52:655 (1983)).

One approach to preserve proteolytic activities of granzymes is to utilize complexation with proteoglycan, since the mature and active form of GrA has been observed in human plasma as a complex with serglycin, a granule-associated proteoglycan (Spaeny-Dekking et al., Blood 95:1465 (2000)). Glycosaminglycan complexes of GrB have also been found proteolytically active (Galvin et al., J. Immunol. 162:5345 (1999)). Thus, it can be possible to preserve the activity of granzyme fusion proteins in plasma through formulations using chondroitin sulfates.

Alternatively, potential candidate proteases can be screened in vitro by interactions with known proteinase inhibitors in plasma or with human plasma directly to avoid potential complications posed by these proteinase inhibitors. Alternatively, proteases for which cognate inhibitors are found in plasma can be engineered to provide mutant forms that resist inhibition. For example, in vitro *E. coli* expression-screening methods have been developed to select mutant proteases that are resistant to known HIV-1 protease inhibitors (Melnick et al., Antimicrob. Agents Chemother. 42:3256 (1998)).

Expression of Protease Fusion Proteins

Methods for the expression of fusion proteins are well known in the art and can be applied to the expression of the protease fusion proteins of the invention. Examples of host systems that can be used in the construction of the fusion proteins of the invention include *E. coli*, baculovirus in insect cells, *Saccharomyces cerevisiae, Pichia pastoris, Hansenula polymorpha*, mammalian cells, and vaccinia virus.

A mammalian expression system can be used to produce a protease fusion protein, particularly when a protease of human origin such as human granzyme B is selected as the protease portion of the fusion. Expressing proteases of human origin in mammalian cells has certain advantages, notably providing glycosylation patterns that are identical to or closely resemble native forms, which are not immunogenic and can help the folding, solubility, and stability of the recombinant protein.

PEGylation of Proteins

One embodiment of the present compositions and methods is the utilization of PEGylated fusion proteins. Preferred embodiments are site-specifically PEGylated fusion proteins. It is known in the art that PEGylated proteins can exhibit a broad range of bioactivities due to the site, number, size, and type of PEG attachment (Harris and Chess Nat. Rev. Drug Discov. 2(3):214-221 (2003)). A preferred composition of a fusion protein in the present compositions and methods is a PEGylated protein that contributes to a desired in vitro or in vivo bioactivity or that is insusceptible to natural actions that would compromise the activity of the fusion protein, such as formation of antibodies, nonspecific adherence to cells or biological surfaces, or degradation or elimination.

A PEG moiety can be attached to the N-terminal amino acid, a cysteine residue (either native or non-native), lysines, or other native or non-native amino acids in a protein's primary sequence. Chemistries for peptide and protein PEGylation have been extensively reviewed (Roberts et al. Adv. Drug Deliv. Rev. 54(4):459-476 (2002)). In addition, specific peptide sequences can be introduced to the primary sequence such that the peptide can be selectively modified by a PEG moiety through a sequence specific enzymatic reaction. Alternatively, a specific peptide sequence can be first modified by a chemically modified group, followed by PEG attachment at the modified group.

Cysteine residues in many proteins can be sequestered in disulfide bonds and are not preferred or available for derivatization. An additional cysteine can be introduced at a location wherein it does not substantially negatively affect the biological activity of the protein, by insertion or substitution through site directed mutagenesis. The free cysteine will serve as the site for the specific attachment of a PEG molecule, thus avoiding the product heterogeneity often observed with amine-specific PEGylation. The preferred site for the added cysteine is exposed on the protein surface and is accessible for PEGylation. The terminal region, C-terminal region, and the linker region of the fusion proteins are potential sites for the cysteine substitution or insertion.

It is also possible to genetically introduce two or more additional cysteines that are not able to form disulfide bonds. In such cases more than one PEG moiety can be specifically attached to the protein. Alternatively, a native, non-essential disulfide bond can be reduced, thus providing two free cysteines for thiol-specific PEGylation.

Free thiol groups can also be introduced by chemical conjugation of a molecule that contains a free cysteine or a thiol group, which can alternatively be modified with a reversible thiol blocking agent.

Another enzyme-catalyzed PEGylation method involves the use of sortases, a family of enzymes from gram-positive bacteria that can recognize a conserved carboxylic sorting motif and catalyze a transpeptidation reaction to anchor surface proteins to the cell wall envelope (Dramsi et al., Res. Microbiol. 156(3):289-297 (2005)). A preferred embodiment comprises the use of a *S. aureus* sortase to catalyze a transpeptidation reaction between a protein that is tagged with LPXTG (SEQ ID NO:79) or NPQTN (SEQ ID NO:80), respectively for sortase A and sortase B, and a PEGylating reagent containing a primary amino group (WO06013202A2). The peptide substrate sequences listed above are for example and non-limiting. It is known in the art that these families of enzymes can recognize and utilize different sequences as substrates, and those sequences are included here as embodiments for the present compositions and methods. The preferred peptide substrate sequences listed above are for example and non-limiting. It is known in the art that these families of enzymes can recognize and utilize different sequences as substrates, and those sequences are included here as embodiments for the present compositions and methods.

Multifunctional PEGs

While a majority of the PEGylated proteins currently on the market have one or more PEGs per protein, it is also possible to construct protein conjugates with two or more proteins attached to one PEG moiety. Heterofunctional PEGs are commercially available, and can be used to covalently link two proteins, or any two moieties of a protein.

Preferred PEGylation Sites

Because both modified antibody derivative or (pro)activators possess regions or domains that are important for their respective functions, the attachment of the bulky PEG substituents on these domains can be detrimental to their function. Accordingly a preferred embodiment of the present compositions and methods is a PEGylated fusion protein wherein the PEG substituent is situated at a position remote from the catalytic site of an activator (either a disabled antibody derivative activator or a proactivator activator) and the cell surface target recognition surface of a target binding moiety.

In one embodiment of the present compositions and methods, the preferred sites of PEGylation are located at or near the N- or C-terminal extremities of proteinaceous target binding moieties. In another embodiment of the present compositions and methods, PEGylation is directed to a linker region between different moieties within the fusion protein.

In another embodiment of the present compositions and methods, reversible PEGylation can be used.

Clearing Agents

The invention optionally includes the use of clearing agents to facilitate the removal of one or more components of the therapeutic composition, for example to reduce or prevent the activation that might result from encounter of the modified antibody derivative or one or more proactivators with an active (pro)activator outside the desired context of contact with a target cell. A clearing agent causes the removal of the administered therapeutic moieties that do not remain contacted with the target cell. The use of clearing agents in ADEPT therapy is well known in the art (see, for example, Syrigos and Epenetos, Anticancer Res. 19:605 (1999)) and can be utilized in the invention.

Methods of Killing a Targeted Cell

Described herein are methods of directing immune effector function against a target cell, such as a human cell or a human cancer cell, by contacting the target cell with (i) a disabled antibody derivative including a first target binding moiety, an antibody effector region, an effector region disabling moiety, and a disabling moiety cleavable linker; and (ii) an activator including a second target binding moiety and an activator domain. Preferably, the first target binding moiety of disabled antibody derivative and the second target binding moiety of the activator each recognize and bind the target cell; they can bind the same or different targets on the cell. Upon binding of both proteins to the target cell the disabling moiety cleavable linker of the disabled antibody derivative is selectively cleaved by the activator and the disabled antibody derivative engages one or more effector functions of the immune system, thereby destroying or inhibiting the target cell. In a separate embodiment, the disabling moiety cleavable linker is not directly cleaved by the activator domain of the activator or proactivator but is rendered by the activator domain in a form susceptible to cleavage by enzymes on or in the environment of the target cell.

The methods can be used to direct immune effector function against a target cell in a subject by administering to the subject (i) a disabled antibody derivative including a first target binding moiety, an antibody effector region, an effector region disabling moiety, and a disabling moiety cleavable linker; and (ii) an activator including a second target binding moiety and an activator domain, and/or a proactivator including a second target binding moiety and an activator domain and a proactivator activation linker. In this aspect, the first target binding moiety of disabled antibody derivative and the second target binding moiety of the activator and/or proactivator each recognize and bind the target cell, i.e., by binding to the same or different targets. Upon binding of both proteins to the target cell, the proactivator activation linker undergoes modification and the proactivator becomes activated. Thereupon the disabling moiety cleavable linker of the disabled antibody derivative is selectively cleaved and the disabled antibody derivative engages one or more effector functions of the immune system, thereby destroying or inhibiting the target cell. In a separate embodiment, the disabling moiety cleavable linker is not directly cleaved by the activator domain of the proactivator that has undergone activation but is rendered by the activator domain in a form susceptible to cleavage by enzymes on or in the environment of the target cell.

Uses of the Invention

The disabled antibody derivatives and activators/proactivators or endogenous activating factors of the invention target and destroy or inhibit specific cell subsets while sparing cells upon which the action of an antibody might have adverse consequences. The utility of the invention lies in the selective elimination of subsets of cells to achieve a desired therapeutic effect. In particular the present compositions can target neoplastic cells while sparing related normal cells, thereby providing a more specific and effective treatment for cancer. The target binding moieties can target cell surface targets on the targeted cancer cells, or on targeted non-neoplastic cells that are preferably eliminated to achieve a therapeutic benefit.

Selective destruction or inhibition of cells or cell populations can be of benefit in the treatment of diseases in which a subset of cells that can be identified or demarcated by specific patterns of cell surface target expression contribute to disease by population expansion, excessive or prolonged activity, or acquisition of abnormal or inappropriately expressed functions that contribute to the symptoms, manifestations or causative factors for a disease. For example autoimmune disorders are widely considered to result from the inappropriate response of the immune system to naturally occurring antigens. The cells that inappropriately respond can belong to a particular subset of cells, for example cells that recognize a specific antigen or plurality of antigens or cells that are derived from the subsequent proliferation and differentiation of such cells or cells that are elicited or recruited by such cells.

In one embodiment, one or both of the target binding moieties can target a cell surface target typical of a specific type of cells, for example by recognizing lineage-specific markers found on subsets of cells and representing their natural origin, such as cell surface targets that demarcate cells arising in the various organs of the body or that demarcate specific cell types within such organs, or cells to which an affiliated organ is not readily provided, such as cells of the hematopoietic, nervous, or vascular systems. In another embodiment, one or both of the target binding moieties can recognize cell surface targets aberrantly expressed on a diseased tissue, such as a cancer cell or a cell eliciting or effecting an autoimmune activity (e.g., B cells, T cells, dendritic cells, NK cells, neutrophils, leukocytes, macrophages, platelets, macrophages, myeloid cells, innate immune cells or granulocytes). One or both agents can target a cell surface marker that is aberrantly overexpressed by a cancer cell. The strategy of engaging multiple targets can be used to destroy or inhibit neoplastic or undesired cells selectively without severe damage to normal or desired cells, thereby providing treatments for neoplastic diseases including leukemias and lymphomas, such as chronic B cell leukemia, mantle cell lymphoma, acute myelogenous leukemia, chronic myelogenous leukemia, acute lymphocytic leukemia, chronic lymphocytic leukemia, multiple myeloma, acute lymphoblastic leukemia, adult T-cell leukemia, Hodgkin's lymphoma, and non-Hodgkin's lymphoma; as well as solid tumors, including melanoma, colon cancer, breast cancer, prostate cancer, ovarian cancer, lung cancer, pancreatic cancer, kidney cancer, stomach cancer, liver cancer, bladder cancer, thyroid cancer, brain cancer, bone cancer, testicular cancer, uterus cancer, soft or connective tissue tumors, nervous system tumors, and head and neck cancer.

The combination of disabled antibody derivative and activator or proactivator compositions can also be used to target non-cancerous cells, including autoreactive B or T cells, providing treatment for chronic inflammatory diseases including multiple sclerosis, rheumatoid arthritis, systemic lupus erythematosus, Sjogren's syndrome, scleroderma, primary biliary cirrhosis, Graves' disease, Hashimoto's thyroiditis, type 1 diabetes, pernicious anemia, myasthenia gravis, Reiter's syndrome, immune thrombocytopenia, celiac disease, inflammatory bowel disease, and asthma and atopic disorders.

In addition the combinatorial therapeutic composition can be used to inhibit or destroy cells in the nervous system that are responsible for pathological or undesired activity, for example nociceptive neurons in the peripheral nervous system, or to treat sensory phantom sensation, or to control neuropathic pain, such as the pain caused by diabetic neuropathy or viral reactivation.

The combination can also target cells infected by viral, microbial, or parasitic pathogens that are difficult to eradicate or that have established persistent associations with the host, providing treatment for acquired syndromes such as HIV, HBV, HCV or papilloma virus infections, tuberculosis, malaria, dengue, Chagas' disease, trypanosomiasis, leishmaniasis, or Lyme disease.

Furthermore, the combination can target specific cell types including, without limitation, parenchymal cells of the major organs of the body, as well as adipocytes, endothelial cells, cells of the nervous system, B cells or T cells or sub-populations thereof, dendritic cells, NK cells, neutrophils, leukocytes, macrophages, platelets, macrophages, myeloid cells, granulocytes, and any other specific tissue cells.

The combination can further target cells which produce disease through proliferation that is not inherently malignant, such as prostate cells in benign prostatic hypertrophy, or the cells of lipomas, chondromas, leiomyomas, pituitary adenomas, insulinomas or intestinal polyps. The combination can be applied in various syndromes leading to hyperproliferation of normal tissues or the expansion of undesired cellular compartments as for example of adipocytes in obesity.

Isolation and Purification of Fusion Proteins

A. General Strategies for Recombinant Protein Purification

There are many established strategies to isolate and purify recombinant proteins known to those skilled in the art, such as those described in Current Protocols in Protein Science (Coligan et al., eds. 2014). Conventional chromatography such as ion exchange chromatography, hydrophobic-interaction (reversed phase) chromatography, and size-exclusion (gel filtration) chromatography, which exploit differences of physicochemical properties between the desired recombinant protein and contaminants, are widely used. HPLC can also been used.

To facilitate the purification of recombinant proteins, a variety of vector systems have been developed to express the target protein as part of a fusion protein appended by an N-terminal or C-terminal polypeptide (tag) that can be subsequently removed using a specific protease. Using such tags, affinity chromatography can be applied to purify the proteins. Examples of such tags include proteins and peptides for which there is a specific antibody (e.g., FLAG fusion purified using anti-FLAG antibody columns), proteins that can specifically bind to columns containing a specific ligand (e.g., GST fusion purified by glutathione affinity gel), histidine tags with affinity to immobilized metal columns (e.g., 6×His tag immobilized on Ni2+ column and eluted by imidazole), and sequences that can be biotinylated by the host during expression or in vitro after isolation and enable purification on an avidin column (e.g., BirA).

B. Isolation and Purification of Fusion Proteins Expressed in Insoluble Form

Many recombinant fusion proteins are expressed as inclusion bodies in *Escherichia coli*, i.e., dense aggregates that consist mainly of a desired recombinant product in a non-native state. In fact, most reported DT-ScFv fusion proteins expressed in *E. coli* are obtained in insoluble forms. Usually the inclusion bodies form because (a) the target protein is insoluble at the concentrations being produced, (b) the target protein is incapable of folding correctly in the bacterial environment, or (c) the target protein is unable to form correct disulfide bonds in the reducing intracellular environment.

Those skilled in the art recognize that different methods that can be used to obtain soluble, active fusion proteins from inclusion bodies. For example, inclusion bodies can be separated by differential centrifugation from other cellular constituents to afford almost pure insoluble product located in the pellet fraction. Inclusion bodies can be partially purified by extracting with a mixture of detergent and denaturant, either urea or guanidine HCl, followed by gel filtration, ion exchange chromatography, or metal chelate chromatography as an initial purification step in the presence of denaturants. The solubilized and partially purified proteins can be refolded by controlled removal of the denaturant under conditions that minimize aggregation and allow correct formation of disulfide bonds. To minimize nonproductive aggregation, low protein concentrations should be used during refolding. In addition, various additives such as nondenaturing concentrations of urea or guanidine HCl, arginine, detergents, and PEG can be used to minimize intermolecular associations between hydrophobic surfaces present in folding intermediates.

C. Isolation and Purification of Fusion Proteins Expressed in Soluble Form

Recombinant proteins can also be expressed and purified in soluble form. Recombinant proteins that are not expressed in inclusion bodies either will be soluble inside the cell or, if using an excretion vector, will be extracellular or periplasmic. Soluble proteins can be purified using conventional methods described above.

Assays for Measuring Cell Death and/or Inhibition of Cell Growth

Various assays well known in the art are useful for determining the efficacy of the fusion protein preparations of the invention, including those assays that measure cell proliferation and death. The following are examples of many assays that can be used for analyzing the cytotoxicity of the reagents in the present compositions and methods.

A. Thymidine Incorporation Assay

The rate of proliferation of cells can be measured by determining the incorporation of [$^3$H]-thymidine into cellular nucleic acids. This assay can be used for analyzing the cytotoxic effects of the compositions of this disclosure.

B. Colony Formation Assay

Colony formation can provide a much more sensitive measure of toxicity than certain other commonly employed methods. The reason for this increased sensitivity can be the fact that colony formation is assessed while the cells are in a state of proliferation, and thus more susceptible to toxic effects. The sensitivity of the colony-formation assay, and the fact that dose and time-dependent effects are detectable, enables acute and chronic exposure periods to be investigated as well as permitting recovery studies.

C. MTS Cytotoxicity Assay

The cytotoxicity of a particular fusion protein or a combination of fusion proteins can be assessed using an MTS cytotoxicity assay. In a typical MTS assay, a tetrazolium salt (MTS: 3-(4,5-dimethylthiazol-2-yl)-5-(3-carboxymethoxyphenyl)-2-(4-sulfophenyl)-2H-tetrazolium) is reduced in metabolically active cells in the presence of the electron coupling reagent phenazine ethosulfate (PES) to form a colored formazan, which is released from the cells and quantified by spectrophotometry at 490 nm. Target cells are grown to 80-100% confluence, washed and incubated in medium containing the cytostatic or cytotoxic agents. After incubation of the cells for 2 to 24 hours, MTS and PES are added and the incubation is continued for one to four hours, after which the samples are analyzed at a wavelength of 490 nm. The amount of color produced is proportional to the number of viable cells.

Cellular Cytotoxicity Assays for Disabled Antibody Derivatives and (Pro)Activators The effector functions of the immune system that directly result in cellular cytotoxic responses are collectively referred to as antibody directed cellular cytotoxicity (ADCC), and they can be measured by a variety of means. Many ADCC assays measure the decrease in viability of the antibody-coated target cell, or the release of antibody-coated target cell contents, following engagement of those cells by effector cells bearing antibody receptors. Typically the effector cells are lymphocytes, either cytotoxic T lymphocytes or natural killer (NK) cells. In some cases the effector cells are myeloid cells, such as monocytes or macrophages. In some cases the effector cells are mixed populations of cells. In other cases they are purified from mixed populations. In yet other cases the effector cells are permanent cell lines.

A. Measurement of Effector Function Activation Using a Model Effector Cell Line

Because the activation pathways engaged by Fc receptors are similar to those engaged by the T and B cell antigen receptors, it is possible to determine the activation of the effector cell by measurement of the induction of response pathways of the T and B cell antigen receptors to determine the effectiveness of a particular antibody to induce ADCC. One convenient form of such effector cell activation assay has been provided in kit form by Promega. According to the kit manufacturer, the kit provides a T cell leukemia cell line, based on the Jurkat T cell line, that has been engineered to express the transmembrane form of CD16, the FcγRIIIa (V158) variant, and a transcriptional reporter that expresses luciferase under the control of NF-AT transcription factor binding sites. Engagement of the CD16 receptor results in activation of NF-AT, and expression of luciferase. The luciferase activity is read in a suitable instrument such as a luminometer or fluorescence plate reader.

B. Measurement of Target Cell Viability

Measurement of the decrease in viability of antibody-coated target cells, or release of the cellular components of antibody-coated target cells, can be carried out to measure the effectiveness of the candidate modified antibody derivatives of the invention. In the design of an ADCC assay it is important to include a facility for distinguishing the target cells from the effector cells. Accordingly, the target cells can be identified by prior labeling with dyes or proteins or radioisotopic compositions that are not provided to the effector cells. The proteins used for labeling can be enzymes, such as luciferases, or fluorescent proteins, such as GFP, that are expressed in the target cells to facilitate their identification and/or aid in the quantitation of their destruction. Alternatively the target cells can be inherently distinguishable from the effector cells as a result of their expression of one or more proteins that identify them as targets. For example the target cells can express one or more cell surface antigens that can be recognized by a cognate antibody. The degree of killing of the target cell population can be assessed by measurement of the release of target cell contents, such as an enzyme such as lactate dehydrogenase, or by the release of a passively incorporated radiolabel, such as $^{51}$Cr-chromate, or by an enzyme such as luciferase, beta-galactosidase, or other conveniently monitored activity. The viability of the target cell population can also be assessed by measurement of the fraction of cells that retain the ability to export fluorescent dyes or pigments that are normally removed from the cell by the action of ATP-requiring pumps that are ubiquitously expressed in mammalian cells. In this type of assay, the cells that have been killed by the action of cytotoxic effector cells lose the ability to export the fluorescent dye or pigment and become fluorescent or colored as a result. Common fluorescent dyes and pigments for this use include ethidium bromide, propidium iodide, 7-aminoactinomycin D and trypan blue. Commercial vendors provide additional fluorescent dyes that include the possibility of actively demarcating both live and dead cells. The detection of live or dead cells by flow cytometry provides, in addition, the option of detecting and removing dead effector cells, for example by selecting only the cells bearing target cell selective surface antigens for analysis.

Humoral Cytotoxicity Assays for Disabled Antibody Derivatives and (Pro)Activators Measurement of the activity of the disabled antibody derivatives and (pro)activators of the invention can also be assessed through the ability of complement proteins to reduce the viability of target cells. In most applications of this type of assay, the target cell is the sole cellular species present, and so a method to distinguish effector cells from target cells need not be provided. Generally a source of complement proteins, frequently from the same species as the cells or proteins being tested, is provided. A convenient source of complement proteins for the present compositions and methods is fresh human plasma. Alternatively complement sources from other species, such as rabbit, or guinea pig, can be used. The target cells can be labeled to facilitate the measurement of loss of viability, for example by transfection with constructs expressing marker proteins such as luciferase or fluorescent proteins. Loss of viability can be assessed by flow cytometry or by the release of cellular constituents that are then measured, such as radiolabel, enzymes, or readily monitored metabolites, such as chromium-51, GAPDH, or ATP.

Administration of Modified Antibody Derivatives and (Pro)Activators

The fusion proteins of the invention are typically administered to the subject by means of injection using any route of administration such as by intramuscular, intrathecal, subcutaneous, submucosal, or intracavitary injection as well as by intravenous or intraarterial injection. Thus, the fusion proteins can be injected systemically, for example, by the intravenous injection of the fusion proteins into the patient's bloodstream or alternatively, the fusion proteins can be directly injected at a specific site.

The modified antibody derivative of the invention can be administered prior to, simultaneously with, or following the administration of the one or more (pro)activators and optionally administered prior to, simultaneously with, for following the administration of the proactivator (pro)activators of the invention. In preferred embodiments the components are administered in such a way as to minimize spontaneous activation during administration. When administered separately, the administration of two or more fusion proteins can be separated from one another by, for example, one minute, 15 minutes, 30 minutes, one hour, two hours, six hours, 12 hours, one day, two days, one week, or longer. Furthermore, one or more of the fusion proteins of the invention can be administered to the subject in a single dose or in multiple doses. When multiple doses are administered, the doses can be separated from one another by, for example, one day, two days, one week, two weeks, or one month. For example, the fusion proteins can be administered once a week for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the fusion proteins. For example, the dosage of the fusion proteins can be increased if the lower dose does not sufficiently destroy or inhibit the growth of the desired target cells. Conversely, the dosage of the fusion proteins can be decreased if the target cells are effectively destroyed or inhibited.

While the attending physician ultimately will decide the appropriate amount and dosage regimen, a therapeutically effective amount of the fusion proteins can be, for example, in the range of about 0.0035 mg to 20 mg/kg body weight/ day or 0.010 mg to 140 mg/kg body weight/week. A therapeutically effective amount can be in the range of about 0.025 mg to 10 mg/kg, for example, about 0.025, 0.035, 0.05, 0.075, 0.1, 0.25, 0.5, 1.0, 1.5, 2.0, 2.5, 3.0, 3.5, 4.0, 5.0, 6.0, 7.0, 8.0, or 9.0 mg/kg body weight administered daily, every other day, or twice a week. In addition, a therapeutically effective amount can be in the range of about 0.05, 0.7, 0.15, 0.2, 1.0, 2.0, 3.0, 4.0, 5.0, 6.0, 7.0, 8.0, 10.0, 12.0, 14.0, 16.0, or 18.0 mg/kg body weight administered weekly, every other week, or once a month. Furthermore, a therapeutically effective amount of the fusion proteins can be, for example in the range of about 100 µg/m$^2$ to 100,000 µg/m$^2$ administered every other day, once weekly, or every other week. The therapeutically effective amount can be in the range of about 1000 µg/m$^2$ to 20,000 µg/m$^2$, for example, about 1000, 1500, 4000, or 14,000 µg/m$^2$ of the fusion proteins administered daily, every other day, twice weekly, weekly, or every other week.

In some cases it can be desirable to modify the plasma half-life of a component of the combinatorial therapeutic agent described herein. The plasma half-lives of therapeutic proteins have been extended using a variety of techniques such as those described by Collen et al., Bollod 71:216-219 (1998); Hotchkiss et al., Thromb. Haemostas. 60:255-261 (1988); Browne wt al., J. Biol. Chem. 263:1599-1602 (1988); Abuchowski et al., Cancer Biochem. Biophys. 7:175 (1984)).

The administration the fusion proteins of the invention can be by any suitable means that results in a concentration of the fusion proteins that, combined with other components, effectively destroys or inhibits the growth of target cells. The fusion proteins can be contained in any appropriate amount in any suitable carrier substance, and is generally present in an amount of 1-95% by weight of the total weight of the composition. The composition can be provided in a dosage form that is suitable for any parenteral (e.g., subcutaneous, intravenous, intramuscular, or intraperitoneal) administration route. The pharmaceutical compositions are formulated according to conventional pharmaceutical practice (see, e.g., Remington: The Science and Practice of Pharmacy (20th ed.), ed. Gennaro, Williams & Wilkins, 2000 and Encyclopedia of Pharmaceutical Technology, eds. Swarbrick and Boylan, 1988-1999, Marcel Dekker, New York).

Kits

Also provided herein are kits for use in a method described herein. The kits can include (i) a disabled antibody derivative, (ii) an activator and/or proactivator, and optionally (iii) instructions for administering the two proteins to a patient diagnosed with cancer or an autoimmune disease.

Alternatively, the kits can include (i) a disabled antibody derivative, and optionally (ii) instructions for administering (i) with an activator or proactivator to a patient diagnosed with cancer or an autoimmune disease. As another example, the kits can include (i) an activator or proactivator, and optionally (ii) instructions for administering (i) with a disabled antibody derivative to a patient diagnosed with cancer or an autoimmune disease.

Each of the components can be included in a separate container, e.g., a microcentrifuge tube or other suitable container.

EXAMPLES

The invention is further described in the following examples, which do not limit the scope of the invention described in the claims.

Example 1: Creation of Disabled Antibody Derivatives

Figure 1A:
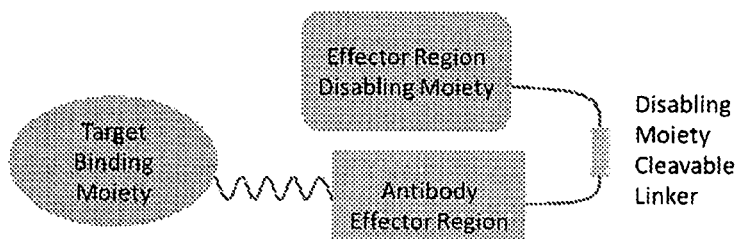
FIGS. 1A-D. Exemplary structures of a disabled antibody derivative. (A), a proactivator (B), an activator (C) and an endogenous activating factor (D). The target binding moiety of the disabled antibody derivative recognizes a different target than the target binding moiety of an activator or proactivator. An activator lacks a proactivator activation linker and does not require activation to be able to act on the disabling moiety cleavable linker. An endogenous activating factor is natively attached to the target or natively located in the vicinity of the target (e.g. because it is secreted by the target) and acts on the disabling moiety cleavable linker to release the effector region disabling moiety. The configurations as shown are nonlimiting examples, as other geometries of connection are possible.
Figure 1B:
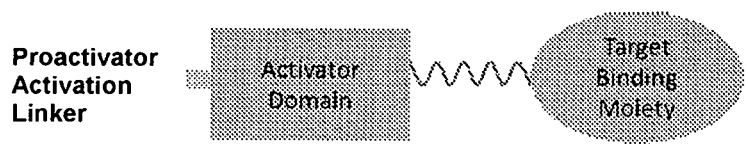
Figure 1C:
Figure 1D:
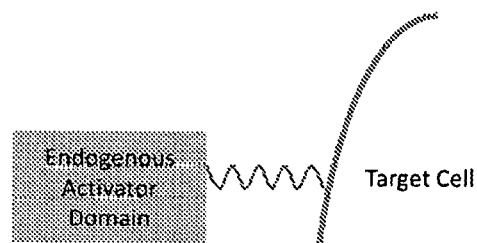
Figure 2A:
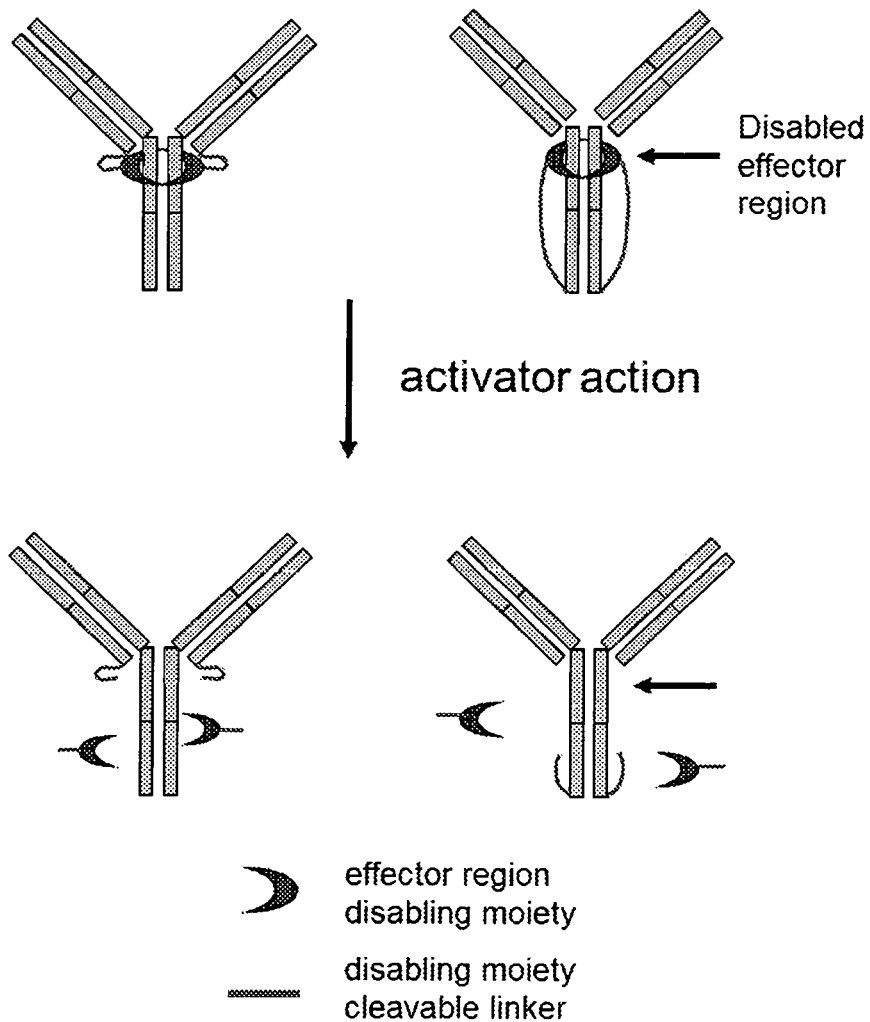
FIGS. 2A-B. Schematic representation of examples of disabled antibody derivatives. A) The light chain or the heavy chain of a therapeutic antibody can be genetically fused at its C-terminus to a disabling moiety cleavable linker and an effector region disabling moiety. The disabling moiety cleavable linker contains specific protease cleavage sites that when cleaved, allow the antibody effector region to be freed from the disabling moiety and exposes the effector region to permit interactions with the immune system. B) Organization of fusion proteins described in the Examples. HC=heavy chain, LC=light chain, H6-BAP=6 measured in Raji CD5+ cells that were incubated with a 3-fold titration of antibody from 10 ug/mL in either the presence or absence of pro-granzyme Bv3-anti-CD5. Disabled Rituximab (circles) is compared with disabled HERCEPTIN® (Squares). B) SKBr3 cells were incubated with the same set of antibodies in the presence or absence of pro-granzyme Bv3-CCPE.
Figure 2B:
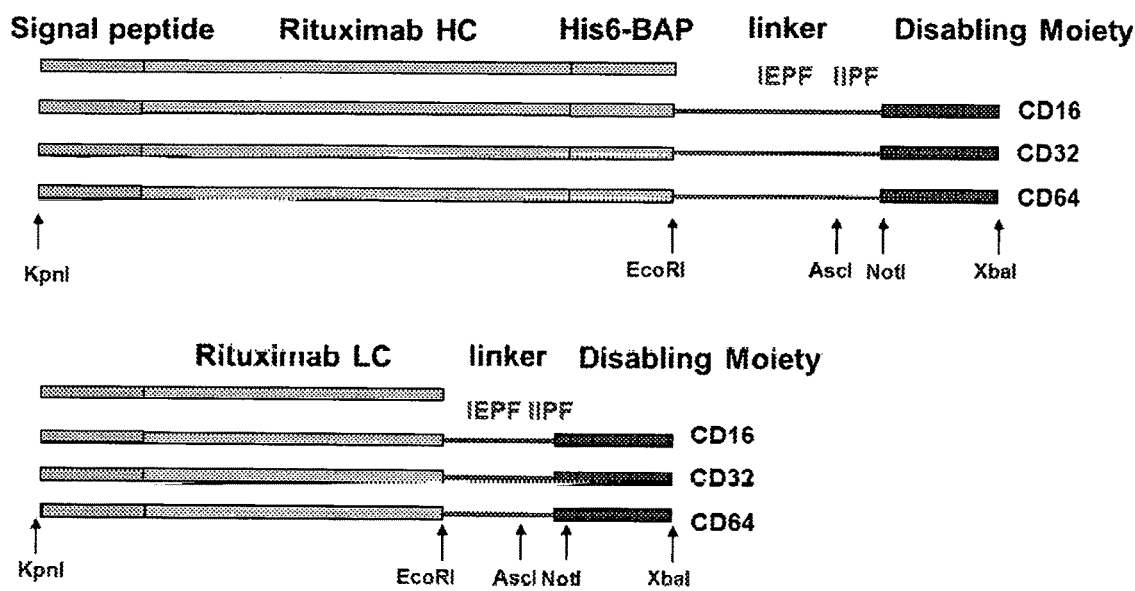
Figure 3A:
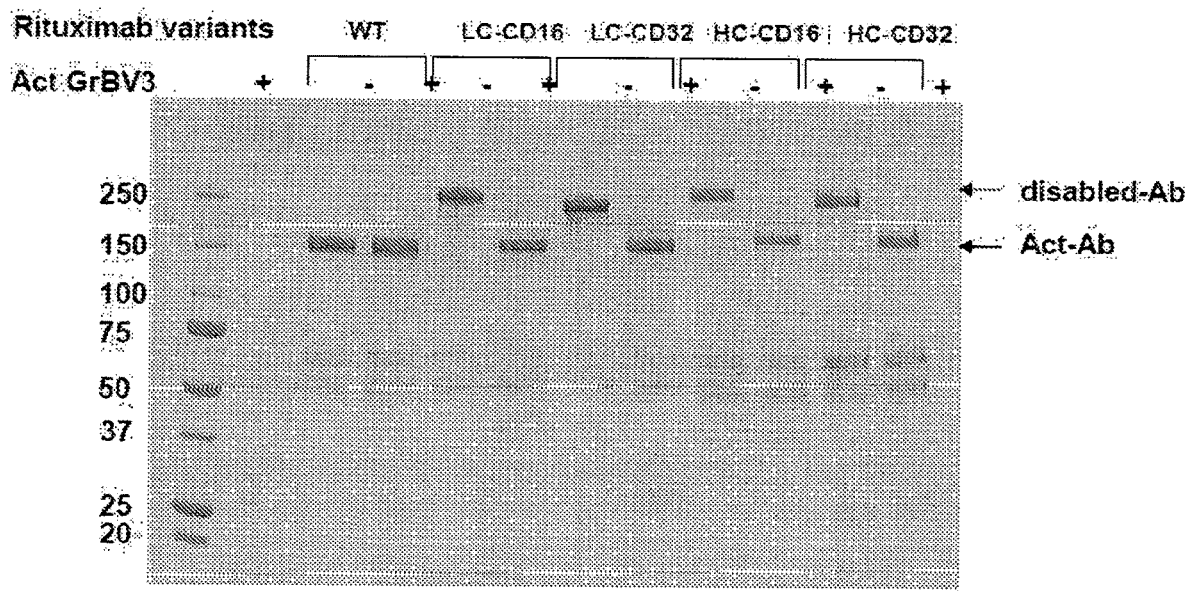
Figure 3B:
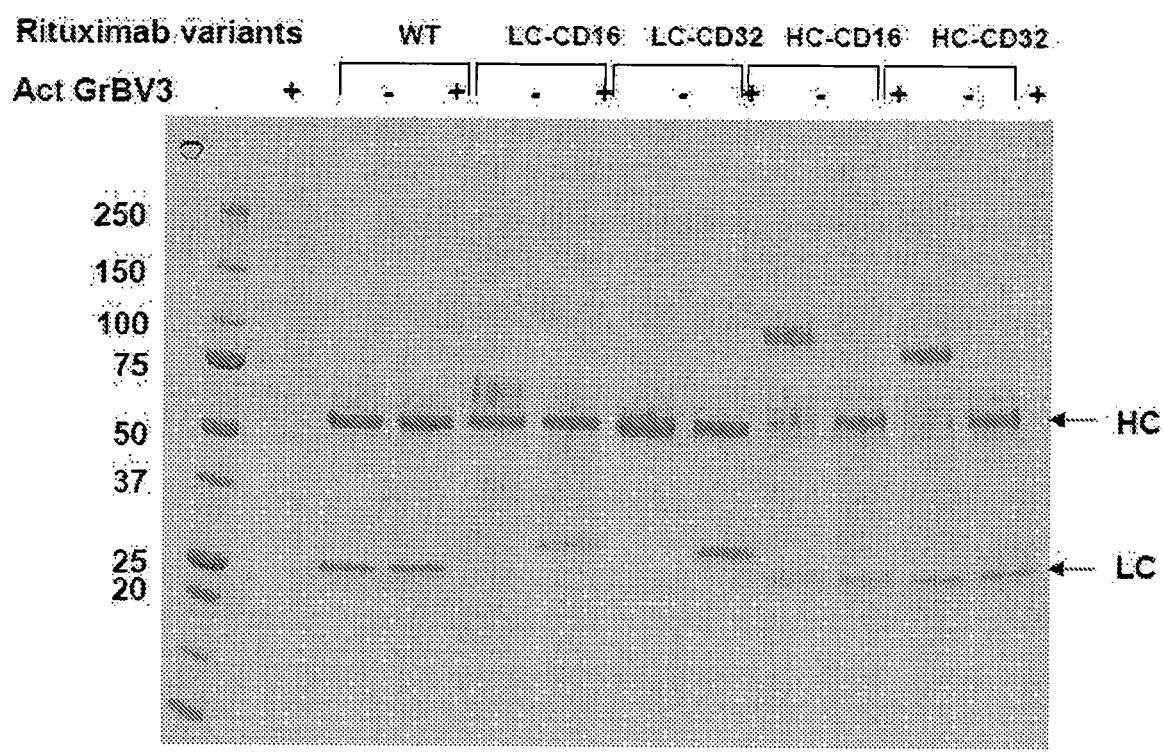

Rituximab was chosen as a model antibody that has been validated as a therapeutic agent and is known to engage both the cellular and humoral immune responses. Rituximab has been shown to activate antibody-dependent cell-mediated cytotoxicity (ADCC) and complement-dependent cytotoxicity (CDC) in vitro and in vivo. The DNA sequences encoding the light chain and heavy chain for the anti-CD20 monoclonal antibody rituximab were chemically synthesized and assembled in a mammalian expression vector. The DNA sequence for the CH1, hinge, CH2 and CH3 domains was derived from the cDNA sequence of native human IgG1 and the murine VH domain sequence was back-translated from protein to DNA. The DNA sequence for the light chain murine VL and human CL domains was back-translated from the protein sequence. A native human IgG heavy chain signal peptide was used as a secretion signal for both the recombinant heavy and light chains, and a sequence encoding a 6-histidine tag and biotin acceptor peptide was appended to the 3' end of the heavy chain coding region. The resulting tagged heavy chain protein is referred to as "unmodified" heavy chain to distinguish it from variants that have been created by fusion with disabling elements. An optimized translational initiation sequence was added to the translational start site and the DNA sequence was modified to remove potential splice donor or acceptor consensus sequences as well as some restriction enzyme recognition sites. The synthetic genes were inserted into a mammalian expression vector pTracer EF (Life Technologies) using the KpnI and XbaI sites in the polylinker region. The flexible linker and the extracellular domains of various Fc-gamma receptors were subsequently appended to these constructs. A disabling moiety cleavable linker sequence was synthesized by extending two annealed overlapping oligonucleotides (Integrated DNA Technologies) using Phusion DNA polymerase (New England Biolabs) and inserted between the EcoRI and AscI sites in the pTracer EF plasmid bearing the rituximab heavy and light chains (FIG. 2B). The sequences for the Fc binding region comprising domains 1 and 2 of the extracellular portion of the Fc-gamma receptors CD16b (Fc-gamma IIIb), CD32a (Fc-gamma IIa) and CD64a (Fc-gamma Ia) were amplified by polymerase chain reaction from cDNA clones from a Seed Laboratory plasmid archive and appended to the 3' end of the linker sequence between the NotI and XbaI sites (FIG. 2B). The disabled antibodies bear an IEPF (SEQ ID NO: 30) protease cleavage site within the flexible linker as well as an IIPF (SEQ ID NO: 31) recognition sequence at the junction of the linker and disabling moiety. A schematic diagram of all the proteins used in these examples with their coding regions and unique restriction sites is described in FIG. 2B. The DNA sequences and their encoded proteins are shown in the sequence listings.

Figure 4:
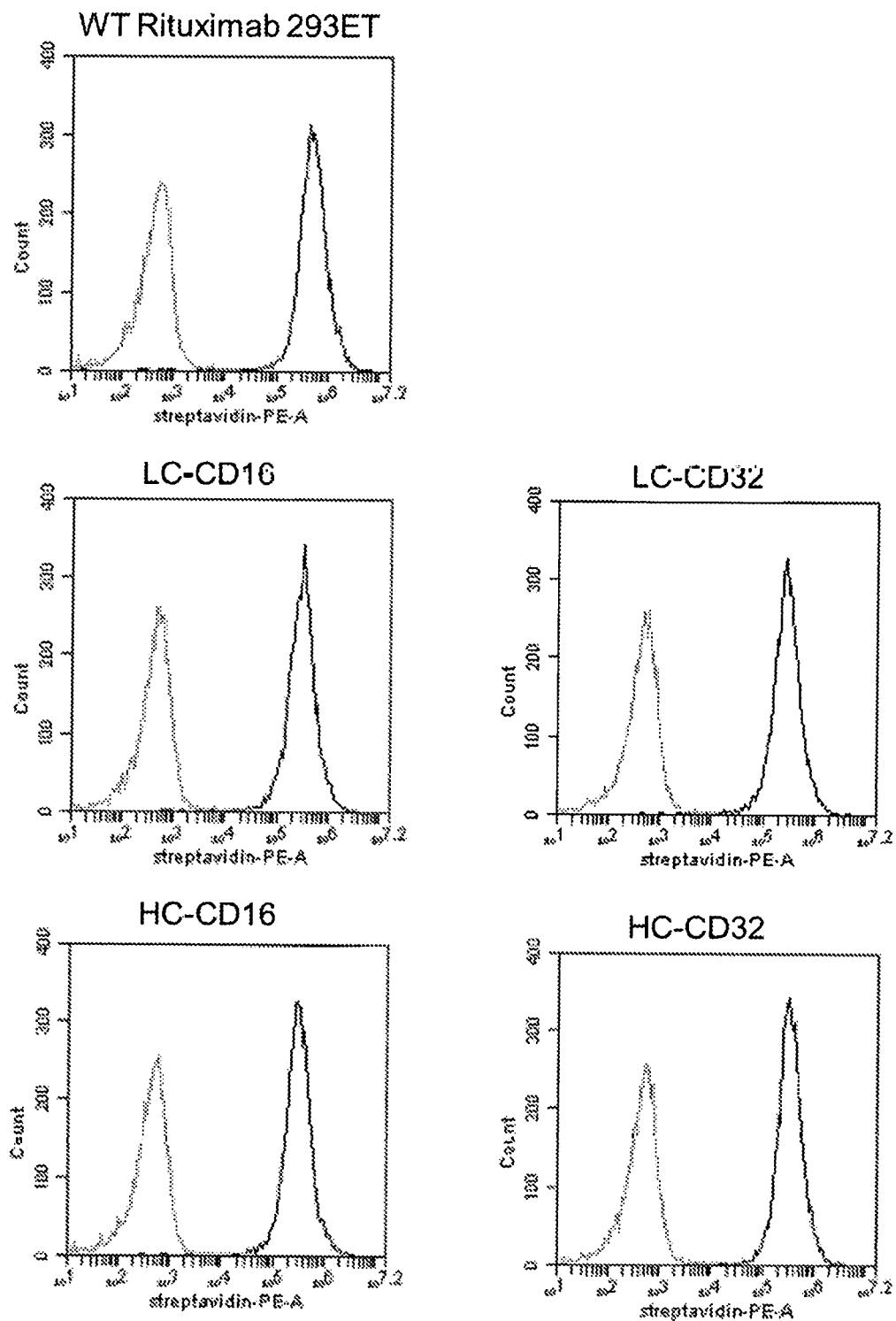
Figure 5A:
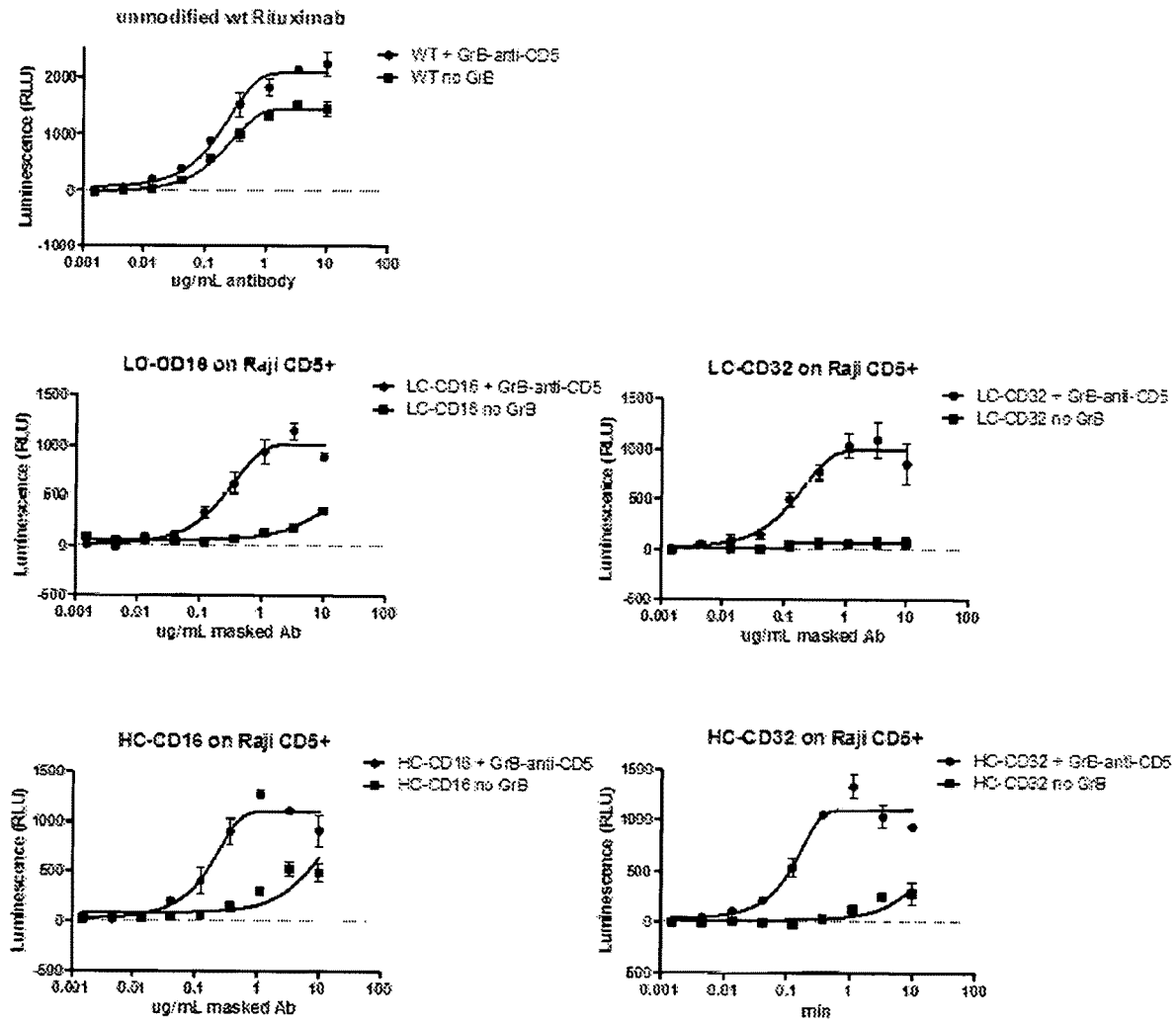
Figure 5B:
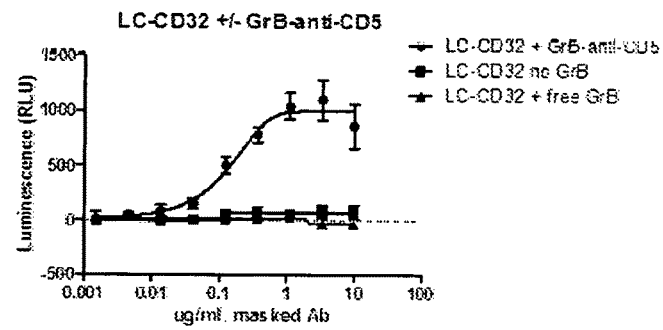
Figure 5C:
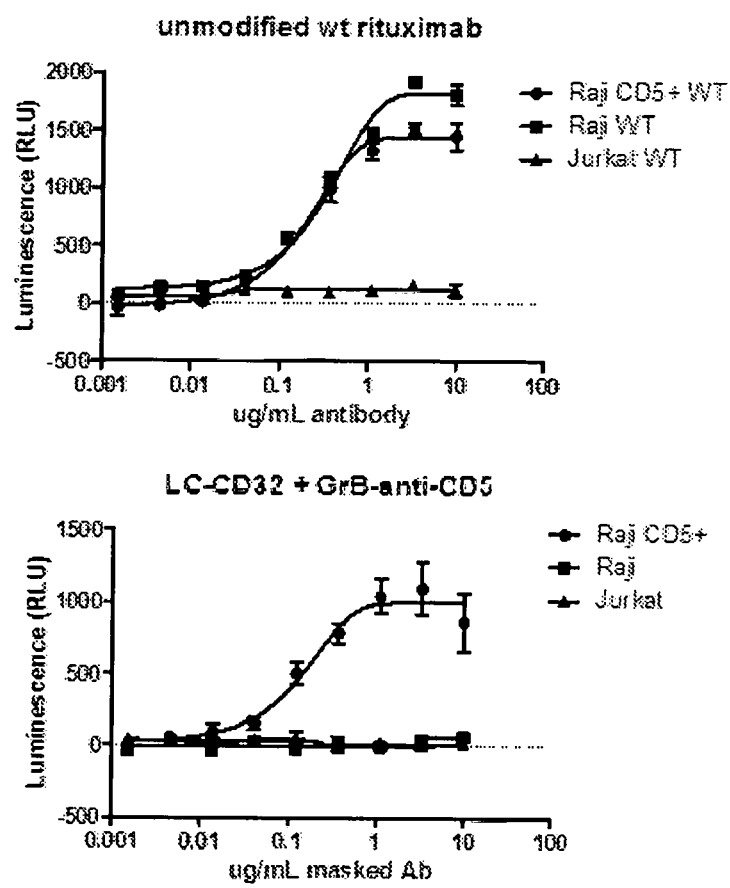

Example 2: Expression and Purification of Antibody Derivative with Disabled Effector Function The structure of the light and heavy chain modified antibodies is diagramed in FIG. 2A. Each antibody derivative was produced by transient expression of plasmids transfected into 293ET cells. The light and heavy chain expression plasmids were mixed in a 1:1 ratio for cotransfection. The C-terminally modified light chain expression plasmids (LC-CD16, -CD32 and -CD64 fusions) were paired with the unmodified heavy chain expression plasmid and the C-terminally modified heavy chain expression plasmids (HC-CD16, -CD32 and -CD64 fusions) were paired with the unmodified light chain expression plasmid. The plasmids encoding the antibody fusions were cotransfected as a 20:1 mixture by mass with a plasmid encoding the *E. coli* BirA enzyme in a form that bears a secretory leader sequence at the N-terminus and an endoplasmic reticulum retention sequence at the C-terminus. The BirA enzyme is secreted into and retained in the endoplasmic reticulum and conjugates biotin to the biotin acceptor polypeptide located at the C terminus of the heavy chain or heavy chain fusion protein. The DNA mixture was mixed in a 1:3 ratio by mass with polyethyleneimine (PEI), provided as a 1 mg/mL solution in serum free Dulbecco's modified Eagle medium (DMEM), incubated 30 min at room temperature and added to the cells. Just prior to DNA:PEI addition the medium for the 293ET cells was exchanged from DMEM with 10% iron-supplemented calf serum to serum free DMEM supplemented with 20 μM biotin. The protein was expressed for 5 days and the medium was collected. The medium was centrifuged to remove cell debris and the pH was adjusted to pH 8 by the addition of 50 mM tris(hydroxymethyl)aminomethane pH 8 and 0.1% Triton™ X-100. The recombinant antibody was purified from the medium by adsorption to Ni-NTA agarose and elution with PBS containing 200 mM imidazole. The antibody was then dialyzed against PBS.

Example 3: Proactivator Protein Production: Progranzyme Bv3 and Anti-CD5 (A2D5) Expression, Purification, and Conjugation A DNA fragment encoding pro-granzyme Bv3 bearing a C-terminal sortase A donor sequence was inserted between the NcoI and NotI sites of pET28a and the protein was expressed and purified from the cytoplasmic fraction of an *E. coli* lysate. A DNA fragment encoding the anti-CD5 scFv (A2D5) with an N-terminal glycine was inserted between the MscI and NotI sites in pET22b (sequence listings), and the protein was expressed and purified from a periplasmic fraction prepared from *E. coli*. The scFv was coexpressed with a pACYC184-based plasmid expressing the periplasmic *E. coli* chaperone Fkp. The proteins were purified using Ni-NTA agarose and eluted with tris(hydroxymethyl)aminomethane buffered saline (TBS) containing 200 mM imidazole and 0.1% Tween®20. Pro-granzyme Bv3 was enzymatically conjugated to anti-CD5 using an engineered SortaseA. Approximately 1 mg/mL of granzyme Bv3 was mixed with a two-fold excess of anti-CD5 scFv protein and 1 μM mutant Sortase A enzyme in conjugation buffer (TBS, 1 mM $CaCl2$, 0.1% Tween®20) and incubated overnight at room temperature. The conjugated protein was further purified by column chromatography (Aktapurifier 10, GE Healthcare) using a Mono S ion exchange column and then dialyzed against PBS.

Example 4. Modified Granzyme Bv3 Action on Antibody Derivatives with Disabled Effector Function Progranzyme Bv3 was converted to granzyme Bv3 by the addition of 0.2 μg of recombinant furin (R&D Systems) to 10 μg of purified progranzyme Bv3 in TBS followed by incubation at 4° C. overnight. 0.1 μg of granzyme Bv3 was added to 5 μg of disabled recombinant rituximab derivative and incubated overnight. A non-reduced sample was analyzed on SDS-PAGE by mixing 2 μg of antibody derivative with gel loading buffer lacking a reducing agent; a reduced sample was obtained by mixing 2 μg of antibody derivative with gel loading buffer containing beta-mercaptoethanol and heating at 95° C. for 1 min. FIG. 3 shows the results of granzyme Bv3 action on the antibody derivatives with disabled effector function. No mobility shift is seen for unmodified antibody chains upon granzyme Bv3 incubation. Incubation of the disabled antibody derivatives with granzyme Bv3 produced a size shift commensurate with the removal of the disabling moieties and a portion of the linker sequence (FIG. 3A). The large fragment of the cleaved antibody derivatives has an electrophoretic mobility similar to that of the unmodified antibody derivative. The observed fragment patterns are consistent with the interpretation that granzyme Bv3 cleaves specifically in the linker region containing the recognition sites. Antibody derivatives that bear effector region disabling moieties attached to the light chain produce a band corresponding to the unmodified heavy chain as well as bands attributable to modified light chains. The light chain fusion to CD16 produces a diffuse band migrating slightly slower than the heavy chain band. The diffuse character of the band can be caused by extensive glycosylation in the CD16a domain; CD16a has 5 recognized N-linked glycosylation sites. The light chain fusion to CD32 has a molecular weight similar to that of the heavy chain and produces a band that comigrates with the unmodified heavy chain band. Upon granzyme Bv3 processing, the light chains migrate with a mobility slightly slower than that of the unmodified counterpart which is accounted for by the linker sequence that remains between the C-terminus of the light chain and the cleavage site within the flexible linker. Disabled antibody derivatives in which the heavy chain has been fused to Fc domains produce a band corresponding to the unmodified light chain and bands that correspond to the heavy chain fusions, linker and disabling moieties. Following incubation with granzyme Bv3 the heavy chain bands adopt approximately the same mobility as the unmodified heavy chains (FIG. 3B). These results show that the granzyme Bv3 cleavage is specific and severs the covalent linkage between the antibody and the Fc-gamma receptor based disabling moieties.

Example 5. Target Cell Binding Properties of Disabled Antibody Derivatives Compared to the Unmodified Rituximab Control We tested the ability of the modified disabled rituximab derivatives to specifically bind to human CD20 expressed on human B-cells. The disabling moiety interacts with the effector region and should not adversely affect the ability of the target binding region to interact with the cell surface antigen. Flow cytometry was used to assess the degree and specificity of binding of the disabled rituximab derivatives to the Raji target cells expressing human CD20 and the Jurkat non-target cells lacking CD20. The C-terminally fused antibodies as well as the wt rituximab were uniformly labeled with biotin during protein expression on the biotin-acceptor peptide found at the C-terminus of the heavy chain. The heavy and light chain constructs were mixed in a 20:1 ratio with a plasmid expressing the BirA enzyme which results in quantitative biotinylation of the expressed antibody during production in HEK 293ET cells. The antibody was added at 10 µg/mL to $1 \times 10^5$ Raji or Jurkat cells preblocked with Fc receptor blocking solution (Human TruStain Fc, Biolegend) in Iscove's modified Dulbecco's media (IMDM) with 10% calf serum. After a 1 hour incubation, the cells were washed and then 1 µL streptavidin-phycoerythrin (Fluka) was added in 100 µL of PBS with 2% calf serum. After a 30 min incubation, the cells were washed once with PBS and then analyzed on an Accuri C6 flow cytometer (BD bioscience). FIG. 4 clearly demonstrates that the target binding properties of the modified disabled antibodies are similar to the unmodified wt rituximab. All of the modified antibodies show strong staining on Raji cells, comparable to the control unmodified rituximab, while no staining is observed on Jurkat cells. The disabled antibodies maintain native target binding properties while not increasing the non-specific interaction with non-target cells.

Figure 6A:
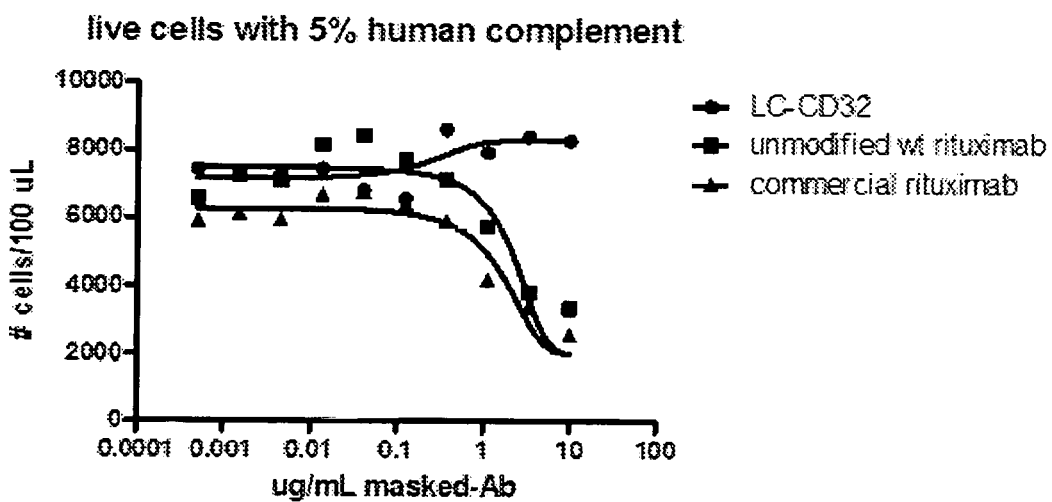

Example 6: ADCC Activity of Antibody Derivatives with Disabled Effector Function The potential for the disabled antibody derivatives to engage ADCC effector functions was measured using a surrogate assay (Promega). The assay relies on a reporter cell that expresses Fc receptor and produces luciferase following contact of the cell with a target bearing bound antibody. The target cells were Burkitt lymphoma derived Raji B-cells that had been transfected with an expression plasmid encoding human CD5 (Raji-CD5). The target cells natively express CD20 as a consequence of their B cell lineage origin. The Promega ADCC luminescent bioassay was performed according to the manufacturer's instructions. The Raji-CD5 cells were incubated with 3-fold serially diluted antibody derivatives starting from 10 µg/mL in RPMI 1640 media containing 10% calf serum. Duplicate wells were assayed for each concentration. For the antibody derivatives modified with disabling moieties, a dilution series was compared with and without 100 nM of the proactivator protein, progranzyme Bv3-anti-CD5 (A2D5 scFv) conjugate. In order to prevent non-specific activation of the disabled antibody derivative in solution, the progranzyme Bv3-anti-CD5 is provided in a form that is initially inactive for granzyme B activity, but can become activated upon furin cleavage of the granzyme B zymogen after cell surface binding. Controls include unmodified rituximab antibody expressed from HEK 293ET cells. The cells, antibodies, and proactivator protein were incubated overnight at 37 C. 75,000 effector cells provided in the kit were added to 7,500 target cells in each well to create a 10:1 ratio of effector cells to target cells. After incubating the plate for 6 hours, the luciferase substrate (Bio-Glo, Promega) was added and the luminescence was read on an M3 spectramax (Molecular Devices). The results were plotted using Graphpad software and fit to a logistic model. Luciferase expression increased with increasing antibody concentration for the control unmodified antibody, indicating that it is capable of inducing an ADCC-mimetic response both in the presence and absence of the granzyme Bv3-anti-CD5 proactivator protein (FIG. 5A). In the case of the modified antibody derivatives however, in the absence of the progranzyme Bv3 proactivator protein, almost no luciferase expression was observed (FIG. 5A). Cells incubated with the modified antibody derivatives and the proactivator granzyme Bv3-anti-CD5 together produced increased luciferase activity with increasing antibody derivative concentration, consistent with the interpretation that progranzyme Bv3 acts on the disabling moiety cleavable linker to allow the release of the effector region disabling moiety (FIG. 5A). For each of the disabled antibody derivatives tested, there was a marked difference in the ADCC activation for cells incubated in the presence of proactivator protein and cells incubated without any proactivator indicating effective disabling of the antibody effector region. The light chain C-terminal fusions, LC-CD16 and LC-CD32, showed superior disabling of the effector region than the corresponding heavy chain C-terminal fusions to the same disabling moieties. In both cases however, the CD32 fusion performed better than the CD16 fusion at disabling the ADCC effect in the absence of proactivator. The improved disabling can be due to the higher affinity of CD32 towards the effector region than CD16. ADCC activation was measured for the LC-CD32 antibody derivative in the presence of a normal proactivator granzyme Bv3-anti-CD5, in the presence of an unconjugated free granzyme Bv3 which cannot bind to the Raji CD5 target cell, and without any granymze Bv3 proactivator present (FIG. 5B). LC-CD32 only elicits an ADCC response only the presence of the granzyme Bv3-anti-CD5 and not the other conditions; this experiment demonstrates that proactivator binding to the target cell is absolutely necessary for eliciting the ADCC response from the disabled antibody derivative. This data supports the idea that the cleavage occurs on the surface of the target cell in which both the disabled antibody derivative and proactivator are both bound. FIG. 5C tests the ADCC signal from cells having both epitopes CD20 and CD5 (Raji-CD5), cells lacking CD5 (Raji), and cells lacking CD20 (Jurkat) in the presence of both the disabled antibody derivative LC-CD32 and the proactivator granzyme Bv3-anti-CD5. As a control, the wt unmodified rituximab shows strong ADCC stimulation in the presence of Raji CD5+ and Raji cells while showing no stimulation from Jurkat cells. This is consistent with CD20 recognition of the wt unmodified rituximab. The combination of the LC-CD32 antibody derivative and the proactivator granzyme Bv3-anti-CD5 shows ADCC activation only on Raji-CD5 cells and not from Raji or Jurkat cells indicating that binding only one of the two compositions is not sufficient for ADCC activation. Both target antigens must be present on the cell to elicit an ADCC response against that cell, and cells expressing only one or none of the epitopes will be spared.

Example 7: Flow Cytometric Analysis of CDC Activity of Disabled Antibodies

The ability of the disabled antibody derivatives to mediate complement-dependent cytotoxicty of Raji-CD5 cells was measured using a LIVE/DEAD stain assay. Raji-CD5 target cells were incubated with 3,3'-dioctadecyloxacarbocyanine perchlorate (DioC18) to uniformly label live and dead cells. Cells were plated at 40,000 cells per well in RPMI with 10% low IgG serum containing a 3-fold serial dilution of antibody starting from 10 μg/mL. After an overnight incubation, human complement (Sigma-Aldrich) was added to 5% (v/v) and the mixture incubated for 2 hours. Propidium iodide was added and a fixed volume from each well was analyzed by flow cytometry (Accuri, BD biosciences). The number of live cells which were propidium iodide negative and DioC18 positive were counted in the 100 µL sample and compared for each antibody concentration. The results were plotted using Graphpad software. No loss in cell titer was observed by flow cytometry after Raji-CD5 cells were incubated with the disabled antibody with light chain CD32 fusion (LC-CD32), whereas cell titer decreased in a concentration dependent manner after the cells were incubated with either HEK293ET expressed unmodified wt rituximab or commercial rituximab (FIG. 6A).

Example 8: GAPDH Release Assay of CDC Activity of Disabled Antibodies

Figure 6B:
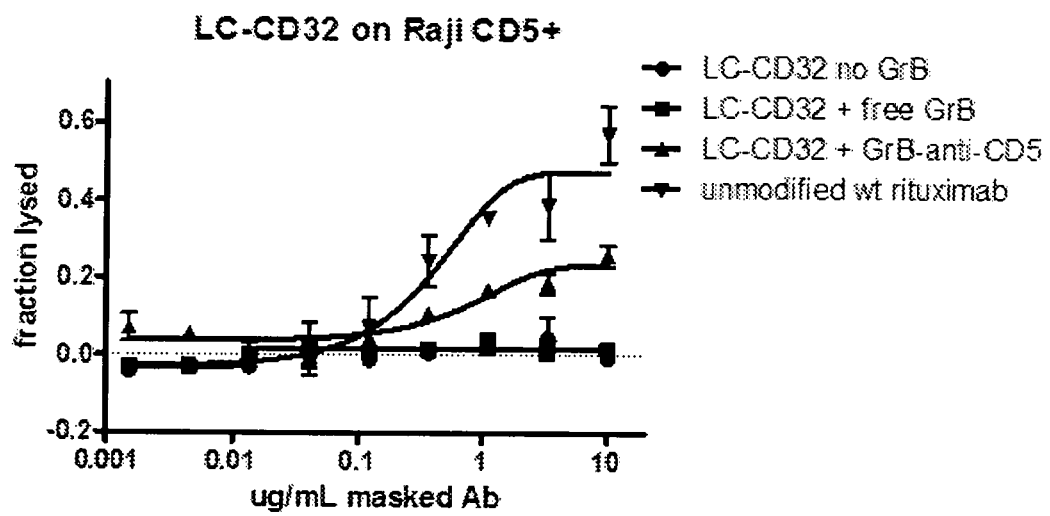
Figure 6C:
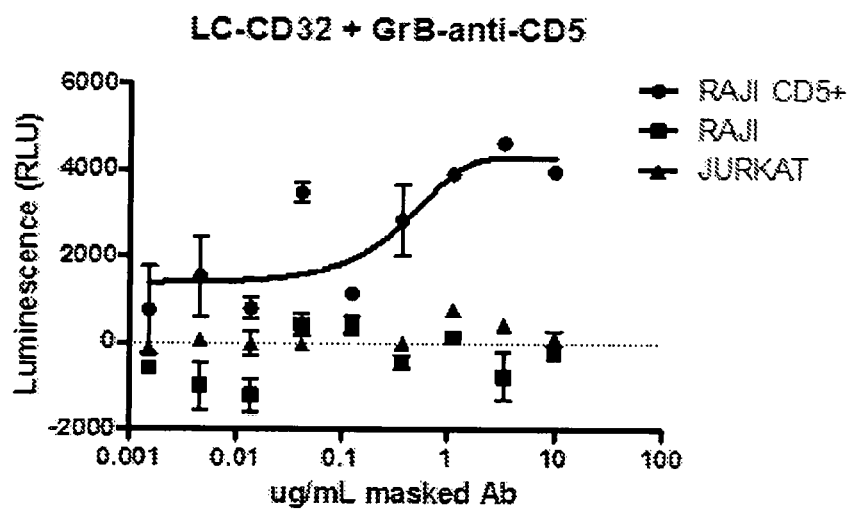

The GAPDH relase assay (aCella-Tox, Cell Technologies) was performed according to manufacturer's instructions. 40,000 target cells in RPMI/10% calf serum were incubated with serial 3-fold dilutions from 10 µg/mL of disabled antibody derivative under different conditions of proactivator addition. After 24 hour incubation with different antibodies concentrations and 100 nM proactivator, human serum was added to 5% (v/v) and the cells were incubated for 2 hours. The cells were centrifuged and the supernatant was mixed with GAPDH luciferase detection solution. Luminescence was measured on a spectramax M3 and the light output was correlated with increased target cell lysis. The fraction of lysed cells was calculated by comparison with wells containing 0.1% Triton™ X-100 (100% lysed) or media (0% lysed). The GAPDH release assay demonstrates activation of CDC activity by the LC-CD32 derivative only when progranzyme Bv3-anti-CD5 fusion is added (FIG. 6B). The LC-CD32 disabled antibody derivative shows concentration dependent CDC activation only in the presence of 100 nM of the proactivator, progranzyme Bv3-anti-CD5, and no activation when co-incubated with either 100 nM of free progranzyme Bv3 or when progranzyme Bv3 is omitted altogether. These results show that the proactivator is absolutely necessary for the disabled antibody to stimulate a CDC response. The combination of the LC-CD32 disabled antibody and the proactivator progranzyme Bv3-anti-CD5 was added to different cell targets with different epitope patterns to test whether binding of both compositions were required for CDC activation. The combination shows CDC activation only on Raji-CD5 cells and not from Raji or Jurkat cells indicating that binding only one of the two compositions is not sufficient for complement activation. Both target antigens must be present on the cell to elicit an CDC response against that cell, and cells expressing only one of the epitopes will not undergo lysis (FIG. 6C). These results are consistent with the cytometric assay in support of the interpretation that the Fc-receptor domain effectively masks (disables) the complement effector region in the IgG1 CH2 domain. Co-binding of the proactivator on the same cell surface is required for the activation of the LC-CD32 disabled antibody derivative to the enabled form.

Example 9: Improved CDC Results Using a Linker with More Granzyme Bv3 Cut Sites

Figure 7A:
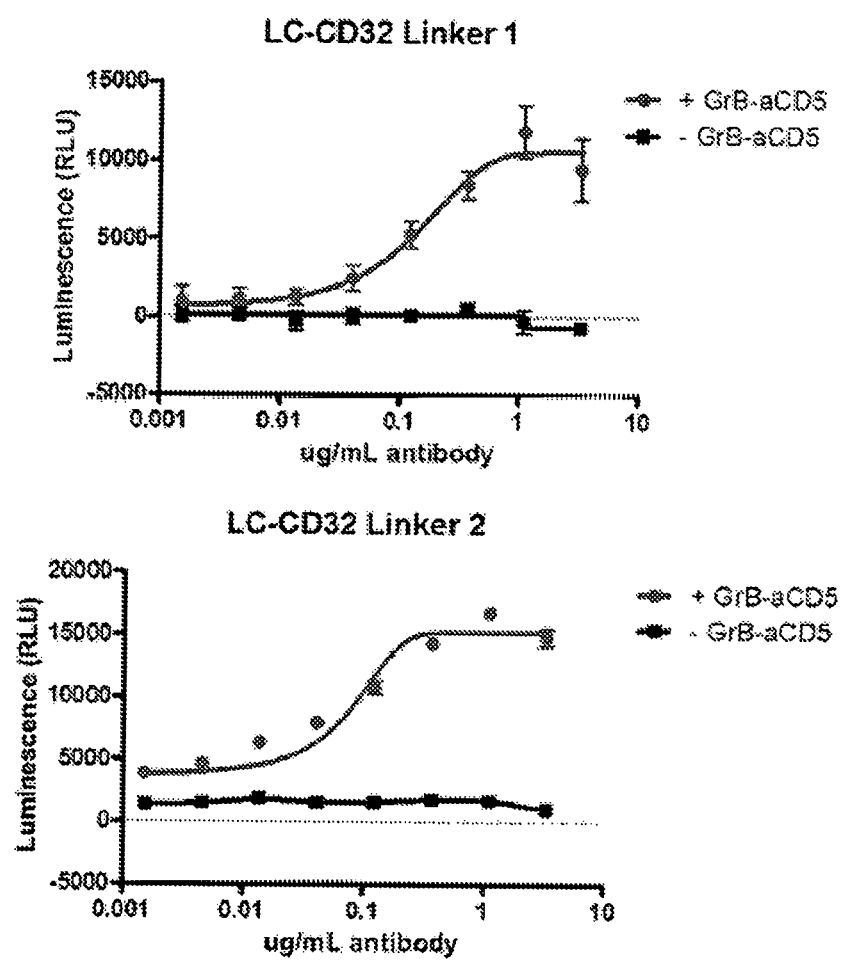
Figure 7B:
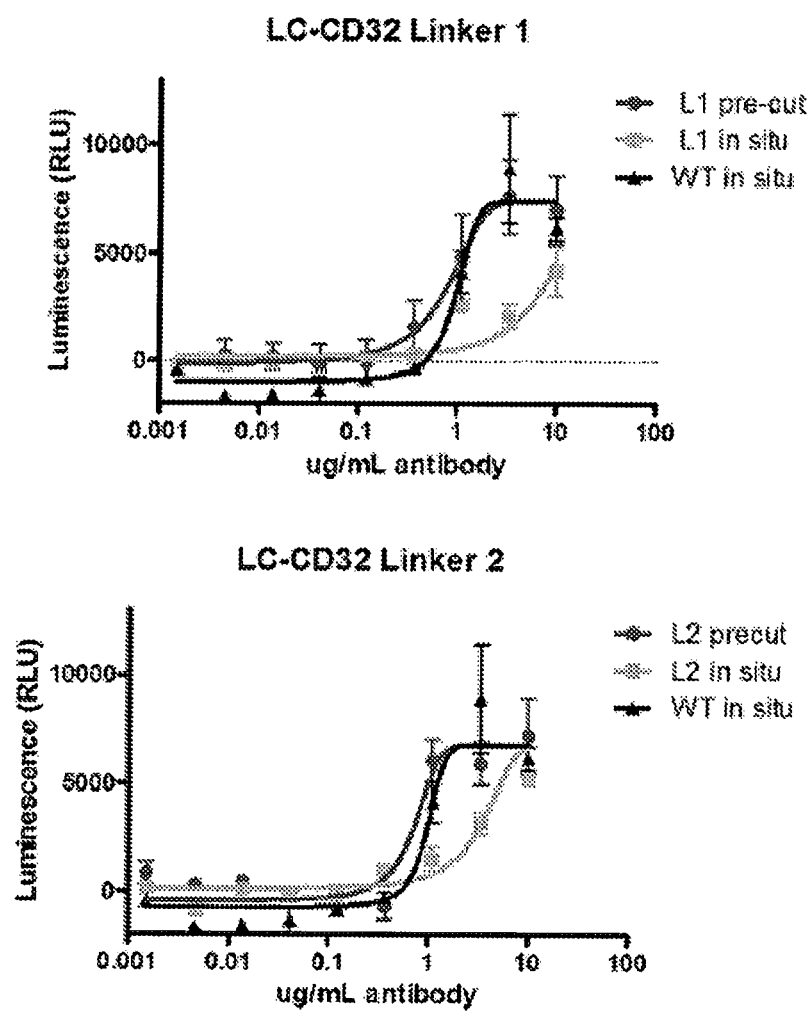
Figure 8A:
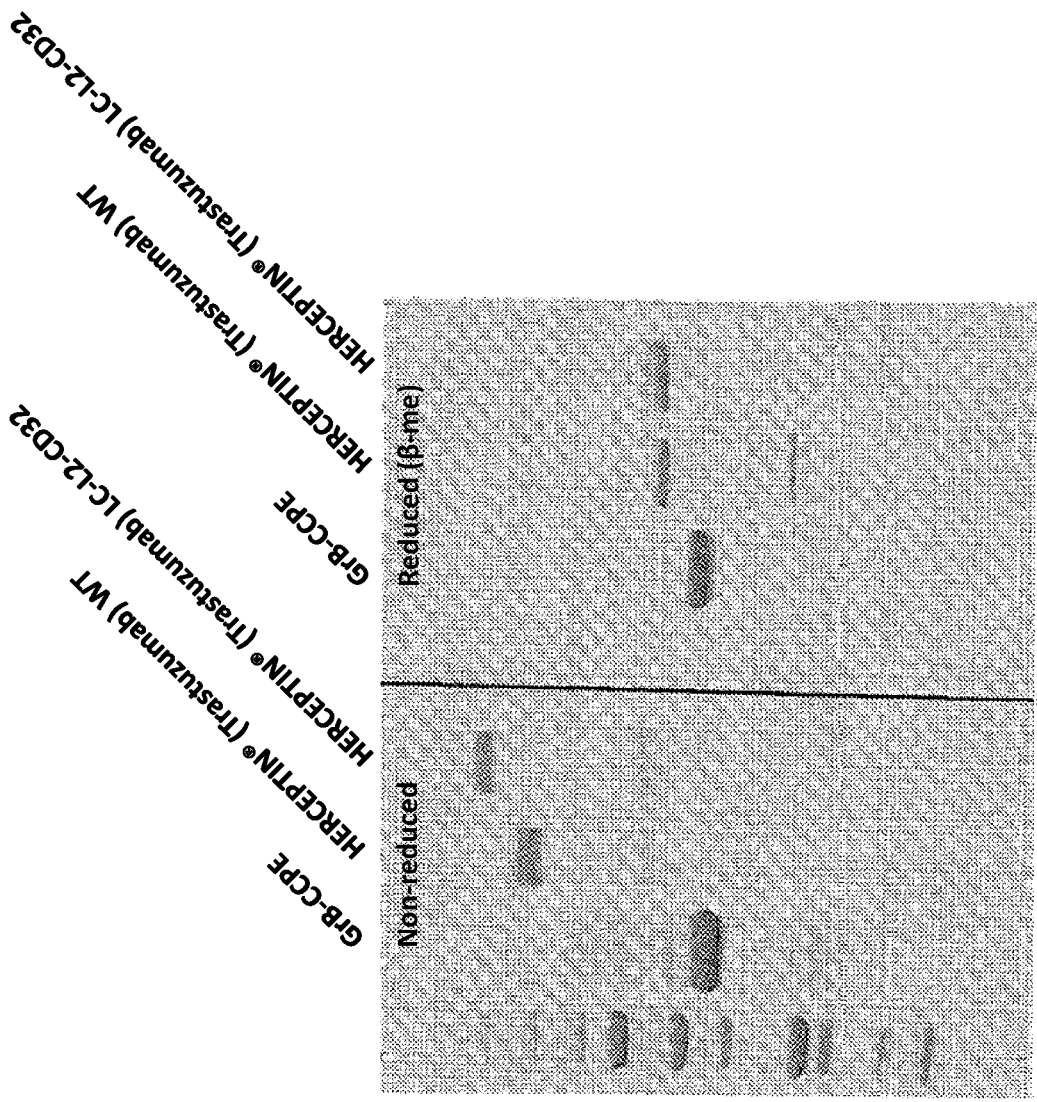
Figure 8B:
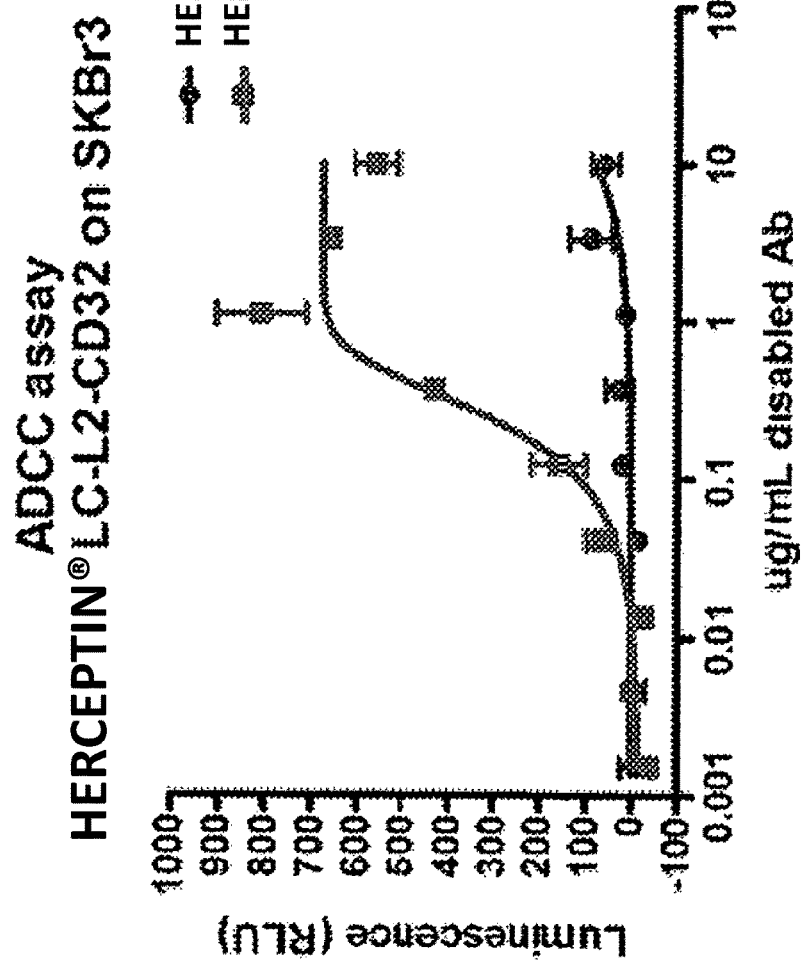
Figure 9A:
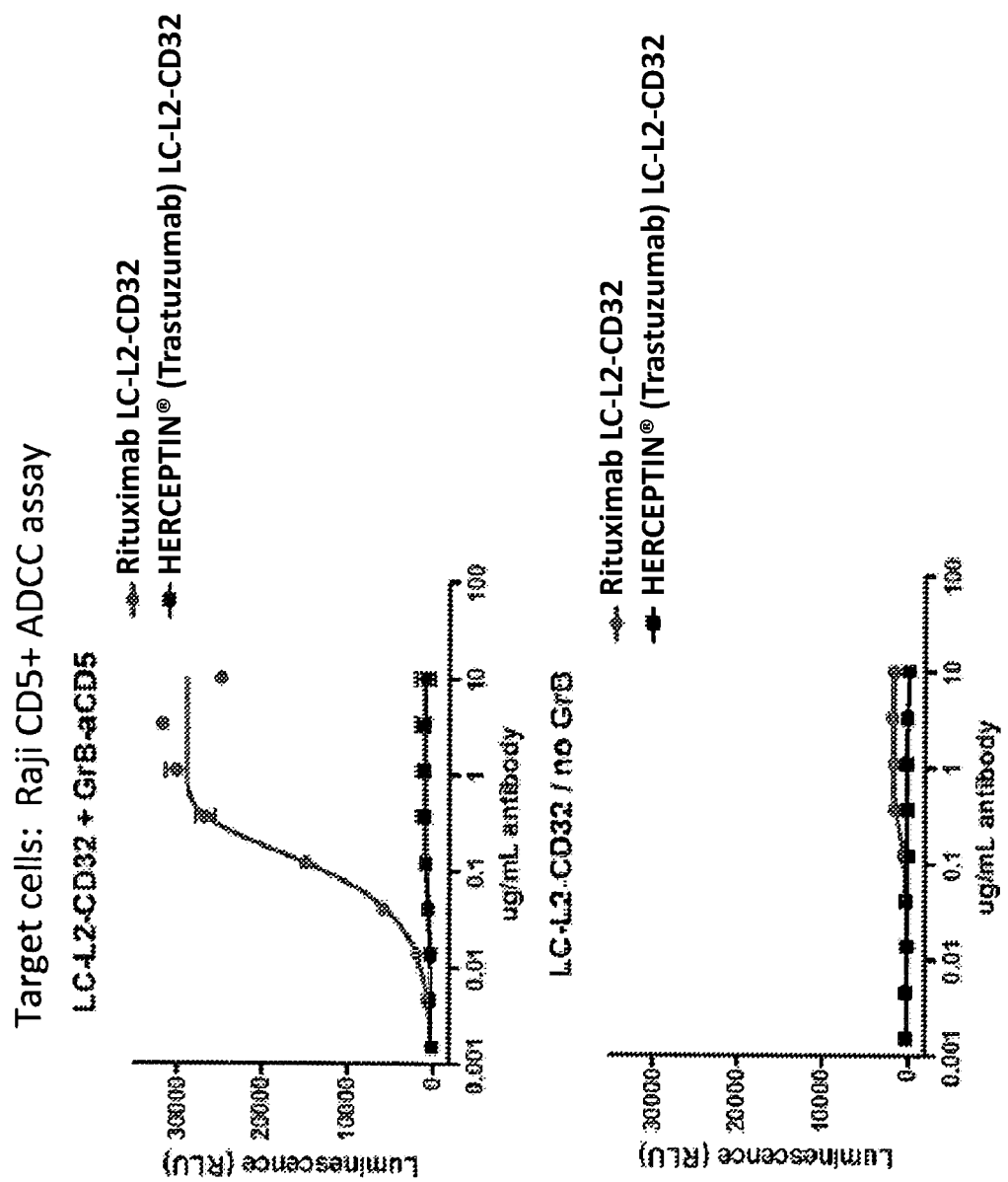
Figure 9B:
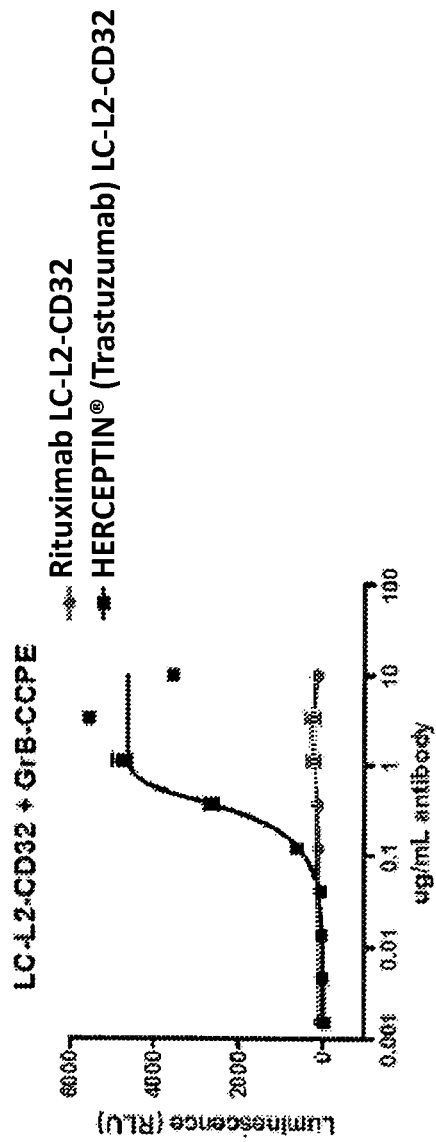
Figure 9B:
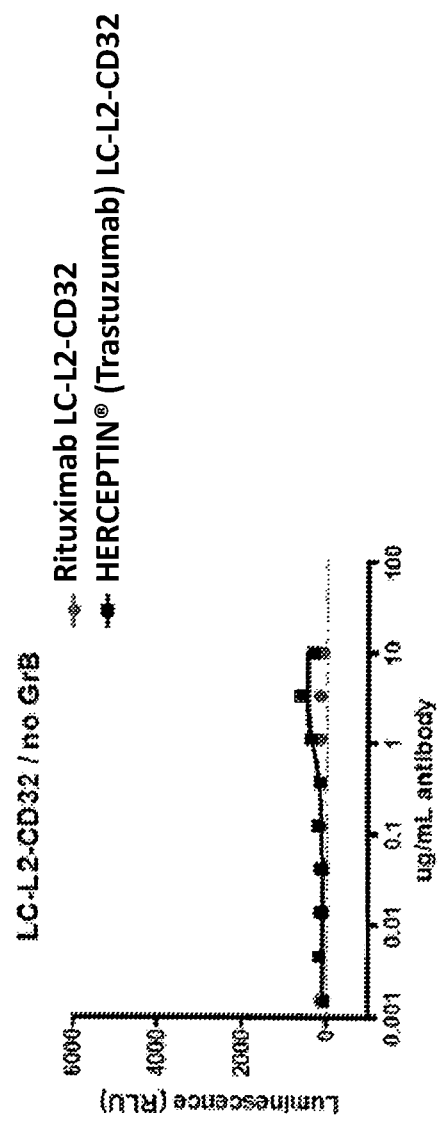

A new linker sequence (SEQ ID NO: 32) was designed, synthesized, and inserted between the EcoRI and NotI regions of the Rituximab LC-CD32 construct (SEQ ID NO: 13, encoding protein of SEQ ID NO:14) creating a new Rituximab LC-L2-CD32 or also called LC-CD32 Linker 2 (SEQ ID NO:33, encoding protein of SEQ ID NO:34). This new linker was designed to add an additional granzyme Bv3 cut side proximal to the C-terminal residue of the normal IgG light chain. After complete digestion with granyzme Bv3 Linker 2 will leave 12 residues at the C-terminus of the light chain while Linker 1 will leave 22 residues. These new constructs were expressed with the Rituximab HC and purified as previously described and tested on their ability to activate an ADCC and CDC response in vitro as compared to the original linker also referred to as LC-CD32 Linker 1. The signal from the in vitro ADCC assay indicates that the new and old linkers behave similarly in terms of activation of a CD16 responsive signal (FIG. 7A). The samples that were coincubated with pro-granzyme Bv3-anti-CD5 at a fixed concentration of 50 nM showed a strong dose dependent signal for the disabled antibody (circles) while the samples lacking the activator showed no activation (black squares). There was no apparent increase in the non-specific activation in the absence of the proactivator granzyme Bv3. The same two proteins were compared using a CDC assay that measures cellular GAPDH (glyceraldehyde 3-phosphate dehydrogenase) release (FIG. 7B). The proteins were either fully activated prior to addition to the cells with activated granzyme Bv3 or allowed to be activated in situ on the cell surface with the addition of pro-granzyme Bv3-anti-CD5. The modified antibodies were compared with the unmodified wt antibody. The antibodies that were precut with granzyme Bv3 prior to addition to the cells (circles) showed a similar response to that of the wt unmodified antibody (triangles). In the case of both the Linker 1 and Linker 2 variants, the in situ activation (squares) and stimulation of CDC was lower perhaps due to incomplete digestion of the antibody on the cell surface. However, the comparison between Linker 1 and Linker 2 showed that there was a stronger CDC response from Linker 2 when the antibody was activated in situ.

Example 10: Demonstration of the Efficacy of Disabled Antibodies Using a Different Antibody, HERCEPTIN® (Trastuzumab)

In order to further demonstrate that disabled antibodies can be used as a general tool, a second unrelated antibody was used to show efficient blocking of effector function. HERCEPTIN® was chosen due to its therapeutic success in treating breast cancer and its documented ability to stimulate ADCC and CDC responses. In addition, HERCEPTIN® targets solid tumors and adherent cells in culture while Rituximab targets hematopoietic cells and suspension cells in culture. We wanted to demonstrate that we can block effector function in both cases and conditionally activate effector function with the addition of pro-activators. The constructs for expressing disabled HERCEPTIN® were created by modifying the vectors encoding the Rituximab LC-L2-CD32 and Rituximab heavy chain. HERCEPTIN® and Rituximab show significant sequence similarity in their constant domains CH1-CH2-CH3 and so the DNA encoding regions unique to HERCEPTIN® were synthesized (Genscript gene synthesis) and cloned onto the existing Rituximab constructs, replacing the sequences unique to Rituximab. The resulting sequence is identical to the reported HERCEPTIN® sequence with the exception of the leader secretion signal peptide, our modifications to the C-terminus of the light chain which is fused directly to the cleavable linker and a domain of CD32, and the heavy chain which has a 6-his tag and biotinylation signal sequence (SEQ ID NOs: 35, 36, 37, 38, 39, 40). The CD32 domain fused to the light chain of the HERCEPTIN® clone should block the effector domains in the CH2 region in the same manner as in the case of the Rituximab example shown above because the sequences involved with the blockage and release are identical in both cases; only the variable antigen binding region and the hinge region between CH1 and CH2 differ between the reported sequence of Rituximab and HERCEPTIN®. The disabled HERCEPTIN® antibody was expressed from 293T cells using transient transfection with PEI and subsequently purified using Ni-NTA agarose. The protein exhibited the expected molecular weight under non-denaturing and denaturing conditions (FIG. 8A). The disabled HERCEPTIN® has an apparent molecular weight around 200 kD due to the added CD32 and linker fusions to the light chain while the wt HERCEPTIN® migrates similar to a normal IgG. Under denaturing conditions, the CD32 modified light chain migrates near the heavy chain due to their similar molecular weight. SKBr3 cells were chosen to test out the disabled HERCEPTIN® antibodies due to its high expression of the HER2 antigen which binds to the HERCEPTIN® antibody. However a second antigen is required for the conditional activation of the disabled HERCEPTIN® antibody. We identified claudin 3 and claudin 4 as potential targets due the SKBr3 cells susceptibility to the *Clostridium perfringens* enterotoxin which requires high expression of claudin 3 and claudin 4. The C-terminal domain of the enterotoxin (termed CCPE) is identified as the region that binds to claudins. A fusion construct was created with pro-granzyme Bv3 fused to CCPE (SEQ ID NO: 41, encoding protein of SEQ ID NO: 42). The pro-granzyme BV3-CCPE protein was soluble when expressed in *E. coli* Shuffle strain (NEB) and purified under native conditions using Ni-NTA agarose. The protein displayed the expected molecular weight under denaturing and non-denaturing SDS-PAGE (FIG. 8A). An ADCC in vitro assay was used to assess the ability of the disabled HERCEPTIN® LC-L2-CD32 to activate a response on condition of pro-granzyme Bv3-CCPE addition. We only see a stimulation of a dose dependent ADCC response in the presence of a fixed amount of 50 nM granzyme Bv3-CCPE activator (squares) and no significant stimulation of ADCC in the absence of the granzyme Bv3-CCPE (circles). The disabled HERCEPTIN® example provides a case in which a different set of epitopes on a completely different target cell line can achieve similar pro-activator dependent effector stimulation. This demonstrates the generalization of the disabled antibody concept.

Example 11: Specificity of the Disabled Rituximab and HERCEPTIN®

This experiment demonstrates that the disabled antibodies still retain their native specificity for the their target antigen, in the case of Rituximab the CD20 expressed on the Raji B-cells while the HERCEPTIN® recognizes the Her2 antigen overexpressed on SKBr3 cells. An in vitro ADCC assay was performed using the disabled Rituximab and HERCEPTIN® LC-L2-CD32 proteins on both Raji CD5+ and SKBr3 cells. Both disabled antibodies were incubated with Raji CD5+ target cells with or without 50 nM fixed amount of pro-granyzme Bv3-anti-CD5 while on SKBr3 cells the antibodies were incubated with or without 50 nM fixed amount of pro-granzyme Bv3-CCPE. For the Raji CD5+ B-cells, a positive ADCC signal is only observed with the Rituximab disabled antibody (circles) in the presence of the coactivator while there is no signal from the HERCEPTIN® disabled antibody (squares) (FIG. 9). In contrast, on the SKBr3 cells, the HERCEPTIN® disabled antibody displayed a positive ADCC signal in the presence of the cognate coactivator while the Rituximab showed no signal. Both antibodies showed no signal in the absence of added coactivator demonstrating that the effector domain for ADCC activation is disabled (FIGS. 9A-B).

Example 12: Alternative Binding Moieties, Disabling Moieties, and Antibody Configurations The antibody architecture was modified to demonstrate that alternative configurations of the antibody derivatives as well as different binding moieties could be used with this method. The variable domain from both the heavy chain and light chain were deleted from the respective constructs by PCR mutagenesis of the mammalian expression vector encoding the rituximab heavy chain (HC, SEQ ID NO: 1) and the light chain fused to CD32 with the linker version 2 (Rituximab LC-L2-CD32, SEQ ID NO: 33). The heavy chain was modified to contain cloning sites in place of the variable domain which allowed for cloning alternative binding moieties in place of the heavy chain variable region. FIG. 10A shows a schematic of the modified antibody with scFv binding moieties fused to the N-terminus of the heavy chain. Ananti-CD20 scFv and an anti-CD19 scFv were PCR amplified and inserted at the 5' end of a fragment encoding the CH1-hinge-CH2-CH3 domains of human IgG1 heavy chain, creating anti-CD20-CH1-CH2-CH3 (SEQ ID NO:43, encoding protein SEQ ID NO:44) and anti-CD19-CH1-CH2-CH3 (SEQ ID NO:45, encoding protein SEQ ID NO:46). Plasmids expressing the modified heavy chain variants were co-transfected with a plasmid encoding a modified light chain fused to CD32 but lacking a variable region (CLk-CD32, SEQ ID NO:47, encoding protein SEQ ID NO:48) and expressed using an Expi293 expression system (Invitrogen). FIG. 10B shows the expression and purification of the two constructs after a tandem purification through Ni-NTA agarose followed by streptactin agarose (Qiagen). The heavy chain contains a 6× His-tag and a strep-tag II sequence is present on the light chain; retention and desorption from both affinity resins ensures that both chains are present. The reducing and non-reducing PAGE experiments demonstrate the presence of both chains in the assembled antibody variant.

These alternative compositions were tested using ADCC and CDC assays as shown in FIGS. 13A-G. The CDC assays in FIGS. 13A-G were done using a modified MTS assay (Promega). Cells were incubated with serially diluted scFv-antibody composite proteins overnight. Reconstituted human serum was added to a final concentration of 5% and the cells incubated for 4 hours. The plates were spun down and ½ of the volume was removed and then MTS reagent was added in ⅕ of the remaining volume. The plates were incubated for 1-2 hours and read on an M3 Spectramax plate reader (Perkin Elmer). The variant tested in the assays is indicated on each of the graphs. The scFv-CH1-hinge-CH2-CH3+CLk-CD32 variants show some attenuation of the ADCC signal in the absence of the granzyme B activator but a significant increase in the signal when granzyme Bv3-anti-CD5 is added at 50 nM. These constructs were not able to completely block the CD16 dependent ADCC signaling. In contrast, there was no detectable CDC response even in the presence of the granzyme B activator so the ability of these constructs to block the CDC response cannot be assessed.

Example 13.Alterative Binding Moieties Fused to the Fc Domain as Binder-Fc-CD32 Fusions Various binding moieties from different sources such as modified antibody fragments (scFv), artificial scaffolds from diversified libraries, native binding ligands to cell surface receptors, and binding protein domains from bacterial sources were tested for their ability to recruit the modified antibodies to cell surface for ADCC and CDC activation. In order to test these new constructs, a direct N-terminal fusion was made of these binders to an Fc domain of the heavy chain which featured a C-terminal fusion to the disabling CD32 domain as described by FIG. 11. These constructs were created by amplifying the Fc-CD32 portion from the vector encoding the HC-CD32 construct (SEQ ID NO: 7) and ligating them into the 3' region of the sequence encoding the various binding domains in pTracer vectors. The examples for antibody fragments include the scFvs for anti-CD20-Fc-CD32 (SEQ ID NO:49, encoding protein SEQ ID NO:50) and anti-CD19-Fc-CD32 (SEQ ID NO:51, encoding protein SEQ ID NO:50). As an example of an artificial scaffold, we synthesized a clone H10-2-G3-Fc-CD32 (SEQ ID NO:57, encoding protein of SEQ ID NO:58) which is an ankyrin repeat scaffold that specifically recognizes the HER2 receptor (ErbB2). H10-2-G3 binds to the HER2 receptor with picomolar affinity (Zahnd et al., J. Mol. Biol. 2007 369:1015-18). A CCPE domain was used as an example of a protein binding domain from a bacterial source. In order to express CCPE in a mammalian expression system, two potential N-linked glycan addition sites were mutated by changing the NXT/S consensus sequence (T212A and S305A in the *Clostridium perfringens* exotoxin). The changes were introduced by PCR mutagenesis with modified primers before ligating the inserts along with the Fc-CD32 domain in the mammalian expression vector to create CCPE-Fc-CD32 (SEQ ID NO:53, encoding protein SEQ ID NO:54). We also tested a natural ligand to a cell surface receptor. CD2 engages the LFA-3 receptor on target B-cells. The CD2 extracellular domain was amplified from a cDNA clone and then ligated to the mammalian expression vector along with the Fc-CD32 to create CD2-Fc-CD32 (SEQ ID NO:55, encoding protein SEQ ID NO:56). These alternative antibody derivatives were transfected as single polypeptide chains in an Expi293 mammalian system and then purified on Ni-NTA. The purified protein is shown in FIG. 11B; the protein exists as a dimer under non-reducing conditions suggesting proper assembly of the Fc-domain and hinge region.

FIGS. 13A-G shows the results of the ADCC and CDC assays for these modified antibodies with alternative binding moieties. Anti-CD20-Fc-CD32, anti-CD19-Fc-CD32, CD2-Fc-CD32 were tested on Raji/CD5+ cells with 50 nM granzyme Bv3-anti-CD5 as the activator reagent. The scFv variants, anti-CD20 and anti-CD19, showed nearly complete suppression of the ADCC signal by the CD32 domain bound to the effector site. When the CD32 domain is removed with the addition of the granzyme B activator, there was a significant stimulation of the ADCC dependent luciferase signal. These modified antibodies did not elicit a CDC response however so the blocking of the CD32 for these modified constructs cannot be assessed. The natural ligand CD2, did not elicit a ADCC or CDC response in the presence of the granzyme B activator perhaps indicating a that the binder does not possess a high enough affinity to LFA-3 in order to show a signal under the parameters of the assay, or the native folding of the binding domain was disrupted in this modified antibody context. CCPE-Fc-CD32 and H10-2-G3-Fc-CD32 were both tested on the breast cancer cell line SKBr3. CCPE targets the claudin 3 and 4 proteins while H10-2-G3 targets the Her2 (ErbB2) receptor overexpressed on these cells. Different activators were used with each of the antibodies. CCPE-Fc-CD32 was paired with Granzyme BV3-H10-2-G3 (SEQ ID NO:57, encoding protein SEQ ID NO:58) while H10-2-G3-Fc-CD32 was paired with Granzyme BV3-CCPE (SEQ ID NO:59, encoding protein SEQ ID NO:60). The binder and the activator in these experiments were reversed. Both CCPE-Fc-CD32 and H10-2-G3-Fc-CD32 show an enhanced ADCC response in the presence of their respective activator granzyme B reagent indicating that the normal ADCC response is attenuated by the presence of the CD32 disabling moiety. There was no detectable CDC response with the H10-2-G3 variant and the CCPE-Fc-CD32 was not tested using a CDC experiment. Many of the Fc-CD32 modified construct demonstrate a significant conditional ADCC signal while there was no CDC signal observed for any of the clones.

Example 14. Modified Antibodies with Alternative Disabling Moieties

The CD16 and CD32 disabling moieties on the light chain C-terminus were also replaced with Fc binding domains from other sources. The configuration of these antibody derivatives are shown in FIG. 12A. Glycoprotein E from Herpes simplex virus, superantigen-like protein 10 from *Staphylococcus aureus*, and darpins from a diversified scaffold were synthesized and cloned into the Rituximab light chain plasmid (SEQ ID NO:4) using the NotI and XbaI restriction sites in place of the CD32 domain to create these clones respectively; Rituximab LC-HSVgE (SEQ ID NO:63, encoding protein SEQ ID NO:64), Rituximab LC-SSL10 (SEQ ID NO:61, encoding protein of SEQ ID NO:62), Rituximab LC-I_02 (SEQ ID NO:65, encoding protein SEQ ID NO:66), Rituximab LC-I_07 (SEQ ID NO:67, encoding protein SEQ ID NO:68), Rituximab LC-I_11 (SEQ ID NO:69, encoding protein SEQ ID NO:70). HSVgE is the glycoprotein E from herpes simplex virus and is well documented as an Fc binder (Dubin et al., J Virol. 1994 68(4) 2478-2486). Superantigen-like protein 10 is an immmunomodulator gene from *Staphylococcus aureus* that has been shown to bind to Fc (SSL10; Patel et al., J Immunol. 2010 184(11):6283-92). I_02, I_07, and I_11 are clones identified from a diversified ankyrin repeat scaffold library using phage display for IgG1-Fc binding (Steiner D. et al., J. Mol. Biol. 2008 382, 1211-1227). These modified Rituximab light chain fusion variants were cotransfected with the Rituximab HC (SEQ ID NO:37, encoding protein SEQ ID NO:38) and expressed in the Expi293 system. The purified protein was analyzed using SDS-PAGE under reducing and non-reducing conditions (FIG. 12B). The heavy chain and light chains for all of the constructs are observed as well as the size difference of the light chain depending on the fusion to its C-terminus.

FIGS. 13A-G shows the ability of compositions with diverse disabling moieties to block ADCC and CDC signaling. Rituximab LC-HSVgE did not show any attenuation of the ADCC signal. The amount of activation was equivalent in the presence or absence of the Granzyme B activator. The CDC lysis was nearly 2 fold greater in the presence of the Granzyme B activator, indicating that the HSVgE binding somewhat disrupts CDC activation. The SSL10 derivative did not show any attenuation of the ADCC or CDC signals in the presence of the Granzyme B activator. The artificial scaffold proteins each showed a slightly different pattern from one another. I_02 showed modest attenuation of ADCC and CDC signals in the absence of the Granzyme B activator, suggesting partial blockage of binding sites on the Fc domain. I_07 showed a greater differential between activated (plus Granzyme B) and unactivated antibody (minus Granzyme B) for ADCC and somewhat less difference in the CDC signal suggesting that the binding site for I_07 interferes with Fc binding more than C1q binding. I_11 showed very weak attenuation of the ADCC signal in the presence of Granzyme B, while CDC was completely blocked, indicating that I_11 binds preferentially in a region that interferes more with CDC activation than ADCC activation. These examples demonstrate alternative methods of disabling the effector function of antibodies.

A summary of all the antibody variants and their results from the in vitro ADCC and CDC assays, with the SEQ ID NO: for the protein, is presented in Table 1.

TABLE 1

| Binders | SEQ ID NO: | Target | Type | ADCC | ADCC Disabled | CDC | CDC Disabled |
|---|---|---|---|---|---|---|---|
| Commercial Rituximab LC | 4 | CD20 | Antibody | + | − | + | − |
| Rituximab-LC-CD32 | 13, 34 | CD20 | Antibody | + | + | + | + |
| Herceptin-LC-CD32 Her2 | 36 | Her2 | Antibody | + | + | − | NA |
| aCD20-CH1-CH2-CH3+CLk-CD32 | 44 + 48 | CD20 | Antibody-like | + | + | − | NA |
| aCD19-CH1-CH2-CH3+CLk-CD32 | 46 + 48 | CD19 | Antibody-like | + | + | − | NA |
| aCD20-Fc-CD32 | 50 | CD20 | scFv-Fc fusion | + | + | − | NA |
| aCD19-Fc-CD32 | 52 | CD19 | scFv-Fc fusion | + | + | − | NA |
| CD2(ECD)-Fc-CD32 | 56 | LFA-3 | natural ligand Fc fusion | − | NA | − | NA |
| CCPE-Fc-CD32 | 54 | claudin 3/4 | bacterial protein-Fc fusion | + | + | − | NA |
| H10-2-G3-Fc-CD32 | 58 | Her2/ErbB2 | artificial scaffold Fc-fusion | + | + | − | NA |

| Disabling moieties Fc-binder | SEQ ID NO: | Type | ADCC | ADCC Disabled | CDC | CDC Disabled |
|---|---|---|---|---|---|---|
| Rituximab LC-I_02 | 66 | Darpin (artificial scaffold) | + | + | + | + |
| Rituximab LC-I_07 | 68 | Darpin (artificial scaffold) | + | + | + | + |
| Rituximab LC-I_11 | 70 | Darpin (artificial scaffold) | + | + | + | + |
| Rituximab LC-SSL10 | 62 | *S. aureus* (bacterial protein) | + | − | + | − |
| Rituximab LC-HSV gE | 64 | Herpes simplex virus (viral protein) | + | − | + | + |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An antibody derivative comprising:
   (i) two first portions, each first portion comprising:
      (a) an antigen-binding domain comprising (1) an antibody variable region comprising a VH heavy chain variable domain and a VL light chain variable domain of a human IgG antibody, or (2) a single chain variable fragment (scFv) region;
      (b) a human IgG antibody heavy chain constant region comprising a CH1 heavy chain constant domain, a hinge region, a CH2 heavy chain constant domain, and a CH3 heavy chain constant domain of human IgG, wherein the CH2 and CH3 heavy chain constant domains represent an antibody effector region comprising an amino acid sequence having at least 95% sequence identity to amino acids 254-470 of SEQ ID NO: 2; and
      (c) a human IgG antibody CL light chain constant domain comprising an amino acid sequence having at least 95% sequence identity to amino acids 126-232 of SEQ ID NO: 4;
   wherein the antigen-binding domain in each of the two first portions is identical;
   wherein the C-terminus of the VH domain of (i)(a)(1) or the scFv region of (i)(a)(2) is linked to the N-terminus of the human IgG heavy chain constant region of (i)(b); and the C-terminus of the VL domain of (i)(a)(1) is linked to the N-terminus of the CL light chain constant domain of (i)(c);
   (ii) two second portions, each second portion comprising an effector region binding moiety comprising an extracellular soluble portion of a human Fc receptor selected from the group consisting of CD16, CD32, and CD64, wherein the extracellular soluble portion of the human Fc receptor comprises domain 1 (D1) and domain 2 (D2) of the extracellular soluble domain of the Fc receptor; and
   (iii) two third portions, each third portion comprising a cleavable linker containing a protease cleavage site that comprises the amino acid sequences of SEQ ID NO: 30 and SEQ ID NO: 31, wherein the cleavable linker is (a) coupled at one end to the C-terminus of the CL light chain constant domain of (i)(c) and (b) coupled at the other end to the effector region binding moiety, wherein the effector region binding moiety binds to the effector region when the cleavable linker is intact.

2. The antibody derivative of claim 1, wherein the extracellular soluble portion of the Fc receptor has the amino acid sequence of any one of the following:
   (1) the extracellular domains D1 and D2 consisting of amino acids 584 to 752 of SEQ ID NO: 6;
   (2) the extracellular domains D1 and D2 consisting of amino acids 584 to 751 of SEQ ID NO: 8; and (3) the extracellular domains D1 and D2 consisting of amino acids 584 to 750 of SEQ ID NO: 10.

3. A kit comprising:
the antibody derivative of claim 1, or a nucleic acid encoding the antibody derivative, and
an activator comprising: a target recognition moiety and an activator domain that cleaves the cleavable linker, wherein the activator domain comprises a protease.

4. The kit of claim 3, wherein the protease is one of the following: (a) pro-granzyme Bv3 comprising the amino acid sequence set forth in SEQ ID NO: 18; or (b) granzyme Bv3 comprising the amino acids 12-240 of the sequence set forth in SEQ ID NO: 60.

5. A nucleic acid encoding the antibody derivative of claim 1.

6. A vector comprising the nucleic acid of claim 5.

7. A host cell expressing the antibody derivative of claim 1.

8. A method of directing immune effector function against a cell, the method comprising:
contacting the cell with an antibody derivative of claim 1, and an activator comprising: a target recognition moiety and an activator domain that cleaves the cleavable linker, wherein the antigen-binding domain and the target recognition moiety bind to targets present on the cell, thereby inducing one or both of a humoral immune response or a cellular immune response against that cell.

9. A method of directing immune effector function against a cell, the method comprising contacting the cell with the antibody derivative of claim 1, wherein the antigen-binding domain binds to a target present on the cell, and the cleavable linker is cleaved by an endogenous activator, to thereby induce one or both of a humoral immune response or a cellular immune response against that cell.

10. The method of claim 8, wherein directing immune effector function against a cell kills the cell.

11. The method of claim 9, wherein directing immune effector function against a cell kills the cell.

* * * * *